(12) United States Patent
Bissantz et al.

(10) Patent No.: US 7,332,501 B2
(45) Date of Patent: Feb. 19, 2008

(54) INDOL-3-YL-CARBONYL-SPIRO-PIPERIDINE DERIVATIVES AS V1A RECEPTOR ANTAGONISTS

(75) Inventors: Caterina Bissantz, Village Neuf (FR); Christophe Grundschober, Rodersdorf (CH); Hasane Ratni, Habsheim (FR); Mark Rogers-Evans, Binningen (CH); Patrick Schnider, Bottmingen (CH)

(73) Assignee: Hoffmann-La Roche Inc., Nutley, NJ (US)

( * ) Notice: Subject to any disclaimer, the term of this patent is extended or adjusted under 35 U.S.C. 154(b) by 23 days.

(21) Appl. No.: 11/483,462

(22) Filed: Jul. 10, 2006

(65) Prior Publication Data

US 2007/0027173 A1    Feb. 1, 2007

(30) Foreign Application Priority Data

Jul. 14, 2005   (EP)  ................................. 05106443
Oct. 7, 2005   (EP)  ................................. 05109364

(51) Int. Cl.
    *A61K 31/438*    (2006.01)
    *C07D 401/14*    (2006.01)
    *C07D 405/14*    (2006.01)

(52) U.S. Cl. ......................... 514/278; 546/17; 544/129; 544/238; 544/242; 544/336; 514/253; 514/256; 514/232.8

(58) Field of Classification Search ................ 514/278, 514/232.8, 253, 256; 546/17; 544/129, 544/238, 242, 336
See application file for complete search history.

(56) References Cited

U.S. PATENT DOCUMENTS 5,686,624 A    11/1997   Di Malta et al.

OTHER PUBLICATIONS

Ebner et al., Eur. J. Neurosci. vol. 15(2), pp. 384-388 (2002).
Liebsch et al., Regul. Pept. vol. 59(2) pp. 229-239 (1995).
Michelini et al., Ann. NY Acad. Sci. vol. 897, pp. 198-211 (1999).
Van Kerckhoven et al., Eur. J. Pharmacol. vol. 449(1-2), pp. 135-141 (2002).

*Primary Examiner*—Charanjit S. Aulakh
(74) *Attorney, Agent, or Firm*—George W. Johnston; Patricia S. Rocha-Tramaloni; Kimberly J. Prior

(57) ABSTRACT

The invention relates to indol-3-yl-carbonyl-spiro-piperidine derivatives which act as V1a receptor antagonists and which are represented by Formula I:

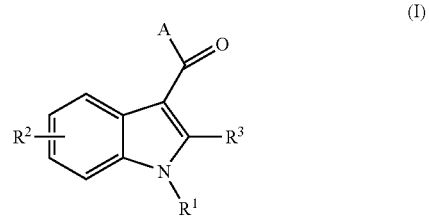

wherein the spiro-piperidine head group A and the residues $R^1$, $R^2$ and $R^3$ are as defined herein. The invention further relates to pharmaceutical compositions containing such compounds, methods for preparing the compounds and pharmaceutical compositions, and their use in the treatment of dysmenorrhea, hypertension, chronic heart failure, inappropriate secretion of vasopressin, liver cirrhosis, nephrotic syndrome, obsessive compulsive disorder, anxious and depressive disorders.

50 Claims, No Drawings

INDOL-3-YL-CARBONYL-SPIRO-PIPERIDINE DERIVATIVES AS V1A RECEPTOR ANTAGONISTS

PRIORITY TO RELATED APPLICATIONS

This application claims the benefit of European Application No. 05106443.4, filed Jul. 14, 2005, as well as European application No. 05109364.9, filed Oct. 7, 2005 which is hereby incorporated by reference in its entirety.

BACKGROUND OF THE INVENTION

Vasopressin is a 9 amino acid peptide mainly produced by the paraventricular nucleus of the hypothalamus. Three vasopressin receptors, all belonging to the class I G-protein coupled receptors, are known. The V1a receptor is expressed in the brain, liver, vascular smooth muscle, lung, uterus and testis, the V1b or V3 receptor is expressed in the brain and pituitary gland, the V2 receptor is expressed in the kidney where it regulates water excretion and mediates the antidiuretic effects of vasopressin.

In the periphery vasopressin acts as a neurohormone and stimulates vasoconstriction, glycogenolysis and antidiuresis. In the brain vasopressin acts as a neuromodulator and is elevated in the amygdala during stress (Ebner, K., C. T. Wotjak, et al. (2002). "Forced swimming triggers vasopressin release within the amygdala to modulate stress-coping strategies in rats." *Eur J Neurosci* 15(2): 384-8). The V1a receptor is extensively expressed in the brain and particularly in limbic areas like the amygdala, lateral septum and hippocampus which are playing an important role in the regulation of anxiety. Indeed V1a knock-out mouse show a reduction in anxious behavior in the plus-maze, open field and light-dark box (Bielsky, I. F., S. B. Hu, et al. (2003). "Profound Impairment in Social Recognition and Reduction in Anxiety-Like Behavior in Vasopressin V1a Receptor Knockout Mice." *Neuropsychopharmacology*). The down-regulation of the V1a receptor using antisense oligonucleotide injection in the septum also causes a reduction in anxious behavior (Landgraf, R., R. Gerstberger, et al. (1995). "V1 vasopressin receptor antisense oligodeoxynucleotide into septum reduces vasopressin binding, social discrimination abilities, and anxiety-related behavior in rats." *Regul Pept* 59(2): 229-39).

The V1a receptor is also mediating the cardiovascular effects of vasopressin in the brain by centrally regulating blood pressure and heart rate in the solitary tract nucleus (Michelini, L. C. and M. Morris (1999). "Endogenous vasopressin modulates the cardiovascular responses to exercise." *Ann NY Acad Sci* 897: 198-211). In the periphery it induces the contraction of vascular smooth muscles and chronic inhibition of the V1a receptor improves hemodynamic parameters in myocardial infarcted rats (Van Kerckhoven, R., I. Lankhuizen, et al. (2002). "Chronic vasopressin V(1A) but not V(2) receptor antagonism prevents heart failure in chronically infarcted rats." *Eur J Pharmacol* 449(1-2): 135-41).

Thus vasopressin receptor antagonists are useful as therapeutics in the conditions of dysmenorrhea, hypertension, chronic heart failure, inappropriate secretion of vasopressin, liver cirrhosis, nephrotic syndrome, obsessive compulsive disorder, anxious and depressive disorders.

SUMMARY OF THE INVENTION

The present invention provides compounds of formula (I)

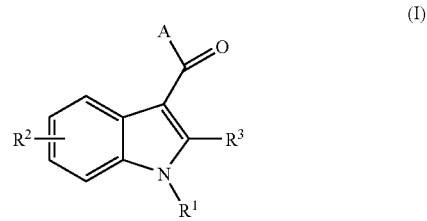

(I)

wherein

A is selected from the following groups (a), (b), (c), (d), (e), (f), (g) and (h):

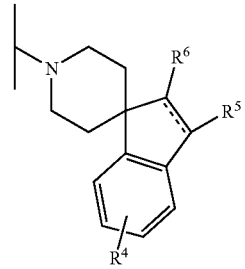

(a)

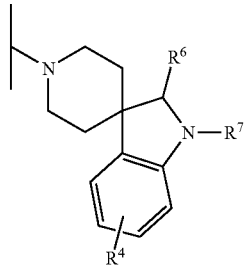

(b)

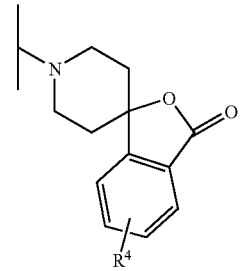

(c)

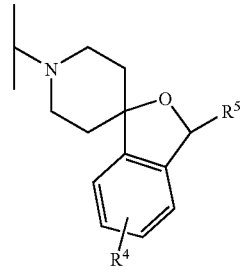

(d)

-continued

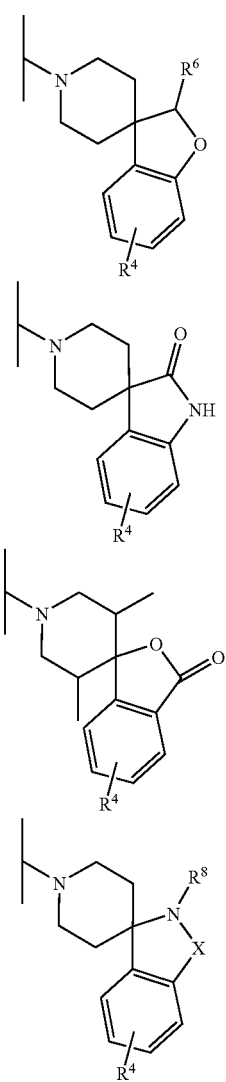

wherein in (a) the dotted line represents an optional double bond;

$R^1$ is H, $C_{1-6}$-alkyl optionally substituted by CN, aryl, 5 or 6 membered heteroaryl or sulfonylaryl each of which is optionally substituted by one or more B, —$(CH_2)_m$—$R^a$ wherein $R^a$ is:

CN, $OR^i$, $NR^iR^{ii}$, or $C_{3-6}$-cycloalkyl, 3 to 7 membered-heterocycloalkyl, aryl, or 5 or 6 membered heteroaryl each of which is optionally substituted by one or more B, or —$(CH_2)_n$—(CO)—$R^b$ or —$(CH_2)_n$—$(SO_2)$—$R^b$, wherein $R^b$ is:

$C_{1-6}$-alkyl, $C_{1-6}$-alkoxy, $C_{3-6}$-cycloalkyl,

—$(CH_2)_m$—$NR^{iii}R^{iv}$, $NR^iR^{ii}$, or $C_{3-6}$-cycloalkyl, 4 to 7 membered-heterocycloalkyl, aryl, or 5 or 6 membered heteroaryl each of which is optionally substituted by one or more B, or $R^1$ and $R^3$ together with the indole ring to which they are attached form a 5 or 6 membered heterocycloalkyl which is optionally substituted by =O, C(O)O—$C_{1-6}$-alkyl or $C_{1-6}$-alkyl;

there is one or more $R^2$, wherein each $R^2$ is the same or different, $R^2$ is one or more H, OH, halo, CN, nitro, $C_{1-6}$-alkyl optionally substituted by —$NR^{iii}R^{iv}$, $C_{1-6}$-alkoxy, —O—$CH_2$—$C_{2-6}$-alkenyl, or benzyloxy, or two $R^2$ together with the indole ring to which they are attached form an oxo or dioxo bridge;

$R^3$ is H, halo,

—(CO)—$R^c$, wherein $R^c$ is:

$C_{1-6}$-alkyl,

—$(CH_2)_n$—$NR^iR^{ii}$, or

—$(CH_2)_n$—$NR^{iii}R^{iv}$, 5 or 6 membered heterocycloalkyl optionally substituted by $C_{1-6}$-alkyl, or $C_{1-6}$-alkyl or aryl, each of which is optionally substituted by halo, —O(CO)—$C_{1-6}$-alkyl, or —NH(CO)$R^d$, wherein $R^d$ is $C_{1-6}$-alkyl optionally substituted by halo or nitro, or $R^d$ is aryl or a 5 or 6 membered heteroaryl each of which is optionally substituted by halo, nitro, $C_{1-6}$-alkyl or $C_{1-6}$-haloalkyl;

there is one or more $R^4$ wherein each $R^4$ is the same or different, $R^4$ is one or more H, halo, $C_{1-6}$-alkyl or $C_{1-6}$-alkoxy each of which is optionally substituted by OH, or two $R^4$ together with the phenyl ring to which they are attached form an oxo or dioxo bridge;

$R^5$ is H, $C_{1-6}$-alkyl or aryl;

$R^6$ is H or $C_{1-6}$-alkyl;

$R^7$ is H or —$SO_2$—$R^e$ wherein $R^e$ is $C_{1-6}$-alkyl or aryl;

$R^8$ is H or $C_{1-6}$-alkyl;

X is $CH_2$ or C=O;

B is halo,

CN, $NR^iR^{ii}$, $C_{1-6}$-alkyl optionally substituted by CN, halo or $C_{1-6}$-alkoxy, $C_{1-6}$-alkoxy, $C_{1-6}$-haloalkoxy, $C_{3-6}$-cycloalkyl, —C(O)O—$C_{1-6}$-alkyl, —C(O)$NR^iR^{ii}$, —C(O)—$C_{1-6}$-alkyl, —$S(O)_2$—$C_{1-6}$-alkyl, —$S(O)_2$—$NR^iR^{ii}$, or $(CR^{iii}R^{iv})_n$-phenyl, or$(CR^{iii}R^{iv})_n$-5 or 6 membered heteroaryl wherein the phenyl or 5 or 6 membered heteroaryl moiety is optionally substituted by one or more substituent(s) selected from the group consisting of:

halo,

CN, $NR^iR^{ii}$, $C_{1-6}$-alkyl optionally substituted by CN, halo or $C_{1-6}$-alkoxy, $C_{1-6}$-alkoxy, $C_{1-6}$-haloalkoxy, $C_{3-6}$-cycloalkyl, —C(O)O—$C_{1-6}$-alkyl, —C(O)—$NR^iR^{ii}$, —C(O)—C$_{1-6}$-alkyl,
—S(O)$_2$—C$_{1-6}$-alkyl, and
—S(O)$_2$—NR$^i$R$^{ii}$;

R$^i$ and R$^{ii}$ are each independently H, C$_{1-6}$-alkyl, C$_{1-6}$-alkyl-NR$^{iii}$R$^{iv}$, —(CO)O—C$_{1-6}$-alkyl, —C(O)—NR$^{iii}$R$^{iv}$, —C(O)—C$_{1-6}$-alkyl, —S(O)$_2$—C$_{1-6}$-alkyl, —S(O)$^2$—NR$^{iii}$R$^{iv}$ or OH;

R$^{iii}$ and R$^{iv}$ are each independently H or C$_{1-6}$-alkyl;

m is 1 to 6; and n is 0 to 4;

and pharmaceutically acceptable salts thereof.

The compounds of formula (I) can contain asymmetric carbon atoms. Accordingly, the present invention includes all stereoisomeric forms of the compounds of formula (I), including each of the individual enantiomers and mixtures thereof.

Compounds of formula (I) have good activity on the V1a receptor. Therefore, the invention provides pharmaceutical compositions containing compounds of formula I or a pharmaceutically acceptable salt thereof and methods for treating dysmenorrhea, hypertension, chronic heart failure, inappropriate secretion of vasopressin, liver cirrhosis, nephrotic syndrome, obsessive compulsive disorder, anxiety, and depressive disorders.

The preferred indications with regard to the present invention are the treatment of anxiety and depressive disorders.

DETAILED DESCRIPTION OF THE INVENTION

The following definitions of general terms used in the present description apply irrespective of whether the terms in question appear alone or in combination. It must be noted that, as used in the specification and the appended claims, the singular forms "a", "an," and "the" include plural forms unless the context clearly dictates otherwise.

As used herein, the term "aryl" means a monovalent cyclic aromatic hydrocarbon moiety consisting of a mono-, bi- or tricyclic aromatic ring system. Examples of aryl moieties include, but are not limited to, optionally substituted phenyl, naphthyl, phenanthryl, fluorenyl, indenyl, pentalenyl, azulenyl, oxydiphenyl, biphenyl, methylenediphenyl, aminodiphenyl, diphenylsulfidyl, diphenylsulfonyl, diphenylisopropylidenyl, benzodioxanyl, benzofuranyl, benzodioxylyl, benzopyranyl, benzoxazinyl, benzoxazinonyl, benzopiperadinyl, benzopiperazinyl, benzopyrrolidinyl, benzomorpholinyl, methylenedioxyphenyl, and ethylenedioxyphenyl, as well as those specifically illustrated by the examples herein below. The aryl group can be substituted. Substituents for aryl include, but are not limited to, halogen, C$_{1-6}$-alkyl, C$_{1-6}$-alkoxy and those groups specifically listed and illustrated by the description and examples herein below. Preferred aryl are phenyl and naphthyl and still preferably phenyl.

The term "C$_{1-6}$-alkyl" denotes a saturated straight- or branched-chain hydrocarbon group containing from 1 to 6 carbon atoms, for example, methyl, ethyl, propyl, isopropyl, n-butyl, i-butyl, 2-butyl, t-butyl and the like. Preferred C$_{1-6}$-alkyl groups are C$_{1-4}$-groups, i.e. groups containing 1-4 carbon atoms.

The term "C$_{1-6}$-alkoxy" denotes an alkyl residue as defined above, which is attached via an oxygen atom. Preferred C$_{1-6}$-alkoxy groups are methoxy and ethoxy as well as those specifically illustrated by the examples herein below.

The term "C$_{2-6}$-alkenyl" denotes a carbon chain of 2 to 6 carbon atoms containing at least one double bond in its chain. C$_{2-6}$-alkenyl groups include ethenyl, propen-1-yl, propen-2-yl, buten-1-yl, buten-3-yl, penten-1-yl, penten-2-yl, penten-3-yl, penten-4-yl, hexen-1-yl, hexen-2-yl, hexen-3-yl, hexen-4-yl and hexen-5-yl, as well as those specifically illustrated by the examples herein below.

The term "benzyloxy" denotes a benzyl group attached via an oxygen atom.

The term "halogen" or "halo" denotes chlorine (Cl), iodine (I), fluorine (F) and bromine (Br).

The term "C$_{1-6}$-haloalkyl" denotes a C$_{1-6}$-alkyl group as defined above which is substituted by one or more halogen atom. Examples of C$_{1-6}$-haloalkyl include, but are not limited to, methyl, ethyl, propyl, isopropyl, isobutyl, sec-butyl, tert-butyl, pentyl and n-hexyl substituted by one or more Cl, F, Br or I atom(s) as well as those groups specifically illustrated by the examples herein below. Preferred C$_{1-6}$-haloalkyl are difluoro- or trifluoro-methyl or ethyl.

"C$_{1-6}$-haloalkoxy" denotes a C$_{1-6}$-alkoxy group as defined above which is substituted by one or more halogen atom. Examples of C$_{1-6}$-haloalkoxy include, but are not limited to, methoxy or ethoxy substituted by one or more Cl, F, Br or I atom(s) as well as those groups specifically illustrated by the examples herein below. Preferred C$_{1-6}$-haloalkoxy are difluoro- or trifluoro-methoxy or ethoxy.

The term "C$_{3-6}$-cycloalkyl" denotes a monovalent or divalent saturated carbocyclic moiety consisting of a monocyclic ring. Cycloalkyl can optionally be substituted with one, two, three or four substituents, wherein each substituent is independently hydroxy, C$_{1-6}$-alkyl, C$_{1-6}$-alkoxy, halogen, amino, unless otherwise specifically indicated. Examples of cycloalkyl moieties include optionally substituted cyclopropyl, optionally substituted cyclobutyl, optionally substituted cyclopentyl and optionally substituted cyclohexyl as well as those specifically illustrated by the examples herein below.

The term "3 to 7 membered heterocycloalkyl" means a monovalent saturated moiety, consisting of one ring of 3 to 7 atoms as ring members, including one, two, or three heteroatoms chosen from nitrogen, oxygen or sulfur, the rest being carbon atoms. 3 to 7 membered heterocycloalkyl can optionally be substituted with one, two, three or four substituents, wherein each substituent is independently hydroxy, C$_{1-6}$-alkyl, C$_{1-6}$-alkoxy, C$_{1-6}$-thioalkyl, halo, C$_{1-6}$-haloalkyl, C$_{1-6}$-hydroxyalkyl, alkoxycarbonyl, amino, C$_{1-6}$-alkylamino, di(C$_{1-6}$)alkylamino, aminocarbonyl, or carbonylamino, unless otherwise specifically indicated. Examples of heterocycloalkyl moieties include, but are not limited to, oxirane, optionally substituted oxetane, optionally substituted tetrahydro-furanyl, optionally substituted piperidinyl, optionally substituted pyrrolidinyl, optionally substituted morpholinyl, optionally substituted piperazinyl, optionally substituted azepane or homopiperazine, and the like and those which are specifically exemplified herein. Substituents can be selected from C$_{1-6}$-alkyl, C$_{1-6}$-alkoxy, C$_{1-6}$-haloalkyl, halo, CN, OH, NH$_2$, as well as those substituents which are specifically illustrated in the examples hereinafter.

The term "5 or 6 membered heteroaryl" means an aromatic ring of 5 or 6 ring atoms as ring members containing one, two, or three ring heteroatoms selected from N, O, or S, the rest being carbon atoms. 5 or 6 heteroaryl can optionally be substituted with one, two, three or four substituents, wherein each substituent is independently hydroxy, C$_{1-6}$-alkyl, C$_{1-6}$-alkoxy, C$_{1-6}$-thioalkyl, halo, C$_{1-6}$-haloalkyl, C$_{1-6}$-hydroxyalkyl, alkoxycarbonyl, amino, C$_{1-6}$-alkylamino, di(C$_{1-6}$)alkylamino, aminocarbonyl, or carbonylamino, unless otherwise specifically indicated.

Examples of heteroaryl moieties include, but are not limited to, optionally substituted imidazolyl, optionally substituted oxazolyl, optionally substituted thiazolyl, optionally substituted pyrazinyl, optionally substituted pyrrolyl, optionally substituted pyrazinyl, optionally substituted pyridinyl, optionally substituted pyrimidinyl, optionally substituted furanyl, and those which are specifically exemplified herein.

The term "sulfonylaryl" denotes an aryl group as defined hereinabove which is attached via a sulfonyl group.

The expression "two $R^2$ together with the indole ring to which they are attached form an oxo or dioxo bridge denotes an oxo or dioxo bridge of the following formulae:

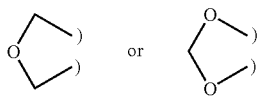

which bind two adjacent carbon atoms of the phenyl or indole ring of the compound of formula (I) to which either $R^2$ is binding.

Examples of group illustrating the expression "$R^1$ and $R^3$ together with the indole ring to which they are attached form a 5 or 6 membered heterocycloalkyl which is optionally substituted by =O, C(O)O—$C_{1-6}$-alkyl or $C_{1-6}$-alkyl" are:

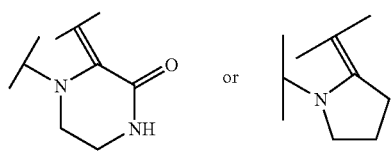

as well as those specifically illustrated by the examples.

"Pharmaceutically acceptable," such as pharmaceutically acceptable carrier, excipient, etc., means pharmacologically acceptable and substantially non-toxic to the subject to which the particular compound is administered.

The term "pharmaceutically acceptable acid addition salts" embraces salts with inorganic and organic acids, such as hydrochloric acid, nitric acid, sulfuric acid, phosphoric acid, citric acid, formic acid, fumaric acid, maleic acid, acetic acid, succinic acid, tartaric acid, methane-sulfonic acid, p-toluenesulfonic acid, as well as those specifically illustrated by the examples herein below.

"Therapeutically effective amount" means an amount that is effective to prevent, alleviate or ameliorate symptoms of disease or prolong the survival of the subject being treated.

The present invention provides compounds of formula (I)

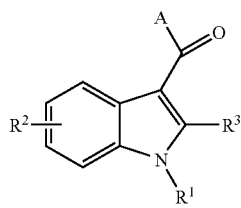

(I)

wherein

A is selected from the following groups (a), (b), (c), (d), (e), (f), (g) and (h):

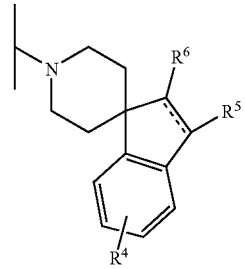

(a)

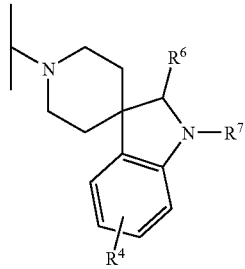

(b)

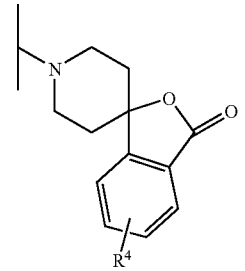

(c)

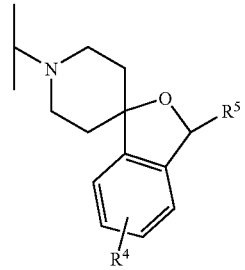

(d)

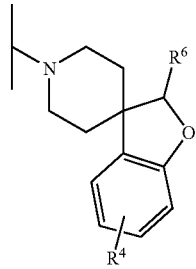

(e)

-continued (f)
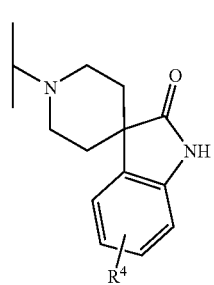

(g)
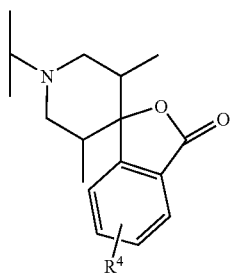

(h)
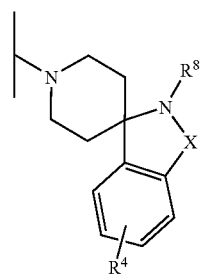

wherein in (a) the dotted line represents an optional double bond;

$R^1$ is H,
$C_{1-6}$-alkyl optionally substituted by CN,
aryl, 5 or 6 membered heteroaryl or sulfonylaryl each of which is optionally substituted by one or more B,
—$(CH_2)_m$—$R^a$ wherein $R^a$ is:
  CN,
  $OR^i$,
  $NR^iR^{ii}$, or
  $C_{3-6}$-cycloalkyl, 3 to 7 membered-heterocycloalkyl, aryl, or 5 or 6 membered heteroaryl each of which is optionally substituted by one or more B,
or —$(CH_2)_n$—(CO)—$R^b$ or —$(CH_2)_n$—$(SO_2)$—$R^b$, wherein $R^b$ is:
  $C_{1-6}$-alkyl,
  $C_{1-6}$-alkoxy,
  $C_{3-6}$-cycloalkyl,
  —$(CH_2)_m$—$NR^{iii}R^{iv}$,
  $NR^iR^{ii}$, or
  $C_{3-6}$-cycloalkyl, 4 to 7 membered-heterocycloalkyl, aryl, or 5 or 6 membered heteroaryl each of which is optionally substituted by one or more B,
or $R^1$ and $R^3$ together with the indole ring to which they are attached form a 5 or 6 membered heterocycloalkyl which is optionally substituted by =O, C(O)O—$C_{1-6}$-alkyl or $C_{1-6}$-alkyl;

there is one or more $R^2$, wherein each $R^2$ is the same or different, $R^2$ is one or more H, OH, halo, CN, nitro, $C_{1-6}$-alkyl optionally substituted by —$NR^{iii}R^{iv}$, $C_{1-6}$-alkoxy, —O—$CH_2$—$C_{2-6}$-alkenyl, or benzyloxy,
or two $R^2$ together with the indole ring to which they are attached form an oxo or dioxo bridge;

$R^3$ is H,
halo,
—(CO)—$R^c$, wherein $R^c$ is:
  $C_{1-6}$-alkyl,
  —$(CH_2)_n$—$NR^iR^{ii}$, or
  —$(CH_2)_n$—$NR^{iii}R^{iv}$,
  5 or 6 membered heterocycloalkyl optionally substituted by $C_{1-6}$-alkyl,
or $C_{1-6}$-alkyl or aryl, each of which is optionally substituted by
  halo,
  —O(CO)—$C_{1-6}$-alkyl, or
  —NH(CO)$R^d$, wherein $R^d$ is $C_{1-6}$-alkyl optionally substituted by halo or nitro, or $R^d$ is aryl or a 5 or 6 membered heteroaryl each of which is optionally substituted by halo, nitro, $C_{1-6}$-alkyl or $C_{1-6}$-haloalkyl;

there is one or more $R^4$ wherein each $R^4$ is the same or different, $R^4$ is one or more H, halo, $C_{1-6}$-alkyl or $C_{1-6}$-alkoxy each of which is optionally substituted by OH,
or two $R^4$ together with the phenyl ring to which they are attached form an oxo or dioxo bridge;

$R^5$ is H, $C_{1-6}$-alkyl or aryl;
$R^6$ is H or $C_{1-6}$-alkyl;
$R^7$ is H or —$SO_2$—$R^e$ wherein $R^e$ is $C_{1-6}$-alkyl or aryl;
$R^8$ is H or $C_{1-6}$-alkyl;
X is $CH_2$ or C=O;
B is halo,
  CN,
  $NR^iR^{ii}$,
  $C_{1-6}$-alkyl optionally substituted by CN, halo or $C_{1-6}$-alkoxy,
  $C_{1-6}$-alkoxy,
  $C_{1-6}$-haloalkoxy,
  $C_{3-6}$-cycloalkyl,
  —C(O)O—$C_{1-6}$-alkyl,
  —C(O)$NR^iR^{ii}$,
  —C(O)—$C_{1-6}$-alkyl,
  —$S(O)_2$—$C_{1-6}$-alkyl,
  —$S(O)_2$—$NR^iR^{ii}$, or
  $(CR^{iii}R^{iv})_n$-phenyl, or $(CR^{iii}R^{iv})_n$-5 or 6 membered heteroaryl wherein the phenyl or 5 or 6 membered heteroaryl moiety is optionally substituted by one or more substituent(s) selected from the group consisting of:
  halo,
  CN,
  $NR^iR^{ii}$,
  $C_{1-6}$-alkyl optionally substituted by CN, halo or $C_{1-6}$-alkoxy,
  $C_{1-6}$-alkoxy,
  $C_{1-6}$-haloalkoxy,
  $C_{3-6}$-cycloalkyl,
  —C(O)O—$C_{1-6}$-alkyl,
  —C(O)—$NR^iR^{ii}$,
  —C(O)—$C_{1-6}$-alkyl,
  —$S(O)_2$—$C_{1-6}$-alkyl, and
  —$S(O)_2$—$NR^iR^{ii}$;

$R^i$ and $R^{ii}$ are each independently H, $C_{1-6}$-alkyl, $C_{1-6}$-alkyl-$NR^{iii}R^{iv}$, —(CO)O—$C_{1-6}$-alkyl, —C(O)—$NR^{iii}R^{iv}$, —C(O)—$C_{1-6}$-alkyl, —$S(O)_2$—$C_{1-6}$-alkyl, —$S(O)^2$—$NR^{iii}R^{iv}$ or OH;

$R^{iii}$ and $R^{iv}$ are each independently H or $C_{1-6}$-alkyl;

m is 1 to 6; and n is 0 to 4;

and pharmaceutically acceptable salts thereof.

In a certain embodiment, the compounds of formula (I) are those compounds wherein:

A is selected from (a), (b), (c), (d), (e), (f), (g) or (h) and wherein $R^1$ is H, $C_{1-6}$-alkyl optionally substituted by CN, aryl, 5 or 6 membered heteroaryl or sulfonylaryl each of which is optionally substituted by one or more B, —$(CH_2)_m$—$R^a$ wherein $R^a$ is:
$OR^i$,
CN,
$NR^iR^{ii}$, or
$C_{3-6}$-cycloalkyl, 3 to 7 membered-heterocycloalkyl, aryl or 5 or 6 membered heteroaryl each of which is optionally substituted by one or more B, or —$(CH_2)_n$—(CO)—$R^b$ or —$(CH_2)_n$—$(SO_2)$—$R^b$, wherein $R^b$ is:
$C_{1-6}$-alkoxy,
$NR^iR^{ii}$, or
4 to 7 membered-heterocycloalkyl, aryl, or 5 or 6 membered heteroaryl each of which is optionally substituted by one or more B, or $R^1$ and $R^3$ together with the indole ring to which they are attached form a 5 or 6 membered heterocycloalkyl which is optionally substituted by =O, C(O)O—$C_{1-6}$-alkyl or $C_{1-6}$-alkyl;

there is one or more $R^2$, wherein each $R^2$ is the same or different, $R^2$ is one or more H, OH, halo, $C_{1-6}$-alkyl optionally substituted by —$NR^{iii}R^{iv}$, or $C_{1-6}$-alkoxy;

$R^3$ is H,
halo
—(CO)—$R^c$, wherein $R^c$ is:
$C_{1-6}$-alkyl
—$(CH_2)_n$—$NR^iR^{ii}$, or
—$(CH_2)_n$—$NR^{iii}R^{iv}$,
5 or 6 membered heterocycloalkyl optionally substituted by $C_{1-6}$-alkyl,
or $C_{1-6}$-alkyl or aryl, each of which is optionally substituted by halo, there is one or more $R^4$, wherein each $R^4$ is the same or different, $R^4$ is one or more H, halo, or $C_{1-6}$-alkoxy optionally substituted by OH,
or two $R^4$ together with the phenyl ring to which they are attached form an oxo or dioxo bridge;

$R^5$ is H or aryl;

$R^6$ is H;

$R^7$ is H or —$SO_2$—$R^e$ wherein $R^e$ is $C_{1-6}$-alkyl or aryl;

$R^8$ is H or $C_{1-6}$-alkyl;

X is $CH_2$ or C=O;

B is halo,
CN,
$NH_2$,
$C_{1-6}$-alkyl optionally substituted by CN or $C_{1-6}$-alkoxy,
$C_{1-6}$-alkoxy,
$C_{1-6}$-haloalkoxy,
$C_{3-6}$-cycloalkyl,
—C(O)O—$C_{1-6}$-alkyl, or
—$(CR^{iii}R^{iv})_n$-phenyl, wherein the phenyl is optionally substituted by one or more substituent(s) selected from the group consisting of:
halo,
$C_{1-6}$-alkyl optionally substituted by CN or halo, and
$C_{1-6}$-alkoxy;

$R^i$ and $R^{ii}$ are each independently H, $C_{1-6}$-alkyl, $C_{1-6}$-alkyl-$NR^{iii}R^{iv}$, —(CO)O—$C_{1-6}$-alkyl, —C(O)—$NR^{iii}R^{iv}$, —C(O)—$C_{1-6}$-alkyl, —$S(O)_2$—$C_{1-6}$-alkyl, —$S(O)^2$—$NR^{iii}R^{iv}$ or OH;

$R^{iii}$ and $R^{iv}$ are H or $C_{1-6}$-alkyl;

m is 1 to 6; and n is 0 to 4;

and pharmaceutically acceptable salts thereof.

In another embodiment, the compounds of formula (I) are those compounds wherein:

A is selected from (a), (b), (c), (d) or (e), and wherein $R^1$ is H, $C_{1-6}$-alkyl optionally substituted by CN, aryl, 5 or 6 membered heteroaryl or sulfonylaryl each of which is optionally substituted by one or more B, —$(CH_2)_m$—$R^a$ wherein $R^a$ is:
CN,
$OR^i$,
$NR^iR^{ii}$, or
$C_{3-6}$-cycloalkyl, 4 to 7 membered-heterocycloalkyl, aryl, or 5 or 6 membered heteroaryl each of which is optionally substituted by one or more B, or —$(CH_2)_n$—(CO)—$R^b$ or —$(CH_2)_n$—$(SO_2)$—$R^b$, wherein $R^b$ is:
$C_{1-6}$-alkyl,
$C_{1-6}$-alkoxy,
$C_{3-6}$-cycloalkyl,
—$(CH_2)_m$—$NR^{iii}R^{iv}$,
$NR^iR^{ii}$, or
$C_{3-6}$-cycloalkyl, 4 to 7 membered-heterocycloalkyl, aryl, or 5 or 6 membered heteroaryl each of which is optionally substituted by one or more B, or $R^1$ and $R^3$ together with the indole ring to which they are attached form a 5 or 6 membered heterocycloalkyl which is optionally substituted by (CO);

there is one or more $R^2$, wherein each $R^2$ is the same or different, $R^2$ is one or more H, OH, halo, CN, nitro, $C_{1-6}$-alkyl optionally substituted by —$NR^{iii}R^{iv}$, $C_{1-6}$-alkoxy, —O—$CH_2$—$C_{2-6}$-alkenyl, or benzyloxy, or two $R^2$ together with the indole ring to which they are attached form an oxo or dioxo bridge;

$R^3$ is H,
halo,
—(CO)—$R^c$, wherein $R^c$ is:
$C_{1-6}$-alkyl,
—$(CH_2)_n$—$NR^iR^{ii}$, or
—$(CH_2)_n$—$NR^{iii}R^{iv}$,
5 or 6 membered heterocycloalkyl optionally substituted by $C_{1-6}$-alkyl,
or $C_{1-6}$-alkyl or aryl, each of which is optionally substituted by
halo,
—O(CO)—$C_{1-6}$-alkyl, or
—NH(CO)$R^d$, wherein $R^d$ is $C_{1-6}$-alkyl optionally substituted by halo or nitro, or $R^d$ is aryl or a 5 or 6 membered heteroaryl, each of which is optionally substituted by halo, nitro, $C_{1-6}$-alkyl or $C_{1-6}$-haloalkyl;

there is one or more $R^4$, wherein each $R^4$ is the same or different, $R^4$ is one or more H, halo, $C_{1-6}$-alkyl or $C_{1-6}$-alkoxy or two $R^4$ together with the phenyl ring to which they are attached form an oxo or dioxo bridge;

$R^5$ is H, $C_{1-6}$-alkyl or aryl;

$R^6$ is H or $C_{1-6}$-alkyl;

$R^7$ is H or —$SO_2$—$R^e$ wherein $R^e$ is $C_{1-6}$-alkyl or aryl;

B is halo,
  CN, $NR^iR^{ii}$,
  $C_{1-6}$-alkyl optionally substituted by CN, halo or $C_{1-6}$-alkoxy,
  $C_{1-6}$-alkoxy,
  $C_{1-6}$-haloalkoxy,
  $C_{3-6}$-cycloalkyl,
  —C(O)O—$C_{1-6}$-alkyl,
  —C(O)$NR^iR^{ii}$,
  —C(O)—$C_{1-6}$-alkyl,
  —S(O)$_2$—$C_{1-6}$-alkyl,
  —S(O)$_2$—$NR^iR^{ii}$, or
  $(CR^{iii}R^{iv})_n$-phenyl or $(CR^{iii}R^{iv})_n$-5 or 6 membered heteroaryl wherein the phenyl or 5 or 6 membered heteroaryl moiety is optionally substituted by one or more substituent(s) selected from the group consisting of:
    halo,
    CN,
    $NR^iR^{ii}$,
    $C_{1-6}$-alkyl optionally substituted by CN or $C_{1-6}$-alkoxy,
    $C_{1-6}$-alkoxy,
    $C_{1-6}$-haloalkoxy,
    $C_{3-6}$-cycloalkyl,
    —C(O)O—$C_{1-6}$-alkyl,
    —C(O)—$NR^iR^{ii}$,
    —C(O)—$C_{1-6}$-alkyl,
    —S(O)$_2$—$C_{1-6}$-alkyl, and
    —S(O)$_2$—$NR^iR^{ii}$;

$R^i$ and $R^{ii}$ are each independently H, $C_{1-6}$-alkyl, $C_{1-6}$-alkyl-$NR^{iii}R^{iv}$, —(CO)O—$C_{1-6}$-alkyl, —C(O)—$NR^{iii}R^{iv}$, —C(O)—$C_{1-6}$-alkyl, —S(O)$_2$—$C_{1-6}$-alkyl or —S(O)$_2$—$NR^{iii}R^{iv}$;

$R^{iii}$ and $R^{iv}$ are each independently H or $C_{1-6}$-alkyl;

m is 1 to 6; and n is 0 to 4;

and pharmaceutically acceptable salts thereof.

In another embodiment, the compounds of formula (I) are those compounds wherein:

A is selected from (a), (b), (c), (d) or (e), and wherein $R^1$ is H,
  $C_{1-6}$-alkyl,
  aryl, 5 or 6 membered heteroaryl or sulfonylaryl which are optionally substituted by one or more B,
  —(CH$_2$)$_m$—$R^a$ wherein $R^a$ is:
    CN,
    $NR^iR^{ii}$, or
    $C_{3-6}$-cycloalkyl, 4 to 7 membered-heterocycloalkyl, aryl or 5 or 6 membered heteroaryl each of which is optionally substituted by one or more B,
  or —(CH$_2$)$_n$—(CO)—$R^b$ or —(CH$_2$)$_n$—(SO$_2$)—$R^b$, wherein $R^b$ is:
    $C_{1-6}$-alkoxy,
    $NR^iR^{ii}$, or
    4 to 7 membered-heterocycloalkyl, aryl, each of which is optionally substituted by one or more B,
  or $R^1$ and $R^3$ together with the indole ring to which they are attached form a 5 or 6 membered heterocycloalkyl which is optiontally substituted by (CO);

there is one or more $R^2$, wherein each $R^2$ is the same or different, $R^2$ is one or more H, OH, halo, $C_{1-6}$-alkyl optionally substituted by —$NR^{iii}R^{iv}$, or $C_{1-6}$-alkoxy;

$R^3$ is H,
  —(CO)—$R^c$, wherein $R^c$ is:
    —(CH$_2$)$_n$—$NR^iR^{ii}$, or
    —(CH$_2$)$_n$—$NR^{iii}R^{iv}$,
    5 or 6 membered heterocycloalkyl optionally substituted by $C_{1-6}$-alkyl,
    or $C_{1-6}$-alkyl or aryl, each of which is optionally substituted by halo, $R^4$, $R^5$ and $R^6$ are H;

$R^7$ is H or —$SO_2$—$R^e$ wherein $R^e$ is $C_{1-6}$-alkyl or aryl;

B is halo,
  NH$_2$,
  $C_{1-6}$-alkyl optionally substituted by CN or $C_{1-6}$-alkoxy,
  $C_{1-6}$-alkoxy,
  $C_{1-6}$-haloalkoxy,
  $C_{3-6}$-cycloalkyl,
  —C(O)O—$C_{1-6}$-alkyl, or
  —(CR$^{iii}$R$^{iv}$)$_n$-phenyl, wherein the phenyl is optionally substituted by one or more substituent(s) selected from the group consisting of:
    halo,
    $C_{1-6}$-alkyl optionally substituted by CN or halo, and
    $C_{1-6}$-alkoxy;

$R^i$ and $R^{ii}$ are each independently H, $C_{1-6}$-alkyl, $C_{1-6}$-alkyl-$NR^{iii}R^{iv}$, —(CO)O—$C_{1-6}$-alkyl, —C(O)—$NR^{iii}R^{iv}$, —C(O)—$C_{1-6}$-alkyl, —S(O)$_2$—$C_{1-6}$-alkyl or —S(O)$_2$—$NR^{iii}R^{iv}$;

$R^{iii}$ and $R^{iv}$ are each independently H or $C_{1-6}$-alkyl;

m is 1 to 6; and n is 0 to 4;

and pharmaceutically acceptable salts thereof.

In another embodiment, the compound of formula (I) are those compounds wherein:

A is selected from (a), (b), (c), (d) or (e), and wherein $R^1$ is H, or
  $C_{1-6}$-alkyl optionally substituted by CN, or
  $C_{1-6}$-alkoxy, or
  aryl, or
  5 or 6 membered heteroaryl, or
  sulfonylaryl, or
  —(CH$_2$)$_m$—$R^a$ wherein $R^a$ is
    $C_{3-6}$-cycloalkyl, or
    5 or 6 membered-heterocycloalkyl, aryl, or 5 or 6 membered heteroaryl each of which is optionally substituted by one or more substituents selected from the group consisting of:
      halo,
      CN,
      $C_{1-6}$-alkyl,
      $C_{1-6}$-alkoxy,
      $C_{1-6}$-haloalkoxy,
      —C(O)O—$C_{1-6}$-alkyl and phenyl each of which is optionally substituted by halo, $C_{1-6}$-alkyl, $C_{1-6}$-haloalkyl or $C_{1-6}$-alkoxy,
      —(CH$_2$)$_m$—$NR^iR^{ii}$, and
      —(CH$_2$)$_n$—(CO)—$R^b$, wherein $R^b$ is aryl or 5 or 6 membered-heterocycloalkyl;

there is one or more R², wherein each R² is the same or different,

R² is one or more H, halo, CN, nitro, C₁₋₆-alkyl, C₁₋₆-alkoxy, —O—CH₂—C₂₋₆-alkenyl, or benzyloxy,
  or two R² together with the indole ring to which they are attached form an oxo or dioxo bridge;

R³ is H, or
  halo, or
  —(CO)—R$^c$, wherein R$^c$ is C₁₋₆-alkyl, 5 or 6 membered heterocycloalkyl optionally substituted by C₁₋₆-alkyl, or R$^c$ is —(CH₂)$_n$—NR$^i$R$^{ii}$, or
  C₁₋₆-alkyl or aryl, each of which is optionally substituted by:
    —O(CO)—C₁₋₆-alkyl,
    or —NH(CO)R$^d$, wherein R$^d$ is C₁₋₆-alkyl optionally substituted by halo or nitro, or R$^d$ is aryl or a 5 or 6 membered heteroaryl, each of which is optionally substituted by halo, nitro, C₁₋₆-alkyl or C₁₋₆-haloalkyl;

there is one or more R⁴, wherein each R⁴ is the same or different,

R⁴ is one or more H, halo, C₁₋₆-alkyl, or C₁₋₆-alkoxy
  or two R⁴ together with the phenyl ring to which they are attached form an oxo or dioxo bridge;

R⁵ is H, C₁₋₆-alkyl or aryl;
R⁶ is H or C₁₋₆-alkyl;
R⁷ is H or —SO₂—R$^e$ wherein R$^e$ is C₁₋₆-alkyl or aryl;
R$^i$ and R$^{ii}$ are each independently selected from H, C₁₋₆-alkyl or —(CO)O—C₁₋₆-alkyl;
m is 1 to 6; and
n is 0 to 4;

and pharmaceutically acceptable salts thereof.

As it can be seen from the definition of A in the compounds of formula (I), said compounds of formula (I) encompass the compounds of formulae (I-a), (I-b), (I-c), (I-d), (I-e), (I-f), (I-g) and (I-h) as follows:

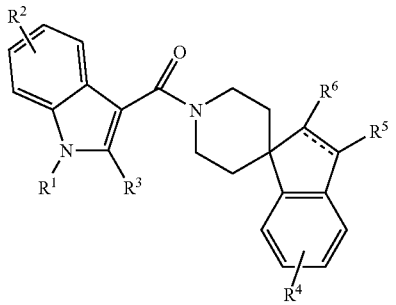
(I-a)

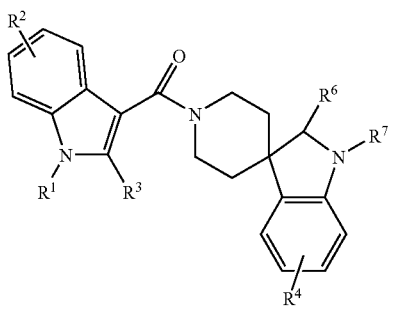
(I-b)

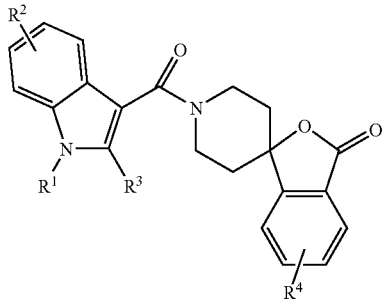
(I-c)

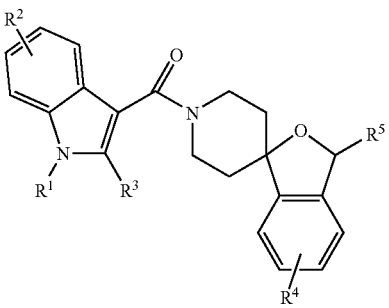
(I-d)

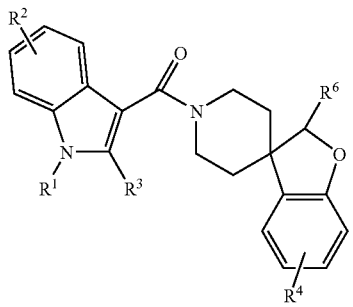
(I-e)

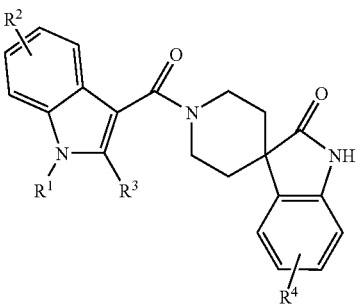
(I-f)

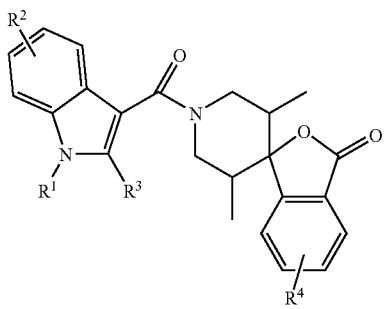
(I-g)

-continued

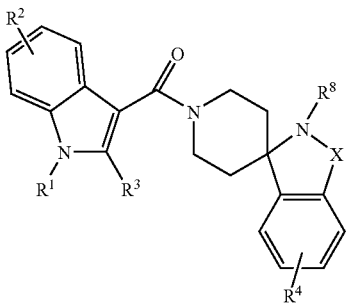

(I-h)

wherein $R^1$ to $R^8$ and X are as defined hereinabove in connection with formula (I).

In a certain embodiment the compounds of the invention are those compounds of formula (I-a):

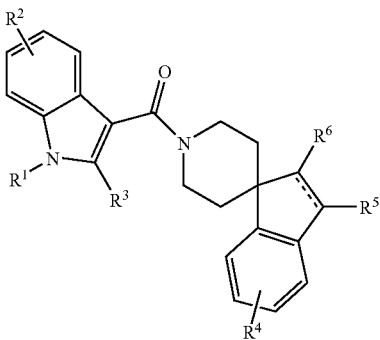

(I-a)

wherein the dotted line represents and optional double bond;
$R^1$ is H,
  $C_{1-6}$-alkyl optionally substituted by CN, sulfonylaryl,
  —$(CH_2)_m$—$R^a$ wherein $R^a$ is:
    $OR^i$,
    CN,
    $NR^iR^{ii}$, or
    $C_{3-6}$-cycloalkyl, 3 to 6 membered-heterocycloalkyl, aryl or 5 or 6 membered heteroaryl each of which is optionally substituted by one or more B,
  or —$(CH_2)_n$—(CO)—$R^b$, wherein $R^b$ is:
    $C_{1-6}$-alkoxy,
    $NR^iR^{ii}$, or
    6 membered-heterocycloalkyl, aryl, or 5 or 6 membered heteroaryl each of which is optionally substituted by one or more B;
there is one or more $R^2$, wherein each $R^2$ is the same or different,
$R^2$ is one or more H, halo, $C_{1-6}$-alkyl;
$R^3$ is H,
  $C_{1-6}$-alkyl,
  or —(CO)—$R^c$, wherein $R^c$ is:
    $C_{1-6}$-alkyl, or
    —$(CH_2)_n$—$NR^iR^{ii}$,
there is one or more $R^4$, wherein each $R^4$ is the same or different,
$R^4$ is one or more H, halo, or $C_{1-6}$-alkoxy optionally substituted by OH, or two $R^4$ together with the phenyl ring to which they are attached form an oxo or dioxo bridge;
$R^5$ is H;
$R^6$ is H;
B is halo,
  CN,
  $C_{1-6}$-alkyl optionally substituted by CN or $C_{1-6}$-alkoxy,
  $C_{1-6}$-alkoxy,
  $C_{1-6}$-haloalkoxy,
  $C_{3-6}$-cycloalkyl,
  —C(O)O—$C_{1-6}$-alkyl,
  —$(CR^{iii}R^{iv})_n$-phenyl, wherein the phenyl is optionally substituted by one or more substituent(s) selected from the group consisting of:
    halo,
    $C_{1-6}$-alkyl optionally substituted by CN or halo, and
    $C_{1-6}$-alkoxy;
$R^i$ and $R^{ii}$ are each independently H, $C_{1-6}$-alkyl, $C_{1-6}$-alkyl-$NR^{iii}R^{iv}$, —C(O)—$C_{1-6}$-alkyl, —S(O)$_2$—$C_{1-6}$-alkyl or OH;
$R^{iii}$ and $R^{iv}$ are each independently H or $C_{1-6}$-alkyl;
m is 1 to 6; and
n is 0 to 4;

and pharmaceutically acceptable salts thereof.

Further, in a certain embodiment the compounds of the invention are those compounds of formula (I-a) as described above, wherein
$R^1$ is H, or
  —$(CH_2)_m$—$R^a$ wherein $R^a$ is aryl which is optionally substituted by one or more substituents selected from the group consisting of:
    halo, CN, $C_{1-6}$-alkyl, $C_{1-6}$-alkoxy, $C_{1-6}$-haloalkoxy, —C(O)O—$C_{1-6}$-alkyl and phenyl optionally substituted by halo, $C_{1-6}$-alkyl, $C_{1-6}$-haloalkyl or $C_{1-6}$-alkoxy;
$R^2$ is H or halo;
$R^3$ is H or $C_{1-6}$-alkyl;
$R^4$, $R^5$ and $R^6$ are H; and
m is 1 to 6;

and pharmaceutically acceptable salts thereof.

The following compounds are examples according to the invention:

1'-[(1-benzyl-2-methyl-1H-indol-3-yl)carbonyl]spiro[indene-1,4'-piperidine];

1'-[(1-benzyl-2-methyl-1H-indol-3-yl)carbonyl]-2,3-dihydrospiro[indene-1,4'-piperidine];

1'-[(1-benzyl-1H-indol-3-yl)carbonyl]spiro[indene-1,4'-piperidine];

1'-[(2-methyl-1H-indol-3-yl)carbonyl]spiro[indene-1,4'-piperidine];

1'-[(6-chloro-1H-indol-3-yl)carbonyl]spiro[indene-1,4'-piperidine]; and

1'-[(6-chloro-1H-indol-3-yl)carbonyl]-2,3-dihydrospiro[indene-1,4'-piperidine].

In a certain embodiment the compounds of the invention are those compounds of formula (I-b):

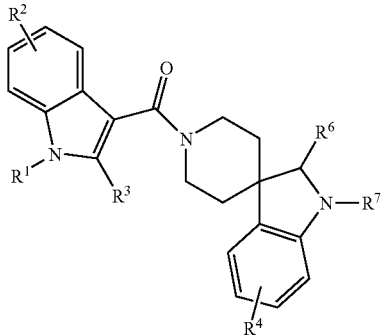

(I-b)

$R^1$ is H,
  $C_{1-6}$-alkyl optionally substituted by CN, sulfonylaryl,
  —$(CH_2)_m$—$R^a$ wherein $R^a$ is:
    $OR^i$,
    CN,
    $NR^iR^{ii}$, or
    $C_{3-6}$-cycloalkyl, 3 to 6 membered-heterocycloalkyl, aryl or 5 or 6 membered heteroaryl each of which is optionally substituted by one or more B,
  —$(CH_2)_n$—(CO)—$R^b$, wherein $R^b$ is:
    $C_{1-6}$-alkoxy, or
    $NR^iR^{ii}$,
    or 5 or 6 membered-heterocycloalkyl, aryl, or 5 or 6 membered heteroaryl each of which is optionally substituted by one or more B;

there is one or more $R^2$, wherein each $R^2$ is the same or different,
$R^2$ is one or more H, halo, $C_{1-6}$-alkyl;
$R^3$ is H,
  $C_{1-6}$-alkyl,
  —(CO)—$R^c$, wherein $R^c$ is:
    $C_{1-6}$-alkyl or
    —$(CH_2)_n$—$NR^iR^{ii}$, there is one or more $R^4$, wherein each $R^4$ is the same or different,
$R^4$ is one or more H, halo, or $C_{1-6}$-alkoxy optionally substituted by OH,
  or two $R^4$ together with the phenyl ring to which they are attached form an oxo or dioxo bridge;
$R^6$ is H;
$R^7$ is H or —$SO_2$—$R^e$ wherein $R^e$ is $C_{1-6}$-alkyl or aryl;
B is halo,
  CN,
  $C_{1-6}$-alkyl optionally substituted by CN or $C_{1-6}$-alkoxy,
  $C_{1-6}$-alkoxy,
  $C_{1-6}$-haloalkoxy,
  $C_{3-6}$-cycloalkyl,
  —C(O)O—$C_{1-6}$-alkyl, or
  —$(CR^{iii}R^{iv})_n$-phenyl, wherein the phenyl is optionally substituted by one or more substituent(s) selected from the group consisting of:
    halo,
    $C_{1-6}$-alkyl optionally substituted by CN or halo, and
    $C_{1-6}$-alkoxy;
$R^i$ and $R^{ii}$ are each independently H, $C_{1-6}$-alkyl, $C_{1-6}$-alkyl-$NR^{iii}R^{iv}$, —C(O)—$C_{1-6}$-alkyl, —$S(O)_2$—$C_{1-6}$-alkyl or OH;

$R^{iii}$ and $R^{iv}$ are each independently H or $C_{1-6}$-alkyl;
m is 1 to 6; and
n is 0 to 4;

and pharmaceutically acceptable salts thereof.

Further, in a certain embodiment the compounds of the invention are those compounds of formula (I-b) as described above, wherein
$R^1$ is H,
  —$(CH_2)_m$—$R^a$ wherein $R^a$ is aryl or 5 or 6 membered heteroaryl each of which is optionally substituted by one or more subsituents selected from the group consisting of:
    halo,
    CN,
    $C_{1-6}$-alkyl,
    $C_{1-6}$-alkoxy,
    $C_{1-6}$-haloalkoxy,
    —C(O)O—$C_{1-6}$-alkyl and
    phenyl optionally substituted by halo, $C_{1-6}$-haloalkyl or $C_{1-6}$-alkoxy,
  —$(CH_2)_m$—$NR^iR^{ii}$,
  —$(CH_2)_n$—(CO)—$R^b$, wherein $R^b$ is aryl or 5 or 6 membered-heterocycloalkyl each of which is optionally substituted by one or more B, or
  —$(CH_2)_n$—(CO)—$R^b$ wherein $R^b$ is $NR^iR^{ii}$,
$R^2$ is H or halo;
$R^3$ is H or $C_{1-6}$-alkyl;
$R^4$ is H or halo;
$R^6$ is H;
$R^7$ is H or —$SO_2$—$R^e$ wherein $R^e$ is $C_{1-6}$-alkyl or aryl;
B is halo, $NH_2$, $C_{1-6}$-alkyl optionally substituted by CN or $C_{1-6}$-alkoxy, $C_{1-6}$-alkoxy, $C_{1-6}$-haloalkoxy, $C_{3-6}$-cycloalkyl, —C(O)O—$C_{1-6}$-alkyl, —$(CR^{iii}R^{iv})_n$-phenyl wherein the phenyl is optionally substituted by one or more substituent(s) selected from the group consisting of:
  halo, $C_{1-6}$-alkyl optionally substituted by CN or halo, and $C_{1-6}$-alkoxy;
$R^i$ and $R^{ii}$ are each independently selected from H and $C_{1-6}$-alkyl;
m is 1 to 6; and
n is 0 to 4;

and pharmaceutically acceptable salts thereof.

In another embodiment thereof,
$R^1$ is H, or
  —$(CH_2)_m$—$R^a$ wherein $R^a$ is aryl which is optionally substituted by one or more subsituents selected from the group consisting of:
    halo,
    CN,
    $C_{1-6}$-alkyl,
    $C_{1-6}$-alkoxy,
    $C_{1-6}$-haloalkoxy,
    —C(O)O—$C_{1-6}$-alkyl and
    phenyl optionally substituted by halo, $C_{1-6}$-haloalkyl or $C_{1-6}$-alkoxy;
$R^2$ is H or halo;
$R^3$ is H or $C_{1-6}$-alkyl;
$R^4$ is H or halo;
$R^6$ is H;
$R^7$ is H or —$SO_2$—$R^e$ wherein $R^e$ is $C_{1-6}$-alkyl; and
m is 1 to 6;

and pharmaceutically acceptable salts thereof.

The following compounds are examples according to the invention:

1'-[(1-benzyl-2-methyl-1H-indol-3-yl)carbonyl]-1-(methylsulfonyl)-1,2-dihydrospiro[indole-3,4'-piperidine];

1'-{[6-chloro-1-(3-fluorobenzoyl)-1H-indol-3-yl]carbonyl}-1,2-dihydrospiro[indole-3,4'-piperidine];
1'-{[6-chloro-1-(2-fluorobenzoyl)-1H-indol-3-yl]carbonyl}-1,2-dihydrospiro[indole-3,4'-piperidine]; 1'-{[6-chloro-1-(3,5-difluorobenzoyl)-1H-indol-3-yl]carbonyl}-1,2-dihydrospiro[indole-3,4'-piperidine];
1'-{[6-chloro-1-(2,3-difluorobenzoyl)-1H-indol-3-yl]carbonyl}-1,2-dihydrospiro[indole-3,4'-piperidine];
1'-({6-chloro-1-[(3,5-difluorophenyl)sulfonyl]-1H-indol-3-yl}carbonyl)-1,2-dihydrospiro[indole-3,4'-piperidine];
2-[6-chloro-3-(1,2-dihydro-1'H-spiro[indole-3,4'-piperidin]-1'-ylcarbonyl)-1H-indol-1-yl]-1-(3,5-difluorophenyl)ethanone;
2-[6-chloro-3-(1,2-dihydro-1'H-spiro[indole-3,4'-piperidin]-1'-ylcarbonyl)-1H-indol-1-yl]-1-(3,4-difluorophenyl)ethanone;
2-[6-chloro-3-(1,2-dihydro-1'H-spiro[indole-3,4'-piperidin]-1'-ylcarbonyl)-1H-indol-1-yl]-1-(2-fluorophenyl)ethanone;
2-[6-chloro-3-(1,2-dihydro-1'H-spiro[indole-3,4'-piperidin]-1'-ylcarbonyl)-1H-indol-1-yl]-N,N-diethylethanamine; and
1'-{[6-chloro-1-(pyridin-2-ylmethyl)-1H-indol-3-yl]carbonyl}-1,2-dihydrospiro[indole-3,4'-piperidine].

Preferred are the following compounds:
1'-[(6-chloro-1H-indol-3-yl)carbonyl]-1,2-dihydrospiro[indole-3,4'-piperidine];
1'-[(1-benzyl-2-methyl-1H-indol-3-yl)carbonyl]-1,2-dihydrospiro[indole-3,4'-piperidine];
1'-{[6-chloro-1-(3,5-difluorobenzyl)-1H-indol-3-yl]carbonyl}-1,2-dihydrospiro[indole-3,4'-piperidine];
1'-{[6-chloro-1-(3-fluorobenzyl)-1H-indol-3-yl]carbonyl}-1,2-dihydrospiro[indole-3,4'-piperidine];
2-[6-chloro-3-(1,2-dihydro-1'H-spiro[indole-3,4'-piperidin]-1'-ylcarbonyl)-1H-indol-1-yl]-N,N-diethylacetamide;
2-[6-chloro-3-(1,2-dihydro-1'H-spiro[indole-3,4'-piperidin]-1'-ylcarbonyl)-1H-indol-1-yl]-N,N-dimethylacetamide;
2-[6-chloro-3-(1,2-dihydro-1'H-spiro[indole-3,4'-piperidin]-1-ylcarbonyl)-1H-indol-1-yl]-1-pyridin-2-ylethanone; and
1'-{[6-chloro-1-(pyridin-3-ylmethyl)-1H-indol-3-yl]carbonyl}-1,2-dihydrospiro[indole-3,4'n-piperidine].

In a certain embodiment the compounds of the invention are those compounds of formula (I-c):

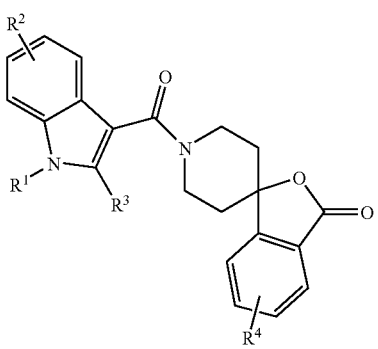

(I-c)

$R^1$ is H,
 $C_{1-6}$-alkyl optionally substituted by CN,
 aryl, 5 or 6 membered heteroaryl or sulfonylaryl each of which is optionally substituted by one or more B,
 —$(CH_2)_m$—$R^a$ wherein $R^a$ is:
  $OR^i$,
  CN,
  $NR^iR^{ii}$,
  $C_{3-6}$-cycloalkyl, or
  4 to 7 membered-heterocycloalkyl, aryl, or 5 or 6 membered heteroaryl each of which is optionally substituted by one or more B, or
 —$(CH_2)_n$—(CO)—$R^b$ wherein $R^b$ is:
  $C_{1-6}$-alkoxy,
  $NR^iR^{ii}$, or
  4 to 7 membered-heterocycloalkyl, aryl, or 5 or 6 membered heteroaryl each of which is optionally substituted by one or more B,
or $R^1$ and $R^3$ together with the indole ring to which they are attached form a 5 or 6 membered heterocycloalkyl which is optionally substituted by =O;

there is one or more $R^2$, wherein each $R^2$ is the same or different,
$R^2$ is one or more H, halo, $C_{1-6}$-alkyl optionally substituted by —$NR^{iii}R^{iv}$, or $C_{1-6}$-alkoxy;
$R^3$ is H,
 $C_{1-6}$-alkyl,
 halo,
 —(CO)—$R^c$, wherein $R^c$ is:
  $C_{1-6}$-alkyl,
  —$(CH_2)_n$—$NR^iR^{ii}$, or
  —$(CH_2)_n$—$NR^{iii}R^{iv}$,
 or 5 or 6 membered heterocycloalkyl optionally substituted by $C_{1-6}$-alkyl;

there is one or more $R^4$, wherein each $R^4$ is the same or different,
$R^4$ is one or more H, halo, or $C_{1-6}$-alkoxy optionally substituted by OH, or
 two $R^4$ together with the phenyl ring to which they are attached form an oxo or dioxo bridge;
B is halo,
 $NH_2$,
 $C_{1-6}$-alkyl optionally substituted by CN or $C_{1-6}$-alkoxy,
 $C_{1-6}$-alkoxy,
 $C_{1-6}$-haloalkoxy,
 $C_{3-6}$-cycloalkyl,
 —C(O)O—$C_{1-6}$-alkyl, or
 —$(CR^{iii}R^{iv})_n$-phenyl, wherein the phenyl is optionally substituted by one or more substituent(s) selected from the group consisting of:
  halo, $C_{1-6}$-alkyl optionally substituted by CN or halo, and $C_{1-6}$-alkoxy;
$R^i$ and $R^{ii}$ are each independently H, $C_{1-6}$-alkyl, $C_{1-6}$-alkyl-$NR^{iii}R^{iv}$, —(CO)O—$C_{1-6}$-alkyl, —C(O)—$NR^{iii}R^{iv}$, —C(O)—$C_{1-6}$-alkyl, —$S(O)_2$—$C_{1-6}$-alkyl, or —$S(O)_2$—$NR^{iii}R^{iv}$;
$R^{iii}$ and $R^{iv}$ are each independently H or $C_{1-6}$-alkyl;
m is 1 to 6; and
n is 0 to 4;

and pharmaceutically acceptable salts thereof.
In a further embodiment thereof,
$R^1$ is H, or
 $C_{1-6}$-alkyl optionally substituted by CN, or
 —$(CH_2)_m$—$R^a$ wherein $R^a$ is aryl which is optionally substituted by one or more subsituents selected from the group consisting of:
  halo, CN, $C_{1-6}$-alkyl, $C_{1-6}$-alkoxy, $C_{1-6}$-haloalkoxy, —C(O)O—$C_{1-6}$-alkyl and phenyl optionally substituted by halo, $C_{1-6}$-haloalkyl or $C_{1-6}$-alkoxy;

R² is H or halo;
R³ is H,
   C$_{1-6}$-alkyl, or
   —(CO)—R$^c$, wherein R$^c$ is 5 or 6 membered heterocycloalkyl optionally substituted by C$_{1-6}$-alkyl, or R$^c$ is —(CH$_2$)$_n$—NR$^i$R$^{ii}$;
R⁴ is H, halo, C$_{1-6}$-alkoxy or
   two R⁴ together with the phenyl ring to which they are attached form a dioxo bridge;
R$^i$ and R$^{ii}$ are each independently selected from H, C$_{1-6}$-alkyl and —(CO)O—C$_{1-6}$-alkyl;
m is 1 to 6; and
n is 0 to 4;

and pharmaceutically acceptable salts thereof.

The following compounds are examples according to the invention:
1'-[(1-benzyl-2-methyl-1H-indol-3-yl)carbonyl]-3H-spiro[2-benzofuran-1,4'-piperidin]-3-one;
4-{6-chloro-3-[(3-oxo-1'H,3H-spiro[2-benzofuran-1,4'-piperidin]-1'-yl)carbonyl]-1H-indol-1-yl}butanenitrile;
2-{6-chloro-3-[(3-oxo-1'H,3H-spiro[2-benzofuran-1,4'-piperidin]-1'-yl)carbonyl]-1H-indol-1-yl}propanenitrile;
1'-({1-[2-(3,4-dimethoxyphenyl)ethyl]-5-methoxy-2-methyl-1H-indol-3-yl}carbonyl)-3H-spiro[2-benzofuran-1,4'-piperidin]-3-one;
1'-{[1-(4-ethoxyphenyl)-5-methoxy-2-methyl-1H-indol-3-yl]carbonyl}-3H-spiro[2-benzofuran-1,4'-piperadin]-3-one;
5-bromo-1'-{[6-chloro-1-(2-fluorobenzoyl)-1H-indol-3-yl]carbonyl}-3H-spiro[2-benzofuran-1,4'-piperidin]-3-one;
5-bromo-1'-{[6-chloro-1-(2,3-difluorobenzoyl)-1H-indol-3-yl]carbonyl}-3H-spiro[2-benzofuran-1,4'-piperidin]-3-one;
5-bromo-1'-({6-chloro-1-[(3,5-difluorophenyl)sulfonyl]-1H-indol-3-yl}carbonyl)-3H-spiro[2-benzofuran-1,4'-piperidin]-3-one; and
1'-[(1-biphenyl-3-yl-6-chloro-1H-indol-3-yl)carbonyl]-3H-spiro[2-benzofuran-1,4'-piperidin]-3-one.

Preferred are the following compounds:
1'-[(6-chloro-1H-indol-3-yl)carbonyl]-6-methoxy-3H-spiro[2-benzofuran-1,4'-piperidin]-3-one;
6-chloro-1'-[(6-chloro-1H-indol-3-yl)carbonyl]-3H-spiro[2-benzofuran-1,4'-piperidin]-3-one;
1'-({6-chloro-2-[(4-methylpiperidin-1-yl)carbonyl]-1H-indol-3-yl}carbonyl)-5-fluoro-3H-spiro[2-benzofuran-1,4'-piperidin]-3-one;
6-chloro-3-[(5-fluoro-3-oxo-1'H,3H-spiro[2-benzofuran-1,4'-piperidin]-1'-yl)carbonyl]-1H-indole-2-carboxamide;
6-chloro-N-[2-(dimethylamino)ethyl]-3-[(5-fluoro-3-oxo-1'H,3H-spiro[2-benzofuran-1,4'-piperidin]-1'-yl)carbonyl]-1H-indole-2-carboxamide;
1'-{[6-chloro-2-(piperazin-1-ylcarbonyl)-1H-indol-3-yl]carbonyl}-5-fluoro-3H-spiro[2-benzofuran-1,4'-piperidin]-3-one;
1'-{[6-chloro-2-(morpholin-4-ylcarbonyl)-1H-indol-3-yl]carbonyl}-5-fluoro-3H-spiro[2-benzofuran-1,4'-piperidin]-3-one;
1'-({6-chloro-2-[(4-methylpiperazin-1-yl)carbonyl]-1H-indol-3-yl}carbonyl)-5-fluoro-3H-spiro[2-benzofuran-1,4'-piperidin]-3-one;
1'-[(1-benzyl-2-methyl-1H-indol-3-yl)carbonyl]-5-bromo-3H-spiro[2-benzofuran-1,4'-piperidin]-3-one;
5-bromo-1'-[(6-chloro-1H-indol-3-yl)carbonyl]-3H-spiro[2-benzofuran-1,4'-piperidin]-3-one;
1'-{[6-chloro-1-(3-fluorobenzoyl)-1H-indol-3-yl]carbonyl}-3H-spiro[2-benzofuran-1,4'-piperidin]-3-one;
1'-{[6-chloro-1-(2-fluorobenzoyl)-1H-indol-3-yl]carbonyl}-3H-spiro[2-benzofuran-1,4'-piperidin]-3-one;
1'-{[6-chloro-1-(2,3-difluorobenzoyl)-1H-indol-3-yl]carbonyl}-3H-spiro[2-benzofuran-1,4'-piperidin]-3-one;
1'-({6-chloro-1-[(3,5-difluorophenyl)sulfonyl]-1H-indol-3-yl}carbonyl)-3H-spiro[2-benzofuran-1,4'-piperidin]-3-one;
1'-{[6-chloro-1-(3-fluorobenzoyl)-1H-indol-3-yl]carbonyl}-5-fluoro-3H-spiro[2-benzofuran-1,4'-piperidin]-3-one;
1'-{[6-chloro-1-(2-fluorobenzoyl)-1H-indol-3-yl]carbonyl}-5-fluoro-3H-spiro[2-benzofuran-1,4'-piperidin]-3-one;
1'-{[6-chloro-1-(3,5-difluorobenzoyl)-1H-indol-3-yl]carbonyl}-5-fluoro-3H-spiro[2-benzofuran-1,4'-piperidin]-3-one;
1'-{[6-chloro-1-(2,3-difluorobenzoyl)-1H-indol-3-yl]carbonyl}-5-fluoro-3H-spiro[2-benzofuran-1,4'-piperidin]-3-one;
1'-({6-chloro-1-[(3,5-difluorophenyl)sulfonyl]-1H-indol-3-yl}carbonyl)-5-fluoro-3H-spiro[2-benzofuran-1,4'-piperidin]-3-one;
5-bromo-1'-{[6-chloro-1-(3-fluorobenzoyl)-1H-indol-3-yl]carbonyl}-3H-spiro[2-benzofuran-1,4'-piperidin]-3-one;
5-bromo-1'-{[6-chloro-1-(3,5-difluorobenzoyl)-1H-indol-3-yl]carbonyl}-3H-spiro[2-benzofuran-1,4'-piperidin]-3-one;
1'-[(1-biphenyl-2-yl-6-chloro-1H-indol-3-yl)carbonyl]-3H-spiro[2-benzofuran-1,4'-piperidin]-3-one;
1'-{[1-(biphenyl-3-ylcarbonyl)-6-chloro-1H-indol-3-yl]carbonyl}-3H-spiro[2-benzofuran-1,4'-piperidin]-3-one;
1'-[(1-{[4-amino-2-(methoxymethyl)pyrimidin-5-yl]methyl}-6-chloro-1H-indol-3-yl)carbonyl]-5-fluoro-3H-spiro[2-benzofuran-1,4'-piperidin]-3-one;
1'-({1-[(4-amino-2-methylpyrimidin-5-yl)methyl]-6-chloro-1H-indol-3-yl}carbonyl)-5-fluoro-3H-spiro[2-benzofuran-1,4'-piperidin]-3-one;
1'-[(7-chloro-1-oxo-1,2,3,4-tetrahydropyrazino[1,2-a]indol-10-yl)carbonyl]-5-fluoro-3H-spiro[2-benzofuran-1,4'-piperidin]-3-one;
1'-({6-chloro-1-[(1,4-dibenzylpiperazin-2-yl)methyl]-1H-indol-3-yl}carbonyl)-5-fluoro-3H-spiro[2-benzofuran-1,4'-piperidin]-3-one;
6-chloro-3-[(5-fluoro-3-oxo-1'H,3H-spiro[2-benzofuran-1,4'-piperidin]-1'-yl)carbonyl]-N-methyl-1H-indole-2-carboxamide;
6-chloro-3-[(5-fluoro-3-oxo-1'H,3H-spiro[2-benzofuran-1,4'-piperidin]-1'-yl)carbonyl]-N-[2-(methylamino)ethyl]-1H-indole-2-carboxamide hydrochloride;
2-{6-chloro-3-[(5-fluoro-3-oxo-1'H,3H-spiro[2-benzofuran-1,4'-piperidin]-1'-yl)carbonyl]-1H-indol-1-yl}-N-[2-(dimethylamino)ethyl]acetamide; and
2-{6-chloro-3-[(3-oxo-1'H,3H-spiro[2-benzofuran-1,4'-piperidin]-1'-yl)carbonyl]-1H-indol-1-yl}-N-[2-(dimethylamino)ethyl]acetamide.

Particularly preferred are the following compounds:
1'-[(1-benzyl-2-methyl-1H-indol-3-yl)carbonyl]-6-chloro-3H-spiro[2-benzofuran-1,4'-piperidin]-3-one;
1'-[(1-benzyl-2-methyl-1H-indol-3-yl)carbonyl]-4-fluoro-3H-spiro[2-benzofuran-1,4'-piperidin]-3-one;
1'-[(1-benzyl-2-methyl-1H-indol-3-yl)carbonyl]-6-methoxy-3H-spiro[2-benzofuran-1,4'-piperidin]-3-one;
1'-[(1-benzyl-2-methyl-1H-indol-3-yl)carbonyl]-5-methoxy-3H-spiro[2-benzofuran-1,4'-piperidin]-3-one;
1'-[(1-benzyl-2-methyl-1H-indol-3-yl)carbonyl]-7-chloro-3H-spiro[2-benzofuran-1,4'-piperidin]-3-one;

1'-[(6-chloro-1H-indol-3-yl)carbonyl]-3H-spiro[2-benzofuran-1,4'-piperidin]-3-one;

1'-[(6-chloro-1H-indol-3-yl)carbonyl]-5-fluoro-3H-spiro[2-benzofuran-1,4'-piperidin]-3-one;

1'-[(1-benzyl-2-methyl-1H-indol-3-yl)carbonyl]-5-fluoro-3H-spiro[2-benzofuran-1,4'-piperidin]-3-one;

6-chloro-3-[(5-fluoro-3-oxo-1'H,3H-spiro[2-benzofuran-1,4'-piperidin]-1'-yl)carbonyl]-N,N-dimethyl-1H-indole-2-carboxamide;

tert-butyl {2-[({6-chloro-3-[(5-fluoro-3-oxo-1'H,3H-spiro[2-benzofuran-1,4'-piperidin]-1'-yl)carbonyl]-1H-indol-2-yl}carbonyl)amino]ethyl}methylcarbamate;

6-chloro-N,N-diethyl-3-[(5-fluoro-3-oxo-1'H,3H-spiro[2-benzofuran-1,4'-piperidin]-1'-yl)carbonyl]-1H-indole-2-carboxamide;

1'-{[6-chloro-2-(piperidin-1-ylcarbonyl)-1H-indol-3-yl]carbonyl}-5-fluoro-3H-spiro[2-benzofuran-1,4'-piperidin]-3-one;

1'-[(1-benzyl-2-methyl-1H-indol-3-yl)carbonyl]-7H-spiro[furo[3,4-f][1,3]benzodioxole-5,4'-piperidin]-7-one;

3-{6-chloro-3-[(3-oxo-1'H,3H-spiro[2-benzofuran-1,4'-piperidin]-1'-yl)carbonyl]-1H-indol-1-yl}propanenitrile;

{6-chloro-3-[(3-oxo-1'H,3H-spiro[2-benzofuran-1,4'-piperidin]-1'-yl)carbonyl]-1H-indol-1-yl}acetonitrile;

1'-[(1-benzyl-2-methyl-1H-indol-3-yl)carbonyl]-6-(2-hydroxyethoxy)-3H-spiro[2-benzofuran-1,4'-piperidin]-3-one;

1'-[(1-benzyl-2-methyl-1H-indol-3-yl)carbonyl]-3H-spiro[2-benzofuran-1,4'-piperidin]-3-one;

1'-{[6-chloro-1-(3,5-difluorophenyl)-1H-indol-3-yl]carbonyl}-3H-spiro[2-benzofuran-1,4'-piperidin]-3-one;

1'-{[6-chloro-1-(3,5-difluorobenzoyl)-1H-indol-3-yl]carbonyl}-3H-spiro[2-benzofuran-1,4'-piperidin]-3-one;

1'-{[6-chloro-1-(3,5-difluorobenzyl)-1H-indol-3-yl]carbonyl}-3H-spiro[2-benzofuran-1,4'-piperidin]-3-one;

1'-{[6-chloro-1-(3-fluorobenzyl)-1H-indol-3-yl]carbonyl}-3H-spiro[2-benzofuran-1,4'-piperidin]-3-one;

1'-({6-chloro-1-[2-(3-fluorophenyl)-2-oxoethyl]-1H-indol-3-yl}carbonyl)-3H-spiro[2-benzofuran-1,4'-piperidin]-3-one;

1'-({6-chloro-1-[2-(2,5-difluorophenyl)-2-oxoethyl]-1H-indol-3-yl}carbonyl)-3H-spiro[2-benzofuran-1,4'-piperidin]-3-one;

1'-{[6-chloro-1-(3,5-difluorobenzyl)-1H-indol-3-yl]carbonyl}-5-fluoro-3H-spiro[2-benzofuran-1,4'-piperidin]-3-one;

1'-{[6-chloro-1-(3-fluorobenzyl)-1H-indol-3-yl]carbonyl}-5-fluoro-3H-spiro[2-benzofuran-1,4'-piperidin]-3-one;

1'-({6-chloro-1-[2-(3-fluorophenyl)-2-oxoethyl]-1H-indol-3-yl}carbonyl)-5-fluoro-3H-spiro[2-benzofuran-1,4'-piperidin]-3-one;

5-bromo-1'-{[6-chloro-1-(3,5-difluorobenzyl)-1H-indol-3-yl]carbonyl}-3H-spiro[2-benzofuran-1,4'-piperidin]-3-one;

5-bromo-1'-{[6-chloro-1-(3-fluorobenzyl)-1H-indol-3-yl]carbonyl}-3H-spiro[2-benzofuran-1,4'-piperidin]-3-one;

5-bromo-1'-({6-chloro-1-[2-(3-fluorophenyl)-2-oxoethyl]-1H-indol-3-yl}carbonyl)-3H-spiro[2-benzofuran-1,4'-piperidin]-3-one;

1'-({6-chloro-1-[2-(2-fluorophenyl)-2-oxoethyl]-1H-indol-3-yl}carbonyl)-3H-spiro[2-benzofuran-1,4'-piperidin]-3-one;

1'-({6-chloro-1-[2-(3,4-difluorophenyl)-2-oxoethyl]-1H-indol-3-yl}carbonyl)-3H-spiro[2-benzofuran-1,4'-piperidin]-3-one;

1'-{[6-chloro-1-(3-fluorophenyl)-1H-indol-3-yl]carbonyl}-3H-spiro[2-benzofuran-1,4'-piperidin]-3-one;

1'-{[6-chloro-1-(2-oxo-2-piperidin-1-ylethyl)-1H-indol-3-yl]carbonyl}-3H-spiro[2-benzofuran-1,4'-piperidin]-3-one;

1'-{[6-chloro-1-(2-morpholin-4-yl-2-oxoethyl)-1H-indol-3-yl]carbonyl}-3H-spiro[2-benzofuran-1,4'-piperidin]-3-one;

2-{6-chloro-3-[(3-oxo-1'H,3H-spiro[2-benzofuran-1,4'-piperidin]-1'-yl)carbonyl]-1H-indol-1-yl}-N,N-dimethylacetamide;

2-{6-chloro-3-[(3-oxo-1'H,3H-spiro[2-benzofuran-1,4'-piperidin]-1'-yl)carbonyl]-1H-indol-1-yl}-N,N-diethylacetamide;

1'-{[6-chloro-1-(piperidin-1-ylcarbonyl)-1H-indol-3-yl]carbonyl}-3H-spiro[2-benzofuran-1,4'-piperidin]-3-one;

tert-butyl {6-chloro-3-[(3-oxo-1'H,3H-spiro[2-benzofuran-1,4'-piperidin]-1'-yl)carbonyl]-1H-indol-1-yl}acetate;

1'-[(6-chloro-1-pyridin-2-yl-1H-indol-3-yl)carbonyl]-3H-spiro[2-benzofuran-1,4'-piperidin]-3-one;

1'-[(6-chloro-1-pyridin-2-yl-1H-indol-3-yl)carbonyl]-5-fluoro-3H-spiro[2-benzofuran-1,4'-piperidin]-3-one;

1'-({6-chloro-1-[(2-methylpyridin-4-yl)methyl]-1H-indol-3-yl}carbonyl)-5-fluoro-3H-spiro[2-benzofuran-1,4'-piperidin]-3-one;

1'-({6-chloro-1-[(6-chloropyridin-3-yl)methyl]-1H-indol-3-yl}carbonyl)-5-fluoro-3H-spiro[2-benzofuran-1,4'-piperidin]-3-one;

1'-({6-chloro-1-[(3-chloro-6-methylpyridazin-4-yl)methyl]-1H-indol-3-yl}carbonyl)-5-fluoro-3H-spiro[2-benzofuran-1,4'-piperidin]-3-one;

1'-{[6-chloro-1-(pyridin-4-ylmethyl)-1H-indol-3-yl]carbonyl}-5-fluoro-3H-spiro[2-benzofuran-1,4'-piperidin]-3-one;

1'-{[6-chloro-1-(2-pyridin-4-ylethyl)-1H-indol-3-yl]carbonyl}-5-fluoro-3H-spiro[2-benzofuran-1,4'-piperidin]-3-one;

1'-{[6-chloro-1-(pyridin-4-ylmethyl)-1H-indol-3-yl]carbonyl}-3H-spiro[2-benzofuran-1,4'-piperidin]-3-one;

1'-{[6-chloro-1-(2-oxo-2-pyridin-2-ylethyl)-1H-indol-3-yl]carbonyl}-5-fluoro-3H-spiro[2-benzofuran-1,4'-piperidin]-3-one;

1'-({6-chloro-1-[2-(5-methyl-2-phenyl-1,3-oxazol-4-yl)-2-oxoethyl]-1H-indol-3-yl}carbonyl)-5-fluoro-3H-spiro[2-benzofuran-1,4'-piperidin]-3-one;

1'-{[6-chloro-1-(pyridin-2-ylmethyl)-1H-indol-3-yl]carbonyl}-5-fluoro-3H-spiro[2-benzofuran-1,4'-piperidin]-3-one;

2-{6-chloro-3-[(5-fluoro-3-oxo-1'H,3H-spiro[2-benzofuran-1,4'-piperidin]-1'-yl)carbonyl]-1H-indol-1-yl}-N,N-dimethylacetamide;

1'-({6-chloro-1-[2-(dimethylamino)ethyl]-1H-indol-3-yl}carbonyl)-5-fluoro-3H-spiro[2-benzofuran-1,4'-piperidin]-3-one;

1'-{[6-chloro-1-(pyridin-3-ylmethyl)-1H-indol-3-yl]carbonyl}-3H-spiro[2-benzofuran-1,4'-piperidin]-3-one;

1'-{[6-chloro-1-(pyrazin-2-ylmethyl)-1H-indol-3-yl]carbonyl}-5-fluoro-3H-spiro[2-benzofuran-1,4'-piperidin]-3-one;

1'-{[6-chloro-1-(pyrimidin-5-ylmethyl)-1H-indol-3-yl]carbonyl}-5-fluoro-3H-spiro[2-benzofuran-1,4'-piperidin]-3-one;

3-{6-chloro-3-[(5-fluoro-3-oxo-1'H,3H-spiro[2-benzofuran-1,4'-piperidin]-1'-yl)carbonyl]-1H-indol-1-yl}propanenitrile;

tert-butyl {6-chloro-3-[(5-fluoro-3-oxo-1'H,3H-spiro[2-benzofuran-1,4'-piperidin]-1'-yl)carbonyl]-1H-indol-1-yl}acetate;

1'-{[6-chloro-1-(2-morpholin-4-yl-2-oxoethyl)-1H-indol-3-yl]carbonyl}-5-fluoro-3H-spiro[2-benzofuran-1,4'-piperidin]-3-one;
1'-({1-[(4-benzylmorpholin-2-yl)methyl]-6-chloro-1H-indol-3-yl}carbonyl)-5-fluoro-3H-spiro[2-benzofuran-1,4'-piperidin]-3-one;
1'-({6-chloro-1-[(5-methylisoxazol-3-yl)methyl]-1H-indol-3-yl}carbonyl)-5-fluoro-3H-spiro[2-benzofuran-1,4'-piperidin]-3-one;
1'-({6-chloro-1-[2-(4-methylpiperazin-1-yl)-2-oxoethyl]-1H-indol-3-yl}carbonyl)-5-fluoro-3H-spiro[2-benzofuran-1,4'-piperidin]-3-one;
1'-{[6-chloro-1-(pyridin-2-ylmethyl)-1H-indol-3-yl]carbonyl}-3H-spiro[2-benzofuran-1,4'-piperidin]-3-one;
1'-({6-chloro-1-[(5-cyclopropyl-2-methyl-1,3-oxazol-4-yl)methyl]-1H-indol-3-yl}carbonyl)-5-fluoro-3H-spiro[2-benzofuran-1,4'-piperidin]-3-one;
1'-({6-chloro-1-[(1-methyl-1H-imidazol-5-yl)methyl]-1H-indol-3-yl}carbonyl)-5-fluoro-3H-spiro[2-benzofuran-1,4'-piperidin]-3-one;
1'-({6-chloro-1-[(3-methylisoxazol-5-yl)methyl]-1H-indol-3-yl}carbonyl)-5-fluoro-3H-spiro[2-benzofuran-1,4'-piperidin]-3-one;
1'-({6-chloro-1-[(1,5-dimethyl-1H-pyrazol-3-yl)methyl]-1H-indol-3-yl}carbonyl)-5-fluoro-3H-spiro[2-benzofuran-1,4'-piperidin]-3-one;
1'-({6-chloro-1-[(3,5-dimethylisoxazol-4-yl)methyl]-1H-indol-3-yl}carbonyl)-5-fluoro-3H-spiro[2-benzofuran-1,4'-piperidin]-3-one;
1'-({6-chloro-1-[(2,5-dimethyl-1,3-oxazol-4-yl)methyl]-1H-indol-3-yl}carbonyl)-5-fluoro-3H-spiro[2-benzofuran-1,4'-piperidin]-3-one;
1'-({6-chloro-1-[(3-fluorooxetan-3-yl)methyl]-1H-indol-3-yl}carbonyl)-5-fluoro-3H-spiro[2-benzofuran-1,4'-piperidin]-3-one;
1'-({6-chloro-1-[(3-fluorooxetan-3-yl)methyl]-1H-indol-3-yl}carbonyl)-3H-spiro[2-benzofuran-1,4'-piperidin]-3-one;
1'-[(6-chloro-1-{[1-(methoxymethyl)-cyclopropyl]methyl}-1H-indol-3-yl)carbonyl]-5-fluoro-3H-spiro[2-benzofuran-1,4'-piperidin]-3-one;
[1-({6-chloro-3-[(5-fluoro-3-oxo-1'H,3H-spiro[2-benzofuran-1,4'-piperidin]-1'-yl)carbonyl]-1H-indol-1-yl}methyl)cyclopropyl]acetonitrile;
1'-[(6-chloro-1-{[1-(methoxymethyl)-cyclopropyl]methyl}-1H-indol-3-yl)carbonyl]-3H-spiro[2-benzofuran-1,4'-piperidin]-3-one;
[1-({6-chloro-3-[(3-oxo-1'H,3H-spiro[2-benzofuran-1,4'-piperidin]-1'-yl)carbonyl]-1H-indol-1-yl}methyl)cyclopropyl]acetonitrile;
1'-({6-chloro-1-[2-(tetrahydro-2H-pyran-4-yl)ethyl]-1H-indol-3-yl}carbonyl)-5-fluoro-3H-spiro[2-benzofuran-1,4'-piperidin]-3-one hydrochloride;
1'-({6-chloro-1-[2-(tetrahydro-2H-pyran-4-yl)ethyl]-1H-indol-3-yl}carbonyl)-3H-spiro[2-benzofuran-1,4'-piperidin]-3-one;
tert-butyl 2-({6-chloro-3-[(5-fluoro-3-oxo-1'H,3H-spiro[2-benzofuran-1,4'-piperidin]-1'-yl)carbonyl]-1H-indol-1-yl}methyl)morpholine-4-carboxylate;
tert-butyl 2-({6-chloro-3-[(3-oxo-1'H,3H-spiro[2-benzofuran-1,4'-piperidin]-1'-yl)carbonyl]-1H-indol-1-yl}methyl)morpholine-4-carboxylate;
1'-{[6-chloro-1-(morpholin-2-ylmethyl)-1H-indol-3-yl]carbonyl}-5-fluoro-3H-spiro[2-benzofuran-1,4'-piperidin]-3-one dihydrochloride;
1'-{[6-chloro-1-(morpholin-2-ylmethyl)-1H-indol-3-yl]carbonyl}-3H-spiro[2-benzofuran-1,4'-piperidin]-3-one hydrochloride;
2-{6-chloro-3-[(5-fluoro-3-oxo-1'H,3H-spiro[2-benzofuran-1,4'-piperidin]-1'-yl)carbonyl]-1H-indol-1-yl}acetamide;
2-{6-chloro-3-[(5-fluoro-3-oxo-1'H,3H-spiro[2-benzofuran-1,4'-piperidin]-1'-yl)carbonyl]-1H-indol-1-yl}-N-methylacetamide;
1'-{[6-chloro-1-(2-oxo-2-piperazin-1-ylethyl)-1H-indol-3-yl]carbonyl}-5-fluoro-3H-spiro[2-benzofuran-1,4'-piperidin]-3-one;
1'-{[1-(3,5-difluorobenzyl)-1H-indol-3-yl]carbonyl}-5-fluoro-3H-spiro[2-benzofuran-1,4'-piperidin]-3-one;
1'-{[1-(3,5-difluorobenzyl)-1H-indol-3-yl]carbonyl}-3H-spiro[2-benzofuran-1,4'-piperidin]-3-one;
N,N-diethyl-2-{3-[(3-oxo-1'H,3H-spiro[2-benzofuran-1,4'-piperidin]-1'-yl)carbonyl]-1H-indol-1-yl}acetamide; and
2-{6-chloro-5-methyl-3-[(3-oxo-1'H,3H-spiro[2-benzofuran-1,4'-piperidin]-1'-yl)carbonyl]-1H-indol-1-yl}-N,N-dimethylacetamide.

In a certain embodiment the compounds of the invention are those compounds of formula (I-d):

(I-d)

wherein
R$^1$ is H,
   C$_{1-6}$-alkyl optionally substituted by CN,
   aryl, 5 or 6 membered heteroaryl or sulfonylaryl each of which is optionally substituted by one or more B,
   —(CH$_2$)$_m$—R$^a$ wherein R$^a$ is:
     OR$^i$,
     CN,
     NR$^i$R$^{ii}$,
     C$_{3-6}$-cycloalkyl, or
     3 to 7 membered-heterocycloalkyl, aryl, or 5 or 6 membered heteroaryl each of which is optionally substituted by one or more B, or
   —(CH$_2$)$_n$—(CO)—R$^b$ wherein R$^b$ is:
     C$_{1-6}$-alkoxy,
     NR$^i$R$^{ii}$, or
     4 to 7 membered-heterocycloalkyl, aryl, or 5 or 6 membered heteroaryl each of which is optionally substituted by one or more B, R¹ and R³ together with the indole ring to which they are attached form a 5 or 6 membered heterocycloalkyl which is optionally substituted by C(O)O—C$_{1-6}$-alkyl or C$_{1-6}$-alkyl;

there is one or more R², wherein each R² is the same or different,

R² is one or more H, halo, C$_{1-6}$-alkyl, or C$_{1-6}$-alkoxy;

R³ is H,
C$_{1-6}$-alkyl, or
—(CO)—R$^c$, wherein R$^c$ is C$_{1-6}$-alkyl, or —(CH$_2$)$_n$—NR$^i$R$^{ii}$;

there is one or more R⁴, wherein each R⁴ is the same or different,

R⁴ is one or more H, halo, or C$_{1-6}$-alkoxy optionally substituted by OH, or
two R⁴ together with the phenyl ring to which they are attached form an oxo or dioxo bridge;

R⁵ is H or aryl;

B is halo, NH$_2$, C$_{1-6}$-alkyl optionally substituted by CN or C$_{1-6}$-alkoxy, C$_{1-6}$-alkoxy, C$_{1-6}$-haloalkoxy, C$_{3-6}$-cycloalkyl, —C(O)O—C$_{1-6}$-alkyl, —(CR$^{iii}$R$^{iv}$)$_n$-phenyl, wherein the phenyl is optionally substituted by one or more substituent(s) selected from the group consisting of: halo, C$_{1-6}$-alkyl optionally substituted by CN or halo, and C$_{1-6}$-alkoxy;

R$^i$ and R$^{ii}$ are each independently H, C$_{1-6}$-alkyl, C$_{1-6}$-alkyl-NR$^{iii}$R$^{iv}$, —(CO)O—C$_{1-6}$-alkyl, —C(O)—NR$^{iii}$R$^{iv}$, —C(O)—C$_{1-6}$-alkyl, —S(O)$_2$—C$_{1-6}$-alkyl, —S(O)$^2$—NR$^{iii}$R$^{iv}$ or OH;

R$^{iii}$ and R$^{iv}$ are each indeptently H or C$_{1-6}$-alkyl;

m is 1 to 6; and n is 0 to 4;

and pharmaceutically acceptable salts thereof.

In a further embodiment thereof,

R¹ is H,
C$_{1-6}$-alkyl optionally substituted by CN,
—(CH$_2$)$_m$—R$^a$ wherein R$^a$ is C$_{3-6}$-cycloalkyl, aryl, or 5 or 6 membered heteroaryl, each of which is optionally substituted by one or more substituents selected from the group consisting of:
halo, CN, C$_{1-6}$-alkyl, C$_{1-6}$-alkoxy, —C(O)O—C$_{1-6}$-alkyl and phenyl optionally substituted by halo, C$_{1-6}$-alkyl C$_{1-6}$-haloalkyl or C$_{1-6}$-alkoxy,
—(CH$_2$)$_m$—NR$^i$R$^{ii}$, or
—(CH$_2$)$_n$—(CO)—R$^b$, wherein R$^b$ is aryl;

R² is H, halo or C$_{1-6}$-alkoxy;

R³ is H,
—(CO)—R$^c$, wherein R$^c$ is C$_{1-6}$-alkyl, or
C$_{1-6}$-alkyl;

R⁴ is H or halo;

R⁵ is H or aryl;

R$^i$ and R$^{ii}$ are each independently C$_{1-6}$-alkyl;

m is 1 to 6; and n is 0 to 4;

and pharmaceutically acceptable salts thereof.

The following compounds are examples according to the invention:

1'-[(1-benzyl-2-methyl-1H-indol-3-yl)carbonyl]-3-phenyl-3H-spiro[2-benzofuran-1,4'-piperidine];

1'-[(1-benzyl-5-methoxy-2-methyl-1H-indol-3-yl)carbonyl]-3H-spiro[2-benzofuran-1,4'-piperidine];

1'-[(1-{[2-(4-chlorophenyl)-1,3-thiazol-4-yl]methyl}-2-methyl-1H-indol-3-yl)carbonyl]-3H-spiro[2-benzofuran-1,4'-piperidine];

1'-[(1-{[2-(4-chlorophenyl)-1,3-thiazol-4-yl]methyl}-2-methyl-1H-indol-3-yl)carbonyl]-3H-spiro[2-benzofuran-1,4'-piperidine];

1'-{[2-methyl-1-({5-methyl-2-[3-(trifluoromethyl)phenyl]-1,3-oxazol-4-yl}methyl)-1H-indol-3-yl]carbonyl}-3H-spiro[2-benzofuran-1,4'-piperidine];

1'-[(1-{[2-(2-fluorophenyl)-5-methyl-1,3-oxazol-4-yl]methyl}-2-methyl-1H-indol-3-yl)carbonyl]-3H-spiro[2-benzofuran-1,4'-piperidine];

1'-[(1-{[2-(4-isopropylphenyl)-5-methyl-1,3-oxazol-4-yl]methyl}-2-methyl-1H-indol-3-yl)carbonyl]-3H-spiro[2-benzofuran-1,4'-piperidine];

1'-[(1-{[2-(4-ethylphenyl)-5-methyl-1,3-oxazol-4-yl]methyl}-2-methyl-1H-indol-3-yl)carbonyl]-3H-spiro[2-benzofuran-1,4'-piperidine];

1'-[(2-methyl-1-{[5-methyl-2-(2-methylphenyl)-1,3-oxazol-4-yl]methyl}-1H-indol-3-yl)carbonyl]-3H-spiro[2-benzofuran-1,4'-piperidine];

1'-{[2-methyl-1-({5-methyl-2-[4-(trifluoromethyl)phenyl]-1,3-oxazol-4-yl}methyl)-1H-indol-3-yl]carbonyl}-3H-spiro[2-benzofuran-1,4'-piperidine];

1'-{[2-methyl-1-({5-methyl-2-[2-(trifluoromethyl)phenyl]-1,3-oxazol-4-yl}methyl)-1H-indol-3-yl]carbonyl}-3H-spiro[2-benzofuran-1,4'-piperidine];

1'-[(5-chloro-1H-indol-3-yl)carbonyl]-3H-spiro[2-benzofuran-1,4'-piperidine];

1'-[(1-methyl-1H-indol-3-yl)carbonyl]-3H-spiro[2-benzofuran-1,4'-piperidine];

1'-(1H-indol-3-ylcarbonyl)-3H-spiro[2-benzofuran-1,4'-piperidine];

2-[6-chloro-3-(1'H,3H-spiro[2-benzofuran-1,4'-piperidin]-1'-ylcarbonyl)-1H-indol-1-yl]propanenitrile;

3-[6-chloro-3-(1'H,3H-spiro[2-benzofuran-1,4'-piperidin]-1'-ylcarbonyl)-1H-indol-1-yl]propanenitrile;

4-[6-chloro-3-(1'H,3H-spiro[2-benzofuran-1,4'-piperidin]-1'-ylcarbonyl)-1H-indol-1-yl]butanenitrile;

1'-({6-chloro-1-[(3,5-difluorophenyl)sulfonyl]-1H-indol-3-yl}carbonyl)-3H-spiro[2-benzofuran-1,4'-piperidine];

1'-{[1-(biphenyl-3-ylcarbonyl)-6-chloro-1H-indol-3-yl]carbonyl}-3H-spiro[2-benzofuran-1,4'-piperidine];

1'-[(1-biphenyl-2-yl-6-chloro-1H-indol-3-yl)carbonyl]-3H-spiro[2-benzofuran-1,4'-piperidine];

1'-[(1-biphenyl-2-yl-6-chloro-1H-indol-3-yl)carbonyl]-3H-spiro[2-benzofuran-1,4'-piperidine];

1'-({6-chloro-1-[(1,4-dibenzylpiperazin-2-yl)methyl]-1H-indol-3-yl}carbonyl)-3H-spiro[2-benzofuran-1,4'-piperidine];

tert-butyl 10-(1'H,3H-spiro[2-benzofuran-1,4'-piperidin]-1'-ylcarbonyl)-3,4-dihydropyrazino[1,2-a]indole-2 (1H)-carboxylate; and 1'-({1-[3,5-bis(trifluoromethyl)benzyl]-6-chloro-2-methyl-1H-indol-3-yl}carbonyl)-3H-spiro[2-benzofuran-1,4'-piperidine].

The following compounds are preferred examples according to the invention:

1'-[(1-benzyl-2-methyl-1H-indol-3-yl)carbonyl]-3H-spiro[2-benzofuran-1,4'-piperidine];

1'-[(1-benzyl-2-methyl-1H-indol-3-yl)carbonyl]-6-chloro-3H-spiro[2-benzofuran-1,4'-piperidine];

1'-[(2-methyl-1H-indol-3-yl)carbonyl]-3H-spiro[2-benzofuran-1,4'-piperidine];

1'-[(1-benzoyl-2-methyl-1H-indol-3-yl)carbonyl]-3H-spiro[2-benzofuran-1,4'-piperidine];

1'-{[2-methyl-1-(phenylsulfonyl)-1H-indol-3-yl]carbonyl}-3H-spiro[2-benzofuran-1,4'-piperidine];

1'-{[1-(cyclohexylmethyl)-2-methyl-1H-indol-3-yl]carbonyl}-3H-spiro[2-benzofuran-1,4'-piperidine];

1'-{[1-(3-fluorobenzyl)-2-methyl-1H-indol-3-yl]carbonyl}-3H-spiro[2-benzofuran-1,4'-piperidine];

1'-({2-methyl-1-[2-(trifluoromethoxy)benzyl]-1H-indol-3-yl}carbonyl)-3H-spiro[2-benzofuran-1,4'-piperidine];

1'-{[1-(3,5-dimethylbenzyl)-2-methyl-1H-indol-3-yl]carbonyl}-3H-spiro[2-benzofuran-1,4'-piperidine];

methyl 4-{[2-methyl-3-(1'H,3H-spiro[2-benzofuran-1,4'-piperidin]-1'-ylcarbonyl)-1H-indol-1-yl]methyl}benzoate;

4-{[2-methyl-3-(1'H,3H-spiro[2-benzofuran-1,4'-piperidin]-1'-ylcarbonyl)-1H-indol-1-yl]methyl}benzonitrile;

1'-{[1-(3,5-difluorobenzyl)-2-methyl-1H-indol-3-yl]carbonyl}-3H-spiro[2-benzofuran-1,4'-piperidine];

1'-{[1-(2-chlorobenzyl)-2-methyl-1H-indol-3-yl]carbonyl}-3H-spiro[2-benzofuran-1,4'-piperidine];

1'-{[1-(2-methoxybenzyl)-2-methyl-1H-indol-3-yl]carbonyl}-3H-spiro[2-benzofuran-1,4'-piperidine];

1'-{[1-(4-methoxybenzyl)-2-methyl-1H-indol-3-yl]carbonyl}-3H-spiro[2-benzofuran-1,4'-piperidine];

1'-[(1-{[2-(2-methoxyphenyl)-5-methyl-1,3-oxazol-4-yl]methyl}-2-methyl-1H-indol-3-yl)carbonyl]-3H-spiro[2-benzofuran-1,4'-piperidine];

1'-[(1-benzyl-1H-indol-3-yl)carbonyl]-3H-spiro[2-benzofuran-1,4'-piperidine];

1'-[(6-chloro-1H-indol-3-yl)carbonyl]-3H-spiro[2-benzofuran-1,4'-piperidine];

N,N-dimethyl-2-[3-(1'H,3H-spiro[2-benzofuran-1,4'-piperidin]-1'-ylcarbonyl)-1H-indol-1-yl]ethanamine;

2-methyl-1-[3-(1'H,3H-spiro[2-benzofuran-1,4'-piperidin]-1'-ylcarbonyl)-1H-indol-2-yl]butan-1-one;

[6-chloro-3-(1'H,3H-spiro[2-benzofuran-1,4'-piperidin]-1'-ylcarbonyl)-1H-indol-1-yl]acetonitrile;

1'-{[6-chloro-1-(3-fluorobenzoyl)-1H-indol-3-yl]carbonyl}-3H-spiro[2-benzofuran-1,4'-piperidine];

1'-{[6-chloro-1-(2-fluorobenzoyl)-1H-indol-3-yl]carbonyl}-3H-spiro[2-benzofuran-1,4'-piperidine];

1'-{[6-chloro-1-(3,5-difluorobenzoyl)-1H-indol-3-yl]carbonyl}-3H-spiro[2-benzofuran-1,4'-piperidine];

1'-{[6-chloro-1-(2,3-difluorobenzoyl)-1H-indol-3-yl]carbonyl}-3H-spiro[2-benzofuran-1,4'-piperidine];

1'-{[6-chloro-1-(3,5-difluorobenzoyl)-1H-indol-3-yl]carbonyl}-3H-spiro[2-benzofuran-1,4'-piperidine];

1'-{[6-chloro-1-(3-fluorobenzyl)-1H-indol-3-yl]carbonyl}-3H-spiro[2-benzofuran-1,4'-piperidine];

1'-{[6-chloro-1-(2-oxo-2-piperidin-1-ylethyl)-1H-indol-3-yl]carbonyl}-3H-spiro[2-benzofuran-1,4'-piperidine];

1'-{[6-chloro-1-(2-morpholin-4-yl-2-oxoethyl)-1H-indol-3-yl]carbonyl}-3H-spiro[2-benzofuran-1,4'-piperidine];

2-[6-chloro-3-(1'H,3H-spiro[2-benzofuran-1,4'-piperidin]-1'-ylcarbonyl)-1H-indol-1-yl]-N,N-dimethylacetamide;

2-[6-chloro-3-(1'H,3H-spiro[2-benzofuran-1,4'-piperidin]-1'-ylcarbonyl)-1H-indol-1-yl]-N,N-diethylacetamide;

1'-{[6-chloro-1-(piperidin-1-ylcarbonyl)-1H-indol-3-yl]carbonyl}-3H-spiro[2-benzofuran-1,4'-piperidine];

tert-butyl[6-chloro-3-(1'H,3H-spiro[2-benzofuran-1,4'-piperidin]-1'-ylcarbonyl)-1H-indol-1-yl]acetate;

1'-{[6-chloro-1-(3,5-difluorophenyl)-1H-indol-3-yl]carbonyl}-3H-spiro[2-benzofuran-1,4'-piperidine];

1'-{[6-chloro-1-(3-fluorophenyl)-1H-indol-3-yl]carbonyl}-3H-spiro[2-benzofuran-1,4'-piperidine];

2-[6-chloro-3-(1'H,3H-spiro[2-benzofuran-1,4'-piperidin]-1'-ylcarbonyl)-1H-indol-1-yl]-1-(2-fluorophenyl)ethanone;

1'-[(6-chloro-1-pyridin-2-yl-1H-indol-3-yl)carbonyl]-3H-spiro[2-benzofuran-1,4'-piperidine];

1'-{[6-chloro-1-(pyridin-4-ylmethyl)-1H-indol-3-yl]carbonyl}-3H-spiro[2-benzofuran-1,4'-piperidine];

2-[6-chloro-3-(1'H,3H-spiro[2-benzofuran-1,4'-piperidin]-1'-ylcarbonyl)-1H-indol-1-yl]-1-pyridin-2-ylethanone;

1'-{[6-chloro-1-(pyridin-3-ylmethyl)-1H-indol-3-yl]carbonyl}-3H-spiro[2-benzofuran-1,4'-piperidine];

1'-{[6-chloro-1-(pyridin-2-ylmethyl)-1H-indol-3-yl]carbonyl}-3H-spiro[2-benzofuran-1,4'-piperidine];

1'-{[6-chloro-1-(pyrazin-2-ylmethyl)-1H-indol-3-yl]carbonyl}-3H-spiro[2-benzofuran-1,4'-piperidine];

1'-{[6-chloro-1-(pyrimidin-5-ylmethyl)-1H-indol-3-yl]carbonyl}-3H-spiro[2-benzofuran-1,4'-piperidine];

2-[6-chloro-3-(1'H,3H-spiro[2-benzofuran-1,4'-piperidin]-1'-ylcarbonyl)-1H-indol-1-yl]-N,N-dimethylethanamine;

1'-{[6-chloro-1-(2-oxo-2-piperazin-1-ylethyl)-1H-indol-3-yl]carbonyl}-3H-spiro[2-benzofuran-1,4'-piperidine];

1'-({1-[(4-benzylmorpholin-2-yl)methyl]-6-chloro-1H-indol-3-yl}carbonyl)-3H-spiro[2-benzofuran-1,4'-piperidine];

1'-({6-chloro-1-[(5-methylisoxazol-3-yl)methyl]-1H-indol-3-yl}carbonyl)-3H-spiro[2-benzofuran-1,4'-piperidine];

1'-({6-chloro-1-[2-(4-methylpiperazin-1-yl)-2-oxoethyl]-1H-indol-3-yl}carbonyl)-3H-spiro[2-benzofuran-1,4'-piperidine];

4-(1-{1-[(2-cyclopropyl-4-methylcyclopenta-1,4-dien-1-yl)methyl]-6-methyl-1H-inden-3-yl}vinyl)-2',3'-dihydrospiro[cyclohexane-1,1'-indene];

1'-({6-chloro-1-[(1-methyl-1H-imidazol-5-yl)methyl]-1H-indol-3-yl}carbonyl)-3H-spiro[2-benzofuran-1,4'-piperidine];

1'-({6-chloro-1-[(3-methylisoxazol-5-yl)methyl]-1H-indol-3-yl}carbonyl)-3H-spiro[2-benzofuran-1,4'-piperidine];

1'-({6-chloro-1-[(1,5-dimethyl-1H-pyrazol-3-yl)methyl]-1H-indol-3-yl}carbonyl)-3H-spiro[2-benzofuran-1,4'-piperidine];

1'-({6-chloro-1-[(3,5-dimethylisoxazol-4-yl)methyl]-1H-indol-3-yl}carbonyl)-3H-spiro[2-benzofuran-1,4'-piperidine];

1'-({6-chloro-1-[(2,5-dimethyl-1,3-oxazol-4-yl)methyl]-1H-indol-3-yl}carbonyl)-3H-spiro[2-benzofuran-1,4'-piperidine];

1'-({6-chloro-1-[(3-fluorooxetan-3-yl)methyl]-1H-indol-3-yl}carbonyl)-3H-spiro[2-benzofuran-1,4'-piperidine];

1'-[(6-chloro-1-{[1-(methoxymethyl)-cyclopropyl]methyl}-1H-indol-3-yl)carbonyl]-3H-spiro[2-benzofuran-1,4'-piperidine];

(1-{[6-chloro-3-(1'H,3H-spiro[2-benzofuran-1,4'-piperidin]-1'-ylcarbonyl)-1H-indol-1-yl]methyl}cyclopropyl)acetonitrile;

1'-({6-chloro-1-[2-(tetrahydro-2H-pyran-4-yl)ethyl]-1H-indol-3-yl}carbonyl)-3H-spiro[2-benzofuran-1,4'-piperidine];

tert-butyl 2-{[6-chloro-3-(1'H,3H-spiro[2-benzofuran-1,4'-piperidin]-1'-ylcarbonyl)-1H-indol-1-yl]methyl}morpholine-4-carboxylate;

1'-{[6-chloro-1-(morpholin-2-ylmethyl)-1H-indol-3-yl]carbonyl}-3H-spiro[2-benzofuran-1,4'-piperidine]hydrochloride;
2-[6-chloro-3-(1'H,3H-spiro[2-benzofuran-1,4'-piperidin]-1'-ylcarbonyl)-1H-indol-1-yl]-N-[2-(dimethylamino)ethyl]acetamide;
2-[6-chloro-5-methyl-3-(1'H,3H-spiro[2-benzofuran-1,4'-piperidin]-1'-ylcarbonyl)-1H-indol-1-yl]-N,N-dimethylacetamide;
2-[6-chloro-3-(1'H,3H-spiro[2-benzofuran-1,4'-piperidin]-1'-ylcarbonyl)-1H-indol-1-yl]acetamide;
2-[6-chloro-3-(1'H,3H-spiro[2-benzofuran-1,4'-piperidin]-1'-ylcarbonyl)-1H-indol-1-yl]-N-[2-(methylamino)ethyl]acetamide;
N-(2-aminoethyl)-2-[6-chloro-3-(1'H,3H-spiro[2-benzofuran-1,4'-piperidin]-1'-ylcarbonyl)-1H-indol-1-yl]acetamide;
2-[6-chloro-3-(1'H,3H-spiro[2-benzofuran-1,4'-piperidin]-1'-ylcarbonyl)-1H-indol-1-yl]ethanamine;
2-[6-chloro-3-(1'H,3H-spiro[2-benzofuran-1,4'-piperidin]-1'-ylcarbonyl)-1H-indol-1-yl]-N-methylethanamine;
2-[6-chloro-3-(1'H,3H-spiro[2-benzofuran-1,4'-piperidin]-1'-ylcarbonyl)-1H-indol-1-yl]-N-methylacetamide;
1'-{[6-chloro-1-(2-morpholin-4-ylethyl)-1H-indol-3-yl]carbonyl}-3H-spiro[2-benzofuran-1,4'-piperidine];
1'-{[6-chloro-1-(3-morpholin-4-ylpropyl)-1H-indol-3-yl]carbonyl}-3H-spiro[2-benzofuran-1,4'-piperidine];
1'-{[6-chloro-1-(oxiran-2-ylmethyl)-1H-indol-3-yl]carbonyl}-3H-spiro[2-benzofuran-1,4'-piperidine];
2-[6-chloro-3-(1'H,3H-spiro[2-benzofuran-1,4'-piperidin]-1'-ylcarbonyl)-1H-indol-1-yl]ethanol;
1'-({6-chloro-1-[(2-methylpyridin-4-yl)methyl]-1H-indol-3-yl}carbonyl)-3H-spiro[2-benzofuran-1,4'-piperidine];
1'-({6-chloro-1-[(3S)-piperidin-3-ylmethyl]-1H-indol-3-yl}carbonyl)-3H-spiro[2-benzofuran-1,4'-piperidine];
2-[6-chloro-3-(1'H,3H-spiro[2-benzofuran-1,4'-piperidin]-1'-ylcarbonyl)-1H-indol-1-yl]-N-hydroxyethanamine;
1'-{[6-chloro-1-(tetrahydro-2H-pyran-4-ylmethyl)-1H-indol-3-yl]carbonyl}-3H-spiro[2-benzofuran-1,4'-piperidine];
1'-({6-chloro-1-[(1-methylpyrrolidin-3-yl)methyl]-1H-indol-3-yl}carbonyl)-3H-spiro[2-benzofuran-1,4'-piperidine];
1'-[(6-chloro-1-{[(3S)-1-methylpiperidin-3-yl]methyl}-1H-indol-3-yl)carbonyl]-3H-spiro[2-benzofuran-1,4'-piperidine];
1'-{[6-chloro-1-(pyrrolidin-3-ylmethyl)-1H-indol-3-yl]carbonyl}-3H-spiro[2-benzofuran-1,4'-piperidine];
1'-({6-chloro-1-[(2S)-pyrrolidin-2-ylmethyl]-1H-indol-3-yl}carbonyl)-3H-spiro[2-benzofuran-1,4'-piperidine];
1'-[(6-chloro-2-methyl-1H-indol-3-yl)carbonyl]-3H-spiro[2-benzofuran-1,4'-piperidine];
1'-(1,2,3,4-tetrahydropyrazino[1,2-a]indol-10-ylcarbonyl)-3H-spiro[2-benzofuran-1,4'-piperidine]hydrochloride;
1'-[(2-methyl-1,2,3,4-tetrahydropyrazino[1,2-a]indol-10-yl)carbonyl]-3H-spiro[2-benzofuran-1,4'-piperidine];
1'-[(6-chloro-2-methyl-1H-indol-3-yl)carbonyl]-3H-spiro[2-benzofuran-1,4'-piperidine];
N-{2-[6-chloro-3-(1'H,3H-spiro[2-benzofuran-1,4'-piperidin]-1'-ylcarbonyl)-1H-indol-1-yl]ethyl}acetamide;
N-{2-[6-chloro-3-(1'H,3H-spiro[2-benzofuran-1,4'-piperidin]-1'-ylcarbonyl)-1H-indol-1-yl]ethyl}methanesulfonamide;
N-{2-[6-chloro-3-(1'H,3H-spiro[2-benzofuran-1,4'-piperidin]-1'-ylcarbonyl)-1H-indol-1-yl]ethyl}-N-methylacetamide;
N-{2-[6-chloro-3-(1'H,3H-spiro[2-benzofuran-1,4'-piperidin]-1'-ylcarbonyl)-1H-indol-1-yl]ethyl}-N-methylmethanesulfonamide;
1'-[(6-chloro-1-{[(2S)-1-methylpyrrolidin-2-yl]methyl}-1H-indol-3-yl)carbonyl]-3H-spiro[2-benzofuran-1,4'-piperidine]; and
1'-[(6-chloro-1-{[(2)-1-methylpyrrolidin-2-yl]methyl}-1H-indol-3-yl)carbonyl]-3H-spiro[2-benzofuran-1,4'-piperidine].

In a certain embodiment the compounds of the invention are those compounds of formula (I-e):

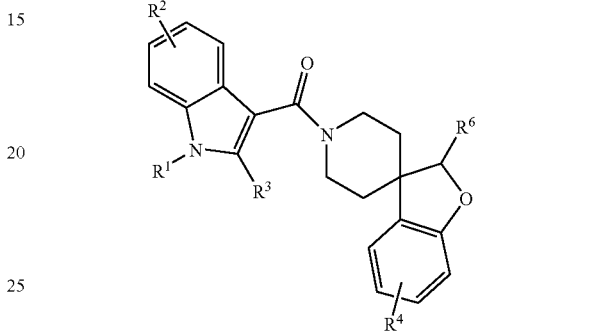

(I-e)

wherein
$R^1$ is H,
  $C_{1-6}$-alkyl optionally substituted by CN, sulfonylaryl,
  —$(CH_2)_m$—$R^a$ wherein $R^a$ is:
    $OR^i$,
    CN,
    $NR^iR^{ii}$, or
    $C_{3-6}$-cycloalkyl, 3 to 6 membered-heterocycloalkyl, aryl or 5 or 6 membered heteroaryl, each of which is optionally substituted by one or more B,
  or —$(CH_2)_n$—(CO)—$R^b$, wherein $R^b$ is:
    $C_{1-6}$-alkoxy,
    $NR^iR^{ii}$, or
    5 or 6 membered-heterocycloalkyl, aryl, or 5 or 6 membered heteroaryl, each of which is optionally substituted by one or more B;

there is one or more $R^2$, wherein each $R^2$ is the same or different,
$R^2$ is one or more H, halo, or $C_{1-6}$-alkyl;
$R^3$ is H,
  $C_{1-6}$-alkyl,
  or —(CO)—$R^c$, wherein $R^c$ is:
    $C_{1-6}$-alkyl or
    —$(CH_2)_n$—$NR^iR^{ii}$, there is one or more $R^4$, wherein each $R^4$ is the same or different,
$R^4$ is one or more H, halo, or $C_{1-6}$-alkoxy optionally substituted by OH, or
  two $R^4$ together with the phenyl ring to which they are attached form an oxo or dioxo bridge;
$R^6$ is H;
B is halo,
  CN,
  $C_{1-6}$-alkyl optionally substituted by CN or $C_{1-6}$-alkoxy,
  $C_{1-6}$-alkoxy,
  $C_{1-6}$-haloalkoxy,
  $C_{3-6}$-cycloalkyl, —C(O)O—$C_{1-6}$-alkyl, or —$(CR^{iii}R^{iv})_n$-phenyl, wherein the phenyl is optionally substituted by one or more substituent(s) selected from the group consisting of:

halo, $C_{1-6}$-alkyl optionally substituted by CN or halo, and $C_{1-6}$-alkoxy;

$R^i$ and $R^{ii}$ are each independently H, $C_{1-6}$-alkyl, $C_{1-6}$-alkyl-$NR^{iii}R^{iv}$, —C(O)—$C_{1-6}$-alkyl, —$S(O)_2$—$C_{1-6}$-alkyl or OH;

$R^{iii}$ and $R^{iv}$ are each independently H or $C_{1-6}$-alkyl;

m is 1 to 6; and n is 0 to 4;

and pharmaceutically acceptable salts thereof.

Further, in a certain embodiment the compounds of the invention are those compounds of formula (I-e), wherein $R^1$ is H, —$(CH_2)_m$—$R^a$ wherein $R^a$ is 5 or 6 membered-heterocycloalkyl, aryl, or 5 or 6 membered heteroaryl, —$(CH_2)_m$—$NR^iR^{ii}$, or —$(CH_2)_n$—(CO)—$R^b$, wherein $R^b$ is 5 or 6 membered-heterocycloalkyl;

there is one or more $R^2$, wherein each $R^2$ is the same or different, $R^2$ is one or more H or halo;

$R^3$ is H or $C_{1-6}$-alkyl;

there is one or more $R^4$, wherein each $R^4$ is the same or different, $R^4$ is one or more H or halo;

$R^6$ is H;

$R^i$ and $R^{ii}$ are each independently $C_{1-6}$-alkyl;

m is 1 to 6; and n is 0 to 4;

and pharmaceutically acceptable salts thereof.

The following compounds are examples according to the invention:

1'-[(6-chloro-1H-indol-3-yl)carbonyl]spiro[1-benzofuran-3,4'-piperidine];

1'-[(1-benzyl-2-methyl-1H-indol-3-yl)carbonyl]spiro[1-benzofuran-3,4'-piperidine];

1'-(1H-indol-3-ylcarbonyl)spiro[1-benzofuran-3,4'-piperidine];

1'-[(6-chloro-5-fluoro-1H-indol-3-yl)carbonyl]spiro[1-benzofuran-3,4'-piperidine];

2-[6-chloro-3-(1'H-spiro[1-benzofuran-3,4'-piperidin]-1'-ylcarbonyl)-1H-indol-1-yl]-N,N-dimethylethanamine;

1'-{[6-chloro-1-(2-pyrrolidin-1-ylethyl)-1H-indol-3-yl]carbonyl}spiro[1-benzofuran-3,4'-piperidine];

3-[6-chloro-3-(1'H-spiro[1-benzofuran-3,4'-piperidin]-1'-ylcarbonyl)-1H-indol-1-yl]-N,N-dimethylpropan-1-amine;

1'-{[6-chloro-1-(2-morpholin-4-ylethyl)-1H-indol-3-yl]carbonyl}spiro[1-benzofuran-3,4'-piperidine];

2-[6-chloro-3-(1'H-spiro[1-benzofuran-3,4'-piperidin]-1'-ylcarbonyl)-1H-indol-1-yl]-N,N-diethylethanamine;

1'-({6-chloro-1-[2-(1H-pyrrol-1-yl)ethyl]-1H-indol-3-yl}carbonyl)spiro[1-benzofuran-3,4'-piperidine]; and 1'-{[6-chloro-1-(2-oxo-2-piperidin-1-ylethyl)-1H-indol-3-yl]carbonyl}spiro[1-benzofuran-3,4'-piperidine].

In a certain embodiment the compounds of the invention are those compounds of formula (I-f):

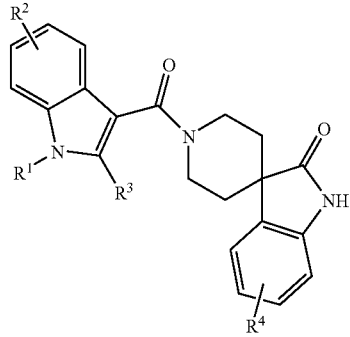

(I-f)

wherein $R^1$ is H, $C_{1-6}$-alkyl optionally substituted by CN, sulfonylaryl,

—$(CH_2)_m$—$R^a$ wherein $R^a$ is:

$OR^i$,

CN, $NR^iR^{ii}$, or $C_{3-6}$-cycloalkyl, 3 to 6 membered-heterocycloalkyl, aryl or 5 or 6 membered heteroaryl, each of which is optionally substituted by one or more B, or —$(CH_2)_n$—(CO)—$R^b$, wherein $R^b$ is:

$C_{1-6}$-alkoxy, $NR^iR^{ii}$, or 6 membered-heterocycloalkyl, aryl, or 5 or 6 membered heteroaryl, each of which is optionally substituted by one or more B;

there is one or more $R^2$, wherein each $R^2$ is the same or different, $R^2$ is one or more H, halo, or $C_{1-6}$-alkyl;

$R^3$ is H, $C_{1-6}$-alkyl,

—(CO)—$R^c$, wherein $R^c$ is:

$C_{1-6}$-alkyl or

—$(CH_2)_n$—$NR^iR^{ii}$, there is one or more $R^4$, wherein each $R^4$ is the same or different, $R^4$ is is one or more H, halo, or $C_{1-6}$-alkoxy optionally substituted by OH, or two $R^4$ together with the phenyl ring to which they are attached form an oxo or dioxo bridge;

B is halo,

CN, $C_{1-6}$-alkyl optionally substituted by CN or $C_{1-6}$-alkoxy, $C_{1-6}$-alkoxy, $C_{1-6}$-haloalkoxy, $C_{3-6}$-cycloalkyl, —C(O)O—$C_{1-6}$-alkyl, —$(CR^{iii}R^{iv})_n$-phenyl, wherein the phenyl is optionally substituted by one or more substituent(s) selected from the group consisting of:

halo, $C_{1-6}$-alkyl optionally substituted by CN or halo, and $C_{1-6}$-alkoxy;

$R^i$ and $R^{ii}$ are each independently H, $C_{1-6}$-alkyl, $C_{1-6}$-alkyl-$NR^{iii}R^{iv}$, —C(O)—$C_{1-6}$-alkyl, —$S(O)_2$—$C_{1-6}$-alkyl or OH;

$R^{iii}$ and $R^{iv}$ are each independently H or $C_{1-6}$-alkyl;

m is 1 to 6; and n is 0 to 4;

and pharmaceutically acceptable salts thereof.

Further, in a certain embodiment the compounds of the invention are those compounds of formula (I-f), wherein
R$^1$ is H;

there is one or more R$^2$, wherein each R$^2$ is the same or different,
R$^2$ is one or more H or halo;
R$^3$ is H;

there is one or more R$^4$, wherein each R$^4$ is the same or different,
R$^4$ is one or more H or halo;

and pharmaceutically acceptable salts thereof.

The following compounds are examples according to the invention:
5-bromo-1'-(1H-indol-3-ylcarbonyl)spiro[indole-3,4'-piperidin]-2(1H)-one; and
5-bromo-1'-[(6-chloro-1H-indol-3-yl)carbonyl]spiro[indole-3,4'-piperidin]-2(1H)-one.

In a certain embodiment the compounds of the invention are those compounds of formula (I-g):

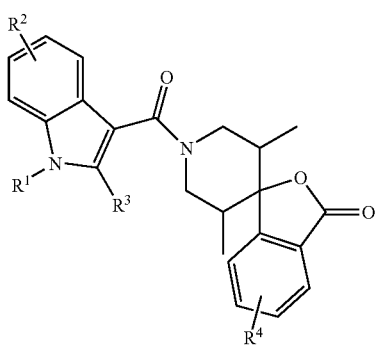

(I-g)

wherein
R$^1$ is H,
C$_{1-6}$-alkyl optionally substituted by CN, sulfonylaryl,
—(CH$_2$)$_m$—R$^a$ wherein R$^a$ is:
OR$^i$,
CN,
NR$^i$R$^{ii}$,
C$_{3-6}$-cycloalkyl, 3 to 6 membered-heterocycloalkyl, aryl or 5 or 6 membered heteroaryl, each of which is optionally substituted by one or more B,
or —(CH$_2$)$_n$—(CO)—R$^b$, wherein R$^b$ is:
C$_{1-6}$-alkoxy,
NR$^i$R$^{ii}$, or
6 membered-heterocycloalkyl, aryl, or 5 or 6 membered heteroaryl, each of which is optionally substituted by one or more B;

there is one or more R$^2$, wherein each R$^2$ is the same or different,
R$^2$ is one or more H or halo;
R$^3$ is H,
or is C$_{1-6}$-alkyl,
or is —(CO)—R$^c$, wherein R$^c$ is:
C$_{1-6}$-alkyl
—(CH$_2$)$_n$—NR$^i$R$^{ii}$, a there is one or more R$^4$, wherein each R$^4$ is the same or different,
R$^4$ is one or more H, halo, or C$_{1-6}$-alkoxy optionally substituted by OH, or two R$^4$ together with the phenyl ring to which they are attached form an oxo or dioxo bridge;
B is halo,
CN,
C$_{1-6}$-alkyl optionally substituted by CN or C$_{1-6}$-alkoxy,
C$_{1-6}$-alkoxy,
C$_{1-6}$-haloalkoxy,
C$_{3-6}$-cycloalkyl,
—C(O)O—C$_{1-6}$-alkyl,
—(CR$^{iii}$R$^{iv}$)$_n$-phenyl, wherein the phenyl is optionally substituted by one or more substituent(s) selected from the group consisting of:
halo, C$_{1-6}$-alkyl optionally substituted by CN or halo, and C$_{1-6}$-alkoxy;
R$^i$ and R$^{ii}$ are each independently H, C$_{1-6}$-alkyl, C$_{1-6}$-alkyl-NR$^{iii}$R$^{iv}$, —C(O)—C$_{1-6}$-alkyl, —S(O)$_2$—C$_{1-6}$-alkyl or OH;
R$^{iii}$ and R$^{iv}$ are each independently H or C$_{1-6}$-alkyl;
m is 1 to 6; and
n is 0 to 4;

and pharmaceutically acceptable salts thereof.

Further, in a certain embodiment the compounds of the invention are those compounds of formula (I-g), wherein
R$^1$ is H or
—(CH$_2$)$_m$—R$^a$ wherein R$^a$ is aryl;
there is one or more R$^2$, wherein each R$^2$ is the same or different,
R$^2$ is one or more H or halo;
R$^3$ is H,
or C$_{1-6}$-alkyl;
R$^4$ is H;
R$^6$ is H;

and pharmaceutically acceptable salts thereof.

The following compounds are examples according to the invention:
(SS,RR)-1'-[(1-benzyl-2-methyl-1H-indol-3-yl)carbonyl]-3',5'-dimethyl-3H-spiro[2-benzofuran-1,4'-piperidin]-3-one;
(RS,SR)-1'-[(6-chloro-1H-indol-3-yl)carbonyl]-3',5'-dimethyl-3H-spiro[2-benzofuran-1,4'-piperidin]-3-one;
(RS,SR)-1'-[(1-benzyl-2-methyl-1H-indol-3-yl)carbonyl]-3',5'-dimethyl-3H-spiro[2-benzofuran-1,4'-piperidin]-3-one; and
(1r,3'R,5'S)-1'-[(1-benzyl-2-methyl-1H-indol-3-yl)carbonyl]-3',5'-dimethyl-3H-spiro[2-benzofuran-1,4'-piperidin]-3-one.

In a certain embodiment the compounds of the invention are those compounds of formula (I-h):

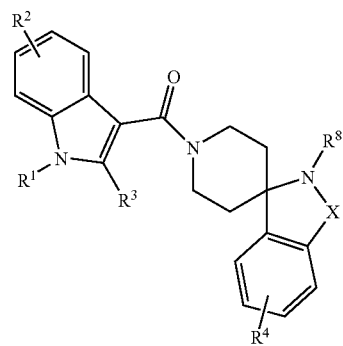

(I-h)

wherein
R¹ is H,
  C$_{1-6}$-alkyl optionally substituted by CN, sulfonylaryl,
    —(CH$_2$)$_m$—R$^a$ wherein R$^a$ is:
      OR$^i$,
      CN,
      NR$^i$R$^{ii}$, or
      C$_{3-6}$-cycloalkyl, 3 to 6 membered-heterocycloalkyl, aryl or 5 or 6 membered heteroaryl, each of which is optionally substituted by one or more B,
  or —(CH$_2$)$_n$—(CO)—R$^b$, wherein R$^b$ is:
    C$_{1-6}$-alkoxy,
    NR$^i$R$^{ii}$, or
    6 membered-heterocycloalkyl, aryl, or 5 or 6 membered heteroaryl, each of which is optionally substituted by one or more B;

there is one or more R², wherein each R² is the same or different,
R² is one or more H, halo, or C$_{1-6}$-alkyl;
R³ is H,
  C$_{1-6}$-alkyl,
  or —(CO)—R$^c$, wherein R$^c$ is:
    C$_{1-6}$-alkyl or
    —(CH$_2$)$_n$—NR$^i$R$^{ii}$, there is one or more R⁴, wherein each R⁴ is the same or different,
R⁴ is is one or more H, halo, or C$_{1-6}$-alkoxy optionally substituted by OH, or
  two R⁴ together with the phenyl ring to which they are attached form an oxo or dioxo bridge;
R⁸ is H or C$_{1-6}$-alkyl;
X is CH$_2$ or C=O;
B is halo,
  CN,
  C$_{1-6}$-alkyl optionally substituted by CN or C$_{1-6}$-alkoxy,
  C$_{1-6}$-alkoxy,
  C$_{1-6}$-haloalkoxy,
  C$_{3-6}$-cycloalkyl,
  —C(O)O—C$_{1-6}$-alkyl, or
  —(CR$^{iii}$R$^{iv}$)$_n$-phenyl, wherein the phenyl is optionally substituted by one or more substituent(s) selected from the group consisting of:
    halo, C$_{1-6}$-alkyl optionally substituted by CN or halo, and C$_{1-6}$-alkoxy;
R$^i$ and R$^{ii}$ are each independently H, C$_{1-6}$-alkyl, C$_{1-6}$-alkyl-NR$^{iii}$R$^{iv}$, —C(O)—C$_{1-6}$-alkyl, —S(O)$_2$—C$_{1-6}$-alkyl or OH;
R$^{iii}$ and R$^{iv}$ are each independently H or C$_{1-6}$-alkyl;
m is 1 to 6; and
n is 0 to 4;
and pharmaceutically acceptable salts thereof.

Further, in a certain embodiment the compounds of the invention are those compounds of formula (I-h), wherein
R¹ is H,
  or —(CH$_2$)$_n$—(CO)—R$^b$, wherein R$^b$ is NR$^i$R$^{ii}$;

there is one or more R², wherein each R² is the same or different,
R² is one or more H or halo;
R³ is H;
R⁴ is H;
R⁸ is H or C$_{1-6}$-alkyl;
X is CH$_2$ or C=O; and
R$^i$ and R$^{ii}$ are each independently H or C$_{1-6}$-alkyl;
and pharmaceutically acceptable salts thereof.

The following compounds are examples according to the invention:
1'-[(6-chloro-1H-indol-3-yl)carbonyl]spiro[isoindole-1,4'-piperidin]-3(2H)-one;
1'-[(6-chloro-1H-indol-3-yl)carbonyl]-2-methyl-2,3-dihydrospiro[isoindole-1,4'-piperidine];
1'-[(6-chloro-1H-indol-3-yl)carbonyl]-2,3-dihydrospiro[isoindole-1,4'-piperidine]; and
2-{6-chloro-3-[(3-oxo-2,3-dihydro-1'H-spiro[isoindole-1,4'-piperidin]-1'-yl)carbonyl]-1H-indol-1-yl}-N-methylacetamide.

The invention also encompasses methods for the treatment or prevention of dysmenorrhea, hypertension, chronic heart failure, inappropriate secretion of vasopressin, liver cirrhosis, nephrotic syndrome, obsessive compulsive disorder, anxious and depressive disorders by administering a compound of formula (I), (I-a), (I-b), (I-c), (I-d), (I-e), (I-f), (I-g) or (I-h).

The invention also encompasses a pharmaceutical composition comprising a compound of formula (I), (I-a), (I-b), (I-c), (I-d), (I-e), (I-f), (I-g) or (I-h) and a pharmaceutically acceptable carrer. Such pharmaceutical compositions are useful for the treatment of dysmenorrhea, hypertension, chronic heart failure, inappropriate secretion of vasopressin, liver cirrhosis, nephrotic syndrome, obsessive compulsive disorder, anxious and depressive disorders.

The invention further encompasses methods for the preparation of compounds of formula (I), (I-a), (I-b), (I-c), (I-d), (I-e), (I-f), (I-g) or (I-h) and pharmaceutical compositions containing them.

In a certain embodiment, the compounds of the invention can be manufactured according to a process comprising the step of reacting a compound of formula (II):

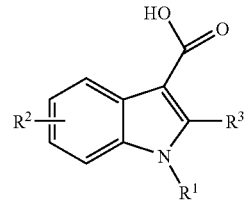

II with a compound of formula A-H to obtain the compound of formula (I), wherein A, R¹, R² and R³ are as defined hereinabove.

In another embodiment, the compounds of the invention can be manufactured according to a oprocess comprising the step of reacting a compound of formula (III):

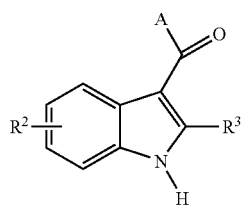

III with an electrophile compound of formula R¹—Y to obtain the compound of formula (I), wherein R¹, R² and R³ are as defined hereinabove and Y is halo, preferably Br or Cl.

In still another embodiment, the compounds of the invention can be manufactured according to a process comprising the step of reacting a compound of formula (IV):

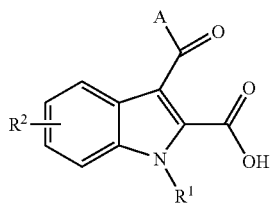

IV with an amine of formula $HNR^iR^{ii}$ to obtain the compound of formula (I), wherein $R^1$, $R^2$, $R^3$, Ri and $R^{ii}$ are as defined hereinabove.

The preparation of the compounds of the invention of formulae (I), (I-a), (I-b), (I-c), (I-d), (I-e), (I-f), (I-g) or (I-h) is described more in details with the following general schemes A, B and C, wherein $R^1$, $R^2$, $R^3$ and A are as defined hereinabove:

General scheme A

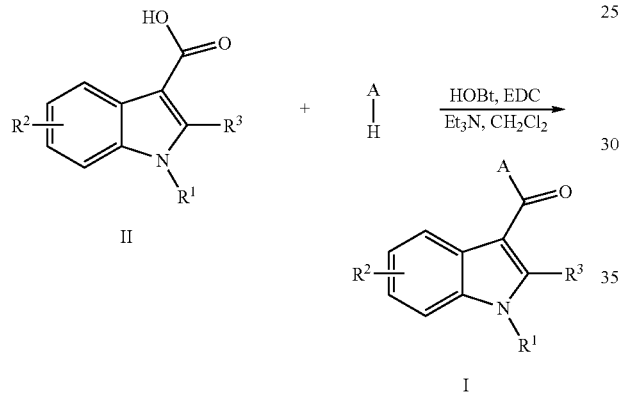

General Scheme A

Compounds of formula (I) can be prepared via an amide coupling between an indole 3-carboxylic acid (II) and a spiropiperidine (A-H). Indole 3-carboxylic acids (II) are either commercially available or readily prepared using a procedure described in *J. Med. Chem.* 1991, 34: 140. Alternatively, they can be prepared following the general scheme D as described hereinafter. The spiropiperidine derivatives A-H are either commercially available or can be prepared using commercially available starting materials and conventional methods. Spiropiperidines A-H of group (h) can be prepared as described in general scheme E. General scheme A is hereinafter further illustrated with general scheme and procedure I to which, e.g., examples 1 to 24, 34, 39-43, 66-70, 77-80 and 123-126 refer.

General scheme B

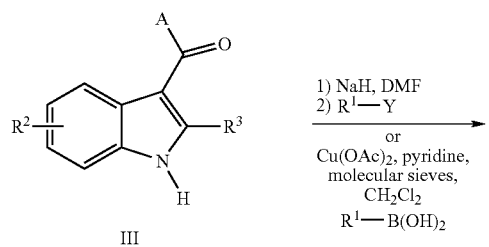

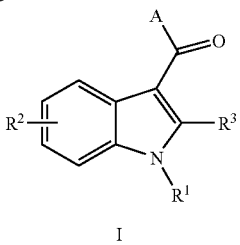

General Scheme B

Compounds of formula (I) with $R^1$ different from H can be prepared by N-deprotonation of an indole derivative (III) (a compound of formula (I) wherein $R^1$ is H) followed by treatment with an electrophilic reactant $R^1$—Y (wherein Y is a leaving group) which is either commercially available or easily prepared according to methods well known in the art and commercially available starting materials. Alternatively, compounds (I) can be prepared by coupling of an indole derivative (III) with a boronic acid $R^1$—B(OH)$_2$ using a transition metal catalyst such as Cu(OAc)$_2$ in the presence of pyridine, molecular sieves and air in dichloromethane. Derivatives (III) are prepared using the method described in the general scheme A. General scheme B is hereinafter further illustrated with general schemes and procedures II and III to which, examples 46 to 65, 81 to 87, 93-103, 133-136, 142-144, 150-154, 161-168, 170, 172-175, 180, 182, 183, 188-193, 195-197, 201-203, 220, 224, 228-247, 253-260, 263, 266, and 267 refer, as well as general schemes and procedures V (e.g. examples 104-115, 117, 204-212), VI (e.g. examples 155-157, 222, 223, 225, 226), VII (e.g. examples 88-92, 128-132, 137-141, 145-149, 158, 214-218, 221) and VIII.

General scheme C

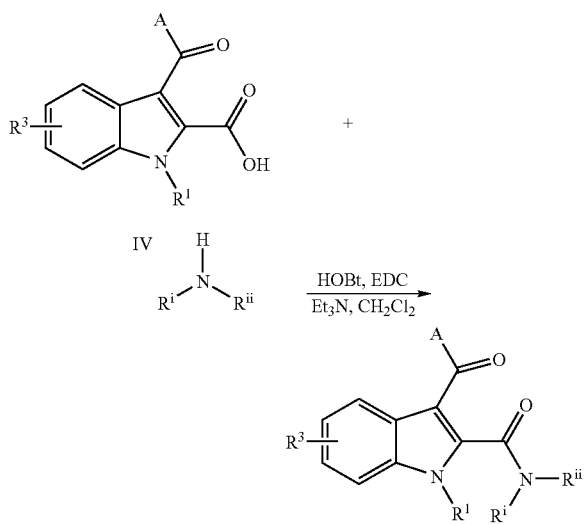

General Scheme C

Compounds of formula (I) wherein $R^3$ is an amide (—$CONR^iR^{ii}$) can be prepared via an amide coupling between an indole 2-carboxylic acid (IV) and an amine $NHR^iR^{ii}$. The indole 2-carboxylic acid derivatives (IV) are readily prepared using commercially available starting products and conventional methods. General scheme C is hereinafter further illustrated with general scheme and procedure IV to which, examples 24 to 33 refer.

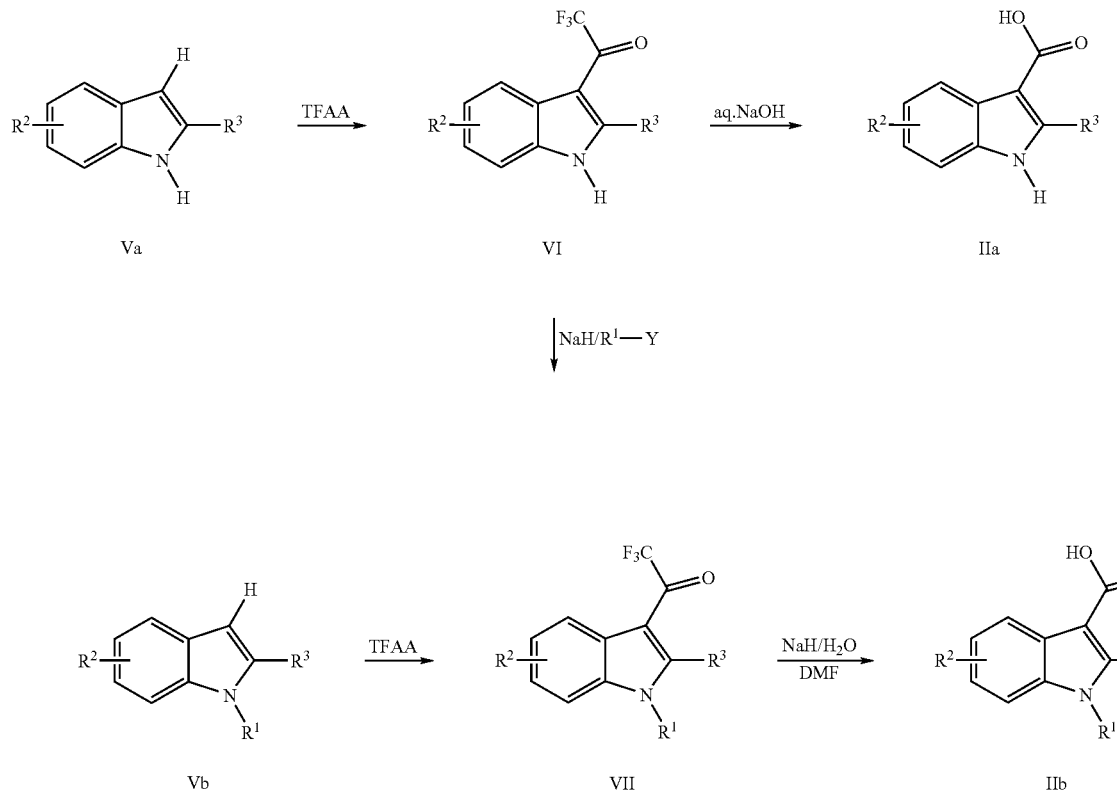

General Scheme D

The treatment of an indole derivative (Va) with trifluoroacetic anhydride in DMF affords intermediate (VI) which can be hydrolysed with an aqueous sodium hydroxide solution to give the 3-carboxylic acid indole derivative (IIa). Alternatively, (VI) can react with an electrophilic reactant $R^1$—Y to give (VII), which is then converted to the corresponding carboxylic acid derivative (IIb) with $NaH/H_2O$ in DMF (see *J. Org Chem.*, 1993, 10, 2862). Intermediate (VII) can alternatively be obtained by treatment of an indole derivative (Vb) with trifluoroacetic anhydride in DMF, dichloromethane or 1,2-dichloroethane. Addition of a suitable base may be advantageous.

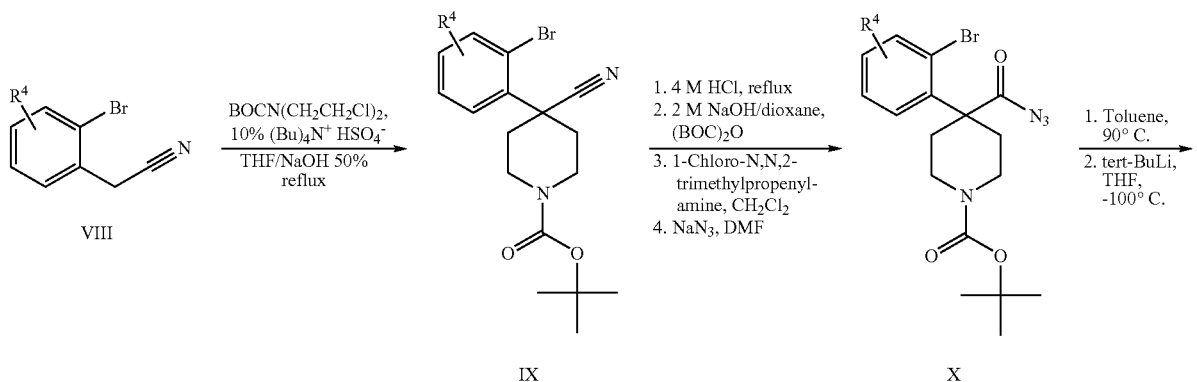

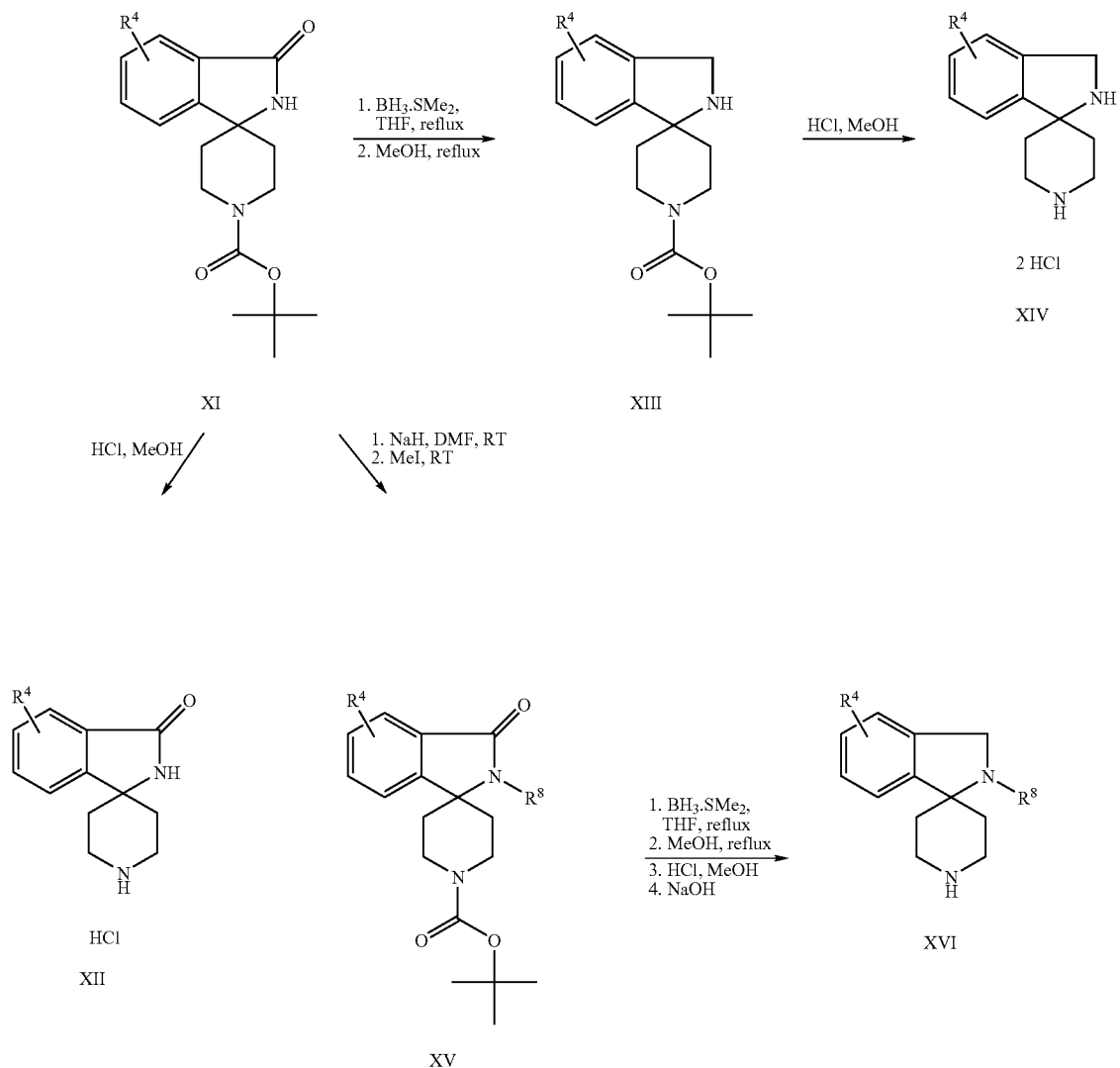

General Scheme E

Cyclization of a bromophenylacetonitrile derivative (VIII) affords a 4-bromoaryl-2-cyanopiperidine derivative (IX). The cyano group is transformed to an azidocarbonyl group using standard functional group transformations to give a compound of formula (X). Upon heating in toluene an azide (X) undergoes a Curtius rearrangement. The crude intermediate isocyanate is trapped to form a lactam of formula (XI) after bromine-lithium exchange using tert-butyllithium at −100° C. N-Deprotection affords spiropiperidine (XII). Alternatively, lactam (XI) can be N-alkylated to give lactam (XV). Both, lactam (XI) and lactam (XV), are reduced using standard conditions to afford spiropiperidines (XIV) and (XVI) after N-deprotection, respectively.

The following general procedures I to VIII are meant to give examples of the preparation of the compounds of the invention according to general schemes A to C.

The following general procedure I is an example of the preparation of the compounds of the invention according to general scheme A.

General procedure I

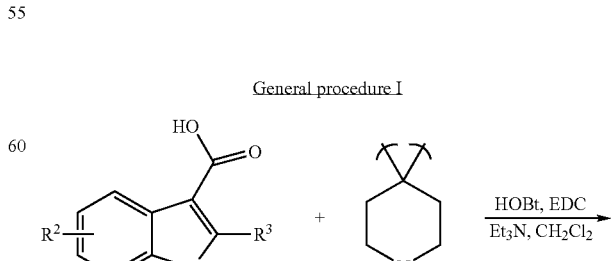

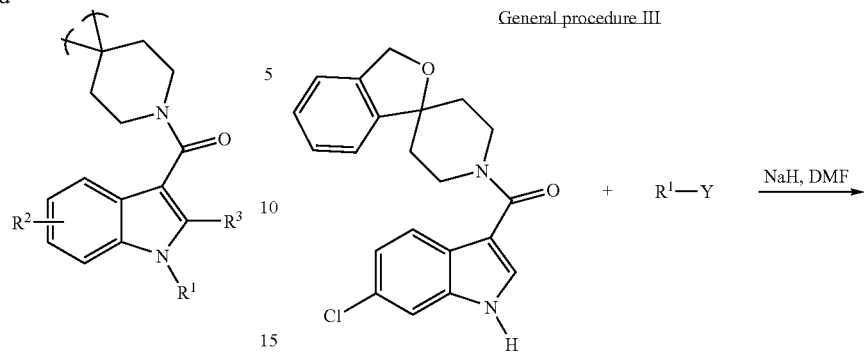

General Procedure I—Amide Coupling:

To a stirred solution of an indole-3-carboxylic acid derivative (1 mmol) in 10 ml $CH_2Cl_2$ was added (1.3 mmol) EDC, (1.3 mmol) HOBt, (1.3 mmol) $Et_3N$ and (1 mmol) of the amine derivative. The mixture was stirred overnight at RT and then poured onto water and extracted with $CH_2Cl_2$. The combined organic phases were dried over $Na_2SO_4$ and concentrated in vacuo. Flash chromatography or preparative HPLC afforded the title compound.

The following general procedures II and III are examples of the preparation of the compounds of the invention according to general scheme B:

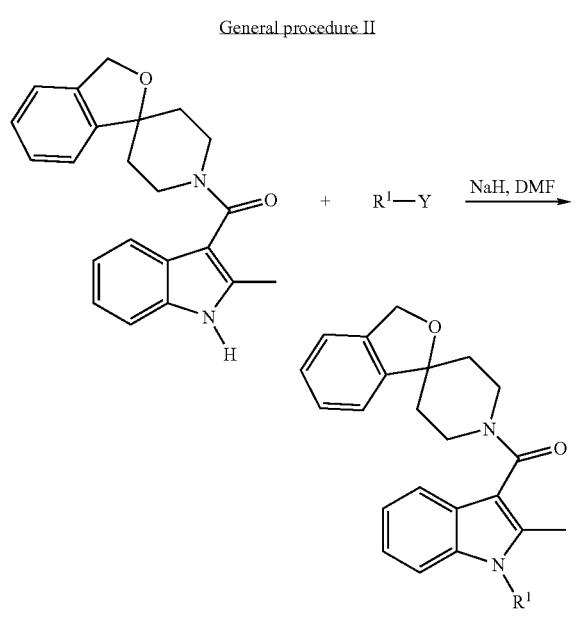

General Procedure II:

To a stirred solution of 30 mg (0.09 mmol) of 1'-[(2-methyl-1H-indol-3-yl)carbonyl]-3H-spiro[2-benzofuran-1,4'-piperidine] (the preparation of which have been described in example 43) in 3 ml DMF was added 4 mg (0.10 mmol) NaH (60% in oil). The mixture was stirred at RT for 30 min., and then the electrophilic reactant $R^1$—Y (0.15 mmol) was added. The mixture was stirred an additional 18 hours and then poured onto water and extracted with ethyl acetate. The combined organic phases were dried over $Na_2SO_4$ and concentrated in vacuo. Purification by preparative HPLC afforded the corresponding derivatives.

General Procedure III:

To a stirred solution of 20 mg (0.054 mmol) of 1'-[(6-chloro-1H-indol-3-yl)carbonyl]spiro[1-benzofuran-3,4'-piperidine](the preparation of which have been described in example 77) in 3 ml DMF was added 8.8 mg (0.11 mmol) NaH (60% in oil). The mixture was stirred at RT for 30 min., and then the electrophilic reactant $R^1$—Y (0.08 mmol) was added. The mixture was stirred an additional 18 hours at 60° C. and then poured onto water and extracted with ethyl acetate. The combined organic phases were dried over $Na_2SO_4$ and concentrated in vacuo. Purification by preparative HPLC afforded the corresponding derivatives.

The following general procedure IV is an example of preparation of the compounds of the invention according to general scheme C:

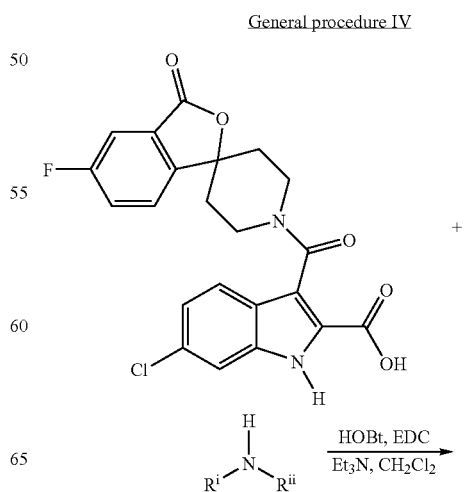

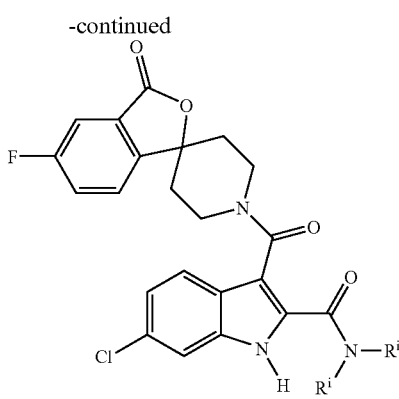

General Procedure IV:

To a stirred solution of 6-chloro-3-[(5-fluoro-3-oxo-1'H, 3H-spiro[2-benzofuran-1,4'-piperidin]-1'-yl)carbonyl]-1H-indole-2-carboxylic acid (1 mmol) (the preparation of which have been described in example 24d) in 10 ml $CH_2Cl_2$ was added (1.3 mmol) EDC, (1.3 mmol) HOBt, (1.3 mmol) $Et_3N$ and (1 mmol) the amine derivative (wherein $R^i$ and $R^{ii}$ are as defined hereinabove). The mixture was stirred overnight at RT and then poured onto water and extracted with $CH_2Cl_2$. The combined organic phases were dried over $Na_2SO_4$ and concentrated in vacuo. Flash chromatography or preparative HPLC afforded the title compound.

The following general procedures V to VIII are examples of the preparation of the compounds of the invention according to general scheme B:

General procedure V

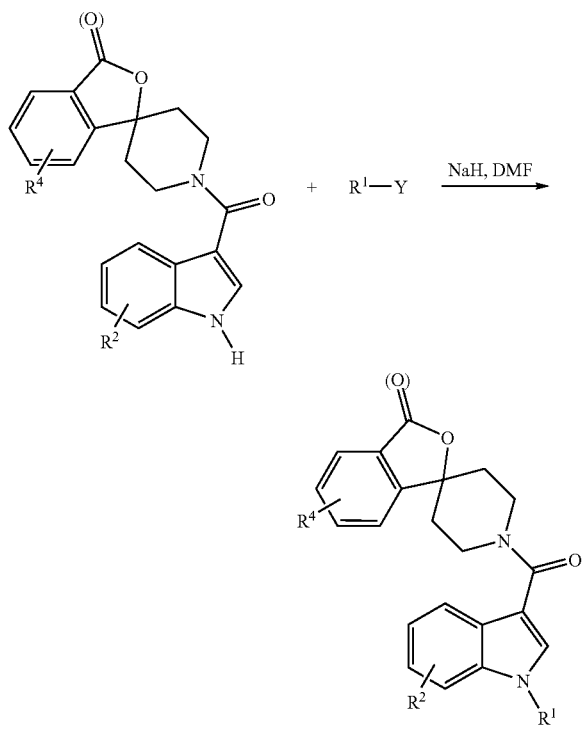

General Procedure V:

To a stirred solution of an indole derivative (III) (0.079 mmol) in 2 ml DMF was added NaH (0.10 mmol, 60% in oil). The mixture was stirred at room temperature for 30 min., and then the electrophile $R^1$—Y (0.15 mmol) was added. The mixture was stirred for an additional 18 hours and then poured onto water and extracted with ethyl acetate. The combined organic phases were dried over $Na_2SO_4$ and concentrated in vacuo. Purification by preparative HPLC afforded the corresponding derivatives.

General procedure VI

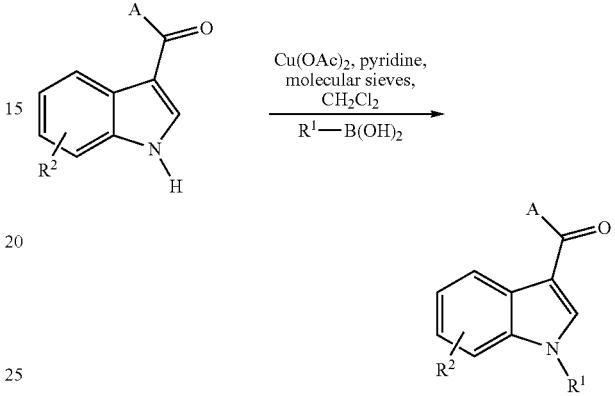

General Procedure VI—Aryl Coupling:

To a solution of the indole in dichloromethane was added anhydrous $Cu(OAc)_2$ (2 eq), the boronic acid (3 eq) and pyridine (4 eq), and the reaction mixture stirred 16 h at room temperature in the presence of 0.4 nm molecular sieve under an open to air atmosphere. Filtration through decalite, washing with dichloromethane and concentration gave the crude product which was purified by silica gel chromatography (hexane/ethyl acetate) to give the desired product.

General procedures VII and VIII

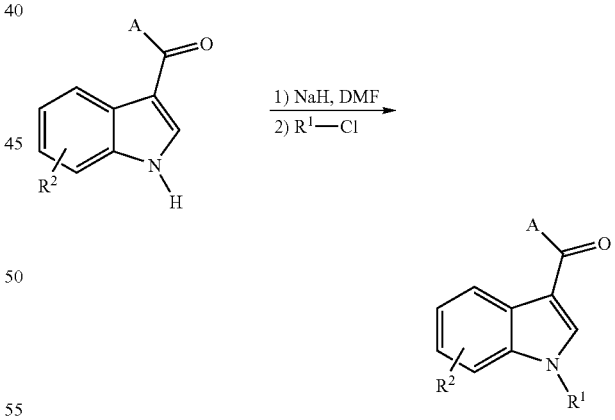

General Procedure VII—Acylation:

A solution of the indole in dry DMF was treated with sodium hydride (1.05 eq) and stirred for 15 min at room temperature, then treated with an acid chloride (1.1 eq) and stirred at room temperature for 2 h. Purification by preparative HPLC yielded the desired product.

General Procedure VIII—Sulphonylation:

A solution of the indole in dry DMF was treated with sodium hydride (1.05 eq) and stirred for 15 min at room temperature, then treated with a sulphonyl chloride (1.1 eq)

and stirred at room temperature for 2 h. Purification by preparative HPLC yielded the desired product.

Results—V1a Activity

Material & Method:

The human V1a receptor was cloned by RT-PCR from total human liver RNA. The coding sequence was subcloned in an expression vector after sequencing to confirm the identity of the amplified sequence. To demonstrate the affinity of the compounds from the present invention to the human V1a receptor binding studies were performed. Cell membranes were prepared from HEK293 cells transiently transfected with the expression vector and grown in 20 liter fermenters with the following protocol.

50 g cells are resuspended in 30 ml freshly prepared ice cold Lysis buffer (50 mM HEPES, 1 mM EDTA, 10 mM MgCl2 adjusted to pH=7.4+complete cocktail of protease inhibitor (Roche Diagnostics)). The cells are homogenized with Polytron for 1 min and sonicated on ice for 2×2 minutes at 80% intensity (Vibracell sonicator). The preparation is centrifuged 20 min at 500 g at 4° C., the pellet is discarded and the supernatant centrifuged 1 hour at 43,000 g at 4° C. (19,000 rpm). The pellet is resuspended in 12.5 ml Lysis buffer+12.5 ml Sucrose 20% and homogenized using a Polytron for 1-2 min. The protein concentration is determined by the Bradford method and aliquots are stored at −80° C. until use. For binding studies 60 mg Yttrium silicate SPA beads (Amersham) are mixed with an aliquot of membrane in binding buffer (50 mM Tris, 120 mM NaCl, 5 mM KCl, 2 mM CaCl2, 10 mM MgCl2) for 15 minutes with mixing. 50 ul of bead/membrane mixture is then added to each well of a 96 well plate, followed by 50 ul of 4 nM 3H-Vasopressin (American Radiolabeled Chemicals). For total binding measurement 100 ul of binding buffer are added to the respective wells, for non-specific binding 100 ul of 8.4 mM cold vasopressin and for compound testing 100 ul of a serial dilution of each compound in 2% DMSO. The plate is incubated 1 h at room temperature, centrifuged 1 min at 1000 g and counted on a Packard Top-Count. Non-specific binding counts are subtracted from each well and data is normalized to the maximum specific binding set at 100%. To calculate an IC 50 the curve is fitted using a non-linear regression model (XLfit), and the Ki is calculated using the Cheng-Prussoff equation.

| Example | Ki (nM) |
|---|---|
| 1 | 6.8 |
| 2 | 16.2 |
| 3 | 10.1 |
| 5 | 8.2 |
| 6 | 19.7 |
| 8 | 27.2 |
| 9 | 9.7 |
| 10 | 12.7 |
| 11 | 11.2 |
| 12 | 3.4 |
| 13 | 9.5 |
| 14 | 11.2 |
| 15 | 14.8 |
| 16 | 4.4 |
| 19 | 6.8 |
| 20 | 15.8 |
| 23 | 11.0 |
| 24 | 33.1 |
| 25 | 20.4 |
| 26 | 39.4 |
| 29 | 10.1 |
| 30 | 5.8 |
| 31 | 12.2 |
| 32 | 27.5 |
| 33 | 10.8 |
| 34 | 2.1 |
| 35 | 2.5 |
| 37 | 6.3 |
| 39 | 1.8 |
| 40 | 2.9 |
| 43 | 11.0 |
| 44 | 11.0 |
| 45 | 9.5 |
| 46 | 0.8 |
| 47 | 0.5 |
| 48 | 2.6 |
| 49 | 2.4 |
| 50 | 10.6 |
| 51 | 5.9 |
| 52 | 2.1 |
| 53 | 1.7 |
| 54 | 2.5 |
| 55 | 7.9 |
| 58 | 12.3 |
| 68 | 6.9 |
| 69 | 4.3 |
| 71 | 5.6 |
| 72 | 2.9 |
| 76 | 1.7 |
| 77 | 15.8 |
| 80 | 7.4 |
| 81 | 5.0 |
| 82 | 12.9 |
| 84 | 3.6 |
| 85 | 10.2 |
| 86 | 13.2 |
| 87 | 3.5 |
| 93 | 13.8 |
| 94 | 4.1 |
| 99 | 5.7 |
| 100 | 3.4 |
| 101 | 27.9 |
| 102 | 25.1 |
| 104 | 1.3 |
| 105 | 2.3 |
| 106 | 0.4 |
| 107 | 1.3 |
| 108 | 6.2 |
| 109 | 1.1 |
| 110 | 0.8 |
| 111 | 2.4 |
| 112 | 2.0 |
| 113 | 1.1 |
| 114 | 1.3 |
| 115 | 10.4 |
| 116 | 1.7 |
| 117 | 1.2 |
| 119 | 24.0 |
| 120 | 2.7 |
| 122 | 5.2 |
| 126 | 3.0 |
| 127 | 3.0 |
| 130 | 11.1 |
| 133 | 0.9 |
| 134 | 1.0 |
| 135 | 1.8 |
| 136 | 3.0 |
| 142 | 0.6 |
| 143 | 1.0 |
| 144 | 2.0 |
| 150 | 3.8 |
| 151 | 4.8 |
| 152 | 4.4 |
| 153 | 1.0 |
| 154 | 1.3 |
| 155 | 5.0 |

-continued

| Example | Ki (nM) |
|---|---|
| 157 | 39.8 |
| 158 | 38.7 |
| 159 | 7.6 |
| 160 | 5.0 |
| 161 | 2.2 |
| 162 | 65.3 |
| 163 | 15.3 |
| 164 | 2.9 |
| 165 | 4.3 |
| 166 | 2.4 |
| 167 | 3.0 |
| 168 | 2.4 |
| 169 | 1.5 |
| 170 | 2.2 |
| 171 | 2.7 |
| 172 | 3.0 |
| 173 | 2.3 |
| 174 | 2.6 |
| 175 | 2.5 |
| 176 | 14.8 |
| 177 | 6.9 |
| 179 | 3.1 |
| 180 | 1.5 |
| 182 | 4.0 |
| 183 | 5.2 |
| 184 | 3.4 |
| 185 | 2.2 |
| 186 | 2.9 |
| 187 | 3.6 |
| 188 | 1.6 |
| 189 | 1.7 |
| 190 | 2.6 |
| 191 | 2.8 |
| 192 | 2.4 |
| 193 | 2.1 |
| 194 | 15.1 |
| 195 | 2.1 |
| 196 | 1.4 |
| 197 | 3.0 |
| 198 | 3.3 |
| 199 | 3.3 |
| 200 | 5.8 |
| 201 | 4.6 |
| 202 | 4.3 |
| 203 | 11.7 |
| 204 | 1.1 |
| 205 | 1.0 |
| 206 | 0.5 |
| 207 | 1.1 |
| 208 | 2.6 |
| 209 | 1.0 |
| 210 | 1.0 |
| 211 | 0.8 |
| 212 | 1.2 |
| 213 | 3.3 |
| 214 | 5.1 |
| 215 | 8.6 |
| 216 | 3.5 |
| 217 | 5.8 |
| 218 | 25.1 |
| 219 | 1.2 |
| 220 | 1.0 |
| 222 | 4.0 |
| 223 | 2.5 |
| 224 | 1.3 |
| 227 | 3.8 |
| 228 | 1.5 |
| 229 | 1.6 |
| 230 | 1.7 |
| 231 | 1.6 |
| 232 | 5.0 |
| 234 | 1.8 |
| 235 | 1.4 |
| 236 | 1.7 |
| 237 | 4.0 |
| 238 | 1.9 |
| 239 | 2.3 |

-continued

| Example | Ki (nM) |
|---|---|
| 240 | 2.0 |
| 241 | 1.5 |
| 242 | 2.2 |
| 243 | 1.4 |
| 244 | 2.6 |
| 245 | 1.7 |
| 246 | 1.9 |
| 247 | 2.3 |
| 248 | 1.5 |
| 249 | 2.4 |
| 250 | 4.1 |
| 251 | 2.1 |
| 252 | 2.3 |
| 253 | 7.7 |
| 254 | 1.9 |
| 255 | 1.4 |
| 256 | 2.4 |
| 257 | 3.1 |
| 258 | 3.7 |
| 259 | 2.6 |
| 260 | 2.8 |
| 261 | 1.7 |
| 262 | 4.3 |
| 263 | 1.7 |
| 264 | 1.8 |
| 265 | 1.4 |
| 266 | 2.7 |
| 267 | 1.4 |
| 268 | 0.07 |
| 269 | 1.0 |
| 270 | 1.3 |
| 271 | 1.5 |
| 272 | 1.3 |
| 273 | 1.1 |
| 274 | 25.1 |
| 275 | 15.7 |
| 276 | 12.0 |
| 277 | 5.2 |
| 280 | 67.6 |
| 281 | 19.1 |
| 283 | 63.1 |
| 284 | 138.0 |

The present invention also provides pharmaceutical compositions containing compounds of formula (I) or their pharmaceutically acceptable acid addition salts thereof and a pharmaceutically acceptable carrier. Such pharmaceutical compositions can be administered orally, e.g. in the form of tablets, coated tablets, dragées, hard and soft gelatine capsules, solutions, emulsions or suspensions. The compositions also can be administered rectally, e.g. in the form of suppositories, or parenterally, e.g. in the form of injectable solutions.

The pharmaceutical compositions of the invention, in addition to one or more compounds of the invention, contain a pharmaceutically acceptable carier. Suitable pharmaceutically acceptable carriers include pharmaceutically inert, inorganic or organic excipients. Lactose, corn starch or derivatives thereof, talc, stearic acid or its salts etc can be used as such excipients e.g. for tablets, dragées and hard gelatin capsules. Suitable excipients for soft gelatine capsules are e.g. vegetable oils, waxes, fats, semi-solid and liquid polyols etc. Suitable excipients for the manufacture of solutions and syrups are e.g. water, polyols, saccharose, invert sugar, glucose etc. Suitable excipients for injection solutions are e.g. water, alcohols, polyols, glycerol, vegetable oils etc. Suitable excipients for suppositories are e.g. natural or hardened oils, waxes, fats, semi-liquid or liquid polyols etc.

Moreover, the pharmaceutical compositions can contain preservatives, solubilizers, stabilizers, wetting agents, emulsifiers, sweeteners, colorants, flavorants, salts for varying the osmotic pressure, buffers, masking agents or antioxidants. They can also contain still other therapeutically valuable substances.

The present invention also provides a method for the manufacture of pharmaceutical compositions. Such process comprises bringing one or more compounds of formula I and/or pharmaceutically acceptable acid addition salts thereof and, if desired, one or more other therapeutically valuable substances into a galenical administration form together with one or more therapeutically inert carriers.

The compounds of the present invention are active on the V1a receptor. Therefore, the invention provides methods for treating dysmenorrhea, hypertension, chronic heart failure, inappropriate secretion of vasopressin, liver cirrhosis, nephrotic syndrome, obsessive compulsive disorder, anxiety, and depressive disorders.

The dosage at which a compound of the invention can be administered can vary within wide limits and will, of course, be fitted to the individual requirements in each particular case. In general, in the case of oral administration a daily dosage of about 10 to 1000 mg per person of a compound of general formula (I) should be appropriate, although the above upper limit can also be exceeded when necessary.

The following Examples illustrate the present invention without limiting it. All temperatures are given in degrees Celsius.

Example A

Tablets of the following composition are manufactured in the usual manner:

|  | mg/tablet |
|---|---|
| Active substance | 5 |
| Lactose | 45 |
| Corn starch | 15 |
| Microcrystalline cellulose | 34 |
| Magnesium stearate | 1 |
| Tablet weight | 100 |

Example B

Capsules of the following composition are manufactured:

|  | mg/capsule |
|---|---|
| Active substance | 10 |
| Lactose | 155 |
| Corn starch | 30 |
| Talc | 5 |
| Capsule fill weight | 200 |

The active substance, lactose and corn starch are firstly mixed in a mixer and then in a comminuting machine. The mixture is returned to the mixer, the talc is added thereto and mixed thoroughly. The mixture is filled by machine into hard gelatine capsules.

Example C

Suppositories of the following composition are manufactured:

|  | mg/supp. |
|---|---|
| Active substance | 15 |
| Suppository mass | 1285 |
| Total | 1300 |

The suppository mass is melted in a glass or steel vessel, mixed thoroughly and cooled to 45° C. Thereupon, the finely powdered active substance is added thereto and stirred until it has dispersed completely. The mixture is poured into suppository moulds of suitable size, left to cool; the suppositories are then removed from the moulds and packed individually in wax paper or metal foil.

EXAMPLES

Where journal references are cited in the examples, the example was performed using the starting material listed with the reactants and conditions cited in the reference. All procedures in such references are well known to those of ordinary skill in the art. All journal references cited herein are incorporated by reference.

Examples of Compounds of Formula (I-a)

Example 1

1'-[(1-benzyl-2-methyl-1H-indol-3-yl)carbonyl]spiro[indene-1,4'-piperidine]

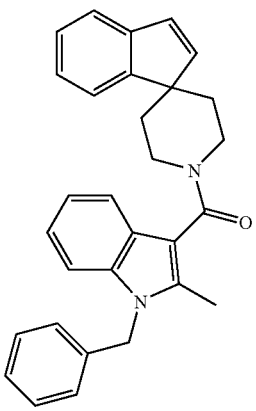

Amide coupling according to general procedure I described hereinabove:
Amine: spiro[indene-1,4'-piperidine] prepared as described in J. Med. Chem. 1992, 35,2033,
Acid: 1-Benzyl-2-methyl-1H-indole-3-carboxylic acid (the preparation of which is described hereinafter),
ES-MS m/e (%): 433.5 (M+H$^+$).

1-Benzyl-2-methyl-1H-indole-3-carboxylic acid

To a stirred solution of 0.50 g (3.10 mmol) 2-methyl-1H-indole-3-carboxylic acid (described in J. Heterocyclic Chem. 1977, 14, 1123) in 5 ml DMF was added 0.27 g (6.75 mmol) of NaH (60% in oil). The mixture was stirred at RT for 30 min. and then 0.39 ml (3.28 mmol) of benzyl bromid was added. The mixture was stirred an additional hour and then poured onto water and extracted with ethyl acetate. The combined organic phases were dried over $Na_2SO_4$ and concentrated in vacuo. Crystallization in $Et_2O$ afforded 1-Benzyl-2-methyl-1H-indole-3-carboxylic acid.

Example 2

1'-[(1-benzyl-2-methyl-1H-indol-3-yl)carbonyl]-2,3-dihydrospiro[indene-1,4'-piperidine]

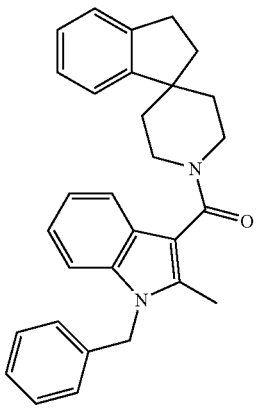

Amide coupling according to general procedure I described hereinabove:
  Amine: 2,3-dihydrospiro[indene-1,4'-piperidine] prepared as described in *J. Med. Chem.* 1992, 35,2033,
  Acid: 1-Benzyl-2-methyl-1H-indole-3-carboxylic acid (described in example 1),
  ES-MS m/e (%): 435.5 (M+H$^+$).

Example 3

1'-[(1-benzyl-1H-indol-3-yl)carbonyl]spiro[indene-1,4'-piperidine]

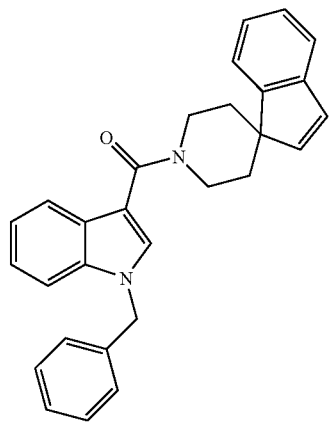

Amide coupling according to general procedure I described hereinabove:
  Amine: spiro[indene-1,4'-piperidine] prepared as described in *J. Med. Chem.* 1992, 35, 2033,
  Acid: 1-benzyl-1H-indole-3-carboxylic acid (the preparation of which is described hereinafter),
  ES-MS m/e (%): 419.4 (M+H$^+$).

1-benzyl-1H-indole-3-carboxylic acid

To a stirred solution of 0.50 g (3.10 mmol) 1H-indole-3-carboxylic acid in 5 ml DMF was added 0.27 g (6.75 mmol) of NaH (60% in oil). The mixture was stirred at RT for 30 min. and then 0.39 ml (3.28 mmol) of benzyl bromid was added. The mixture was stirred an additional hour and then poured onto water and extracted with ethyl acetate. The combined organic phases were dried over $Na_2SO_4$ and concentrated in vacuo. Crystallization in $Et_2O$ afforded 0.61 g (78%) of 1-benzyl-1H-indole-3-carboxylic acid as a white solid. ES-MS m/e (%): 250 (M−H$^+$).

Example 4

1'-[(2-methyl-1H-indol-3-yl)carbonyl]spiro[indene-1,4'-piperidine]

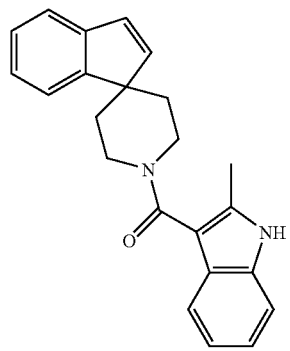

Amide coupling according to general procedure I described hereinabove:
  Amine: spiro[indene-1,4'-piperidine] prepared as described in *J. Med. Chem.* 1992, 35, 2033,
  Acid: 2-Methyl-1H-indole-3-carboxylic acid prepared as described in *J. Heterocyclic Chem.* 1977, 14, 1123,
  ES-MS m/e (%): 343.2. (M+H$^+$).

Example 5

1'-[(6-chloro-1H-indol-3-yl)carbonyl]spiro[indene-1,4'-piperidine]

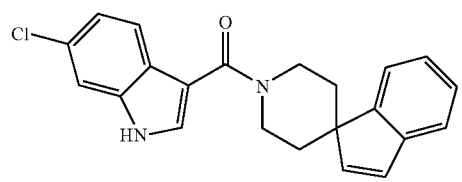

Amide coupling according to general procedure I described hereinabove:
  Amine: spiro[indene-1,4'-piperidine] prepared as described in *J. Med. Chem.* 1992, 35, 2033, Acid: 6-chloro-1H-indole-3-carboxylic acid (the preparation of which is described hereinafter),
ES-MS m/e (%): 363.4 (M+H⁺).

6-chloro-1H-indole-3-carboxylic acid

Using a procedure described in *J. Med. Chem.* 1991, 34, 140, from 7.0 g (0.046 mmol) of 6-chloro-1H-indole was prepared 5.80 g (64%) of 6-chloro-1H-indole-3-carboxylic acid as a light brown solid. ES-MS m/e (%): 194 (M−H⁺).

Example 6

1'-[(6-chloro-1H-indol-3-yl)carbonyl]-2,3-dihydrospiro[indene-1,4'-piperidine]

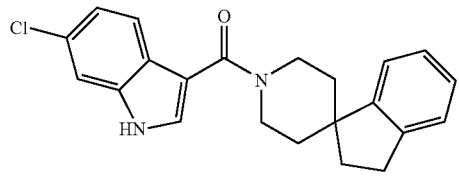

Amide coupling according to general procedure I described hereinabove:
Amine: 2,3-dihydrospiro[indene-1,4'-piperidine] prepared as described in *J. Med. Chem.* 1992, 35, 2033,
Acid: 6-chloro-1H-indole-3-carboxylic acid (described in example 5),
ES-MS m/e (%): 365.4 (M+H⁺).

Examples of Compounds of Formula (I-b)

Example 7

1'-[(1-benzyl-2-methyl-1H-indol-3-yl)carbonyl]-1-(methylsulfonyl)-1,2-dihydrospiro[indole-3,4'-piperidine]

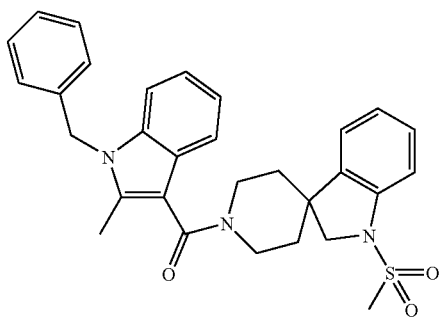

Amide coupling according to general procedure I described hereinabove:
Amine: 1-(methylsulfonyl)-1,2-dihydrospiro[indole-3,4'-piperidine] prepared as described in *Tetrahedron*, 1997, 53, 10983,
Acid: 1-Benzyl-2-methyl-1H-indole-3-carboxylic acid (described in example 1),
ES-MS m/e (%): 514.6 (M+H⁺).

Example 8

1'-[(6-chloro-1H-indol-3-yl)carbonyl]-1,2-dihydrospiro[indole-3,4'-piperidine]

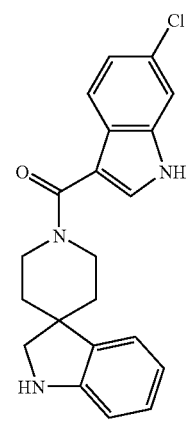

Amide coupling according to general procedure I described hereinabove:
Amine: 1,2-dihydrospiro[indole-3,4'-piperidine] prepared as described in *Tetrahedron*, 2004, 60, 4875-4878,
Acid: 6-chloro-1H-indole-3-carboxylic acid (described in example 5),
ES-MS m/e (%): 366.4 (M+H⁺).

Example 9

1'-[(1-benzyl-2-methyl-1H-indol-3-yl)carbonyl]-1,2-dihydrospiro[indole-3,4'-piperidine]

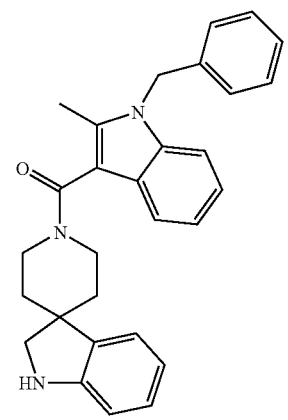

Amide coupling according to general procedure I described hereinabove:
Amine: 1,2-dihydrospiro[indole-3,4'-piperidine] prepared as described in *Tetrahedron*, 2004, 60, 4875-4878,
Acid: 1-Benzyl-2-methyl-1H-indole-3-carboxylic acid (described in example 1),
ES-MS m/e (%): 436.6 (M+H⁺).

Examples of Compounds of Formula (I-c)

Example 10

1'-[(1-benzyl-2-methyl-1H-indol-3-yl)carbonyl]-6-chloro-3H-spiro[2-benzofuran-1,4'-piperidin]-3-one

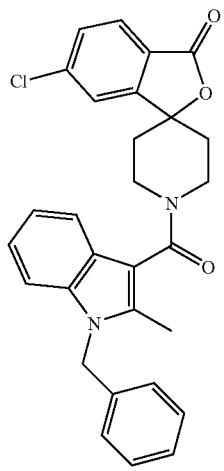

Amide coupling according to general procedure I described hereinabove:
Amine: 6-chloro-3H-spiro[2-benzofuran-1,4'-piperidin]-3-one prepared as described in European patent application EP722941,
Acid: 1-Benzyl-2-methyl-1H-indole-3-carboxylic acid (described in example 1),
ES-MS m/e (%): 485.5 (M+H$^+$).

Example 11

1'-[(1-benzyl-2-methyl-1H-indol-3-yl)carbonyl]-4-fluoro-3H-spiro[2-benzofuran-1,4'-piperidin]-3-one

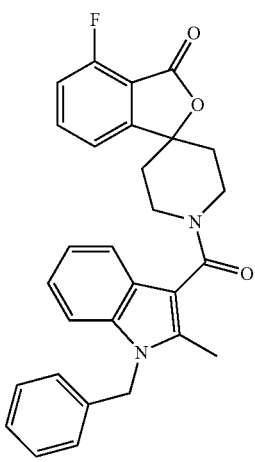

Amide coupling according to general procedure I described hereinabove:
Amine: 4-fluoro-3H-spiro[2-benzofuran-1,4'-piperidin]-3-one prepared as described in EP722941,
Acid: 1-Benzyl-2-methyl-1H-indole-3-carboxylic acid (described in example 1),
ES-MS m/e (%): 469.5 (M+H$^+$).

Example 12

1'-[(1-benzyl-2-methyl-1H-indol-3-yl)carbonyl]-6-methoxy-3H-spiro[2-benzofuran-1,4'-piperidin]-3-one

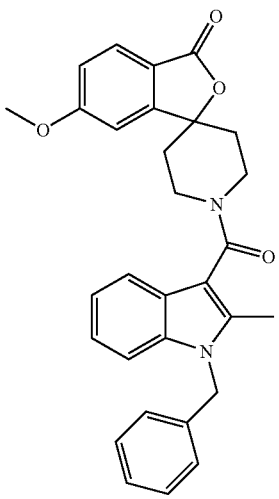

Amide coupling according to general procedure I described hereinabove:
Amine: 6-methoxy-3H-spiro[2-benzofuran-1,4'-piperidin]-3-one prepared as described in EP722941, incorporated by reference herein.
Acid: 1-Benzyl-2-methyl-1H-indole-3-carboxylic acid (described in example 1),
ES-MS m/e (%): 481.4 (M+H$^+$).

Example 13

1'-[(1-benzyl-2-methyl-1H-indol-3-yl)carbonyl]-5-methoxy-3H-spiro[2-benzofuran-1,4'-piperidin]-3-one

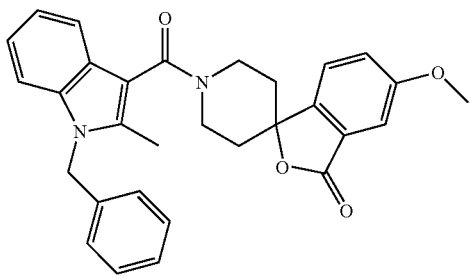

Amide coupling according to general procedure I described hereinabove:
Amine: 5-methoxy-3H-spiro[2-benzofuran-1,4'-piperidin]-3-one prepared as described in EP722941, incorporated by reference herein.
Acid: 1-Benzyl-2-methyl-1H-indole-3-carboxylic acid (described in example 1),
ES-MS m/e (%): 481.6 (M+H$^+$).

Example 14

1'-[(1-benzyl-2-methyl-1H-indol-3-yl)carbonyl]-7-chloro-3H-spiro[2-benzofuran-1,4'-piperidin]-3-one

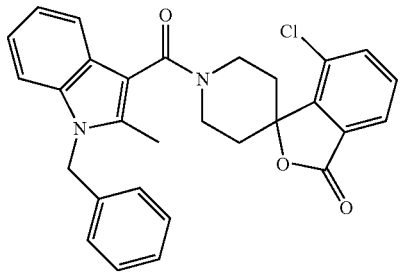

Amide coupling according to general procedure I described hereinabove:
Amine: 7-chloro-3H-spiro[2-benzofuran-1,4'-piperidin]-3-one (the preparation of which is described hereinafter),
Acid: 1-Benzyl-2-methyl-1H-indole-3-carboxylic acid (described in example 1),
ES-MS m/e (%): 485.5 (M+H$^+$).

7-chloro-3H-spiro[2-benzofuran-1,4'-piperidin]-3-one

Following the general procedure described in *J. Org. Chem.* 1976, 41, 2628, from 2-bromo-3-chloro-benzoic acid (the preparation of which is described in *J. Org. Chem.* 203, 68, 2030) and 1-benzyl-piperidin-4-one was prepared 7-chloro-3H-spiro[2-benzofuran-1,4'-piperidin]-3-one, after debenzylation (Pd/C, H$_2$, MeOH/HCl), as a white solid. ES-MS m/e (%): 238.7 (M+H$^+$).

Example of Compounds of Formula (I-g)

Example 15

(SS,RR)-1'-[(1-benzyl-2-methyl-1H-indol-3-yl)carbonyl]-3',5'-dimethyl-3H-spiro[2-benzofuran-1,4'-piperidin]-3-one

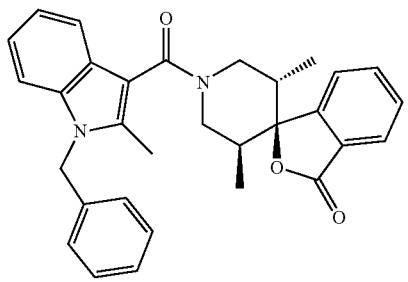

Amide coupling according to general procedure I described hereinabove:
Amine: (SS,RR)-3',5'-dimethyl-3H-spiro[2-benzofuran-1,4'-piperidin]-3-one prepared as described in WO9929696,
Acid: 1-Benzyl-2-methyl-1H-indole-3-carboxylic acid (described in example 1),
ES-MS m/e (%): 479.6 (M+H$^+$).

Examples of Compounds of Formula (I-c)

Example 16

1'-[(6-chloro-1H-indol-3-yl)carbonyl]-3H-spiro[2-benzofuran-1,4'-piperidin]-3-one

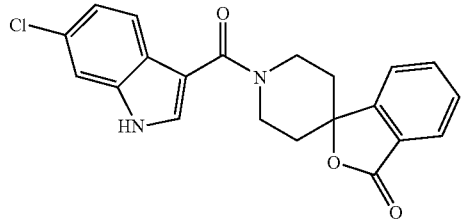

Amide coupling according to general procedure I described hereinabove:
Amine: 3H-spiro[2-benzofuran-1,4'-piperidin]-3-one prepared as described in *J. Org. Chem,* 1976, 41, 2628,
Acid: 6-chloro-1H-indole-3-carboxylic acid (described in example 5),
ES-MS m/e (%): 381.4 (M+H$^+$).

Example 17

1'-[(6-chloro-1H-indol-3-yl)carbonyl]-6-methoxy-3H-spiro[2-benzofuran-1,4'-piperidin]-3-one

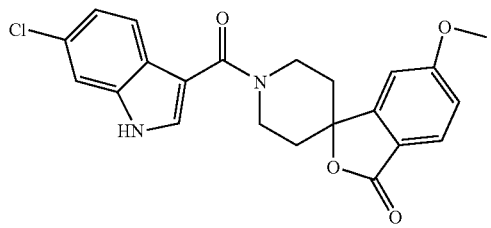

Amide coupling according to general procedure I described hereinabove:
Amine: 6-methoxy-3H-spiro[2-benzofuran-1,4'-piperidin]-3-one prepared as described in EP722941,
Acid: 6-chloro-1H-indole-3-carboxylic acid (described in example 5),
ES-MS m/e (%): 411.4 (M+H$^+$).

Example of Compounds of Formula (I-g)

Example 18

(RS,SR)-1'-[(6-chloro-1H-indol-3-yl)carbonyl]-3',5'-dimethyl-3H-spiro[2-benzofuran-1,4'-piperidin]-3-one

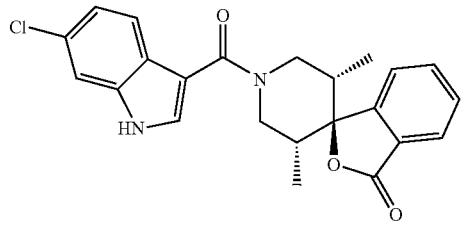

Amide coupling according to general procedure I described hereinabove:
Amine: (1r,3'R,5'S)-3',5'-dimethyl-3H-spiro[2-benzofuran-1,4'-piperidin]-3-one prepared as described in WO9929696;
Acid: 6-chloro-1H-indole-3-carboxylic acid (described in example 5),
ES-MS m/e (%): 409.4 (M+H$^+$).

Examples of Compounds of Formula (I-c)

Example 19

1'-[(6-chloro-1H-indol-3-yl)carbonyl]-5-fluoro-3H-spiro[2-benzofuran-1,4'-piperidin]-3-one

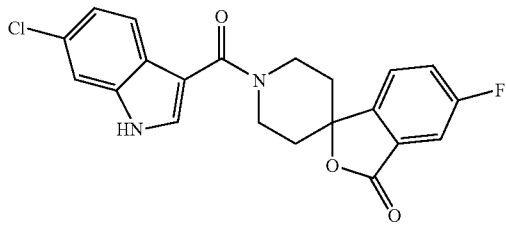

Amide coupling according to general procedure I described hereinabove:
Amine: 5-fluoro-3H-spiro[2-benzofuran-1,4'-piperidin]-3-one prepared as described in WO2001014376,
Acid: 6-chloro-1H-indole-3-carboxylic acid (described in example 5),
ES-MS m/e (%): 399.4 (M+H$^+$).

Example 20

6-chloro-1'-[(6-chloro-1H-indol-3-yl)carbonyl]-3H-spiro[2-benzofuran-1,4'-piperidin]-3-one

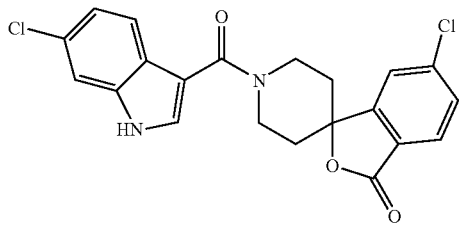

Amide coupling according to general procedure I described hereinabove:
Amine: 6-chloro-3H-spiro[2-benzofuran-1,4'-piperidin]-3-one prepared as described in EP722941,
Acid: 6-chloro-1H-indole-3-carboxylic acid (described in example 88),
ES-MS m/e (%): 415.3 (M$^+$).

Example of Compounds of Formula (I-g)

Example 21

(RS,SR)-1'-[(1-benzyl-2-methyl-1H-indol-3-yl)carbonyl]-3',5'-dimethyl-3H-spiro[2-benzofuran-1,4'-piperidin]-3-one

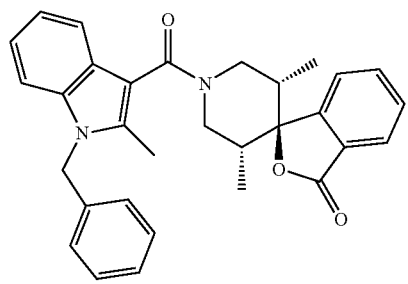

Amide coupling according to general procedure I described hereinabove:
Amine: (1r,3'R,5'S)-3',5'-dimethyl-3H-spiro[2-benzofuran-1,4'-piperidin]-3-one prepared as described in WO9929696,
Acid: 1-Benzyl-2-methyl-1H-indole-3-carboxylic acid (described in example 1),
ES-MS m/e (%): 479.6 (M+H$^+$).

Examples of Compounds of Formula (I-c)

Example 22

1'-[(1-benzyl-2-methyl-1H-indol-3-yl)carbonyl]-3H-spiro[2-benzofuran-1,4'-piperidin]-3-one

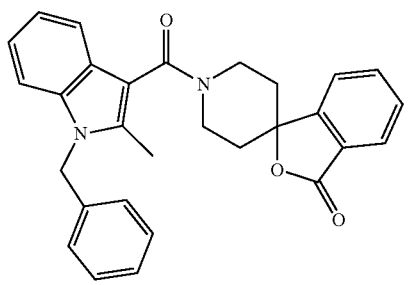

Amide coupling according to general procedure I described hereinabove:
Amine: 3H-spiro[2-benzofuran-1,4'-piperidin]-3-one prepared as described in *J. Org. Chem.* 1976, 41, 2628,
Acid: 1-Benzyl-2-methyl-1H-indole-3-carboxylic acid (described in example 1),
ES-MS m/e (%): 451.6 (M+H$^+$).

Example 23

1'-[(1-benzyl-2-methyl-1H-indol-3-yl)carbonyl]-5-fluoro-3H-spiro[2-benzofuran-1,4'-piperidin]-3-one

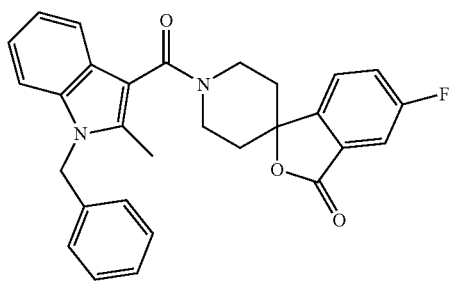

Amide coupling according to general procedure I described hereinabove:
Amine: 5-fluoro-3H-spiro[2-benzofuran-1,4'-piperidin]-3-one prepared as described in WO2001014376,
Acid: 1-Benzyl-2-methyl-1H-indole-3-carboxylic acid (described in example 1),
ES-MS m/e (%): 469.6 (M+H$^+$).

Example 24

1'-({6-chloro-2-[(4-methylpiperidin-1-yl)carbonyl]-1H-indol-3-yl}carbonyl)-5-fluoro-3H-spiro[2-benzofuran-1,4'-piperidin]-3-one

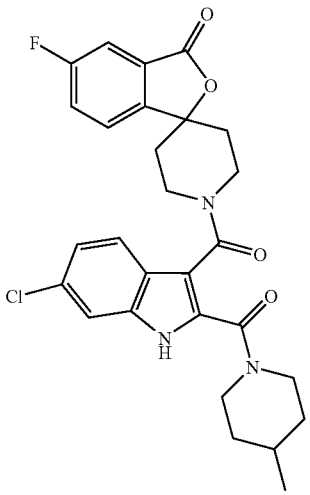

a) 6-Chloro-3-formyl-1H-indole-2-carboxylic acid ethyl ester

To a stirred solution of 2.36 g (0.011 mol) of 6-chloro-1H-indole-2-carboxylic acid ethyl ester in DMF (20 ml) was added phosphorus oxychloride (1.08 ml, 0.012 mol) at RT. The solution was heated at 60° C. for 2 hours, then cooled to RT, and poured into water. The ph was adjusted to 7 by careful addition of aq. NaOH 2N. The resulting brown precipitate was collected by filtration and dried over night in a vacuum oven (50° C.). The title compound was obtained as light brown solid, 2.05 g (77%).

b) 6-Chloro-1H-indole-2,3-dicarboxylic acid 2-ethyl ester

To a solution of 0.104 g (0.413 mmol) of 6-Chloro-3-formyl-1H-indole-2-carboxylic acid ethyl ester in a mixture of tert-butanol (10 ml) and $H_2O$ (5 ml), was added 2-methyl-2-butene (2 ml) followed by a solution of $NaClO_2$ (0.344 g, 3.80 mmol) and $NaH_2PO_4$ (0.399 g, 2.90 mmol) in water (2 ml). The mixture was stirred overnight at RT. The organic solvents were removed, and then the aqueous solution diluted with water, and washed twice with hexane. The ph of the aqueous phase was adjusted to 3 by addition of aq. HCl 1N, and the product extracted with EtOAc. The combined organic phases were dried over $Na_2SO_4$ and concentrated in vacuo to afford 15 mg (14%) of 6-chloro-1H-indole-2,3-dicarboxylic acid 2-ethyl ester as a light yellow solid.

c) 1H-indole-2-carboxylic acid, 6-chloro-3-[(5-fluoro-3-oxospiro[isobenzofuran-1(3H),4'-piperidin]-1'-yl)carbonyl]-ethyl ester Amide coupling according to general procedure I described hereinabove:
  Amine: 5-fluoro-3H-spiro[2-benzofuran-1,4'-piperidin]-3-one prepared as described in WO2001014376,
  Acid: 6-chloro-1H-indole-2,3-dicarboxylic acid 2-ethyl Ester (the preparation of which is described hereinafter), d) 6-chloro-3-[(5-fluoro-3-oxo-1'H,3H-spiro[2-benzofuran-1,4'-piperidin]-1'-yl)carbonyl]-1H-indole-2-carboxylic acid To a solution of 1.89 g (4.02 mmol) of 1H-indole-2-carboxylic acid, 6-chloro-3-[(5-fluoro-3-oxospiro[isobenzofuran-1(3H), 4'-piperidin]-1'-yl)carbonyl]-, ethyl ester in EtOH (150 ml), was added an aqueous solution of LiOH (7.8 ml, 1M). The resulting white suspension was stirred at 80° C. overnight, cooled to RT, and then poured in 500 ml aq. HCl (1N). The product was extracted with 3 times 500 ml of $CH_2Cl_2$, and the combined organic phases were dried over $Na_2SO_4$ and concentrated in vacuo to afford 1.42 g (72%) of 6-chloro-3-[(5-fluoro-3-oxo-1'H,3H-spiro[2-benzofuran-1, 4'-piperidin]-1'-yl)carbonyl]-1H-indole-2-carboxylic acid as a white solid.

e) 1'-({6-chloro-2-[(4-methylpiperidin-1-yl)carbonyl]-1H-indol-3-yl}carbonyl)-5-fluoro-3H-spiro[2-benzofuran-1,4'-piperidin]-3-one Amide coupling according to general procedure IV described hereinabove:
  Amine: commercially available 4-methyl-piperidine,
  Acid: 6-chloro-3-[(5-fluoro-3-oxo-1'H,3H-spiro[2-benzofuran-1,4'-piperidin]-1'-yl)carbonyl]-1H-indole-2-carboxylic acid (described in step d hereinabove),
  ES-MS m/e (%): 525 (M+H$^+$)

Example 25

6-chloro-3-[(5-fluoro-3-oxo-1'H,3H-spiro[2-benzofuran-1,4'-piperidin]-1'-yl)carbonyl]-1H-indole-2-carboxamide

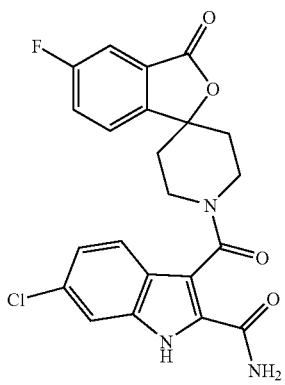

Amide coupling according to general procedure IV described hereinabove:
  Amine: commercial available ammonium hydroxide,
  Acid: 6-chloro-3-[(5-fluoro-3-oxo-1'H,3H-spiro[2-benzofuran-1,4'-piperidin]-1'-yl)carbonyl]-1H-indole-2-carboxylic acid (described in example 24),
  ES-MS m/e (%): 442 (M+H$^+$).

Example 26

6-chloro-N-[2-(dimethylamino)ethyl]-3-[(5-fluoro-3-oxo-1'H,3H-spiro[2-benzofuran-1,4'-piperidin]-1'-yl)carbonyl]-1H-indole-2-carboxamide

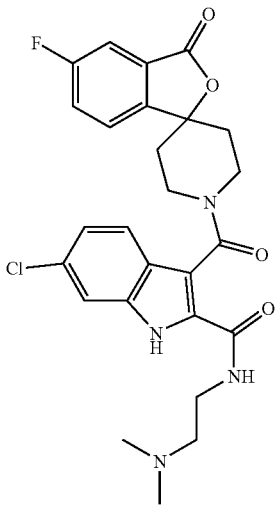

Amide coupling according to general procedure IV described hereinabove:
Amine: commercially available N1,N1-dimethyl-ethane-1,2-diamine,
Acid: 6-chloro-3-[(5-fluoro-3-oxo-1'H,3H-spiro[2-benzofuran-1,4'-piperidin]-1'-yl)carbonyl]-1H-indole-2-carboxylic acid (described in example 24),
ES-MS m/e (%): 513 (M+H$^+$).

Example 27

1'-{[6-chloro-2-(piperazin-1-ylcarbonyl)-1H-indol-3-yl]carbonyl}-5-fluoro-3H-spiro[2-benzofuran-1,4'-piperidin]-3-one

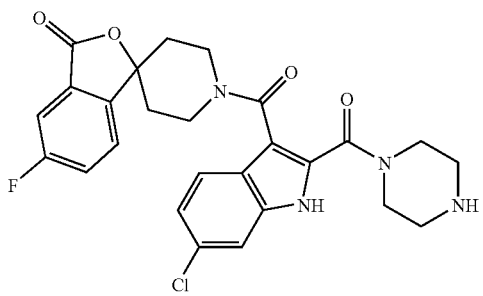

Amide coupling according to general procedure IV described hereinabove:
Amine: commercially available piperazine,
Acid: 6-chloro-3-[(5-fluoro-3-oxo-1'H,3H-spiro[2-benzofuran-1,4'-piperidin]-1'-yl)carbonyl]-1H-indole-2-carboxylic acid (described in example 24),
ES-MS m/e (%): 511 (M+H$^+$).

Example 28

1'-{[6-chloro-2-(morpholin-4-ylcarbonyl)-1H-indol-3-yl]carbonyl}-5-fluoro-3H-spiro[2-benzofuran-1,4'-piperidin]-3-one

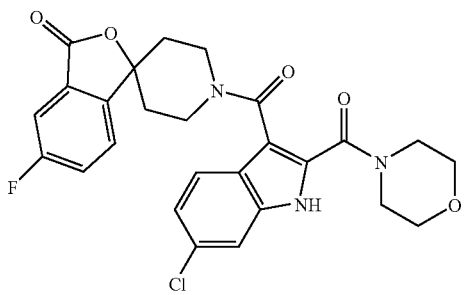

Amide coupling according to general procedure IV described hereinabove:
Amine: commercially available morpholine,
Acid: 6-chloro-3-[(5-fluoro-3-oxo-1'H,3H-spiro[2-benzofuran-1,4'-piperidin]-1'-yl)carbonyl]-1H-indole-2-carboxylic acid (described in example 24),
ES-MS m/e (%): 512 (M+H$^+$).

Example 29

6-chloro-3-[(5-fluoro-3-oxo-1'H,3H-spiro[2-benzofuran-1,4'-piperidin]-1'-yl)carbonyl]-N,N-dimethyl-1H-indole-2-carboxamide

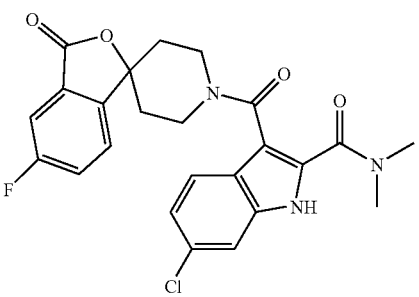

Amide coupling according to general procedure IV described hereinabove:
Amine: commercially available dimethylamine,
Acid: 6-chloro-3-[(5-fluoro-3-oxo-1'H, 3H-spiro[2-benzofuran-1,4'-piperidin]-1'-yl)carbonyl]-1H-indole-2-carboxylic acid (described in example 24),
ES-MS m/e (%): 471 (M+H$^+$).

Example 30 tert-butyl {2-[({6-chloro-3-[(5-fluoro-3-oxo-1'H,3H-spiro[2-benzofuran-1,4'-piperidin]-1'-yl)carbonyl]-1H-indol-2-yl}carbonyl)amino]ethyl}methylcarbamate

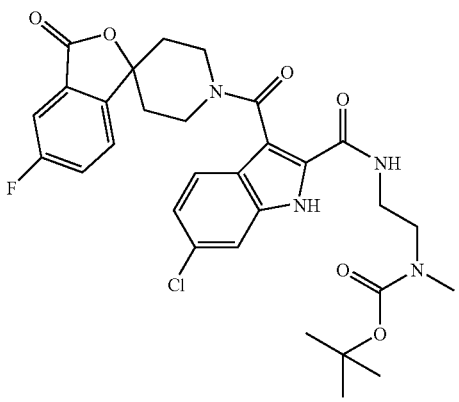

Amide coupling according to general procedure IV described hereinabove:
Amine: commercially available (2-Amino-ethyl)-methyl-carbamic acid tert-butyl ester,
Acid: 6-chloro-3-[(5-fluoro-3-oxo-1'H,3H-spiro[2-benzofuran-1,4'-piperidin]-1'-yl)carbonyl]-1H-indole-2-carboxylic acid (described in example 24),
ES-MS m/e (%): 599 (M+H$^+$).

Example 31

6-chloro-N,N-diethyl-3-[(5-fluoro-3-oxo-1'H,3H-spiro[2-benzofuran-1,4'-piperidin]-1'-yl)carbonyl]-1H-indole-2-carboxamide

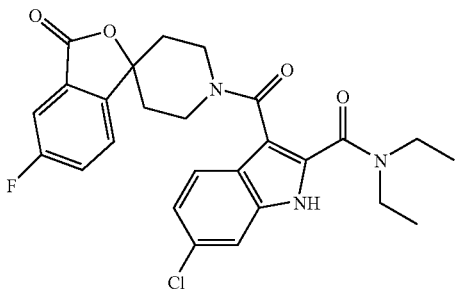

Amide coupling according to general procedure IV described hereinabove:
Amine: commercially available diethyl-amine,
Acid: 6-chloro-3-[(5-fluoro-3-oxo-1'H,3H-spiro[2-benzofuran-1,4'-piperidin]-1'-yl)carbonyl]-1H-indole-2-carboxylic acid (described in example 24),
ES-MS m/e (%): 498 (M+H$^+$).

Example 32

1'-({6-chloro-2-[(4-methylpiperazin-1-yl)carbonyl]-1H-indol-3-yl}carbonyl)-5-fluoro-3H-spiro[2-benzofuran-1,4'-piperidin]-3-one

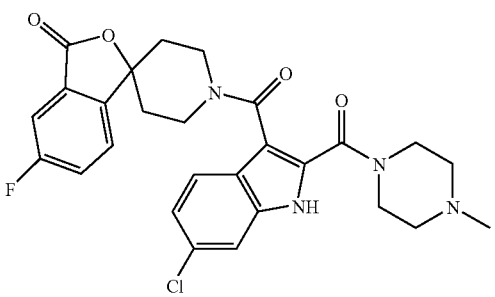

Amide coupling according to general procedure IV described hereinabove:
Amine: commercially available 1-methyl-piperazine,
Acid: 6-chloro-3-[(5-fluoro-3-oxo-1'H, 3H-spiro[2-benzofuran-1,4'-piperidin]-1'-yl)carbonyl]-1H-indole-2-carboxylic acid (described in example 24),
ES-MS m/e (%): 524 (M+H$^+$).

Example 33

1'-{[6-chloro-2-(piperidin-1-ylcarbonyl)-1H-indol-3-yl]carbonyl}-5-fluoro-3H-spiro[2-benzofuran-1,4'-piperidin]-3-one

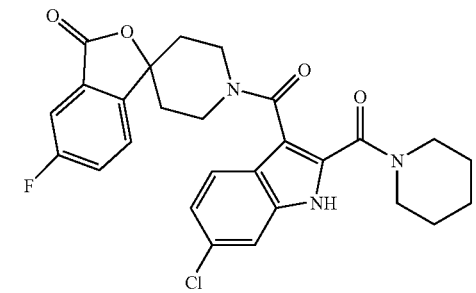

Amide coupling according to general procedure IV described hereinabove:
Amine: commercially available piperidine,
Acid: 6-chloro-3-[(5-fluoro-3-oxo-1'H,3H-spiro[2-benzofuran-1,4'-piperidin]-1'-yl)carbonyl]-1H-indole-2-carboxylic acid (described in example 24),
ES-MS m/e (%): 510 (M+H$^+$).

Example 34

1'-[(1-benzyl-2-methyl-1H-indol-3-yl)carbonyl]-7H-spiro[furo[3,4-f][1,3]benzodioxole-5,4'-piperidin]-7-one

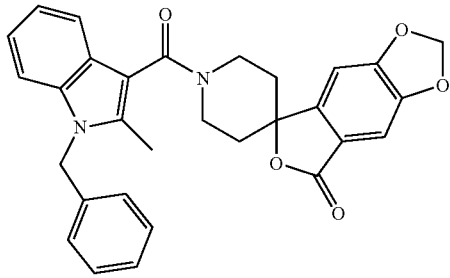

Amide coupling according to general procedure I described hereinabove:
Amine: 7H-spiro[furo[3,4-f][1,3]benzodioxole-5,4'-piperidin]-7-one prepared as described in DE2458176A1,
Acid: 1-Benzyl-2-methyl-1H-indole-3-carboxylic acid (described in example 1),
ES-MS m/e (%): 495 (M+H$^+$).

Example 35

3-{6-chloro-3-[(3-oxo-1'H,3H-spiro[2-benzofuran-1,4'-piperidin]-1'-yl)carbonyl]-1H-indol-1-yl}propanenitrile

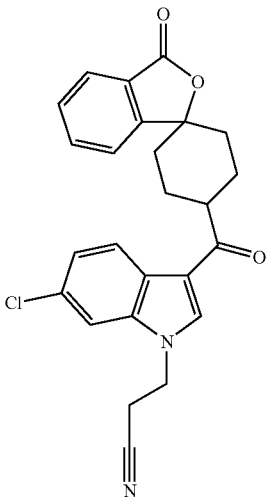

To a stirred solution of 100 mg (0.26 mmol) of 1'-[(6-chloro-1H-indol-3-yl)carbonyl]-3H-spiro[2-benzofuran-1,4'-piperidine]-3-one (the preparation of which has been described in example 16) in 5 ml DMF was added 11.5 mg (0.28 mmol) NaH (60% in oil). The mixture was stirred at RT for 30 min. and then 35 mg (0.26 mmol) of 3-bromopropionitrile was added. The mixture was stirred an additional hour and then poured onto water and extracted with ethyl acetate. The combined organic phases were dried over Na$_2$SO$_4$ and concentrated in vacuo. Flash chromatography (CH$_2$Cl$_2$MeOH, 99:1; SiO$_2$) afforded 48 mg (29%) of 3-{6-chloro-3-[(3-oxo-1'H,3H-spiro[2-benzofuran-1,4'-piperidin]-1'-yl)carbonyl]-1H-indol-1-yl}propanenitrile as a light yellow solid. ES-MS m/e (%): 434(M+H$^+$).

Example 36

4-{6-chloro-3-[(3-oxo-1'H,3H-spiro[2-benzofuran-1,4'-piperidin]-1'-yl)carbonyl]-1H-indol-1-yl}butanenitrile

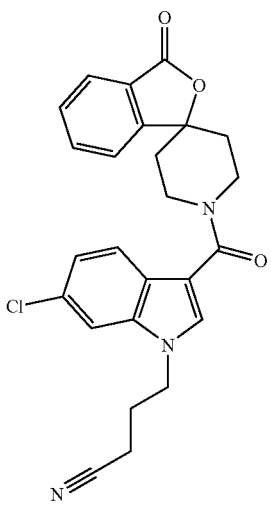

To a stirred solution of 100 mg (0.26 mmol) of 1'-[(6-chloro-1H-indol-3-yl)carbonyl]-3H-spiro[2-benzofuran-1,4'-piperidine]-3-one (the preparation of which has been described in example 16) in 5 ml DMF was added 11.5 mg (0.28 mmol) NaH (60% in oil). The mixture was stirred at RT for 30 min. and then 37 mg (0.26 mmol) of 4-bromobutyronitrile was added. The mixture was stirred overnight and then poured onto water and extracted with ethyl acetate. The combined organic phases were dried over Na$_2$SO$_4$ and concentrated in vacuo. Flash chromatography (CH$_2$Cl$_2$/MeOH, 99:1; SiO$_2$) afforded 69 mg (59%) of 4-{6-chloro-3-[(3-oxo-1'H,3H-spiro[2-benzofuran-1,4'-piperidin]-1'-yl)carbonyl]-1H-indol-1-yl}butanenitrile as a light yellow solid.
ES-MS m/e (%): 448(M+H$^+$).

Example 37

{6-chloro-3-[(3-oxo-1'H,3H-spiro[2-benzofuran-1,4'-piperidin]-1'-yl)carbonyl]-1H-indol-1-yl}acetonitrile

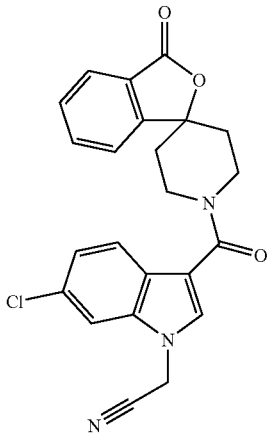

To a stirred solution of 100 mg (0.26 mmol) of 1'-[(6-chloro-1H-indol-3-yl)carbonyl]-3H-spiro[2-benzofuran-1,4'-piperidine]-3-one (the preparation of which has been described in example 16) in 5 ml DMF was added 11.5 mg (0.28 mmol) NaH (60% in oil). The mixture was stirred at RT for 30 min. and then 31 mg (0.26 mmol) of bromoacetonitrile was added. The mixture was stirred overnight and then poured onto water and extracted with ethyl acetate. The combined organic phases were dried over Na$_2$SO$_4$ and concentrated in vacuo. Flash chromatography (EtOAc/Hx, 1:6; SiO$_2$) afforded 58 mg (34%) of {6-chloro-3-[(3-oxo-1'H,3H-spiro[2-benzofuran-1,4'-piperidin]-1'-yl)carbonyl]-1H-indol-1-yl}acetonitrile as a light yellow solid.

ES-MS m/e (%): 420(M+H$^+$).

Example 38

2-{6-chloro-3-[(3-oxo-1'H,3H-spiro[2-benzofuran-1,4'-piperidin]-1'-yl)carbonyl]-1H-indol-1-yl}propanenitrile

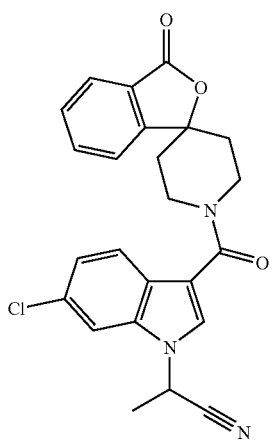

To a stirred solution of 100 mg (0.26 mmol) of 1'-[(6-chloro-1H-indol-3-yl)carbonyl]-3H-spiro[2-benzofuran-1,4'-piperidine]-3-one (the preparation of which has been described in example 16) in 5 ml DMF was added 11.5 mg (0.28 mmol) NaH (60% in oil). The mixture was stirred at RT for 30 min. and then 35 mg (0.26 mmol) of 2-bromopropionitrile was added. The mixture was stirred overnight and then poured onto water and extracted with ethyl acetate. The combined organic phases were dried over Na$_2$SO$_4$ and concentrated in vacuo. Flash chromatography (EtOAc/Hx, 2:1; SiO$_2$) afforded 54 mg (34%) of 2-{6-chloro-3-[(3-oxo-1'H,3H-spiro[2-benzofuran-1,4'-piperidin]-1'-yl) carbonyl]-1H-indol-1-yl}propanenitrile as a light yellow solid.

ES-MS m/e (%): 434(M+H$^+$).

Examples of Compounds of Formula (I-d)

Example 39

1'-[(1-benzyl-2-methyl-1H-indol-3-yl)carbonyl]-3H-spiro[2-benzofuran-1,4'-piperidine]

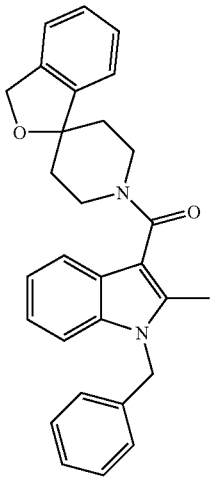

Amide coupling according to general procedure I described hereinabove:
- Amine: spiro[isobenzofuran-1(3H), 4'-piperidine] pepared as described in *J. Org. Chem.* 1976, 41, 2628,
- Acid: 1-Benzyl-2-methyl-1H-indole-3-carboxylic acid (described in example 1).
- ES-MS m/e (%): 437.5 (M+H$^+$).

Example 40

1'-[(1-benzyl-2-methyl-1H-indol-3-yl)carbonyl]-6-chloro-3H-spiro[2-benzofuran-1,4'-piperidine]

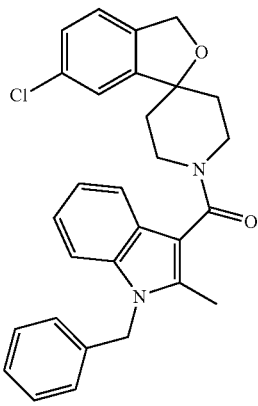

Amide coupling according to general procedure I described hereinabove:
- Amine: 6-chloro-3H-spiro[2-benzofuran-1,4'-piperidine] prepared as described in WO2004004714,
- Acid: 1-Benzyl-2-methyl-1H-indole-3-carboxylic acid (described in example 1)
- ES-MS m/e (%): 471.3 (M+H$^+$).

Example 41

1'-[(1-benzyl-2-methyl-1H-indol-3-yl)carbonyl]-3-phenyl-3H-spiro[2-benzofuran-1,4'-piperidine]

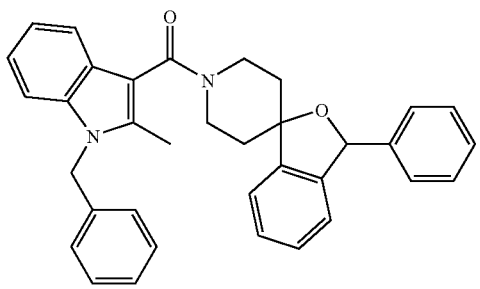

Amide coupling according to general procedure I described hereinabove:
Amine: 3-phenyl-3H-spiro[2-benzofuran-1,4'-piperidine] prepared as described in *J. Med. Chem.* 1976, 19, 1315,
Acid: 1-Benzyl-2-methyl-1H-indole-3-carboxylic acid (described in example 1)
ES-MS m/e (%): 513.6 (M+H$^+$).

Example 42

1'-[(1-benzyl-5-methoxy-2-methyl-1H-indol-3-yl)carbonyl]-3H-spiro[2-benzofuran-1,4'-piperidine]

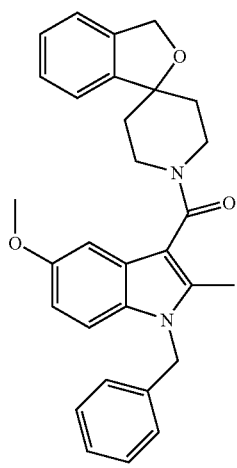

Amide coupling according to general procedure I described hereinabove:
Amine: spiro[isobenzofuran-1(3H), 4'-piperidine] prepared as described in *J. Org. Chem.* 1976, 41, 2628,
Acid: 1-benzyl-5-methoxy-2-methyl-1H-indole-3-carboxylic acid (commercially available),
ES-MS m/e (%): 467.4 (M+H$^+$).

Example 43

1'-[(2-methyl-1H-indol-3-yl)carbonyl]-3H-spiro[2-benzofuran-1,4'-piperidine]

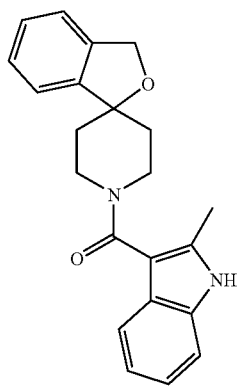

Amide coupling according to general procedure I described hereinabove:
Amine: spiro[isobenzofuran-1(3H), 4'-piperidine] prepared as described in *J. Org. Chem.* 1976, 41, 2628,
Acid: 2-Methyl-1H-indole-3-carboxylic acid (described in *J. Heterocyclic Chem.* 1977, 14, 1123),
ES-MS m/e (%): 347.3 (M+H$^+$).

Example 44

1'-[(1-benzoyl-2-methyl-1H-indol-3-yl)carbonyl]-3H-spiro[2-benzofuran-1,4'-piperidine]

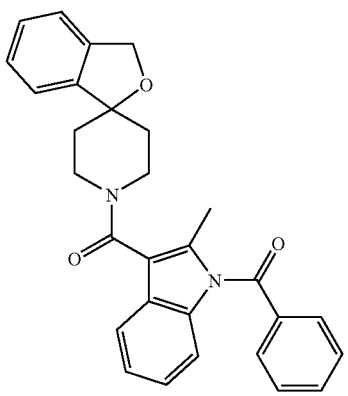

To a stirred solution of 40 mg (0.11 mmol) of 1'-[(2-methyl-1H-indol-3-yl)carbonyl]-3H-spiro[2-benzofuran-1,4'-piperidine] (the preparation of which has been described in example 43) in 3 ml DMF was added 5 mg (0.11 mmol) NaH (60% in oil). The mixture was stirred at RT for 30 min. and then 19 mg (0.13 mmol) of benzoyl chloride was added. The mixture was stirred an additional hour and then poured onto water and extracted with ethyl acetate. The combined organic phases were dried over Na$_2$SO$_4$ and concentrated in vacuo. Re-crystallization in Et$_2$O afforded 51 mg (98%) of 1'-[(1-benzoyl-2-methyl-1H-indol-3-yl)carbonyl]-3H-spiro[2-benzofuran-1,4'-piperidine] as white crystals.
ES-MS m/e (%): 451.3 (M+H$^+$).

Example 45

1'-{[2-methyl-1-(phenylsulfonyl)-1H-indol-3-yl]carbonyl}-3H-spiro[2-benzofuran-1,4'-piperidine]

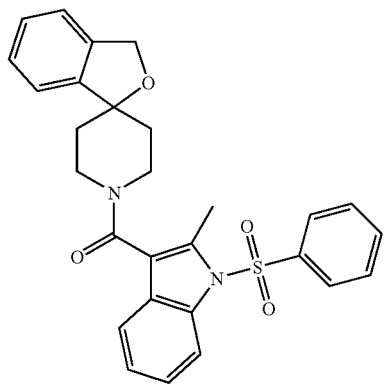

To a stirred solution of 40 mg (0.11 mmol) of 1'-[(2-methyl-1H-indol-3-yl)carbonyl]-3H-spiro[2-benzofuran-1, 4'-piperidine] (the preparation of which has been described in example 43) in 3 ml DMF was added 5 mg (0.11 mmol) NaH (60% in oil). The mixture was stirred at RT for 30 min. and then 24 mg (0.14 mmol) of benzenesulfonyl chloride was added. The mixture was stirred an additional hour and then poured onto water and extracted with ethyl acetate. The combined organic phases were dried over $Na_2SO_4$ and concentrated in vacuo. Re-crystallization in $Et_2O$ afforded 45 mg (80%) of 1'-{[2-methyl-1-(phenylsulfonyl)-1H-indol-3-yl]carbonyl}-3H-spiro[2-benzofuran-1,4'-piperidine] as white crystals. ES-MS m/e (%): 487.4 (M+H$^+$).

Example 46

1'-{[1-(cyclohexylmethyl)-2-methyl-1H-indol-3-yl]carbonyl}-3H-spiro[2-benzofuran-1,4'-piperidine]

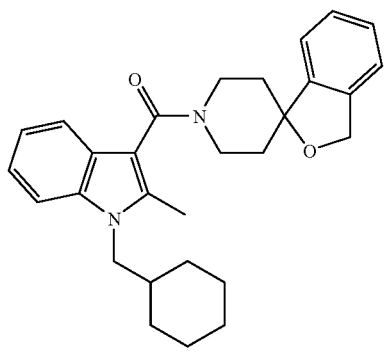

Following the general procedure II described hereinabove above with bromomethyl-cyclohexane as electrophile; the title compound was obtained as white solid.
ES-MS m/e (%): 443.5 (M+H$^+$).

Example 47

1'-{[1-(3-fluorobenzyl)-2-methyl-1H-indol-3-yl]carbonyl}-3H-spiro[2-benzofuran-1,4'-piperidine]

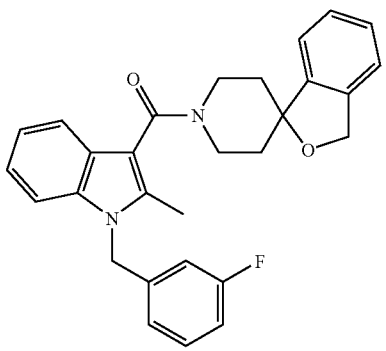

Following the general procedure II described hereinabove with 1-bromomethyl-3-fluoro-benzene as electrophile; the title compound was obtained as white solid.
ES-MS m/e (%): 455.4 (M+H$^+$).

Example 48

1'-({2-methyl-1-[2-(trifluoromethoxy)benzyl]-1H-indol-3-yl}carbonyl)-3H-spiro[2-benzofuran-1,4'-piperidine]

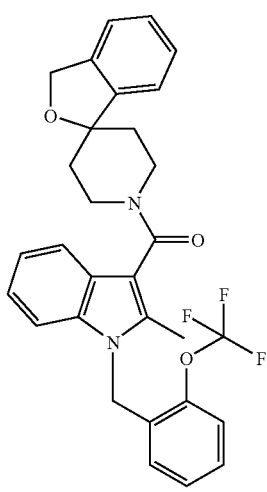

Following the general procedure II described hereinabove with 1-bromomethyl-2-trifluoromethoxy-benzene as electrophile; the title compound was obtained as white solid.
ES-MS m/e (%): 521.4 (M+H$^+$).

Example 49

1'-{[1-(3,5-dimethylbenzyl)-2-methyl-1H-indol-3-yl]carbonyl}-3H-spiro[2-benzofuran-1,4'-piperidine]

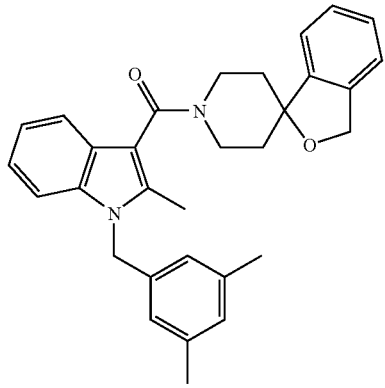

Following the general procedure II described hereinabove with 1-bromomethyl-3,5-dimethyl-benzene as electrophile, the title compound was obtained as white solid.

ES-MS m/e (%): 465.4 (M+H$^+$).

Example 50 methyl 4-{[2-methyl-3-(1'H,3H-spiro[2-benzofuran-1,4'-piperidin]-1'-ylcarbonyl)-1H-indol-1-yl]methyl}benzoate

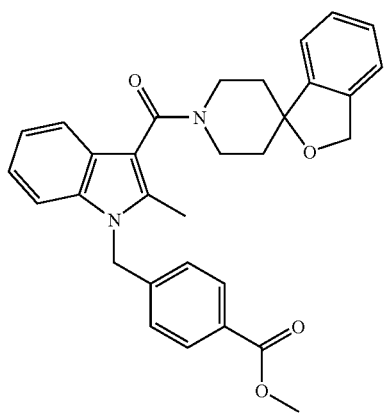

Following the general procedure II described hereinabove with 4-bromomethyl-benzoic acid methyl ester as electrophile; the title compound was obtained as white solid.

ES-MS m/e (%): 495.5 (M+H$^+$).

Example 51

4-{[2-methyl-3-(1'H,3H-spiro[2-benzofuran-1,4'-piperidin]-1'-ylcarbonyl)-1H-indol-1-yl]methyl}benzonitrile

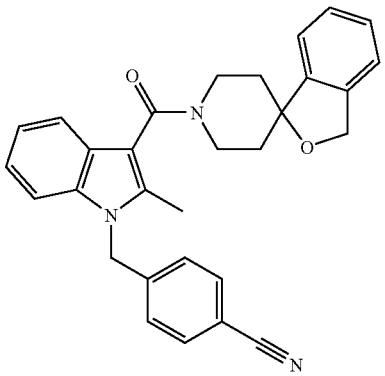

Following the general procedure II described hereinabove with 4-bromomethyl-benzonitrile as electrophile; the title compound was obtained as white solid.

ES-MS m/e (%): 462.4 (M+H$^+$).

Example 52

1'-[{(1-(3,5-difluorobenzyl)-2-methyl-1H-indol-3-yl]carbonyl}-3H-spiro[2-benzofuran-1,4'-piperidine]

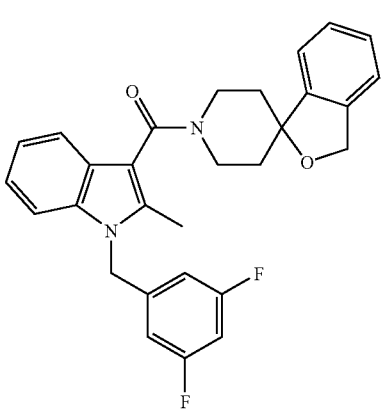

Following the general procedure II described hereinabove with 1-bromomethyl-3,5-difluoro-benzene as electrophile; the title compound was obtained as white solid.

ES-MS m/e (%): 473.4 (M+H$^+$).

Example 53

1'-{[1-(2-chlorobenzyl)-2-methyl-1H-indol-3-yl]carbonyl}-3H-spiro[2-benzofuran-1,4'-piperidine]

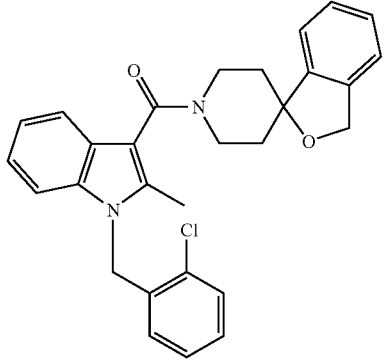

Following the general procedure II described hereinabove with 1-bromomethyl-2-chloro-benzene as electrophile; the title compound was obtained as white solid.

ES-MS m/e (%): 471.3 (M+H$^+$).

Example 54

1'-{[1-(2-methoxybenzyl)-2-methyl-1H-indol-3-yl]carbonyl}-3H-spiro[2-benzofuran-1,4'-piperidine]

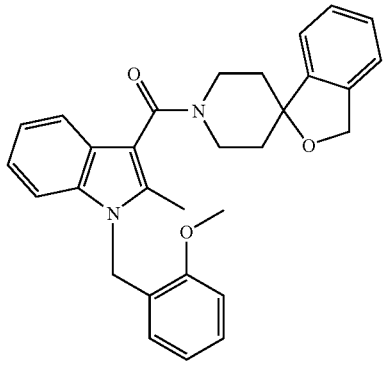

Following the general procedure II described hereinabove with 1-chloromethyl-2-methoxy-benzene as electrophile; the title compound was obtained as white solid.

ES-MS m/e (%): 467.4 (M+H$^+$).

Example 55

1'-{[1-(4-methoxybenzyl)-2-methyl-1H-indol-3-yl]carbonyl}-3H-spiro[2-benzofuran-1,4'-piperidine]

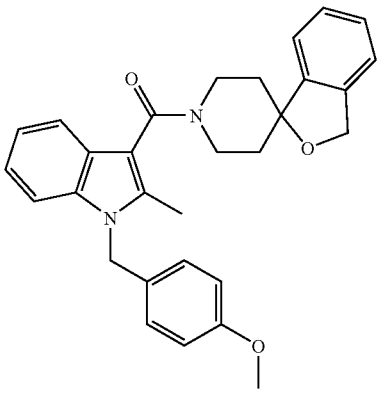

Following the general procedure II described hereinabove with 1-chloromethyl-4-methoxy-benzene as electrophile; the title compound was obtained as white solid.

ES-MS m/e (%): 467.4 (M+H$^+$).

Example 56

1'-[(1-{[2-(4-chlorophenyl)-1,3-thiazol-4-yl]methyl}-2-methyl-1H-indol-3-yl)carbonyl]-3H-spiro[2-benzofuran-1,4'-piperidine]

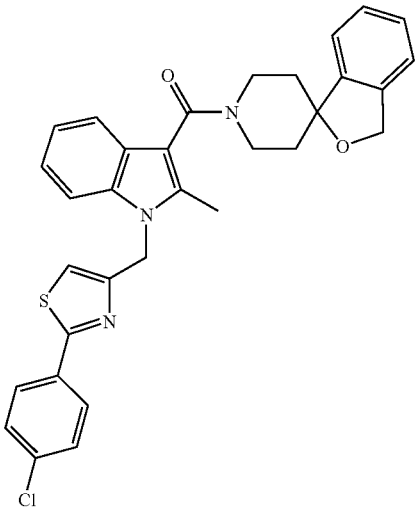

Following the general procedure II described hereinabove with 4-chloromethyl-2-(4-chloro-phenyl)-thiazole (commercially available) as electrophile, the title compound was obtained as a white solid.

ES-MS m/e (%): 554.3.(M+H$^+$).

Example 57

1'-[(1-{[2-(4-chlorophenyl)-1,3-thiazol-4-yl]methyl}-2-methyl-1H-indol-3-yl)carbonyl]-3H-spiro[2-benzofuran-1,4'-piperidine]

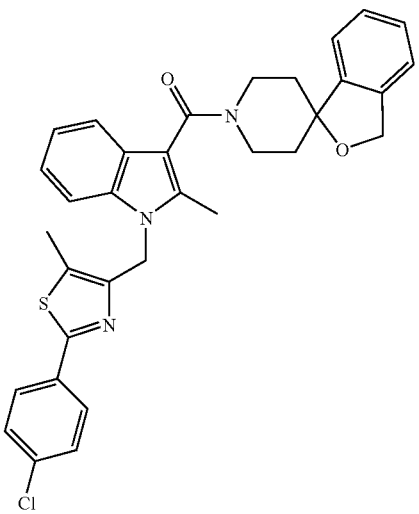

Following the general procedure II described hereinabove with 4-bromomethyl-2-(4-chloro-phenyl)-5-methyl-thiazole (the preparation of which has been described in WO2004020420) as electrophile, the title compound was obtained as a white solid.

ES-MS m/e (%):.568.3 (M+H$^+$).

Example 58

1'-[(1-{[2-(2-methoxyphenyl)-5-methyl-1,3-oxazol-4-yl]methyl}-2-methyl-1H-indol-3-yl)carbonyl]-3H-spiro[2-benzofuran-1,4'-piperidine]

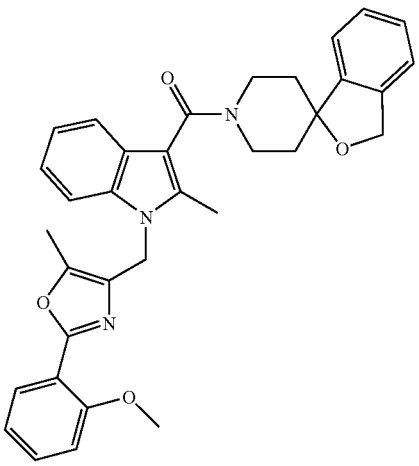

Following the general procedure II described hereinabove with 4-chloromethyl-2-(2-methoxy-phenyl)-5-methyl-oxazole (the preparation of which has been described in WO2002092084 & WO2004031162) as electrophile, the title compound was obtained as a white solid.

ES-MS m/e (%): 548.5 (M+H$^+$).

Example 59

1'-{[2-methyl-1-({5-methyl-2-[3-(trifluoromethyl)phenyl]-1,3-oxazol-4-yl}methyl)-1H-indol-3-yl]carbonyl}-3H-spiro[2-benzofuran-1,4'-piperidine]

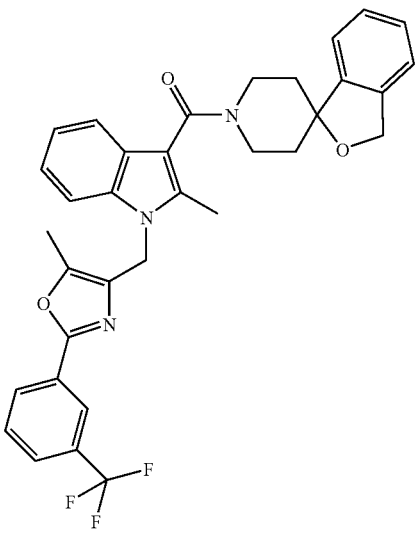

Following the general procedure II described hereinabove with 4-chloromethyl-5-methyl -2-(3-trifluoromethyl-phenyl)-oxazole (the preparation of which has been described in WO2004031162) as electrophile, the title compound was obtained as a white solid.

ES-MS m/e (%):.586.3 (M+H$^+$).

Example 60

1'-[(1-{[2-(2-fluorophenyl)-5-methyl-1,3-oxazol-4-yl]methyl}-2-methyl-1H-indol-3-yl)carbonyl]-3H-spiro[2-benzofuran-1,4'-piperidine]

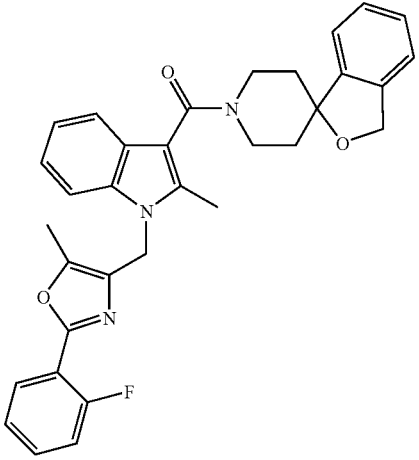

Following the general procedure II described hereinabove with 4-chloromethyl-2-(2-fluoro-phenyl)-5-methyl-oxazole (commercially available) as electrophile, the title compound was obtained as a white solid.

ES-MS m/e (%):.536.4 (M+H$^+$).

Example 61

1'-[(1-{[2-(4-isopropylphenyl)-5-methyl-1,3-oxazol-4-yl]methyl}-2-methyl-1H-indol-3-yl)carbonyl]-3H-spiro[2-benzofuran-1,4'-piperidine]

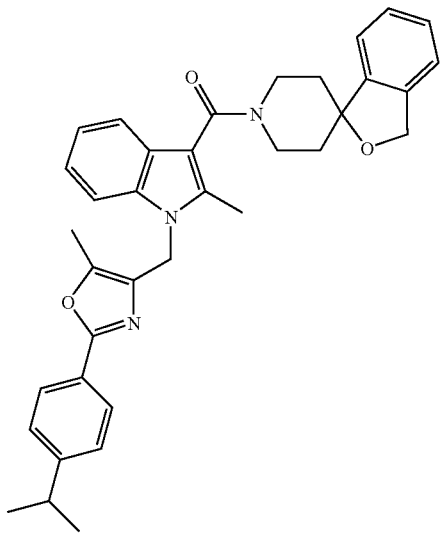

Following the general procedure II described hereinabove with 4-chloromethyl-2-(4-isopropyl-phenyl)-5-methyl-oxazole (the preparation of which has been described in WO2002092084 & WO2004031162) as electrophile, the title compound was obtained as a white solid. ES-MS m/e (%):.560.4 (M+H$^+$).

Example 62

1'-[(1-{[2-(4-ethylphenyl)-5-methyl-1,3-oxazol-4-yl]methyl}-2-methyl-1H-indol-3-yl)carbonyl]-3H-spiro[2-benzofuran-1,4'-piperidine]

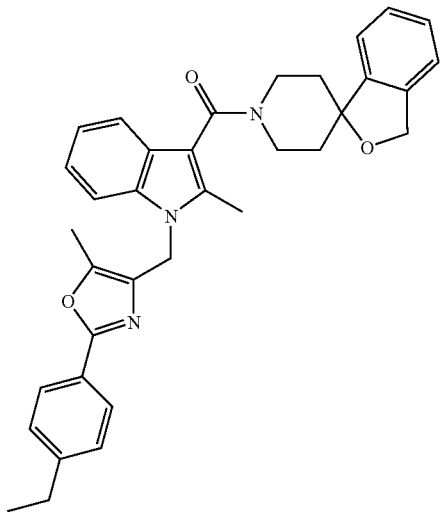

Following the general procedure II described hereinabove with 4-chloromethyl-2-(4-ethyl-phenyl)-5-methyl-oxazole (the preparation of which has been described in WO2002092084) as electrophile, the title compound was obtained as a white solid.

ES-MS m/e (%):.546.4 (M+H$^+$).

Example 63

1'-[(2-methyl-1-{[5-methyl-2-(2-methylphenyl)-1,3-oxazol-4-yl]methyl}-1H-indol-3-yl)carbonyl]-3H-spiro[2-benzofuran-1,4'-piperidine]

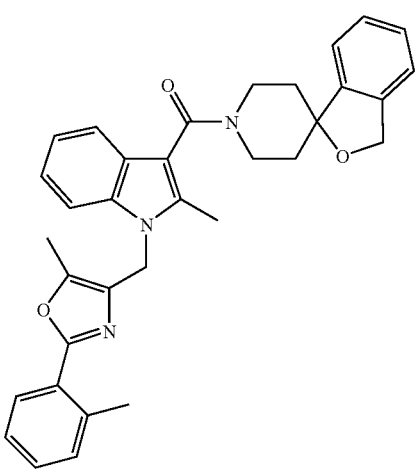

Following the general procedure II described hereinabove with 4-chloromethyl-5-methyl-2-o-tolyl-oxazole (the preparation of which has been described in WO2004031162) as electrophile, the title compound was obtained as a white solid.

ES-MS m/e (%):532.3 (M+H$^+$).

Example 64

1'-{[2-methyl-1-({5-methyl-2-[4-(trifluoromethyl)phenyl]-1,3-oxazol-4-yl}methyl)-1H-indol-3-yl]carbonyl}-3H-spiro[2-benzofuran-1,4'-piperidine]

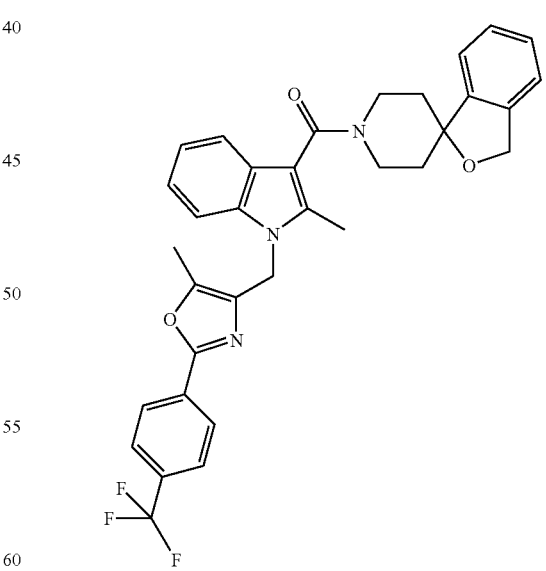

Following the general procedure II described hereinabove with 4-chloromethyl-5-methyl -2-(4-trifluoromethyl-phenyl)-oxazole (the preparation of which has been described in J. Med. Chem. 2000, 43, 995-1010) as electrophile, the title compound was obtained as a white solid.

ES-MS m/e (%):.586.3 (M+H$^+$).

Example 65

1'-{[2-methyl-1-({5-methyl-2-[2-(trifluoromethyl)phenyl]-1,3-oxazol-4-yl}methyl)-1H-indol-3-yl]carbonyl}-3H-spiro[2-benzofuran-1,4'-piperidine]

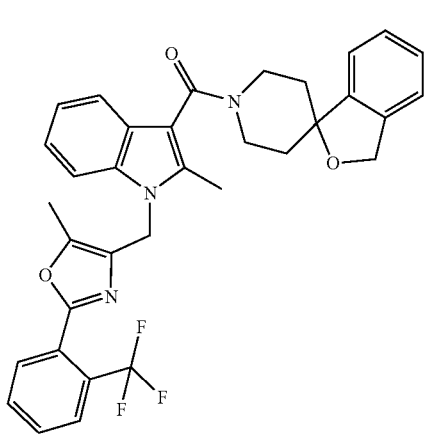

Following the general procedure II described hereinabove with 4-chloromethyl-5-methyl-2-(2-trifluoromethyl-phenyl)-oxazole (the preparation of which has been described in WO2004031162) as electrophile, the title compound was obtained as a white solid.

ES-MS m/e (%):.586.5 (M+H$^+$).

Example 66

1'-[(5-chloro-1H-indol-3-yl)carbonyl]-3H-spiro[2-benzofuran-1,4'-piperidine]

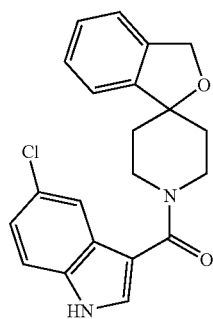

Amide coupling according to general procedure I described hereinabove:
- Amine: spiro[isobenzofuran-1 (3H), 4'-piperidine] prepared as described in *J. Org. Chem.* 1976, 41, 2628,
- Acid: 5-Chloro-1H-indole-3-carboxylic acid (commercially available),
- ES-MS m/e (%):.367.1 (M+H$^+$).

Example 67

1'-[(1-methyl-1H-indol-3-yl)carbonyl]-3H-spiro[2-benzofuran-1,4'-piperidine]

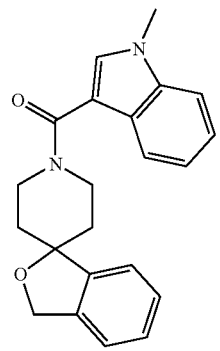

Amide coupling according to general procedure I described hereinabove:
- Amine: spiro[isobenzofuran-1 (3H), 4'-piperidine] prepared as described in *J. Org. Chem.* 1976, 41, 2628,
- Acid: 1-Methyl-1H-indole-3-carboxylic acid (commercially available),
- ES-MS m/e (%): 347.5 (M+H$^+$).

Example 68

1'-[(1-benzyl-1H-indol-3-yl)carbonyl]-3H-spiro[2-benzofuran-1,4'-piperidine]

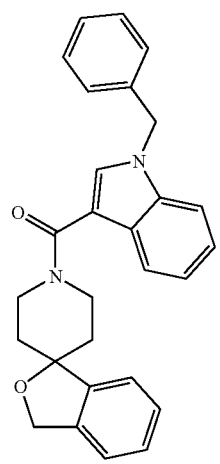

Amide coupling according to general procedure I described hereinabove:
- Amine: spiro[isobenzofuran-1 (3H), 4'-piperidine] prepared as described in *J. Org. Chem.* 1976, 41, 2628,
- Acid: 1-benzyl-1H-indole-3-carboxylic acid (described in example 3),
- ES-MS m/e (%): 423.6 (M+H$^+$).

Example 69

1'-[(6-chloro-1H-indol-3-yl)carbonyl]-3H-spiro[2-benzofuran-1,4'-piperidine]

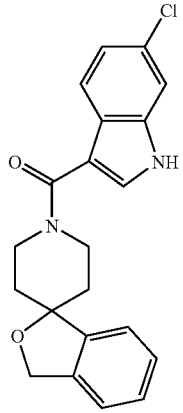

Amide coupling according to general procedure I described hereinabove:
Amine: spiro[isobenzofuran-1 (3H), 4'-piperidine] prepared as described in *J. Org. Chem.* 1976, 41, 2628,
Acid: 6-chloro-1H-indole-3-carboxylic acid (the preparation of which is described hereinafter),
ES-MS m/e (%):.367.2 (M+H$^+$).

6-chloro-1H-indole-3-carboxylic acid

Using a procedure described in *J. Med. Chem.* 1991, 34, 140, from 7.0 g (0.046 mmol) of 6-chloro-1H-indole was prepared 5.80 g (64%) of 6-chloro-1H-indole-3-carboxylic acid as a light brown solid.
ES-MS m/e (%): 194 (M−H$^+$).

Example 70

1'-(1H-indol-3-ylcarbonyl)-3H-spiro[2-benzofuran-1,4'-piperidine]

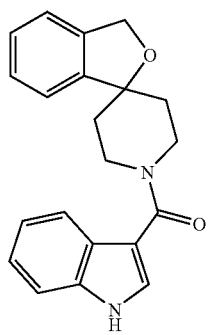

Amide coupling according to general procedure I described hereinabove:
Amine: spiro[isobenzofuran-1(3H), 4'-piperidine] prepared as described in *J. Org. Chem.* 1976, 41, 2628,
Acid: 1H-Indole-3-carboxylic acid (commercially available),
ES-MS m/e (%):.333.3 (M+H$^+$).

Example 71

N,N-dimethyl-2-[3-(1'H,3H-spiro[2-benzofuran-1,4'-piperidin]-1'-ylcarbonyl)-1H-indol-1-yl]ethanamine

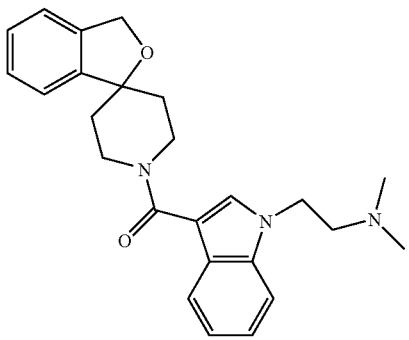

To a stirred solution of 20 mg (0.060 mmol) of 1'-(1H-indol-3-ylcarbonyl)-3H-spiro[2-benzofuran-1,4'-piperidine] (the preparation of which has been described in example 70) in DMF (3 ml) at RT, was added 2.9 mg (0.072 mmol) of NaH (60% in oil). The mixture was stirred 20 min. and then 13 mg (0.072 mmol) of (2-chloro-ethyl)-dimethyl-amine in 1 ml of DMF was added. The mixture was stirred an additional 5 hours at 50° C. and then poured onto water and extracted with ethyl acetate. The combined organic phases were dried over Na$_2$SO$_4$ and concentrated in vacuo. Flash chromatography (CH$_2$Cl$_2$/MeOH 8/2) afforded 11 mg (48%) of N,N-dimethyl-2-[3-(1'H,3H-spiro[2-benzofuran-1,4'-piperidin]-1'-ylcarbonyl)-1H-indol-1-yl]ethanamine as a viscous oil. ES-MS m/e (%): 404.3 (M+H$^+$).

Example 72

2-methyl-1-[3-(1'H,3H-spiro[2-benzofuran-1,4'-piperidin]-1'-ylcarbonyl)-1H-indol-2-yl]butan-1-one

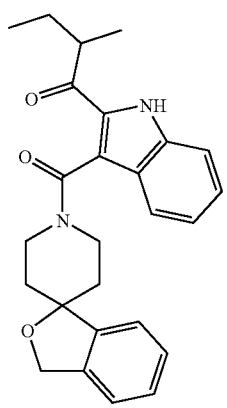

Amide coupling according to general procedure I described hereinabove:
Amine: spiro[isobenzofuran-1(3H), 4'-piperidine] prepared as described in *J. Org. Chem.* 1976, 41, 2628,
Acid: 2-(2-Methyl-butyryl)-1H-indole-3-carboxylic acid (commercially available),
ES-MS m/e (%):.417 (M+H$^+$).

Example 73

2-[6-chloro-3-(1'H,3H-spiro[2-benzofuran-1,4'-piperidin]-1'-ylcarbonyl)-1H-indol-1-yl]propanenitrile

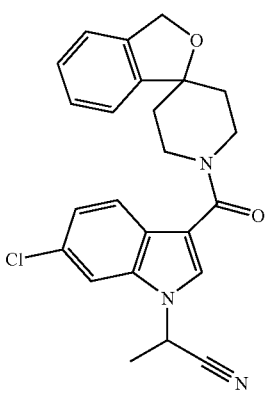

To a stirred solution of 100 mg (0.26 mmol) of 1'-[(6-chloro-1H-indol-3-yl)carbonyl]-3H-spiro[2-benzofuran-1,4'-piperidine] (the preparation of which has been described in example 69) in 5 ml DMF was added 11.5 mg (0.28 mmol) NaH (60% in oil). The mixture was stirred at RT for 30 min. and then 35 mg (0.26 mmol) of 2-bromo-propionitrile was added. The mixture was stirred overnight and then poured onto water and extracted with ethyl acetate. The combined organic phases were dried over Na$_2$SO$_4$ and concentrated in vacuo. Flash chromatography (EtOAc/Hx, 1:1; SiO$_2$) afforded 93 mg (91%) of 2-[6-chloro-3-(1'H,3H-spiro[2-benzofuran-1,4'-piperidin]-1'-ylcarbonyl)-1H-indol-1-yl] propanenitrile as a light yellow solid.

ES-MS m/e (%): 420(M+H$^+$).

Example 74

3-[6-chloro-3-(1'H,3H-spiro[2-benzofuran-1,4'-piperidin]-1'-ylcarbonyl)-1H-indol-1-yl]propanenitrile

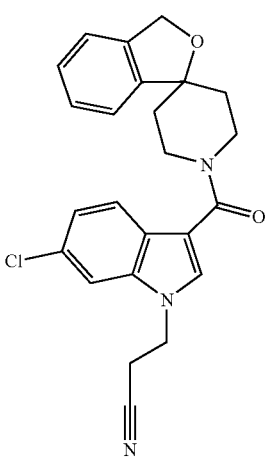

To a stirred solution of 100 mg (0.26 mmol) of 1'-[(6-chloro-1H-indol-3-yl)carbonyl]-3H-spiro[2-benzofuran-1,4'-piperidine] (the preparation of which has been described in example 69) in 5 ml DMF was added 11.5 mg (0.28 mmol) NaH (60% in oil). The mixture was stirred at RT for 30 min. and then 35 mg (0.26 mmol) of 3-bromo-propionitrile was added. The mixture was stirred for two days at RT and then poured onto water and extracted with ethyl acetate. The combined organic phases were dried over Na$_2$SO$_4$ and concentrated in vacuo. Flash chromatography (EtOAc/Hx, 2:1; SiO$_2$) afforded 105 mg (96%) of 3-[6-chloro-3-(1'H,3H-spiro[2-benzofuran-1,4'-piperidin]-1'-ylcarbonyl)-1H-indol-1-yl] propanenitrile as a white solid.

ES-MS m/e (%): 420(M+H$^+$).

Example 75

4-[6-chloro-3-(1'H,3H-spiro[2-benzofuran-1,4'-piperidin]-1'-ylcarbonyl)-1H-indol-1-yl]butanenitrile

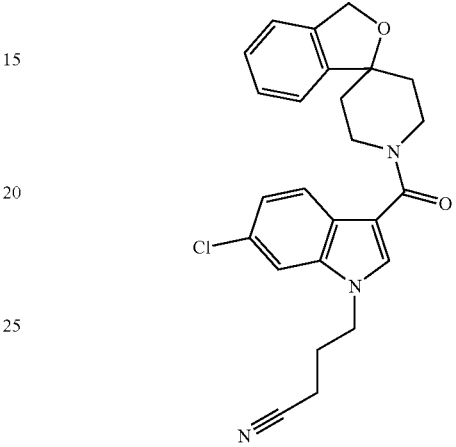

To a stirred solution of 100 mg (0.26 mmol) of 1'-[(6-chloro-1H-indol-3-yl)carbonyl]-3H-spiro[2-benzofuran-1,4'-piperidine] (the preparation of which has been described in example 69) in 5 ml DMF was added 11.5 mg (0.28 mmol) NaH (60% in oil). The mixture was stirred at RT for 30 min. and then 35 mg (0.26 mmol) of 4-bromo-butyronitrile was added. The mixture was stirred for two days at RT and then poured onto water and extracted with ethyl acetate. The combined organic phases were dried over Na$_2$SO$_4$ and concentrated in vacuo. Flash chromatography (EtOAc/Hx, 2:1; SiO$_2$) afforded 99 mg (88%) of 4-[6-chloro-3-(1'H,3H-spiro[2-benzofuran-1,4'-piperidin]-1'-ylcarbonyl)-1H-indol-1-yl]butanenitrile as a white solid.

ES-MS m/e (%): 434(M+H$^+$).

Example 76

[6-chloro-3-(1'H,3H-spiro[2-benzofuran-1,4'-piperidin]-1'-ylcarbonyl)-1H-indol-1-yl]acetonitrile

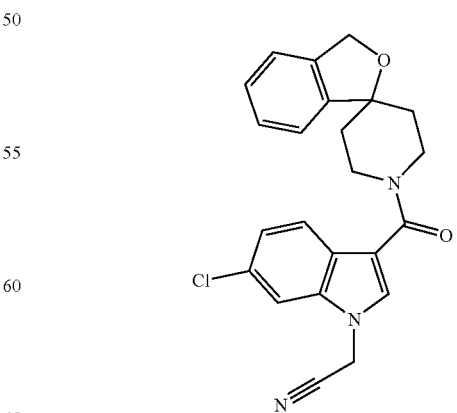

To a stirred solution of 100 mg (0.26 mmol) of 1'-[(6-chloro-1H-indol-3-yl)carbonyl]-3H-spiro[2-benzofuran-1, 4'-piperidine] (the preparation of which has been described in example 69) in 5 ml DMF was added 11.5 mg (0.28 mmol) NaH (60% in oil). The mixture was stirred at RT for 30 min. and then 35 mg (0.26 mmol) of bromo-acetonitrile was added. The mixture was stirred overnight at RT and then poured onto water and extracted with ethyl acetate. The combined organic phases were dried over $Na_2SO_4$ and concentrated in vacuo. Flash chromatography (EtOAc/Hx, 2:1; $SiO_2$) afforded 43 mg (41%) of [6-chloro-3-(1'H,3H-spiro[2-benzofuran-1,4'-piperidin]-1'-ylcarbonyl)-1H-indol-1-yl]acetonitrile as a white solid.

ES-MS m/e (%): 406(M+H$^+$).

Examples of Compounds of Formula (I-e)

Example 77

1'-[(6-chloro-1H-indol-3-yl)carbonyl]spiro[1-benzofuran-3,4'-piperidine]

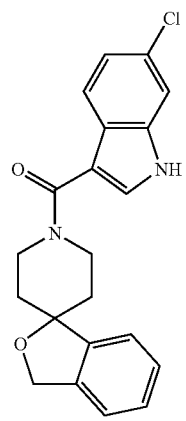

Amide coupling according to general procedure I described hereinabove:
  Amine: commercially available spiro[1-benzofuran-3,4'-piperidine],
  Acid: 6-chloro-1H-indole-3-carboxylic acid (described in example 5),
  ES-MS m/e (%): 367.4 (M+H$^+$).

Example 78

1'-[(1-benzyl-2-methyl-1H-indol-3-yl)carbonyl]spiro[1-benzofuran-3,4'-piperidine]

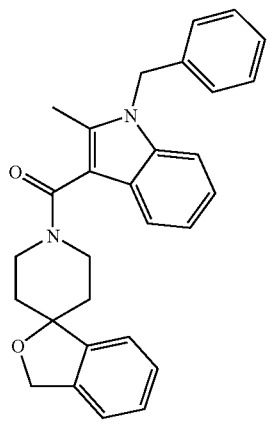

Amide coupling according to general procedure I described hereinabove:
  Amine: commercially available spiro[1-benzofuran-3,4'-piperidine],
  Acid: 1-Benzyl-2-methyl-1H-indole-3-carboxylic acid (described in example 1),
  ES-MS m/e (%): 437.6 (M+H$^+$).

Example 79

1'-(1H-indol-3-ylcarbonyl)spiro[1-benzofuran-3,4'-piperidine]

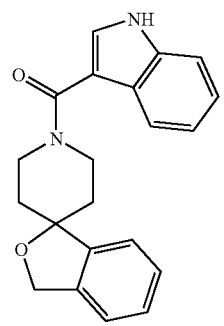

Amide coupling according to general procedure I described hereinabove:
  Amine: commercially available spiro[1-benzofuran-3,4'-piperidine],
  Acid: 1H-Indole-3-carboxylic acid (commercially available), ES-MS m/e (%): 333.4 (M+H$^+$).

Example 80

1'-[(6-chloro-5-fluoro-1H-indol-3-yl)carbonyl]spiro[1-benzofuran-3,4'-piperidine]

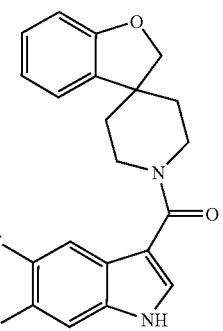

Amide coupling according to general procedure I described hereinabove:
  Amine: commercially available spiro[1-benzofuran-3,4'-piperidine],
  Acid: 6-chloro-5-fluoro-1H-indole-3-carboxylic acid (the preparation of which is described hereinafter), ES-MS m/e (%): 385.1 (M+H$^+$).

a) 6-chloro-5-fluoro-1H-indole

Following the procedure described in WO9747598, from 6-chloro-5-fluoro-1H-indole-2,3-dione was prepared 6-chloro-5-fluoro-1H-indole.

b) 6-chloro-5-fluoro-1H-indole-3-carboxylic acid

Following a procedure described in *J. Med. Chem.* 1991, 34, 140, from 0.25 g (1.47 mmol) of 6-chloro-5-fluoro-1H-indole was prepared 0.35 g (90%) of 6-chloro-5-fluoro-1H-indole-3-carboxylic acid as a light brown solid. ES-MS m/e (%): 213 (M–H$^+$).

Example 81

2-[6-chloro-3-(1'H-spiro[1-benzofuran-3,4'-piperidin]-1'-ylcarbonyl)-1H-indol-1-yl]-N,N-dimethyl-ethanamine

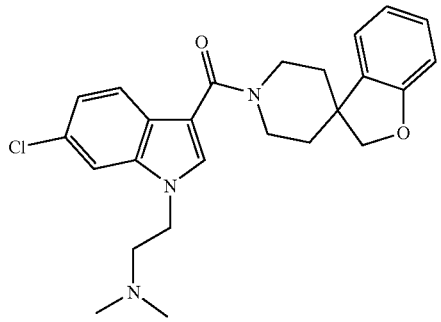

Following the general procedure III as described hereinabove with commercially available (2-chloro-ethyl)-dimethyl-amine as electrophile, the title compound was obtained as colorless viscous oil. ES-MS m/e (%): 438.1 (M+H$^+$).

Example 82

1'-{[6-chloro-1-(2-pyrrolidin-1-ylethyl)-1H-indol-3-yl]carbonyl}spiro[1-benzofuran-3,4'-piperidine]

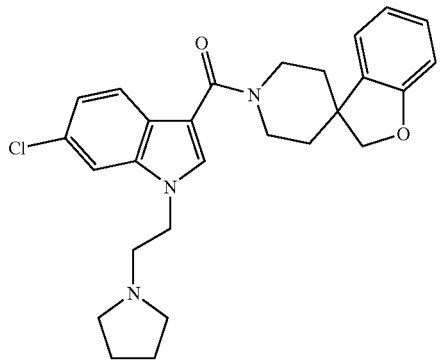

Following the general procedure III as described hereinabove with commercially available 1-(2-chloro-ethyl)-pyrrolidine as electrophile, the title compound was obtained as a colorless viscous oil. ES-MS m/e (%): 464.0 (M+H$^+$).

Example 83

3-[6-chloro-3-(1'H-spiro[1-benzofuran-3,4'-piperidin]-1'-ylcarbonyl)-1H-indol-1-yl]-N,N-dimethyl-propan-1-amine

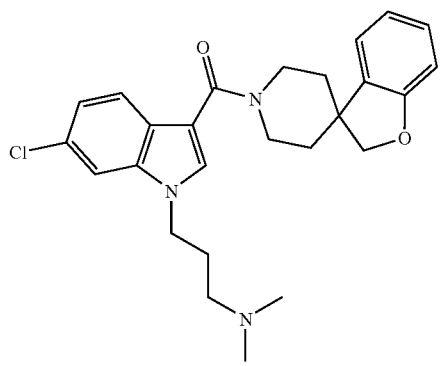

Following the general procedure III as described hereinabove with commercially available (3-chloro-propyl)-dimethyl-amine as electrophile, the title compound was obtained as colorless viscous oil. ES-MS m/e (%): 452.0 (M+H$^+$).

Example 84

1'-{[6-chloro-1-(2-morpholin-4-ylethyl)-1H-indol-3-yl]carbonyl}spiro[1-benzofuran-3,4'-piperidine]

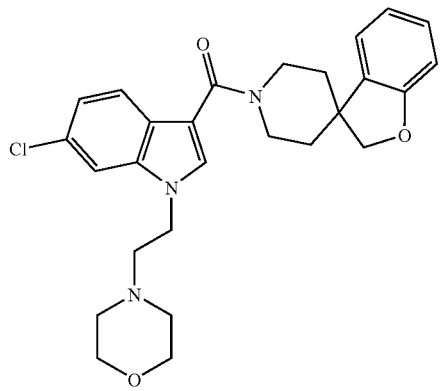

Following the general procedure III as described hereinabove with commercially available 4-(2-chloro-ethyl)-morpholine as electrophile, the title compound was obtained as a colorless viscous oil. ES-MS m/e (%): 480.1 (M+H$^+$).

Example 85

2-[6-chloro-3-(1'H-spiro[1-benzofuran-3,4'-piperidin]-1'-ylcarbonyl)-1H-indol-1-yl]-N,N-diethylethanamine

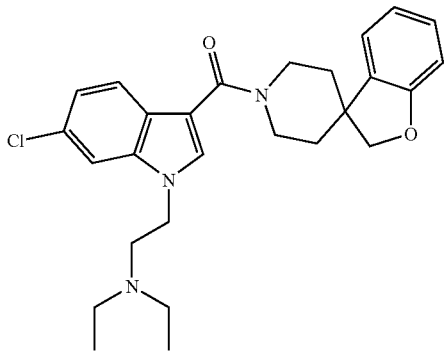

Following the general procedure III as described hereinabove with commercially available (2-bromo-ethyl)-diethylamine as electrophile, the title compound was obtained as colorless viscous oil. ES-MS m/e (%): 466.2 (M+H$^+$).

Example 86

1'-({6-chloro-1-[2-(1H-pyrrol-1-yl)ethyl]-1H-indol-3-yl}carbonyl)spiro[1-benzofuran-3,4'-piperidine]

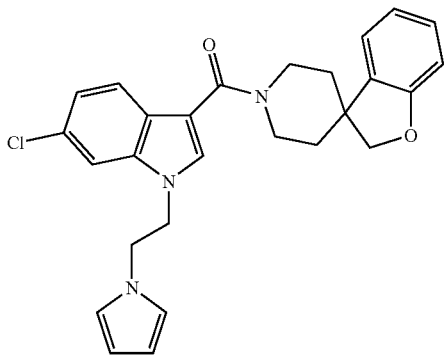

Following the general procedure III as described hereinabove with commercially available 1-(2-chloro-ethyl)-1H-pyrrole as electrophile, the title compound was obtained as a white solid.
ES-MS m/e (%): 460.2 (M+H$^+$).

Example 87

1'-{[6-chloro-1-(2-oxo-2-piperidin-1-ylethyl)-1H-indol-3-yl]carbonyl}spiro[1-benzofuran-3,4'-piperidine]

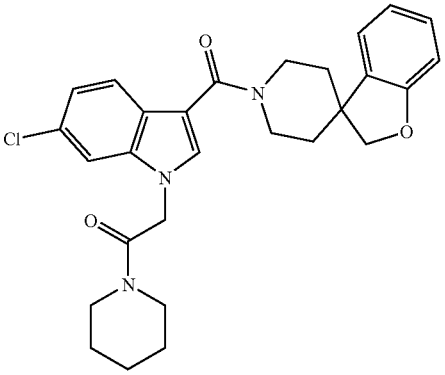

Following the general procedure III as described hereinabove with commercially available 2-chloro-1-piperidin-1-yl-ethanone as electrophile, the title compound was obtained as a white solid. ES-MS m/e (%): 492.2 (M+H$^+$).

Examples of Compounds of Formula (I-b)

Example 88

1'-{[6-Chloro-1-(3-fluorobenzoyl)-1H-indol-3-yl]carbonyl}-3H-spiro[2-benzofuran-1,4'-piperidine

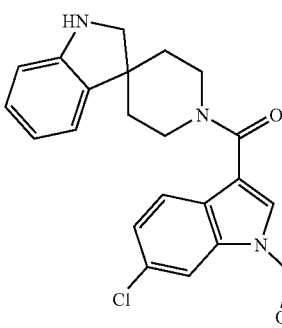

Following the general procedure VII as described above, the acylation of 1'-[(6-chloro-1H-indol-3-yl)carbonyl]-1,2-dihydrospiro[indole-3,4'-piperidine] (prepared according to example 8) with commercially available 3-fluorobenzoyl chloride gave the title compound.
ES-MS m/e (%): 488.5(M+H$^+$).

Example 89

1'-{[6-Chloro-1-(2-fluorobenzoyl)-1H-indol-3-yl]carbonyl}-1,2-dihydrospiro[indole-3,4'-piperidine

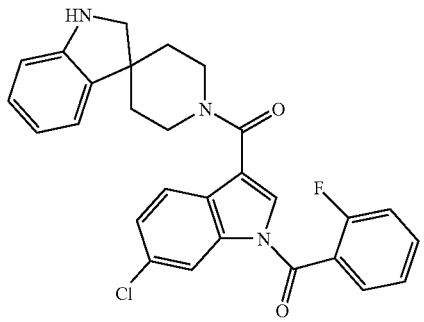

Following the general procedure VII as described above, the acylation of 1'-[(6-chloro-1H-indol-3-yl)carbonyl]-1,2-dihydrospiro[indole-3,4'-piperidine] (prepared according to example 8) with commercially available 2-fluorobenzoyl chloride gave the title compound.

ES-MS m/e (%): 488.4(M+H$^+$).

Example 90

1'-{[6-Chloro-1-(3,5-difluorobenzoyl)-1H-indol-3-yl]carbonyl}-1,2-dihydrospiro[indole-3,4'-piperidine

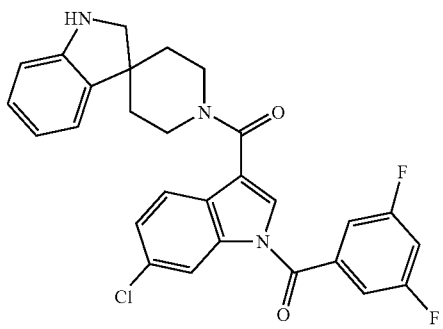

Following the general procedure VII as described above, the acylation of 1'-[(6-chloro-1H-indol-3-yl)carbonyl]-1,2-dihydrospiro[indole-3,4'-piperidine] (prepared according to example 8 above) with commercially available 3,5-difluorobenzoyl chloride gave the title compound. ES-MS m/e (%): 506.4(M+H$^+$).

Example 91

1'-{[6-Chloro-1-(2,3-difluorobenzoyl)-1H-indol-3-yl]carbonyl}-1,2-dihydrospiro[indole-3,4'-piperidine

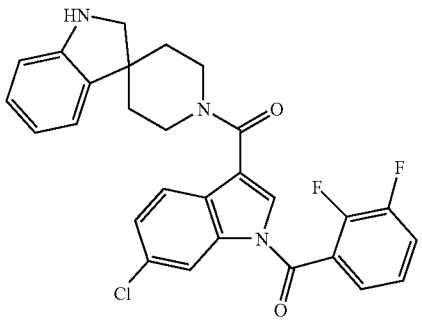

Following the general procedure VII as described above, the acylation of 1'-[(6-chloro-1H-indol-3-yl)carbonyl]-1,2-dihydrospiro[indole-3,4'-piperidine] (prepared according to example 8) with commercially available 2,3-difluorobenzoyl chloride gave the title compound.

ES-MS m/e (%): 506.4(M+H$^+$).

Example 92

1'-({6-Chloro-1-[(3,5-difluorophenyl)sulfonyl]-1H-indol-3-yl}carbonyl)-1,2-dihydrospiro[indole-3,4'-piperidine

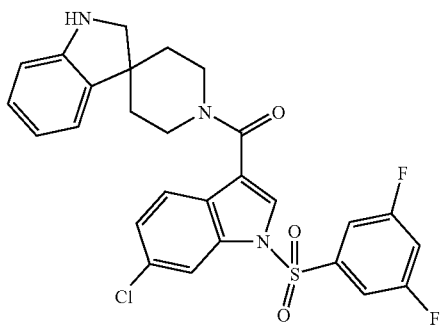

Following the general procedure VII as described above, the sulphonylation of 1'-[(6-chloro-1H-indol-3-yl)carbonyl]-1,2-dihydrospiro[indole-3,4'-piperidine] (prepared according to example 8) with commercially available 3,5-difluorobenzenesulfonyl chloride gave the title compound. ES-MS m/e (%): 542.4(M−H$^+$).

Example 93

1'-{[6-Chloro-1-(3,5-difluorobenzyl)-1H-indol-3-yl]carbonyl}-1,2-dihydrospiro[indole-3,4'-piperidine

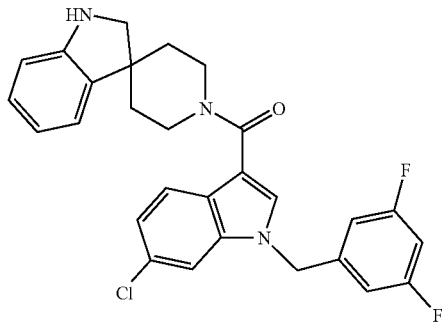

Following the general procedure III as described above, the alkylation of 1'-[(6-chloro-1H-indol-3-yl)carbonyl]-1,2-dihydrospiro[indole-3,4'-piperidine] (prepared according to example 8) with commercially available 3,5-difluorobenzyl chloride gave the title compound.

ES-MS m/e (%): 492.4(M+H$^+$).

Example 94

1'-{[6-Chloro-1-(3-fluorobenzyl)-1H-indol-3-yl]carbonyl}-1,2-dihydrospiro[indole-3,4'-piperidine

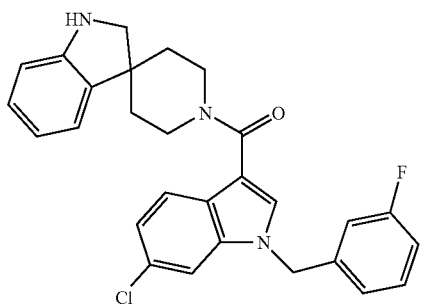

Following the general procedure III as described above, the alkylation of 1'-[(6-chloro-1H-indol-3-yl)carbonyl]-1,2-dihydrospiro[indole-3,4'-piperidine] (prepared according to example 8) with commercially available 3-fluorobenzyl chloride gave the title compound.

ES-MS m/e (%): 474.4(M+$^+$).

Example 95

2-[6-Chloro-3-(1,2-dihydro-1'H-spiro[indole-3,4'-piperidin]-1'-ylcarbonyl)-1H-indol-1-yl]-1-(3,5-difluorophenyl)ethanone

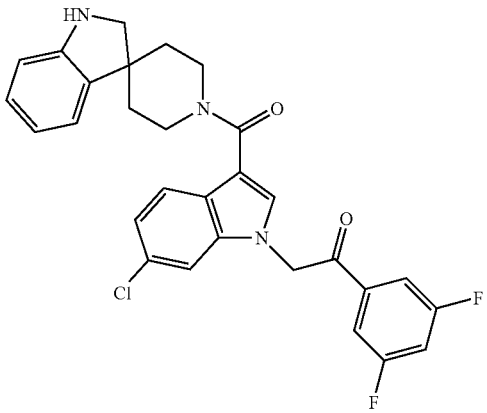

Following the general procedure III as described above, the alkylation of 1'-[(6-chloro-1H-indol-3-yl)carbonyl]-1,2-dihydrospiro[indole-3,4'-piperidine] (prepared according to example 8) with commercially available 2-chloro-1-(3,5-difluoro-phenyl)-ethanone gave the title compound. ES-MS m/e (%): 520.4(M+H$^+$).

Example 96

2-[6-Chloro-3-(1,2-dihydro-1'H-spiro[indole-3,4'-piperidin]-1'-ylcarbonyl)-1H-indol-1-yl]-1-(3,4-difluorophenyl)ethanone

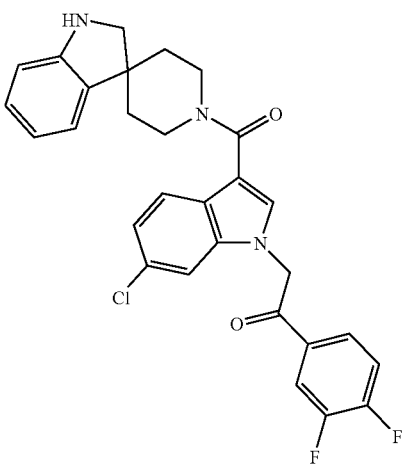

Following the general procedure III as described above, the alkylation of 1'-[(6-chloro-1H-indol-3-yl)carbonyl]-1,2-dihydrospiro[indole-3,4'-piperidine] (prepared according to example 8) with commercially available 2-chloro-1-(3,4-difluoro-phenyl)-ethanone gave the title compound. ES-MS m/e (%): 520.4(M+H$^+$).

Example 97

2-[6-Chloro-3-(1,2-dihydro-1'H-spiro[indole-3,4'-piperidin]-1'-ylcarbonyl)-1H-indol-1-yl]-1-(2-fluorophenyl)ethanone

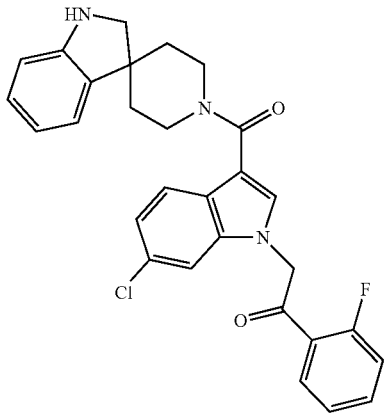

Following the general procedure III as described above, the alkylation of 1'-[(6-chloro-1H-indol-3-yl)carbonyl]-1,2-dihydrospiro[indole-3,4'-piperidine] (prepared according to example 8) with commercially available 2-chloro-1-(2-fluoro-phenyl)-ethanone gave the title compound. ES-MS m/e (%): 502.5(M+H⁺).

Example 98

2-[6-Chloro-3-(1,2-dihydro-1'H-spiro[indole-3,4'-piperidin]-1'-ylcarbonyl)-1H-indol-1-yl]-N,N-diethylethanamine

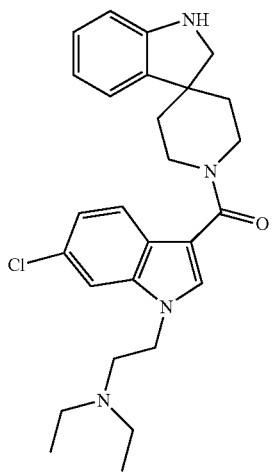

Following the general procedure III as described above, the alkylation of 1'-[(6-chloro-1H-indol-3-yl)carbonyl]-1,2-dihydrospiro[indole-3,4'-piperidine] (prepared according to example 8) with commercially available diethylaminoethyl bromide gave the title compound.
ES-MS m/e (%): 465.4(M+H⁺).

Example 99

2-[6-Chloro-3-(1,2-dihydro-1'H-spiro[indole-3,4'-piperidin]-1'-ylcarbonyl)-1H-indol-1-yl]-N,N-diethylacetamide

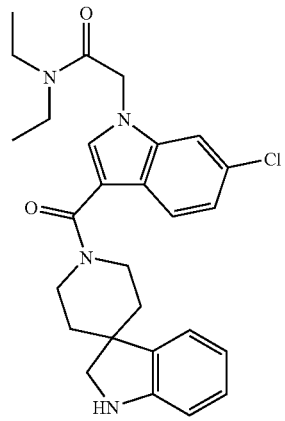

Following the general procedure III as described above, the alkylation of 1'-[(6-chloro-1H-indol-3-yl)carbonyl]-1,2-dihydrospiro[indole-3,4'-piperidine] (prepared according to example 8) with commercially available 2-chloro-N,N-diethyl-acetamide gave the title compound. ES-MS m/e (%): 479.5 (M+H⁺).

Example 100

2-[6-Chloro-3-(1,2-dihydro-1'H-spiro[indole-3,4'-piperidin]-1'-ylcarbonyl)-1H-indol-1-yl]-N,N-dimethylacetamide

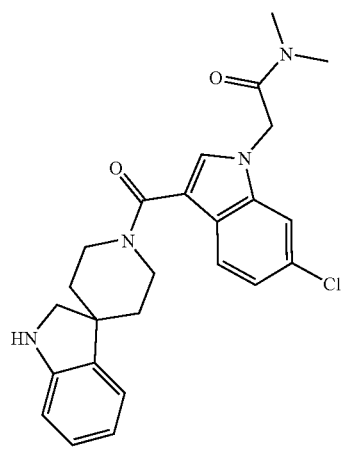

Following the general procedure III as described above, the alkylation of 1'-[(6-chloro-1H-indol-3-yl)carbonyl]-1,2-dihydrospiro[indole-3,4'-piperidine] (prepared according to example 8) with commercially available 2-chloro-N,N-diethyl-acetamide gave the title compound. ES-MS m/e (%): 451.5(M+H⁺).

Example 101

2-[6-Chloro-3-(1,2-dihydro-1'H-spiro[indole-3,4'-piperidin]-1'-ylcarbonyl)-1H-indol-1-yl]-1-pyridin-2-ylethanone

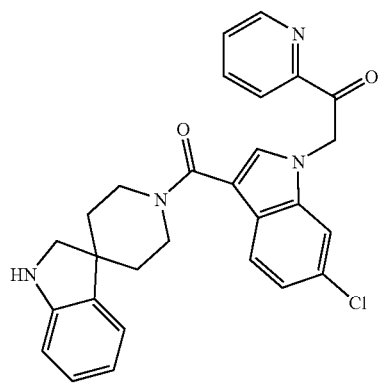

Following the general procedure III as described above, the alkylation of 1'-[(6-chloro-1H-indol-3-yl)carbonyl]-1,2-dihydrospiro[indole-3,4'-piperidine] (prepared according to example 8) with commercially available 2-chloro-1-pyridin-2-yl-ethanone gave the title compound. ES-MS m/e (%): 485.4(M+H$^+$).

Example 102

1'-{[6-Chloro-1-(pyridin-3-ylmethyl)-1H-indol-3-yl]carbonyl}-1,2-dihydrospiro[indole-3,4'-piperidine]

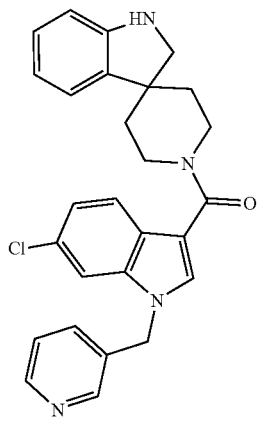

Following the general procedure III as described above, the alkylation of 1'-[(6-chloro-1H-indol-3-yl)carbonyl]-1,2-dihydrospiro[indole-3,4'-piperidine] (prepared according to example 8) with commercially available 3-bromomethyl-pyridine gave the title compound.

ES-MS m/e (%): 457.2(M+H$^+$).

Example 103

1'-{[6-Chloro-1-(pyridin-2-ylmethyl)-1H-indol-3-yl]carbonyl}-1,2-dihydrospiro[indole-3,4'-piperidine]

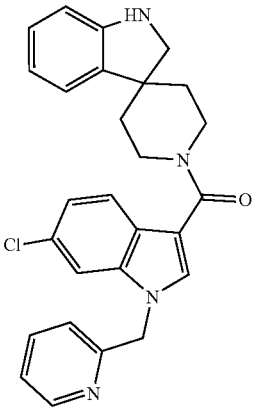

Following the general procedure III as described above, the alkylation of 1'-[(6-chloro-1H-indol-3-yl)carbonyl]-1,2-dihydrospiro[indole-3,4'-piperidine] (prepared according to example 8) with methanesulfonic acid pyridin-2-ylmethyl ester (described in WO 9955318) gave the title compound. ES-MS m/e (%): 457.2(M+H$^+$).

Examples of Compounds of Formula (I-c)

Example 104

1'-{[6-Chloro-1-(2-oxo-2-piperidin-1-ylethyl)-1H-indol-3-yl]carbonyl}-3H-spiro[2-benzofuran-1,4'-piperidin]-3-one

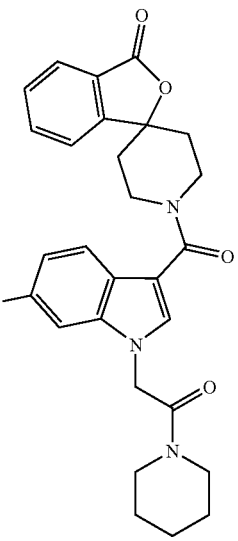

Following the general procedure V as described hereinabove, the alkylation of 1'-[(6-chloro-1H-indol-3-yl)carbonyl]-3H-spiro[2-benzofuran-1,4'-piperidin]-3-one (the preparation of which has been described in example 16) with commercially available 2-chloro-1-piperidin-1-yl-ethanone as electrophile, the title compound was obtained as a white powder.

ES-MS m/e (%): 506.0 (M+H$^+$).

Example 105

1'-{[6-Chloro-1-(2-morpholin-4-yl-2-oxoethyl)-1H-indol-3-yl]carbonyl}-3H-spiro[2-benzofuran-1,4'-piperidin]-3-one

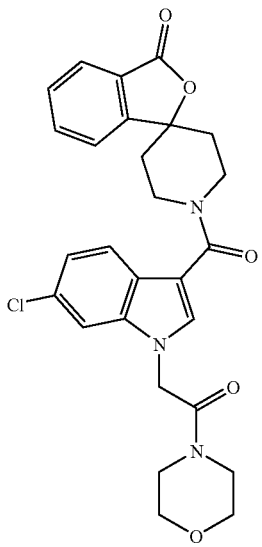

Following the general procedure V as described hereinabove, the alkylation of 1'-[(6-chloro-1H-indol-3-yl)carbonyl]-3H-spiro[2-benzofuran-1,4'-piperidin]-3-one (the preparation of which has been described in example 16) with commercially available 2-chloro-1-morpholin-4-yl-ethanone as electrophile, the title compound was obtained as a white powder.

ES-MS m/e (%): 508.1 (M+H$^+$).

Example 106

2-{6-Chloro-3-[(3-oxo-1'H,3H-spiro[2-benzofuran-1,4'-piperidin]-1'-yl)carbonyl]-1H-indol-1-yl}-N,N-dimethylacetamide

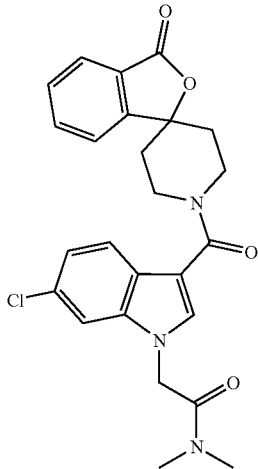

Following the general procedure V as described hereinabove, the alkylation of 1'-[(6-chloro-1H-indol-3-yl)carbonyl]-3H-spiro[2-benzofuran-1,4'-piperidin)-3-one (the preparation of which has been described in example 16) with commercially available 2-chloro-N,N-dimethyl-acetamide as electrophile, the title compound was obtained as a white powder.

ES-MS m/e (%): 466.1 (M+H$^+$).

Example 107

2-{6-Chloro-3-[(3-oxo-1'H,3H-spiro[2-benzofuran-1,4'-piperidin]-1'-yl)carbonyl]-1H-indol-1-yl}-N,N-diethylacetamide

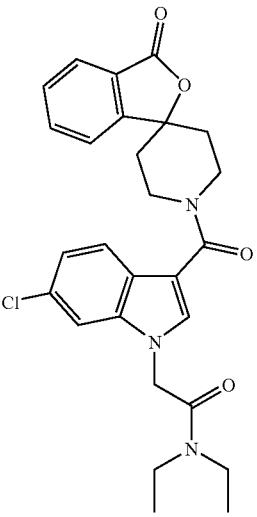

Following the general procedure V as described hereinabove, the alkylation of 1'-[(6-chloro-1H-indol-3-yl)carbonyl]-3H-spiro[2-benzofuran-1,4'-piperidin]-3-one (the preparation of which has been described in example 16) with commercially available 2-chloro-N,N-diethyl-acetamide as electrophile, the title compound was obtained as a white powder.

ES-MS m/e (%): 494.1 (M+H$^+$).

Example 108

1'-{[6-Chloro-1-(piperidin-1-ylcarbonyl)-1H-indol-3-yl]carbonyl}-3H-spiro[2-benzofuran-1,4'-piperidin]-3-one

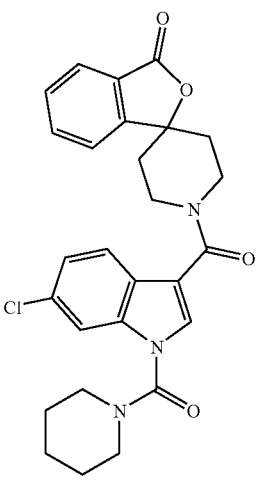

Following the general procedure V as described hereinabove, the alkylation of 1'-[(6-chloro-1H-indol-3-yl)carbonyl]-3H-spiro[2-benzofuran-1,4'-piperidin]-3-one (the preparation of which has been described in example 16) with commercially available piperidine-1-carbonyl chloride as electrophile, the title compound was obtained as a white powder.

ES-MS m/e (%): 492.1 (M+H⁺).

Example 109 tert-Butyl {6-chloro-3-[(3-oxo-1'H,3H-spiro[2-benzofuran-1,4'-piperidin]-1'-yl)carbonyl]-1H-indol-1-yl}acetate

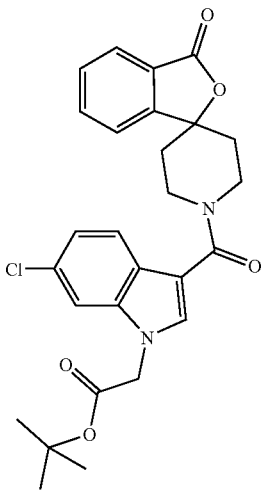

Following the general procedure V as described hereinabove, the alkylation of 1'-[(6-chloro-1H-indol-3-yl)carbonyl]-3H-spiro[2-benzofuran-1,4'-piperidin]-3-one (the preparation of which has been described in example 16) with commercially available chloro-acetic acid tert-butyl ester as electrophile, the title compound was obtained as a white powder.

ES-MS m/e (%): 495.2 (M+H⁺).

Example 110

2-{6-Chloro-3-[(5-fluoro-3-oxo-1'H,3H-spiro[2-benzofuran-1,4'-piperidin]-1'-yl)carbonyl]-1H-indol-1-yl}-N,N-dimethylacetamide

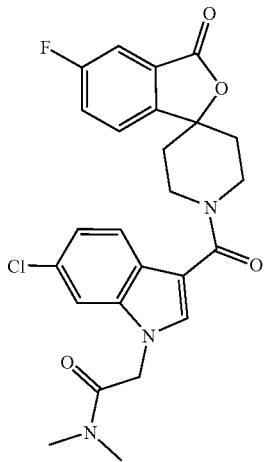

Following the general procedure V as described hereinabove, the alkylation of 1'-[(6-chloro-1H-indol-3-yl)carbonyl]-5-fluoro-3H-spiro[2-benzofuran-1,4'-piperidin]-3-one (the preparation of which has been described in example 19) with commercially available 2-chloro-N,N-dimethyl-acetamide as electrophile, the title compound was obtained as a white solid.

ES-MS m/e (%): 484.0 (M+H⁺).

Example 111

1'-({6-Chloro-1-[2-(dimethylamino)ethyl]-1H-indol-3-yl}carbonyl)-5-fluoro-3H-spiro[2-benzofuran-1,4'-piperidin]-3-one

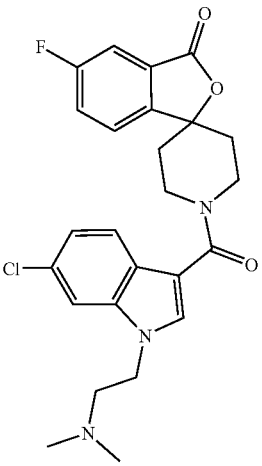

Following the general procedure V as described hereinabove, the alkylation of 1'-[(6-chloro-1H-indol-3-yl)carbonyl]-5-fluoro-3H-spiro[2-benzofuran-1,4'-piperidin]-3-one (the preparation of which have been described in example 19) with commercially available (2-chloro-ethyl)-dimethyl-amine as electrophile, the title compound was obtained as a white solid.

ES-MS m/e (%): 470.1 (M+H⁺).

Example 112 tert-Butyl {6-chloro-3-[(5-fluoro-3-oxo-1'H,3H-spiro[2-benzofuran-1,4'-piperidin]-1'-yl)carbonyl]-1H-indol-1-yl}acetate

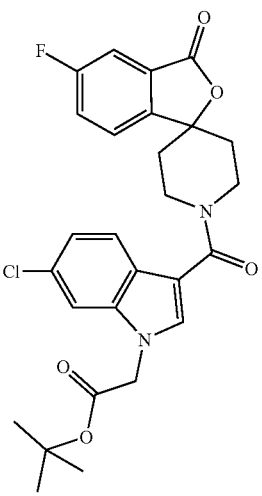

Following the general procedure V as described hereinabove, the alkylation of 1'-[(6-chloro-1H-indol-3-yl)carbonyl]-5-fluoro-3H-spiro[2-benzofuran-1,4'-piperidin]-3-one (the preparation of which have been described in example 19) with commercially available chloro-acetic acid tert-butyl ester as electrophile, the title compound was obtained as a white solid.

ES-MS m/e (%): 513.2 (M+H⁺).

Example 113

1'-{[6-Chloro-1-(2-morpholin-4-yl-2-oxoethyl)-1H-indol-3-yl]carbonyl}-5-fluoro-3H-spiro[2-benzofuran-1,4'-piperidin]-3-one

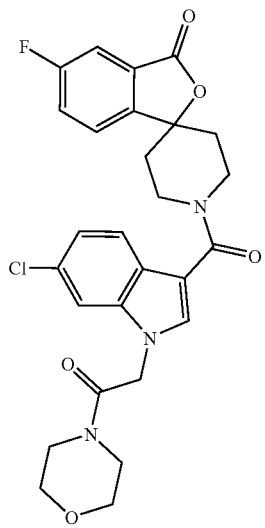

Following the general procedure V as described hereinabove, the alkylation of 1'-[(6-chloro-1H-indol-3-yl)carbonyl]-5-fluoro-3H-spiro[2-benzofuran-1,4'-piperidin]-3-one (the preparation of which have been described in example 19) with commercially available 2-chloro-1-morpholin-4-yl-ethanone as electrophile, the title compound was obtained as a white solid.

ES-MS m/e (%): 526.2 (M+H⁺).

Example 114

1'-({6-Chloro-1-[2-(4-methylpiperazin-1-yl)-2-oxoethyl]-1H-indol-3-yl}carbonyl)-5-fluoro-3H-spiro[2-benzofuran-1,4'-piperidin]-3-one

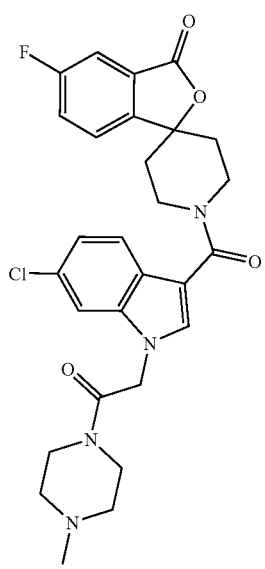

Following the general procedure V as described hereinabove, the alkylation of 1'-[(6-chloro-1H-indol-3-yl)carbonyl]-5-fluoro-3H-spiro[2-benzofuran-1,4'-piperidin]-3-one (the preparation of which have been described in example 19) with commercially available 2-chloro-1-(4-methyl-piperazin-1-yl)-ethanone as electrophile, the title compound was obtained as a white solid. ES-MS m/e (%): 539.4 (M+H⁺).

Example 115

2-{6-Chloro-3-[(5-fluoro-3-oxo-1'H,3H-spiro[2-benzofuran-1,4'-piperidin]-1'-yl)carbonyl]-1H-indol-1-yl}acetamide

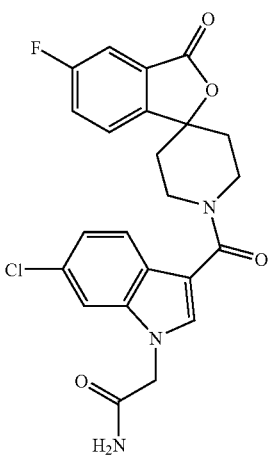

Following the general procedure V as described hereinabove, the alkylation of 1'-[(6-chloro-1H-indol-3-yl)carbonyl]-5-fluoro-3H-spiro[2-benzofuran-1,4'-piperidin]-3-one (the preparation of which have been described in example 19) with commercially available chloro-acetic acid methyl ester as electrophile, an ester intermediate methyl {6-chloro-3-[(5-fluoro-3-oxo-1'H,3H-spiro[2-benzofuran-1,4'-piperidin]-1'-yl)carbonyl]-1H-indol-1-yl}acetate was obtained as a white solid. This intermediate compound, methyl {6-chloro-3-[(5-fluoro-3-oxo-1'H,3H-spiro[2-benzofuran-1,4'-piperidin]-1'-yl)carbonyl]-1H-indol-1-yl}acetate, was then hydrolysed using standard conditions (aq.NaOH 1M, MeOH, room temperature) to give {6-chloro-3-[(5-fluoro-3-oxo-1'H,3H-spiro[2-benzofuran-1,4'-piperidin]-1'-yl)carbonyl]-1H-indol-1-yl}acetic acid as a white solid.

An amide coupling between {6-chloro-3-[(5-fluoro-3-oxo-1'H,3H-spiro[2-benzofuran-1,4'-piperidin]-1'-yl)carbonyl]-1H-indol-1-yl}acetic acid and NH₄OH (25% in water) afforded the title coumpound as a white solid.

ES-MS m/e (%): 456.4 (M+H⁺).

Example 116

2-{6-Chloro-3-[(5-fluoro-3-oxo-1'H,3H-spiro[2-benzofuran-1,4'-piperidin]-1'-yl)carbonyl]-1H-indol-1-yl}-N-methylacetamide

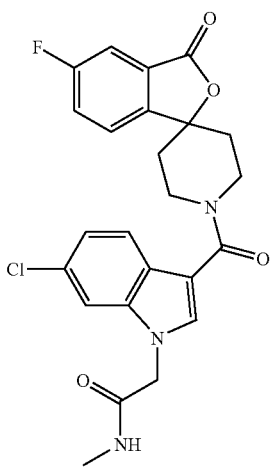

An amide coupling between {6-chloro-3-[(5-fluoro-3-oxo-1'H,3H-spiro[2-benzofuran-1,4'-piperidin]-1'-yl)carbonyl]-1H-indol-1-yl}acetic acid (described herein above) and methyl amine afforded the title coumpound as a white solid.
ES-MS m/e (%): 470.3 (M+H$^+$).

Example 117

1'-{[6-Chloro-1-(2-oxo-2-piperazin-1-ylethyl)-1H-indol-3-yl]carbonyl}-5-fluoro-3H-spiro[2-benzofuran-1,4'-piperidin]-3-one

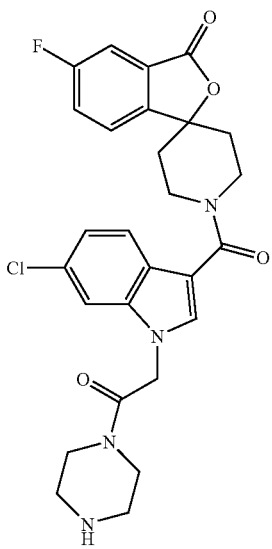

Following the general procedure V as described hereinabove, the alkylation of 1'-[(6-chloro-1H-indol-3-yl)carbonyl]-5-fluoro-3H-spiro[2-benzofuran-1,4'-piperidin]-3-one (the preparation of which have been described in example 19) with commercially available 4-(2-Chloro-acetyl)-piperazine-1-carboxylic acid tert-butyl ester as electrophile, the title compound was obtained as a white solid after removal of the Boc protecting group under standard conditions (TFA/dichloromethane, room temperature).
ES-MS m/e (%): 525.1 (M+H$^+$).

Example 118

2-{6-Chloro-3-[(5-fluoro-3-oxo-1'H,3H-spiro[2-benzofuran-1,4'-piperidin]-1'-yl)carbonyl]-1H-indol-1-yl}-N-[2-(dimethylamino)ethyl]acetamide

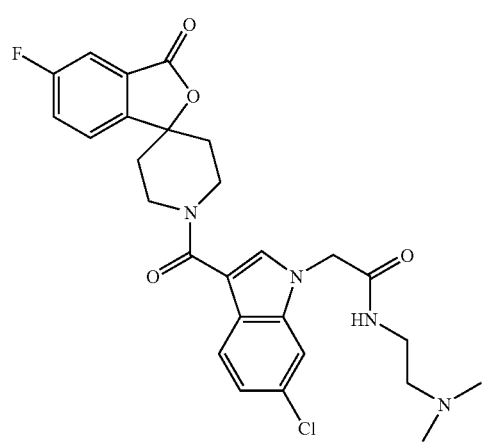

An amide coupling between {6-chloro-3-[(5-fluoro-3-oxo-1'H,3H-spiro[2-benzofuran-1,4'-piperidin]-1'-yl)carbonyl]-1H-indol-1-yl]acetic acid (described herein above) and N,N-dimethyl-ethane-1,2-diamine afforded the title coumpound as a white solid.
ES-MS m/e (%): 527.2 (M+H$^+$).

Example 119

2-{6-Chloro-3-[(3-oxo-1'H,3H-spiro[2-benzofuran-1,4'-piperidin]-1'-yl)carbonyl]-1H-indol-1-yl}-N-[2-(dimethylamino)ethyl]acetamide

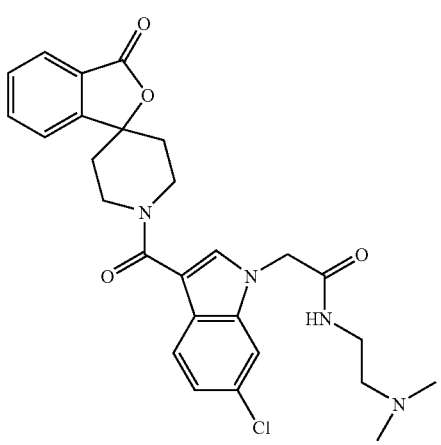

An amide coupling between {6-chloro-3-[(3-oxo-1'H,3H-spiro[2-benzofuran-1,4'-piperidin]-1'-yl)carbonyl]-1H-indol-1-yl}acetic acid (described herein above) and N,N-dimethyl-ethane-1,2-diamine afforded the title coumpound as a white solid.
ES-MS m/e (%): 509.2 (M+H$^+$).

Example 120

2-{6-Chloro-5-methyl-3-[(3-oxo-1'H,3H-spiro[2-benzofuran-1,4'-piperidin]-1'-yl)carbonyl]-1H-indol-1-yl}-N,N-dimethylacetamide a) 1-(6-Chloro-5-methyl-1H-indol-3-yl)-2,2,2-trifluoro-ethanone

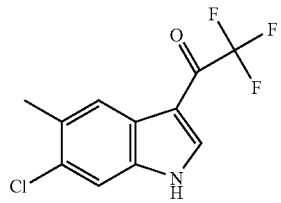

Using a procedure described in *J. Med. Chem.* 1991, 34, 140, from 0.250 g (0.002 mol) of 6-chloro-5-methyl-1H-indole were prepared 0.38 g (96%) of 1-(6-chloro-5methyl-1H-indol-3-yl)-2,2,2-trifluoro-ethanone as a white solid.

b) 2-[6-Chloro-5-methyl-3-(2,2,2-trifluoro-acetyl)-indol-1-yl]-N,N-dimethyl-acetamide

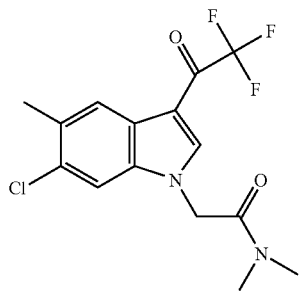

To a stirred solution of 1-(6-chloro-5methyl-1H-indol-3-yl)-2,2,2-trifluoro-ethanone (0.38 g) in 10 ml of DMF at 0° C. were added 64 mg (1.1 eq.) of NaH (60% in oil). After stirring the mixture for 30 min. were added 0.16 ml (1.1 eq.) of dimethylamino-acetyl chloride. The mixture was stirred for an additional hour and then poured onto water and extracted with ethyl acetate. The combined organic phases were dried over $Na_2SO_4$ and concentrated in vacuo to afford 300 mg (60%) of the title compound as a white solid.

c) 6-Chloro-1-dimethylcarbamoylmethyl-5-methyl-1H-indole-3-carboxylic acid

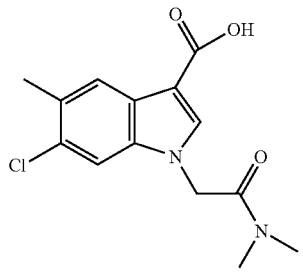

Using a similar procedure as described in *J. Med. Chem.* 1991, 34, 140, from 0.280 g of 2-[6-chloro-5-methyl-3-(2,2,2-trifluoro-acetyl)-indol-1-yl]-N,N-dimethyl-acetamide were prepared 0.18 g (76%) of the title compound as a white solid.

d) 2-[6-chloro-5-methyl-3-[(3-oxo-1'H,3H-spiro[2-benzofuran-1,4'-piperidin]-1'-yl)carbonyl]-1H-indol-1-yl]-N,N-dimethylacetamide

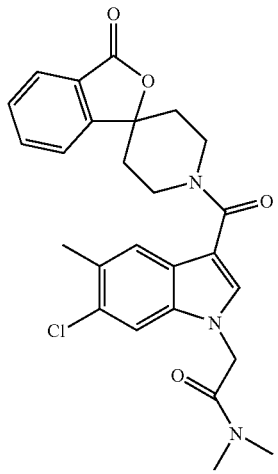

Amide coupling according to general procedure I described hereinabove:
Amine: 3H-spiro[2-benzofuran-1,4'-piperidin]-3-one prepared as described in *J. Org. Chem,* 1976, 41, 2628,
Acid: 6-Chloro-1-dimethylcarbamoylmethyl-5-methyl-1H-indole-3-carboxylic acid,
ES-MS m/e (%): 480.3 (M+H$^+$).

Example 121

1'-[(1-Benzyl-2-methyl-1H-indol-3-yl)carbonyl]-5-bromo-3H-spiro[2-benzofuran-1,4'-piperidin]-3-one a) 5-Bromo-1'-methyl-3H-spiro[2-benzofuran-1,4'-piperidin]-3-one

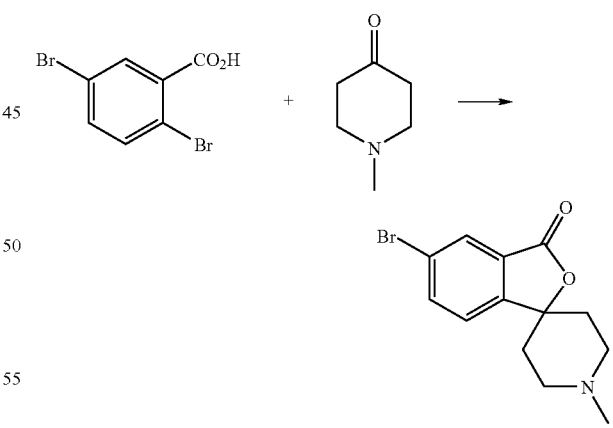

Butyllithium (97.2 ml of 1.47 M solution in hexane, 143 mmol) was added dropwise to a solution of 2,5-Dibromo-benzoic acid (20 g, 72 mmol) in dry THF (300 ml) at −78° C. over a period of 3.5 h under a nitrogen atmosphere. The reaction mixture was stirred at −78° C. for 2 h. A solution of N-methyl piperidone (11.31 g, 99 mmol) in hexane (40 mL) was added dropwise during 30 min to the reaction mixture at −78° C. The reaction mixture was allowed to come to room temperature and stirring was continued for overnight.

The reaction mixture was added to a mixture of water (500 ml) and ether (300 mL). The aqueous layer was extracted with ether (5×150 mL) and acidified with concentrated HCl (to pH 2-3) and extracted with ether (2×150 ml). The acidic solution was boiled for 1 h and then cooled to 0-5° C. and made alkaline (to pH 9-10) with aqueous NaOH. The cold solution was rapidly extracted with chloroform (5×300 mL). The combined chloroform extracts were washed with water (150 ml), dried over sodium sulfate and evaporated under reduced pressure. The residue was purified was purified by silica gel (100-200) column chromatography eluting with methanol in dichloromethane (0.5% to 2.5%) to afford the desired product (4.2 g, 20%).

$^1$H-NMR (400 MHz, CDCl$_3$): δ 1.71 (d, J=14.2 Hz, 2H), 2.15-2.24 (m, 2H), 2.37 (s, 3H), 2.45-2.52 (m, 2H), 2.83-2.87 (m, 2H), 7.26 (d, J=8.25 Hz, 1H), 7.75 (dd, J=7.8, 1.7 Hz, 1H). $^{13}$C-NMR (100 MHz, CDCl$_3$): δ 35.95, 46.05, 51.42, 84.00, 122.54, 122.97, 127.52, 128.64, 137.06, 152.24, 167.77.

b) 5-Bromo-3-oxo-1'H,3H-spiro[2-benzofuran-1,4'-piperidine]-1'-carbonitrile

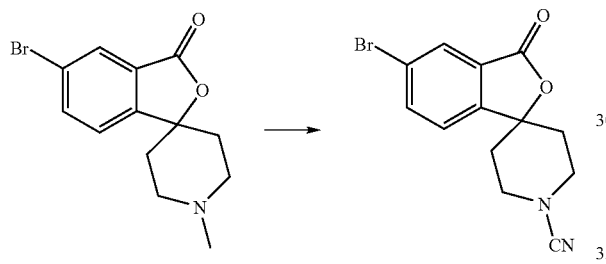

A solution of the N-methylpiperidine (3.0 g, 10 mmol) in choloroform (50 ml) was added dropwise to a stirred boiling solution of cyanogen bromide (12.16 g, 120 mmol) in chloroform (100 ml) under a nitrogen atmosphere and the resulting solution was refluxed for overnight. The reaction mixture was cooled and washed with 25 mL of 5% HCl and then with 20 ml of water. The organic layer was dried over sodium sulfate and evaporated under reduced pressure. The residue was purified by silica gel column chromatography (100-200) eluting with methanol in dichloromethane (0.5% to 1.0%) to get the pure product (1.6 g, 51%).

$^1$H-NMR (400 MHz, CDCl$_3$): δ 1.72 (d, J=14.2 Hz, 2H), 2.24-2.32 (m, 2H), 3.37-3.59 (m, 4H), 7.32 (d, J=8.2 Hz, 1H), 7.83 (dd, J=8.0, 1.7 Hz, 1H), 8.03 (d, J=1.7 Hz, 1H).

c) 5-Bromo-3H-spiro[2-benzofuran-1,4'-piperidin]-3-one

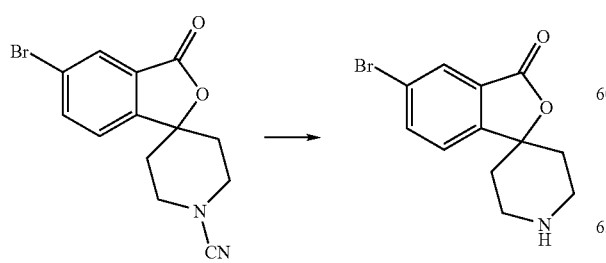

A mixture of cyanoamine (1.0 g, 3.2 mmol) and 20% HCl (12 ml) was heated under reflux under a nitrogen atmosphere for 6 h. The reaction mixture was cooled to 0-5° C. and pH was adjusted to 9-10 with aqueous NaOH solution and rapidly extracted with chloroform (3×50 ml). The combined extracts were washed with water, the organic layer was dried over sodium sulfate and evaporated under reduced pressure. The residue was washed with distilled hexane and dried under high vacuum to get the pure product (0.64 g, 70%).

IR (KBr) 3333.84, 290.53, 283525, 2811.07, 2749.38, 1756.04, 1470.28, 1415.14, 1271.03, 1196.28, 1083.84, 929.07, 831.50, 792.35, 734.78, 691.24, 548.46, 534.50 cm$^{-1}$. $^1$H-NMR (400 MHz, CDCl$_3$): δ 1.66-1.72 (m, 2H), 2.02-2.09 (m, 2H), 3.07-3.18 (m, 4H), 7.29 (d, J=7.8 Hz, 1H), 7.77 (dd, J=7.8, 1.7 Hz, 1H), 7.99 (d, J=1.7 Hz, 1H).$^{13}$C-NMR (100 MHz, CDCl$_3$): δ 6.33, 42.49, 85.23, 122.61, 122.93, 127.39, 128.64, 137.07, 152.44, 167.91. FIA-MS: 282.1 and 284.1; C$_{12}$H$_{12}$$^{79}$BrNO$_2$ [MH$^+$] requires 282.1. mp: 162-163° C.

d) 1'-[(1-Benzyl-2-methyl-1H-indol-3-yl)carbonyl]-5-bromo-3H-spiro[2-benzofuran-1,4'-piperidin]-3-one

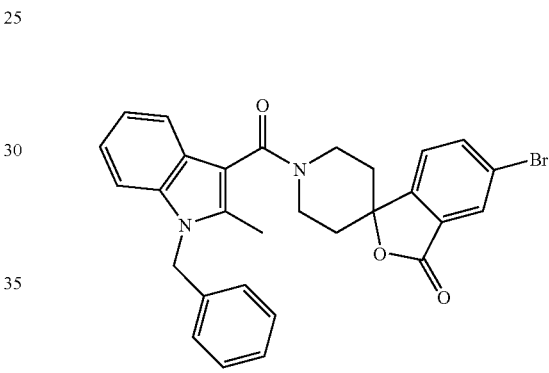

Following the general procedure I as described above, the acylation of 5-bromo-3H-spiro[2-benzofuran-1,4'-piperidin]-3-one with 1-benzyl-2-methyl-1H-indole-3-carboxylic acid (preparation described in example 1), gave the title compound.

ES-MS m/e (%): 531.5(M+H$^+$).

Example 122

1'-[(1-benzyl-2-methyl-1H-indol-3-yl)carbonyl]-6-(2-hydroxyethoxy)-3H-spiro[2-benzofuran-1,4'-piperidin]-3-one a) 6-fluoro-1'-methyl-3H-spiro[2-benzofuran-1,4'-piperidin]-3-one

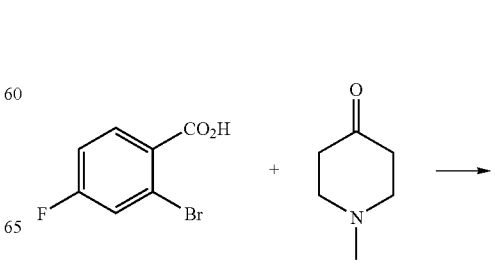

-continued

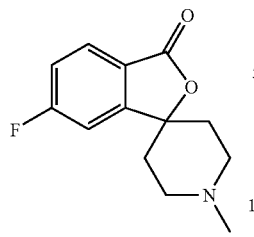

To a solution of the substituted 2-bromo-4-fluoro-benzoic acid (10.9 g, 50 mmol) in dry THF (200 ml) at −78° C. n-butyllithium (1.6 M in hexanes) (100 mmol) was added drop wise (3 h) and the resulting solution was stirred for an additional 2 h at the same temperature. Freshly distilled N-methyl 4-piperidone (7.91 g, 70 mmol) in dry hexane (25 ml) was added over 30 min at the same temperature. The mixture was then allowed to stir at rt and was finally added to ether (200 ml) and water (300 ml). The basic (aqueous) layer was extracted with ether (5×100 ml) and the aqueous layer was acidified with concentrated hydrochloric acid (pH 2-3) and extracted with ether. The aqueous solution was boiled for 1 h and was then cooled to 0-5° C. and made alkaline (pH 9-10) with cold aqueous sodium hydroxide. The cold solution was rapidly extracted with chloroform (5×200 ml). The combined chloroform extracts were washed with water, dried, concentrated to give light yellow solid which was purified over neutral alumina eluting with a gradient of 30-50% ethyl acetate-hexane to obtain 1.75 g (15%) of the desired product as a white solid.

$^1$H-NMR (CDCl$_3$, 400 MHz): δ 1.68-1.75 (m, 2H), 2.18-2.19 (m, 1H), 2.38 (s, 3H), 2.44-2.52 (m, 2H), 2.68-2.84 (m, 2H), 2.84-2.85 (m, 1H), 7.02-7.05 (m, 1H), 7.19-7.22 (m, 1H), 7.84-7.87 (m, 1H); FIA-MS: 236 (M+1).

b) 6-Fluoro-3-oxo-1'H,3H-spiro[2-benzofuran-1,4'-piperidine]-1'-carbonitrile

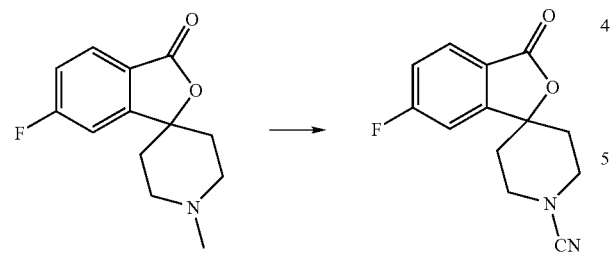

To a solution of the 6-fluoro-1'-methyl-3H-spiro[2-benzofuran-1,4'-piperidin]-3-one (1.17 g, 5 mmol) in dry chloroform (10 ml) was added cyanogenbromide (60 mnol) and the resulting solution was refluxed for 36 h. The reaction mixture was extracted with 5% HCl (5 ml) and then with water (2.5 ml). The chloroform solution was dried (anhydrous MgSO$_4$) and concentrated to give a pale yellow soild which was chromatographed over SiO$_2$ eluting with 1% MeOH-dichloromethane to give 858 mg (70%) the desired product as a white solid.

$^1$H-NMR (CDCl$_3$, 400 MHz): δ 1.72-1.76 (m, 2H), 2.22-2.30 (m, 1H), 3.48-3.60 (m, 4H), 7.09-7.11 (m, 1H), 7.11-7.28 (m, 1H), 7.89-7.92 (m, 1H); IR (KBr): 3492, 3043, 2216, 1760, 1602, 1478 cm$^{-1}$.

c) 5-(2-hydroxyethoxy)-3H-spiro[2-benzofuran-1,4'-piperidin]-3-one

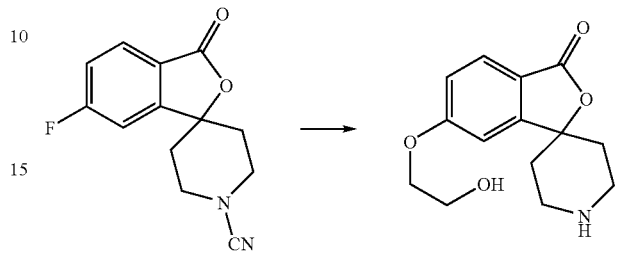

6-Fluoro-3-oxo-1'H,3H-spiro[2-benzofuran-1,4'-piperidine]-1'-carbonitrile (1.23 g, 5 mmol) was heated with ethylene glycol (5 ml) and sodium hydroxide (0.82 g, 20.5 mmol) for 15-20 min at 130° C. Most of the ethylene glycol was removed by distillation under high vaccum. The residual reaction mixture was diluted with water and extracted repeatedly with chloroform. The combined organics was dried and concentrated to give a semi solid material which was purified over Al$_2$O$_3$ column upon elution with 5-7% MeOH/CH$_2$Cl$_2$ containing NH$_3$ (aqueous) to yield 789 mg (60%) of the desired product as a pale yellow solid.

$^1$H-NMR (d$_6$-DMSO, 400 MHz): δ 1.47-1.50 (m, 2H), 2.03-2.10 (m, 2H), 2.79-2.85 (m, 2H), 2.95-2.97 (m, 2H), 3.73-3.76 (m, 2H), 4.12-4.14 (m, 2H), 7.09 (d, J=8.4 Hz, 1H), 7.20 (s, 1H), 7.69 (d, J=8.4 Hz, 1H); $^{13}$C-NMR (d$_6$-DMSO, 100 MHz): δ 35.9, 42.3, 59.3, 70.4, 84.6, 106.4, 116.6, 117.0, 126.8, 156.9, 163.9, 168.5; FIA-MS: 264.3 (M+1).

d) 1'-[(1-Benzyl-2-methyl-1H-indol-3-yl)carbonyl]-6-(2-hydroxyethoxy)-3H-spiro[2-benzofuran-1,4'-piperidin]-3-one

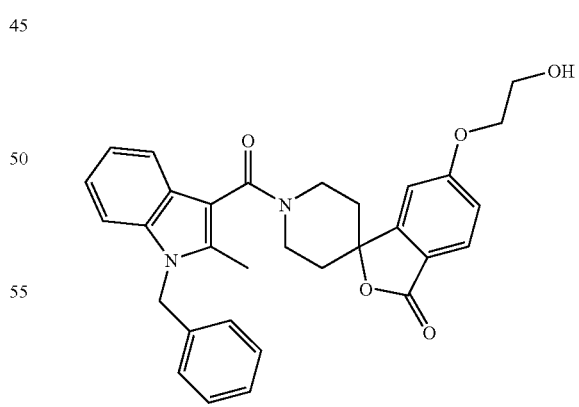

Following the general procedure I as described above, the acylation of 5-(2-hydroxyethoxy)-3H-spiro[2-benzofuran-1,4'-piperidin]-3-one with 1-benzyl-2-methyl-1H-indole-3-carboxylic acid (preparation described in example 1), gave the title compound.

ES-MS m/e (%): 511.6(M+H$^+$).

Example 123

1'-({1-[2-(3,4-Dimethoxyphenyl)ethyl]-5-methoxy-2-methyl-1H-indol-3-yl}carbonyl)-3H-spiro[2-benzofuran-1,4'-piperidin]-3-one

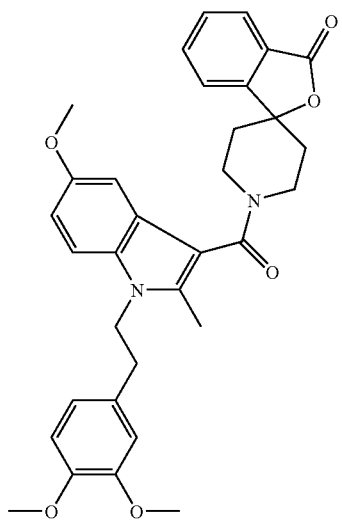

Following the general procedure I as described above, the acylation of 3H-spiro[2-benzofuran-1,4'-piperidin]-3-one prepared as described in example 16 above, with commercially available 1-[2-(3,4-dimethoxy-phenyl)-ethyl]-5-methoxy-2-methyl-1H-indole-3-carboxylic acid, gave the title compound. ES-MS m/e (%): 555.3 (M+H⁺).

Example 124

1'-{[1-(4-Ethoxyphenyl)-5-methoxy-2-methyl-1H-indol-3-yl]carbonyl}-3H-spiro[2-benzofuran-1,4'-piperidin]-3-one

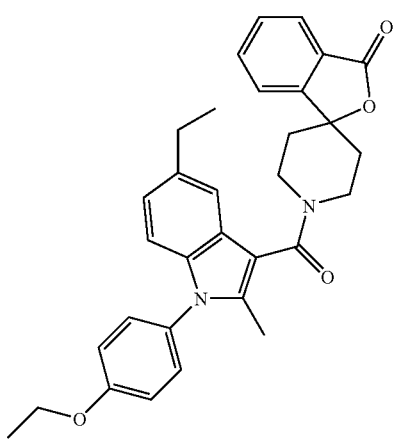

Following the general procedure I as described above, acylation of 3H-spiro[2-benzofuran-1,4'-piperidin]-3-one prepared as described in example 16, with commercially available 1-(4-ethoxyphenyl)-5-methoxy-2-methyl-1H-indole-3-carboxylic acid, gave the title compound. ES-MS m/e (%): 511.5 (M+H⁺).

Example 125

5-Bromo-1'-[(6-chloro-1H-indol-3-yl)carbonyl]-3H-spiro[2-benzofuran-1,4'-piperidin]-3-one

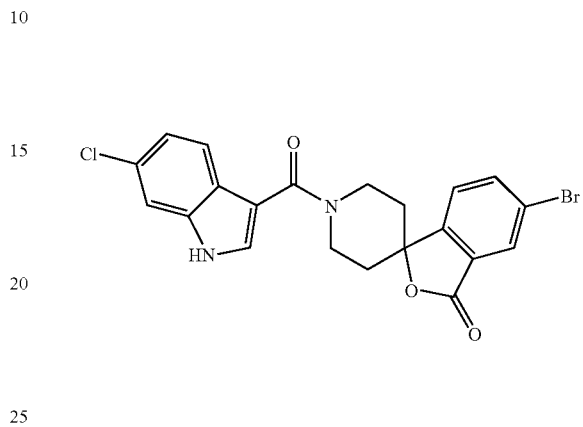

Following the general procedure I as described above, the acylation of 5-bromo-3H-spiro[2-benzofuran-1,4'-piperidin]-3-one with 1H-indole-3-carboxylic acid (commercially available), gave the title compound. ES-MS m/e (%): 459.3 (M+H⁺).

Example 126

1'-[(1-Benzyl-2-methyl-1H-indol-3-yl)carbonyl]-3H-spiro[2-benzofuran-1,4'-piperidin]-3-one

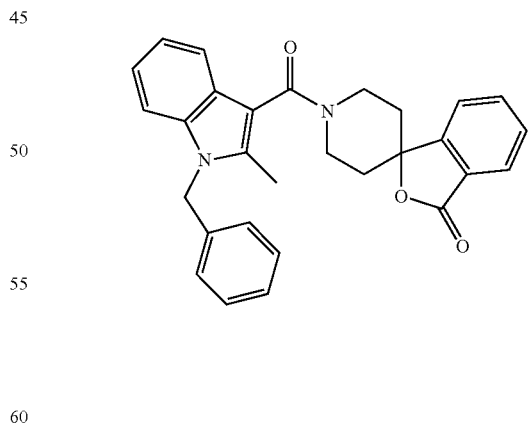

Following the general procedure I as described above, the acylation of 3H-spiro[2-benzofuran-1,4'-piperidin]-3-one prepared as described in example 16 above with 1-benzyl-2-methyl-1H-indole-3-carboxylic acid (preparation described in example 1), gave the title compound. ES-MS m/e (%): 451.6 (M+H⁺).

Example 127

1'-{[6-Chloro-1-(3,5-difluorophenyl)-1H-indol-3-yl]carbonyl}-3H-spiro[2-benzofuran-1,4'-piperidin]-3-one

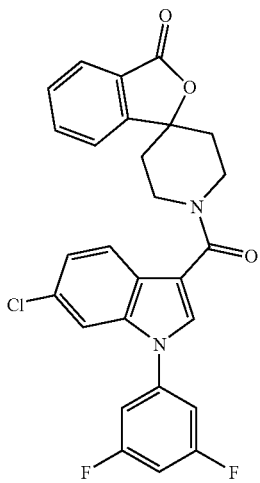

Following the general procedure VI as described above, the arylation of 1'-[(6-chloro-1H-indol-3-yl)carbonyl]-3H-spiro[2-benzofuran-1,4'-piperidin]-3-one (prepared according to example 16) with commercially available 3,5-difluorophenylboronic acid gave the title compound. ES-MS m/e (%): 493.1(M+H$^+$).

Example 128

1'-{[6-chloro-1-(3-fluorobenzoyl)-1H-indol-3-yl]carbonyl}-3H-spiro[2-benzofuran-1,4'-piperidin]-3-one

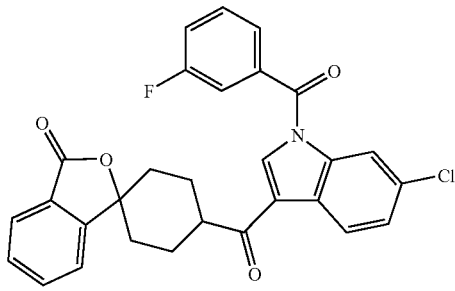

Following the general procedure VII as described above, the acylation of 1'-[(6-chloro-1H-indol-3-yl)carbonyl]-3H-spiro[2-benzofuran-1,4'-piperidin]-3-one (prepared according to example 16 above) with commercially available 3-fluorobenzoyl chloride gave the title compound. ES-MS m/c (%): 503.4 (M+H$^+$).

Example 129

1'-{[6-Chloro-1-(2-fluorobenzoyl)-1H-indol-3-yl]carbonyl}-3H-spiro[2-benzofuran-1,4'-piperidin]-3-one

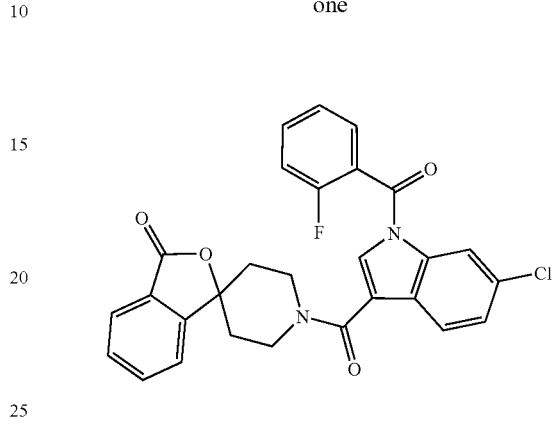

Following the general procedure VII as described above, the acylation of 1'-[(6-chloro-1H-indol-3-yl)carbonyl]-3H-spiro[2-benzofuran-1,4'-piperidin]-3-one (prepared according to example 16) with commercially available 2-fluorobenzoyl chloride gave the title compound.

ES-MS m/c (%): 503.4 (M+H$^+$).

Example 130

1'-{[6-Chloro-1-(3,5-difluorobenzoyl)-1H-indol-3-yl]carbonyl}-3H-spiro[2-benzofuran-1,4'-piperidin]-3-one

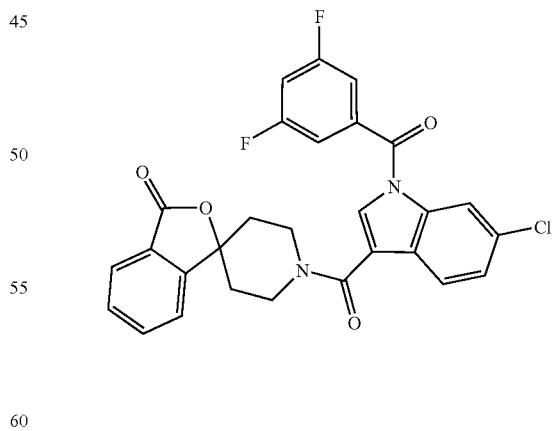

Following the general procedure VII as described above, the acylation of 1'-[(6-chloro-1H-indol-3-yl)carbonyl]-3H-spiro[2-benzofuran-1,4'-piperidin]-3-one (prepared according to example 16) with commercially available 3,5-difluorobenzoyl chloride gave the title compound.

ES-MS m/e (%): 521.4(M+H$^+$).

Example 131

1'-{[6-Chloro-1-(2,3-difluorobenzoyl)-1H-indol-3-yl]carbonyl}-3H-spiro[2-benzofuran-1,4'-piperidin]-3-one

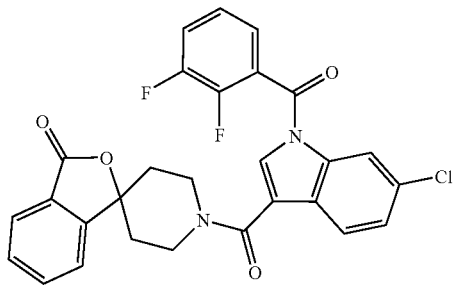

Following the general procedure VII as described above, the acylation of 1'-[(6-chloro-1H-indol-3-yl)carbonyl]-3H-spiro[2-benzofuran-1,4'-piperidin]-3-one (prepared according to example 16) with commercially available 2,3-difluorobenzoyl chloride gave the title compound.

ES-MS m/e (%): 521.4(M+H$^+$).

Example 132

1'-({6-Chloro-1-[(3,5-difluorophenyl)sulfonyl]-1H-indol-3-yl}carbonyl)-3H-spiro[2-benzofuran-1,4'-piperidin]-3-one

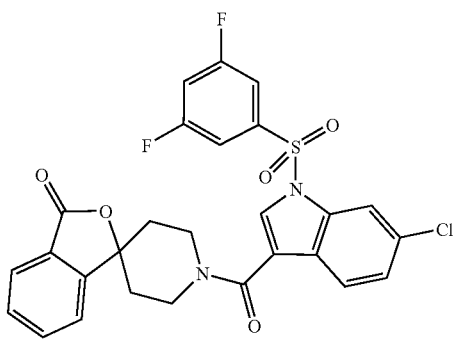

Following the general procedure VII as described above, the sulphonylation of 1'-[(6-chloro-1H-indol-3-yl)carbonyl]-3H-spiro[2-benzofuran-1,4'-piperidin]-3-one (prepared according to example 16 above) with commercially available 3,5-difluorobenzenesulfonyl chloride gave the title compound.

ES-MS m/e (%): 557.4(M+H$^+$).

Example 133

1'-{[6-Chloro-1-(3,5-difluorobenzyl)-1H-indol-3-yl]carbonyl}-3H-spiro[2-benzofuran-1,4'-piperidin]-3-one

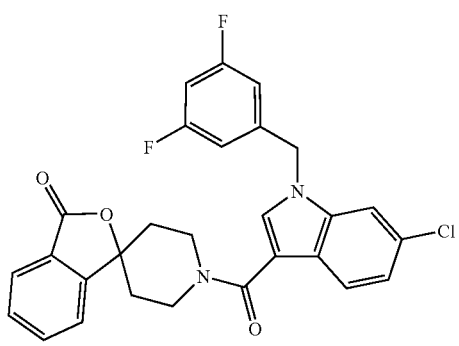

Following the general procedure III as described above, the acylation of 1'-[(6-chloro-1H-indol-3-yl)carbonyl]-3H-spiro[2-benzofuran-1,4'-piperidin]-3-one (prepared according to example 16 above) with commercially available 3,5-difluorobenzyl chloride gave the title compound. ES-MS m/e (%): 507.4(M+H$^+$).

Example 134

1'-{[6-Chloro-1-(3-fluorobenzyl)-1H-indol-3-yl]carbonyl}-3H-spiro[2-benzofuran-1,4'-piperidin]-3-one

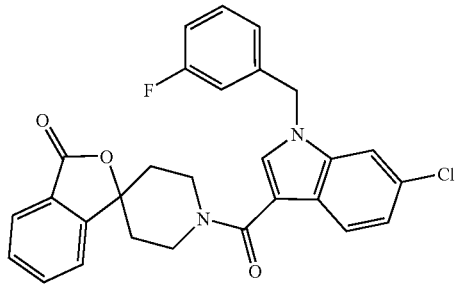

Following the general procedure III as described above, the acylation of 1'-[(6-chloro-1H-indol-3-yl)carbonyl]-3H-spiro[2-benzofuran-1,4'-piperidin]-3-one (prepared according to example 16) with commercially available 3-fluorobenzyl chloride gave the title compound.

ES-MS m/e (%): 489.4(M+H$^+$).

Example 135

1'-({6-Chloro-1-[2-(3-fluorophenyl)-2-oxoethyl]-1H-indol-3-yl}carbonyl)-3H-spiro[2-benzofuran-1,4'-piperidin]-3-one

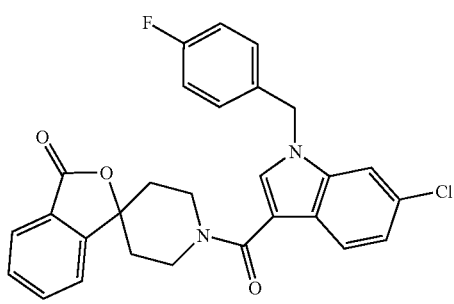

Following the general procedure III as described above, the acylation of 1'-[(6-chloro-1H-indol-3-yl)carbonyl]-3H-spiro[2-benzofuran-1,4'-piperidin]-3-one (prepared according to example 16) with commercially available 2-chloro-1-(3-fluoro-phenyl)-ethanone gave the title compound. ES-MS m/e (%): 517.4(M+H$^+$).

Example 136

1'-({6-Chloro-1-[2-(2,5-difluorophenyl)-2-oxoethyl]-1H-indol-3-yl]carbonyl)-3H-spiro[2-benzofuran-1,4'-piperidin]-3-one

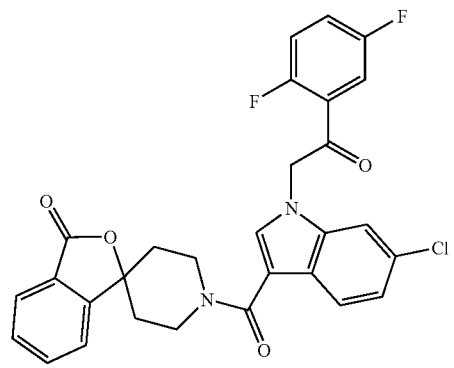

Following the general procedure III as described above, the acylation of 1'-[(6-chloro-1H-indol-3-yl)carbonyl]-3H-spiro[2-benzofuran-1,4'-piperidin]-3-one (prepared according to example 16) with commercially available 2-chloro-1-(2,5-difluoro-phenyl)-ethanoneethanone gave the title compound. ES-MS m/e (%): 535.4(M+H$^+$).

Example 137

1'-{[6-Chloro-1-(3-fluorobenzoyl)-1H-indol-3-yl]carbonyl}-5-fluoro-3H-spiro[2-benzofuran-1,4'-piperidin]-3-one

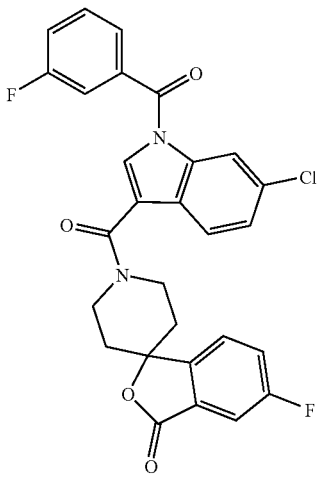

Following the general procedure VII as described above, the acylation of 1'-[(6-chloro-1H-indol-3-yl)carbonyl]-5-fluoro-3H-spiro[2-benzofuran-1,4'-piperidin]-3-one (prepared according to example 19) with commercially available 3-fluorobenzoyl chloride gave the title compound. ES-MS m/e (%): 521.4(M+H$^+$).

Example 138

1'-{[6-Chloro-1-(2-fluorobenzoyl)-1H-indol-3-yl]carbonyl}-5-fluoro-3H-spiro[2-benzofuran-1,4'-piperidin]-3-one

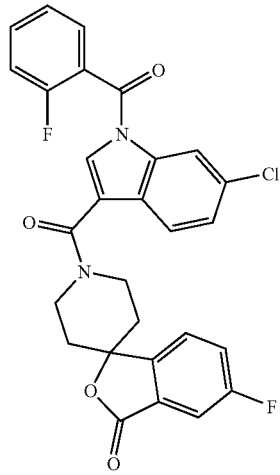

Following the general procedure VII as described above, the acylation of 1'-[(6-chloro-1H-indol-3-yl)carbonyl]-5-fluoro-3H-spiro[2-benzofuran-1,4'-piperidin]-3-one (prepared according to example 19) with commercially available 2-fluorobenzoyl chloride gave the title compound. ES-MS m/e (%): 521.4(M+H$^+$).

Example 139

1'-{[6-Chloro-1-(2,3-difluorobenzoyl)-1H-indol-3-yl]carbonyl}-5-fluoro-3H-spiro[2-benzofuran-1,4'-piperidin]-3-one

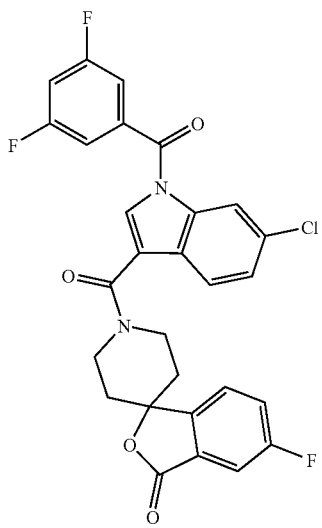

Following the general procedure VII as described above, the acylation of 1'-[(6-chloro-1H-indol-3-yl)carbonyl]-5-fluoro-3H-spiro[2-benzofuran-1,4'-piperidin]-3-one (prepared according to example 19) with commercially available 3,5-difluorobenzoyl chloride gave the title compound. ES-MS m/e (%): 539.4(M+H$^+$).

Example 140

1'-{[6-Chloro-1-(2,3-difluorobenzoyl)-1H-indol-3-yl]carbonyl}-5-fluoro-3H-spiro[2-benzofuran-1,4'-piperidin]-3-one

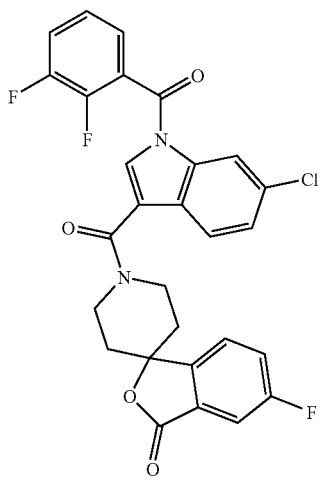

Following the general procedure VII as described above, the acylation of 1'-[(6-chloro-1H-indol-3-yl)carbonyl]-5-fluoro-3H-spiro[2-benzofuran-1,4'-piperidin]-3-one (prepared according to example 19) with commercially available 2,3-difluorobenzoyl chloride gave the title compound. ES-MS m/e (%): 539.3(M+H$^+$).

Example 141

1'-({6-Chloro-1-[(3,5-difluorophenyl)sulfonyl]-1H-indol-3-yl}carbonyl)-5-fluoro-3H-spiro[2-benzofuran-1,4'-piperidin]-3-one

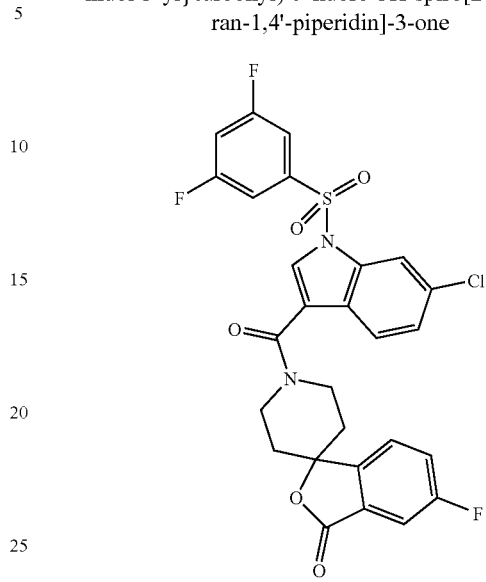

Following the general procedure VII as described above, the sulphonylation of 1'-[(6-chloro-1H-indol-3-yl)carbonyl]-5-fluoro-3H-spiro[2-benzofuran-1,4'-piperidin]-3-one (prepared according to example 19) with commercially available 3,5-difluorobenzenesulfonyl chloride gave the title compound. ES-MS m/e (%): 575.3(M+H$^+$).

Example 142

1'-{[6-Chloro-1-(3,5-difluorobenzyl)-1H-indol-3-yl]carbonyl}-5-fluoro-3H-spiro[2-benzofuran-1,4'-piperidin]-3-one

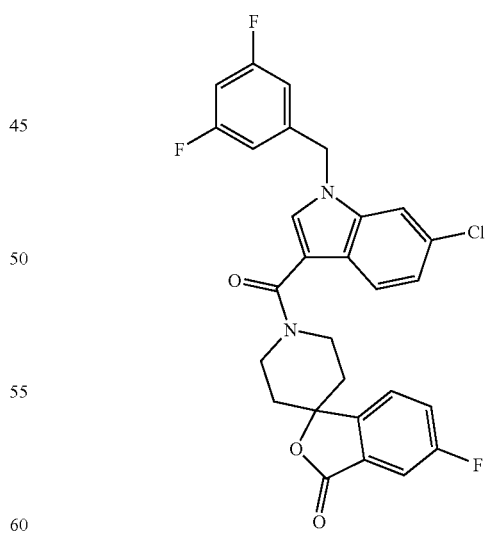

Following the general procedure III as described above, the alkylation of 1'-[(6-chloro-1H-indol-3-yl)carbonyl]-5-fluoro-3H-spiro[2-benzofuran-1,4'-piperidin]-3-one (prepared according to example 19) with commercially available 3,5-difluorobenzyl chloride gave the title compound. ES-MS m/e (%): 525.4(M+H$^+$).

Example 143

1'-{[6-Chloro-1-(3-fluorobenzyl)-1H-indol-3-yl]carbonyl}-5-fluoro-3H-spiro[2-benzofuran-1,4'-piperidin]-3-one

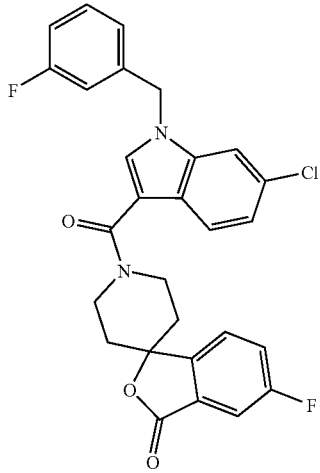

Following the general procedure III as described above, the alkylation of 1'-[(6-chloro-1H-indol-3-yl)carbonyl]-5-fluoro-3H-spiro[2-benzofuran-1,4'-piperidin]-3-one (prepared according to example 19) with commercially available 3-fluorobenzyl chloride gave the title compound. ES-MS m/e (%): 507.4(M+H$^+$).

Example 144

1'-({6-Chloro-1-[2-(3-fluorophenyl)-2-oxoethyl]-1H-indol-3-yl}carbonyl)-5-fluoro-3H-spiro[2-benzofuran-1,4'-piperidin]-3-one

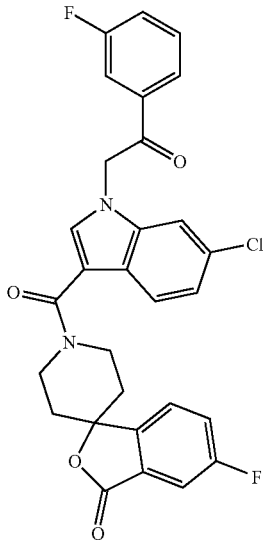

Following the general procedure III as described above, the alkylation of 1'-[(6-chloro-1H-indol-3-yl)carbonyl]-5-fluoro-3H-spiro[2-benzofuran-1,4'-piperidin]-3-one (prepared according to example 19) with commercially available 2-chloro-1-(3-fluoro-phenyl)-ethanone gave the title compound.
ES-MS m/e (%): 535.4 (M+H$^+$).

Example 145

5-Bromo-1'-{[6-chloro-1-(3-fluorobenzoyl)-1H-indol-3-yl]carbonyl}-3H-spiro[2-benzofuran-1,4'-piperidin]-3-one

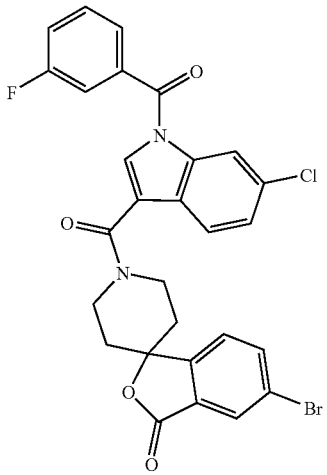

Following the general procedure VII as described above, the acylation of 5-bromo-1'-[(6-chloro-1H-indol-3-yl)carbonyl]-3H-spiro[2-benzofuran-1,4'-piperidin]-3-one with commercially available 3-fluorobenzoyl chloride gave the title compound. ES-MS m/e (%): 581.2(M+H$^+$).

Example 146

5-Bromo-1'-{[6-chloro-1-(2-fluorobenzoyl)-1H-indol-3-yl]carbonyl}-3H-spiro[2-benzofuran-1,4'-piperidin]-3-one

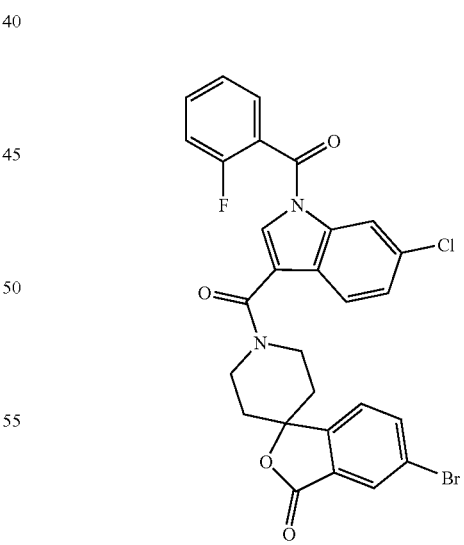

Following the general procedure VII as describeed above, the acylation of 5-bromo-1'-[(6-chloro-1H-indol-3-yl)carbonyl]-3H-spiro[2-benzofuran-1,4'-piperidin]-3-one with commercially available 3-fluorobenzoyl chloride gave the title compound.
ES-MS m/e (%): 581.2(M+H$^+$).

Example 147

5-Bromo-1'-[6-chloro-1-(3,5-difluorobenzoyl)-1H-indol-3-yl]carbonyl}-3H-spiro[2-benzofuran-1,4'-piperidin]-3-one

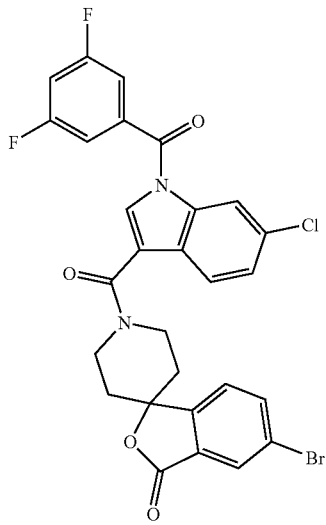

Following the general procedure VII as describeed above, the acylation of 5-bromo-1'-[(6-chloro-1H-indol-3-yl)carbonyl]-3H-spiro[2-benzofuran-1,4'-piperidin]-3-one with commercially available 3,5-difluorobenzoyl chloride gave the title compound.

ES-MS m/e (%): 599.2(M+H$^+$).

Example 148

5-Bromo-1'-{[6-chloro-1-(2,3-difluorobenzoyl)-1H-indol-3-yl]carbonyl}-3H-spiro[2-benzofuran-1,4'-piperidin]-3-one

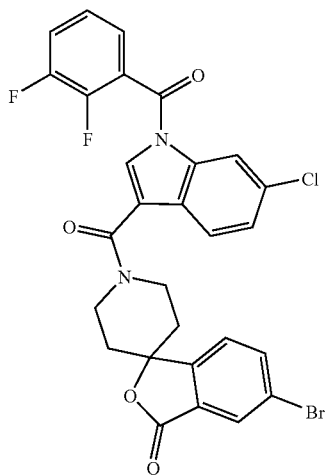

Following the general procedure VII as describeed above, the acylation of 5-bromo-1'-[(6-chloro-1H-indol-3-yl)carbonyl]-3H-spiro[2-benzofuran-1,4'-piperidin]-3-one with commercially available 2,3-difluorobenzoyl chloride gave the title compound.

ES-MS m/e (%): 599.2(M+H$^+$)

Example 149

5-Bromo-1'-({6-chloro-1-[(3,5-difluorophenyl)sulfonyl]-1H-indol-3-yl}carbonyl)-3H-spiro[2-benzofuran-1,4'-piperidin]-3-one

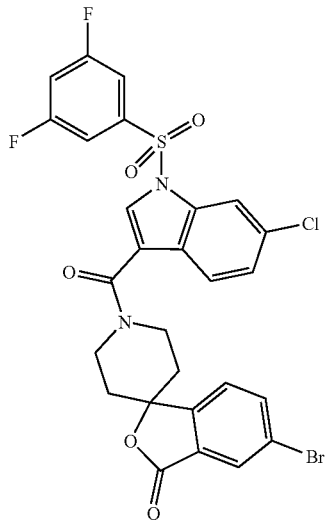

Following the general procedure VII as described above, the sulphonylation of 5-bromo-1'-[(6-chloro-1H-indol-3-yl)carbonyl]-3H-spiro[2-benzofuran-1,4'-piperidin]-3-one with commercially available 3,5-difluorobenzenesulfonyl chloride gave the title compound.

ES-MS m/e (%): 635.2(M+H$^+$).

Example 150

5-Bromo-1'-{[6-chloro-1-(3,5-difluorobenzyl)-1H-indol-3-yl]carbonyl}-3H-spiro[2-benzofuran-1,4'-piperidin]-3-one

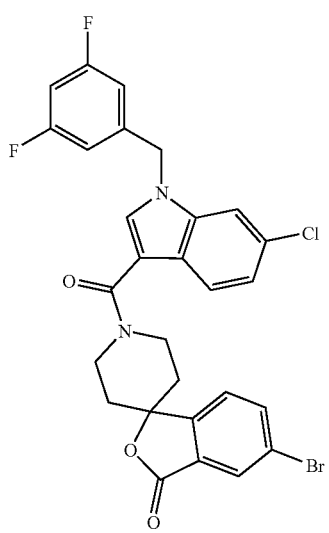

Following the general procedure III as described above, the alkylation of 5-bromo-1'-[(6-chloro-1H-indol-3-yl)carbonyl]-3H-spiro[2-benzofuran-1,4'-piperidin]-3-one with commercially available 3,5-difluorobenzyl chloride gave the title compound.

ES-MS m/e (%): 585.2(M+H$^+$).

Example 151

5-Bromo-1'-{[6-chloro-1-(3-fluorobenzyl)-1H-indol-3-yl]carbonyl}-3H-spiro[2-benzofuran-1,4'-piperidin]-3-one

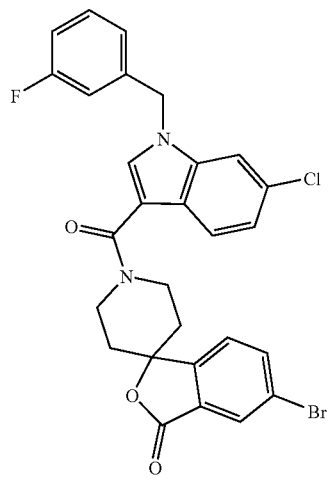

Following the general procedure III as described above, the alkylation of 5-bromo-1'-[(6-chloro-1H-indol-3-yl)carbonyl]-3H-spiro[2-benzofuran-1,4'-piperidin]-3-one with commercially available 3-fluorobenzyl chloride gave the title compound. ES-MS m/e (%): 567.3(M+H$^+$).

Example 152

5-Bromo-1'-({6-chloro-1-[2-(3-fluorophenyl)-2-oxo-ethyl]-1H-indol-3-yl}carbonyl)-3H-spiro[2-benzofuran-1,4'-piperidin]-3-one

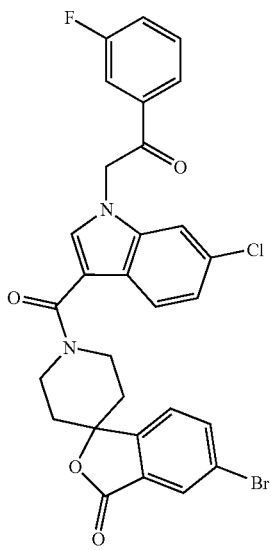

Following the general procedure III as described above, the alkylation of 5-bromo-1'-[(6-chloro-1H-indol-3-yl)carbonyl]-3H-spiro[2-benzofuran-1,4'-piperidin]-3-one with commercially available 2-chloro-1-(3-fluoro-phenyl)-ethanone gave the title compound.
ES-MS m/e (%): 595.3(M+H$^+$).

Example 153

1'-({6-Chloro-1-[2-(2-fluorophenyl)-2-oxoethyl]-1H-indol-3-yl}carbonyl)-3H-spiro[2-benzofuran-1,4'-piperidin]-3-one

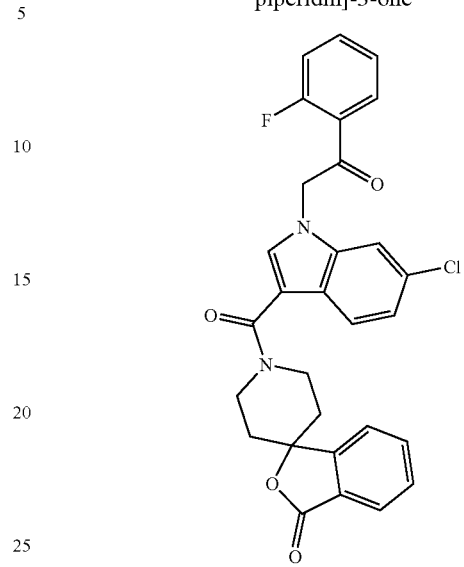

Following the general procedure III as described above, the alkylation of 3H-spiro[2-benzofuran-1,4'-piperidin]-3-one prepared as described in example 16 with commercially available 2-chloro-1-(3-fluoro-phenyl)-ethanone gave the title compound.
ES-MS m/e (%): 517.4(M+H$^+$).

Example 154

1'-({6-Chloro-1-[2-(3,4-difluorophenyl)-2-oxoethyl]-1H-indol-3-yl}carbonyl)-3H-spiro[2-benzofuran-1,4'-piperidin]-3-one

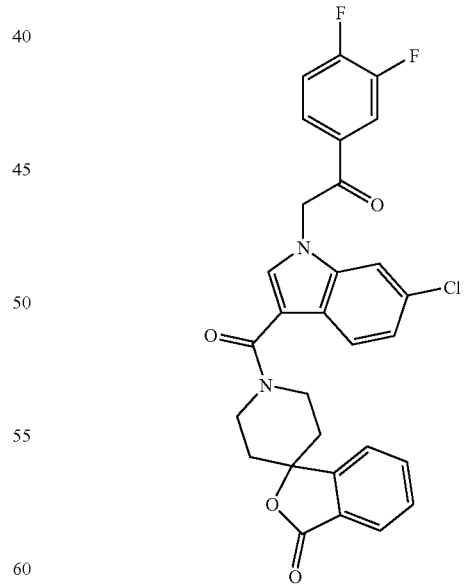

Following the general procedure III as described above, the alkylation of 3H-spiro[2-benzofuran-1,4'-piperidin]-3-one prepared as described in example 16 above with commercially available 2-chloro-1-(3,4-difluoro-phenyl)-ethanone gave the title compound.
ES-MS m/e (%): 535.4(M+H$^+$).

Example 155

1'-{[6-Chloro-1-(3-fluorophenyl)-1H-indol-3-yl]carbonyl}-3H-spiro[2-benzofuran-1,4'-piperidin]-3-one

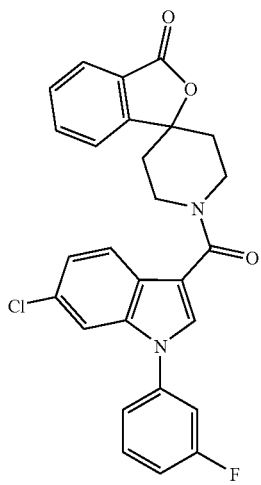

Following the general procedure VI as described above, the arylation of 1'-[(6-chloro-1H-indol-3-yl)carbonyl]-3H-spiro[2-benzofuran-1,4'-piperidin]-3-one (prepared according to example 16 above) with commercially available 3-fluorophenylboronic acid gave the title compound. ES-MS m/e (%): 475.0(M+H⁺).

Example 156

1'-[(1-Biphenyl-3-yl-6-chloro-1H-indol-3-yl)carbonyl]-3H-spiro[2-benzofuran-1,4'-piperidin]-3-one

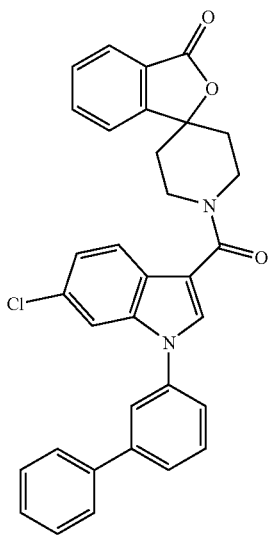

Following the general procedure VI as described above, the arylation of 1'-[(6-chloro-1H-indol-3-yl)carbonyl]-3H-spiro[2-benzofuran-1,4'-piperidin]-3-one (prepared according to example 16) with commercially available 3-biphenylboronic acid gave the title compound.

ES-MS m/e (%): 533.0(M+H⁺).

Example 157

1'-[(1-Biphenyl-2-yl-6-chloro-1H-indol-3-yl)carbonyl]-3H-spiro[2-benzofuran-1,4'-piperidin]-3-one

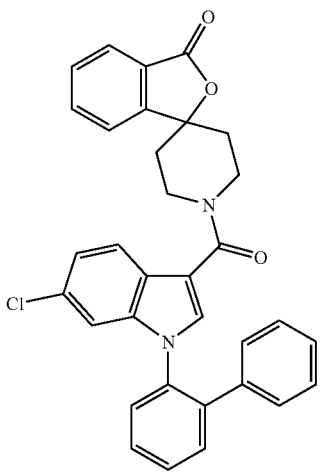

Following the general procedure VI as described above, the arylation of 1'-[(6-chloro-1H-indol-3-yl)carbonyl]-3H-spiro[2-benzofuran-1,4'-piperidin]-3-one (prepared according to example 16) with commercially available 2-biphenylboronic acid gave the title compound.

ES-MS m/e (%): 533.0(M+H⁺).

Example 158

1'-{[1-(Biphenyl-3-ylcarbonyl)-6-chloro-1H-indol-3-yl]carbonyl}-3H-spiro[2-benzofuran-1,4'-piperidin]-3-one

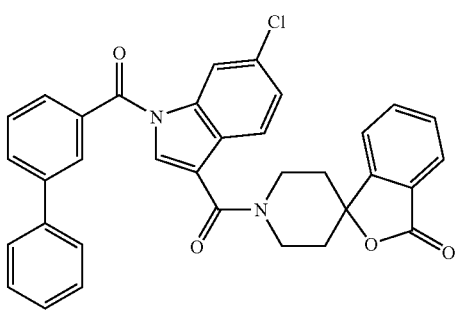

Following the general procedure VII as described above, the acylation of 1'-[(6-chloro-1H-indol-3-yl)carbonyl]-3H-spiro[2-benzofuran-1,4'-piperidin]-3-one (prepared according to example 16) with commercially available biphenyl-3-carbonyl chloride gave the title compound.

ES-MS m/e (%): 561.4(M+H⁺).

Example 159

1-[(6-Chloro-1-pyridin-2-yl-1H-indol-3-yl)carbonyl]-3H-spiro[2-benzofuran-1,4'-piperidin]-3-one

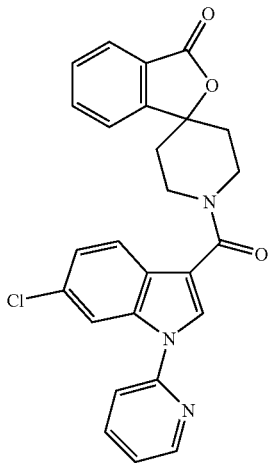

To a solution of 1'-[(6-chloro-1H-indol-3-yl)carbonyl]-3H-spiro[2-benzofuran-1,4'-piperidin]-3-one (prepared according to example 16 above) in dry DMF was added NaH (1 eq) and the reaction mixture stirred at room temperature for 30 min and then treated with 2-fluoropyridine (1.5 eq) and heated at 140° C. under microwave irradiation for 15 min. Purification by preparative HPLC gave the desired product in 38% yield.

ES-MS m/e (%): 458.1(M+H$^+$).

Example 160

1-[(6-Chloro-1-pyridin-2-yl-1H-indol-3-yl)carbonyl]-5-fluoro-3H-spiro[2-benzofuran-1,4'-piperidin]-3-one

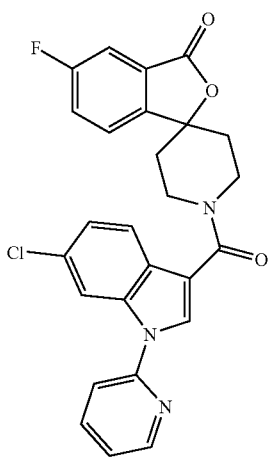

To a solution of 1'-[(6-chloro-1H-indol-3-yl)carbonyl]-5-fluoro-3H-spiro[2-benzofuran-1,4'-piperidin]-3-one (prepared according to example 19) in dry DMF was added NaH (1 eq) and the reaction mixture stirred at room temperature for 30 min and then treated with 2-fluoropyridine (1.5 eq) and heated at 140° C. under microwave irradiation for 15 min. Purification by preparative HPLC gave the desired product in 36% yield.

ES-MS m/e (%): 476.0(M+H$^+$).

Example 161

1'-({6-Chloro-1-[(2-methylpyridin-4-yl)methyl]-1H-indol-3-yl}carbonyl)-5-fluoro-3H-spiro[2-benzofuran-1,4'-piperidin]-3-one

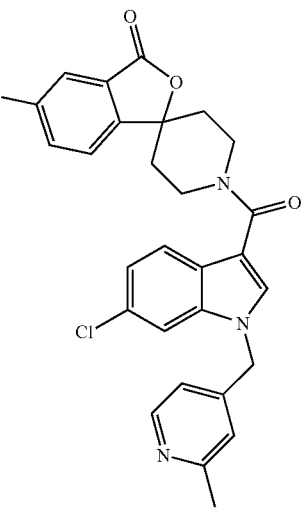

Following the general procedure III as described above, the alkylation of 1'-[(6-chloro-1H-indol-3-yl)carbonyl]-5-fluoro-3H-spiro[2-benzofuran-1,4'-piperidin]-3-one (prepared according to example 19) with 4-chloromethyl-2-methyl-pyridine (described in WO 2006023707) gave the title compound. ES-MS m/e (%): 504.2(M+H$^+$).

Example 162

1'-[(1-{[4-Amino-2-(methoxymethyl)pyrimidin-5-yl]methyl}-6-chloro-1H-indol-3-yl)carbonyl]-5-fluoro-3H-spiro[2-benzofuran-1,4'-piperidin]-3-one

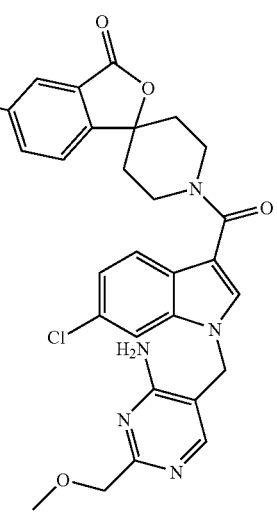

Following the general procedure III as described above, the alkylation of 1'-[(6-chloro-1H-indol-3-yl)carbonyl]-5-fluoro-3H-spiro[2-benzofuran-1,4'-piperidin]-3-one (prepared according to example 19) with 5-chloromethyl-2-methoxy-pyrimidin-4-ylamine gave the title compound. ES-MS m/e (%): 550.2(M+H$^+$).

Example 163

1'-({1-[(4-Amino-2-methylpyrimidin-5-yl)methyl]-6-chloro-1H-indol-3-yl}carbonyl)-5-fluoro-3H-spiro[2-benzofuran-1,4'-piperidin]-3-one

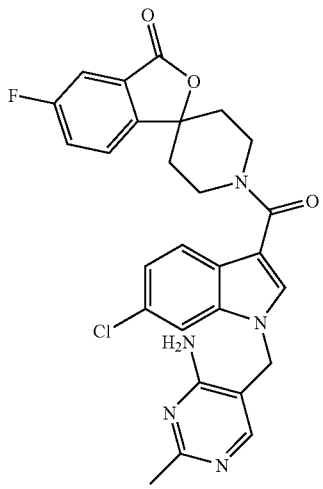

Following the general procedure III as described above, the alkylation of 1'-[(6-chloro-1H-indol-3-yl)carbonyl]-5-fluoro-3H-spiro[2-benzofuran-1,4'-piperidin]-3-one (prepared according to example 19 above) with 5-chloromethyl-2-methyl-pyrimidin-4-ylamine (described in Pharmaceutical Chemistry Journal (Translation of Khimiko-Farmatsevticheskii Zhurnal) (1999), 33(2), 101-103) gave the title compound.
ES-MS m/e (%): 520.2(M+H$^+$).

Example 164

1'-({6-Chloro-1-[(6-chloropyridin-3-yl)methyl]-1H-indol-3-yl}carbonyl)-5-fluoro-3H-spiro[2-benzofuran-1,4'-piperidin]-3-one

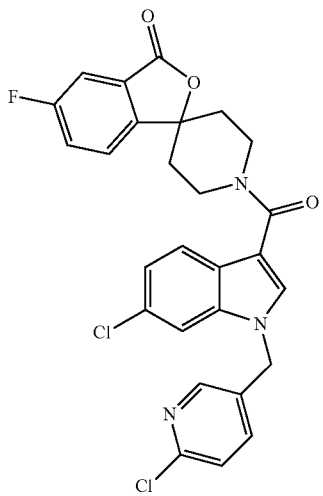

Following the general procedure III as described above, the alkylation of 1'-[(6-chloro-1H-indol-3-yl)carbonyl]-5-fluoro-3H-spiro[2-benzofuran-1,4'-piperidin]-3-one (prepared according to example 19) with commercially available 2-chloro-5-chloromethylpyridine gave the title compound.
ES-MS m/e (%): 524.1(M+H$^+$).

Example 165

1'-({6-Chloro-1-[(3-chloro-6-methylpyridazin-4-yl)methyl]-1H-indol-3-yl}carbonyl)-5-fluoro-3H-spiro[2-benzofuran-1,4'-piperidin]-3-one

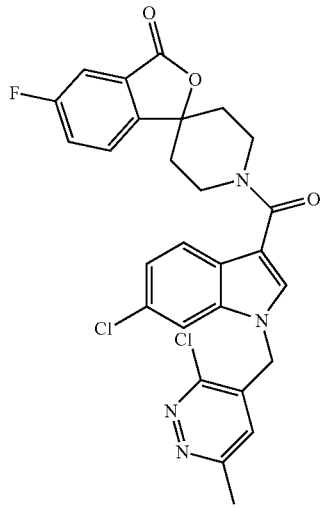

Following the general procedure III as described above, the alkylation of 1'-[(6-chloro-1H-indol-3-yl)carbonyl]-5-fluoro-3H-spiro[2-benzofuran-1,4'-piperidin]-3-one (prepared according to example 19 above) with 3-chloro-4-chloromethyl-6-methyl-pyridazine (prepared by U.S. Pat. No. 3,453,277) gave the title compound. ES-MS m/e (%): 539.1(M+H$^+$).

Example 166

1'-{[6-Chloro-1-(pyridin-4-ylmethyl)-1H-indol-3-yl]carbonyl}-5-fluoro-3H-spiro[2-benzofuran-1,4'-piperidin]-3-one

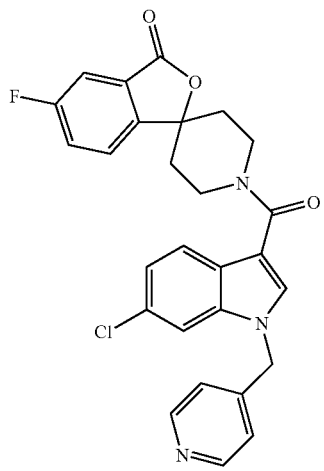

Following the general procedure III as described above, the alkylation of 1'-[(6-chloro-1H-indol-3-yl)carbonyl]-5-fluoro-3H-spiro[2-benzofuran-1,4'-piperidin]-3-one (prepared according to example 19) with commercially available 4-bromomethyl-pyridine gave the title compound.

$^1$H-NMR (300 MHz, CDCl$_3$): δ 1.75 (m, 2H), 2.26-2.39 (m, 2H), 3.3 (m, 2H), 4.45 (m, 2H), 5.6 (s, 2H), 7.15 (m, 3H), 7.65 (m, 3H), 7.8 (d,1H), 7.92 (m,1H), 8.03 (s,1H), 8.52(d,2H)

Example 167

1'-{[6-Chloro-1-(2-pyridin-4-ylethyl)-1H-indol-3-yl]carbonyl}-5-fluoro-3H-spiro[2-benzofuran-1,4'-piperidin]-3-one

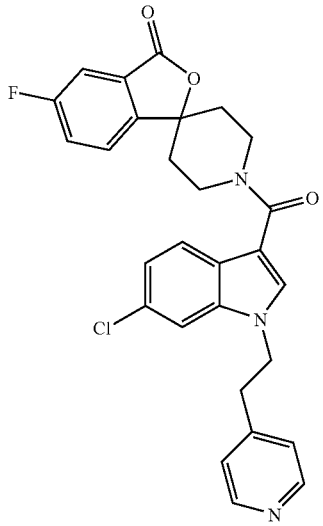

Following the general procedure III as described above, the alkylation of 1'-[(6-chloro-1H-indol-3-yl)carbonyl]-5-fluoro-3H-spiro[2-benzofuran-1,4'-piperidin]-3-one (prepared according to example 19) with commercially available 4-(2-bromo-ethyl)-pyridine gave the title compound. ES-MS m/e (%): 504.2(M+H$^+$).

Example 168

1'-{[6-Chloro-1-(pyridin-4-ylmethyl)-1H-indol-3-yl]carbonyl}-3H-spiro[2-benzofuran-1,4'-piperidin]-3-one

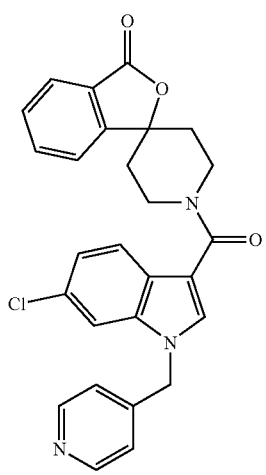

Following the general procedure III as described above, the alkylation of 1'-[(6-chloro-1H-indol-3-yl)carbonyl]-3H-spiro[2-benzofuran-1,4'-piperidin]-3-one (prepared according to example 16) with commercially available 4-bromomethyl-pyridine gave the title compound.
ES-MS m/e (%): 472.3(M+H$^+$).

Example 169

1'-{[6-Chloro-1-(2-oxo-2-pyridin-2-ylethyl)-1H-indol-3-yl]carbonyl}-5-fluoro-3H-spiro[2-benzofuran-1,4'-piperidin]-3-one

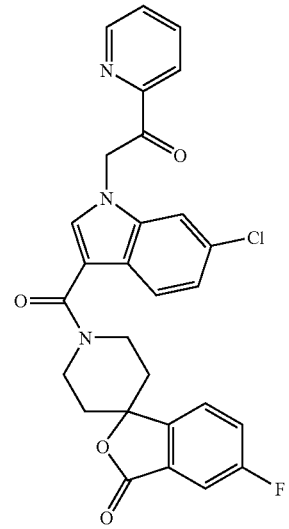

Following the general procedure III as described above, the alkylation of 1'-[(6-chloro-1H-indol-3-yl)carbonyl]-5-fluoro-3H-spiro[2-benzofuran-1,4'-piperidin]-3-one (prepared according to example 19 above) with commercially available 2-bromo-1-pyridin-2-ylethanone gave the title compound.
ES-MS m/e (%): 518.4(M+H$^+$).

Example 170

1'-({6-Chloro-1-[2-(5-methyl-2-phenyl-1,3-oxazol-4-yl)-2-oxoethyl]-1H-indol-3-yl}carbonyl)-5-fluoro-3H-spiro[2-benzofuran-1,4'-piperidin]-3-one

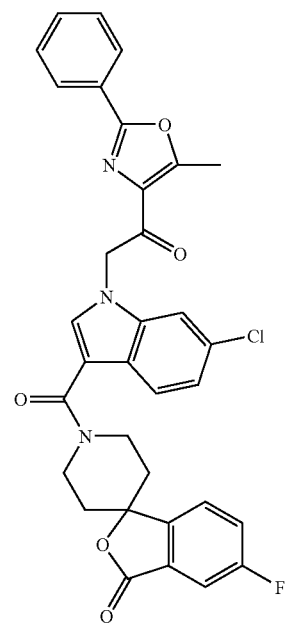

Following the general procedure III as described above, the alkylation of 1'-[(6-chloro-1H-indol-3-yl)carbonyl]-5-fluoro-3H-spiro[2-benzofuran-1,4'-piperidin]-3-one (prepared according to example 19) with 2-bromo-1-(5-methyl-2-phenyl-oxazol-4-yl)-ethanone (described in Journal of Medicinal Chemistry (1992), 35(14), 2617-26) gave the title compound.

ES-MS m/e (%): 598.4(M+H⁺).

Example 171

1'-{[6-Chloro-1-(pyridin-2-ylmethyl)-1H-indol-3-yl]carbonyl}-5-fluoro-3H-spiro[2-benzofuran-1,4'-piperidin]-3-one a) Methanesulfonic acid pyridin-3-ylmethyl ester To a mixture of 2-(hydroxymethyl)pyridine, DMAP and NEt₃ was slowly added MsCl at 0° C. and the reaction mixture was stirred at room temperature for 1 h. The reaction mixture was extracted with water and dichloromethane The organic phase was dried on Na₂SO₄, filtered and the solvent was evaporated. Silica gel column chromatography (dichloromethane/MeOH 99:1) gave the title compound in 52% yield.

ES-MS m/e (%): 188.1 (M+H⁺).

b) 1'-{[6-chloro-1-(pyridin-2-ylmethyl)-1H-indol-3-yl]carbonyl}-5-fluoro-3H-spiro[2-benzofuran-1,4'-piperidin]-3-one

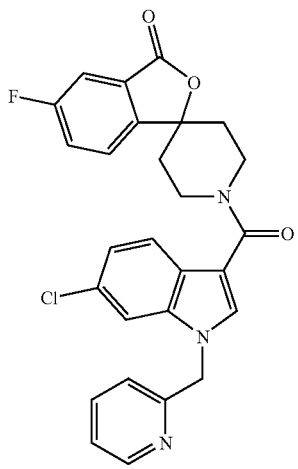

Following the general procedure III as described above, the alkylation of 1'-[(6-chloro-1H-indol-3-yl)carbonyl]-5-fluoro-3H-spiro[2-benzofuran-1,4'-piperidin]-3-one (prepared according to example 19) with methanesulfonic acid pyridin-2-ylmethyl ester (described in WO 9955318) gave the desired product in 29% yield;

ES-MS m/e (%): 490.0(M+H⁺).

Example 172

1'-{[6-Chloro-1-(pyridin-3-ylmethyl)-1H-indol-3-yl]carbonyl}-3H-spiro[2-benzofuran-1,4'-piperidin]-3-one

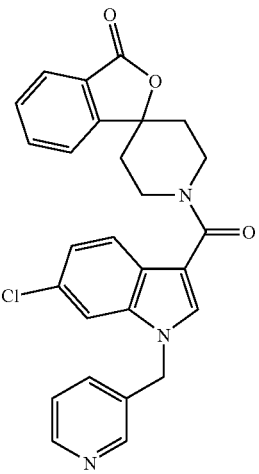

Following the general procedure III as described above, the alkylation of 1'-[(6-chloro-1H-indol-3-yl)carbonyl]-3H-spiro[2-benzofuran-1,4'-piperidin]-3-one (prepared according to example 16) with commercially available 3-bromomethyl-pyridine gave the title compound.

ES-MS m/e (%): 472.1(M+H⁺).

Example 173

1'-{[6-Chloro-1-(pyrazin-2-ylmethyl)-1H-indol-3-yl]carbonyl}-5-fluoro-3H-spiro[2-benzofuran-1,4'-piperidin]-3-one

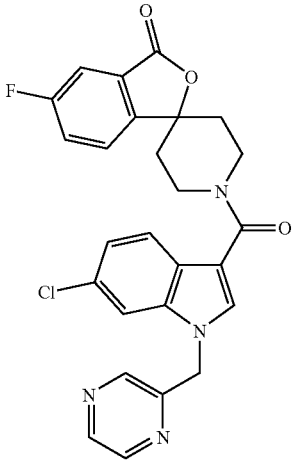

Following the general procedure III as described above, the alkylation of 1'-[(6-chloro-1H-indol-3-yl)carbonyl]-5-fluoro-3H-spiro[2-benzofuran-1,4'-piperidin]-3-one (prepared according to example 19) with methanesulfonic acid pyrazin-2-ylmethyl ester (preparation described in WO 2002064574) gave the title compound.

ES-MS m/e (%): 491.0(M+H⁺).

Example 174

1'-{[6-Chloro-1-(pyrimidin-5-ylmethyl)-1H-indol-3-yl]carbonyl}-5-fluoro-3H-spiro[2-benzofuran-1,4'-piperidin]-3-one a) Methanesulfonic acid pyrimidin-5-ylmethyl ester To a mixture of pyrimidin-5-yl-methanol, DMAP and NEt₃ was slowly added MsCl at 0° C. and the reaction mixture was stirred at room temperature for 3 h. The reaction mixture was extracted with water and dichloromethane. The organic phase was dried on Na₂SO₄, filtered and the solvent was evaporated. Silica gel column chromatography (Ethyl acetate/hexane 1:1) gave the title compound in 40% yield.

b) 1'-{[6-Chloro-1-(pyrimidin-5-ylmethyl)-1H-indol-3-yl]carbonyl}-5-fluoro-3H-spiro[2-benzofuran-1,4'-piperidin]-3-one

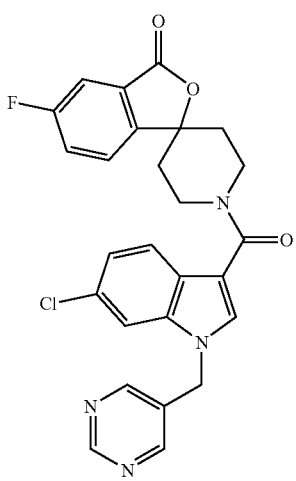

Following the general procedure III as described above, the alkylation of 1'-[(6-chloro-1H-indol-3-yl)carbonyl]-5-fluoro-3H-spiro[2-benzofuran-1,4'-piperidin]-3-one (prepared according to example 19) with methanesulfonic acid pyrimidin-5-ylmethyl ester gave the title compound. ES-MS m/e (%): 491.0(M+H⁺).

Example 175

3-{6-Chloro-3-[(5-fluoro-3-oxo-1'H,3H-spiro[2-benzofuran-1,4'-piperidin]-1'-yl)carbonyl]-1H-indol-1-yl}propanenitrile

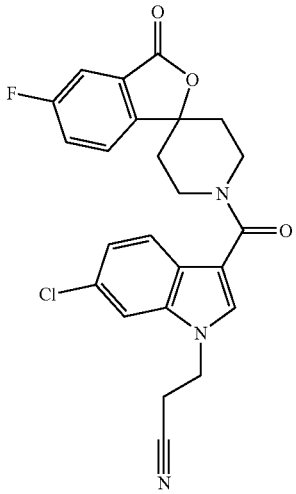

Following the general procedure III as described above, the alkylation of 1'-[(6-chloro-1H-indol-3-yl)carbonyl]-5-fluoro-3H-spiro[2-benzofuran-1,4'-piperidin]-3-one (prepared according to example 19) with commercially available 3-bromo-propionitrile gave the title compound.

ES-MS m/e (%): 452.0(M+H⁺).

Example 176

1'-[(7-Chloro-1-oxo-1,2,3,4-tetrahydropyrazino[1,2-a]indol-10-yl)carbonyl]-5-fluoro-3H-spiro[2-benzofuran-1,4'-piperidin]-3-one a) 6-Chloro-1H-indole-2,3-dicarboxylic acid 2-ethyl ester

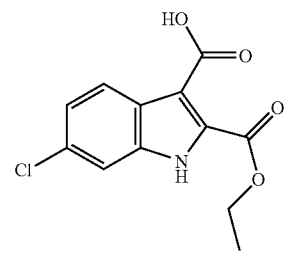

To a solution of commercially available 6-chloro-3-formyl-1H-indole-2-carboxylic acid ethyl ester in t-BuOH and 2-methyl-2-butene (50 eq) was added 9.2 eq NaClO₂ (9 eq) and aq. NaH₂PO₄ (7 eq) and stirred 12 h at room temperature. After concentration the mixture was dissolved in H₂O and adjusted to pH7 and then extracted with EtOAc; partial concentration of the organic phase precipitated the product in 52% yield.

b) Ethyl 6-chloro-3-[(5-fluoro-3-oxo-1'H,3H-spiro[2-benzofuran-1,4'-piperidin]-1'-yl)carbonyl]-1H-indole-2-carboxylate

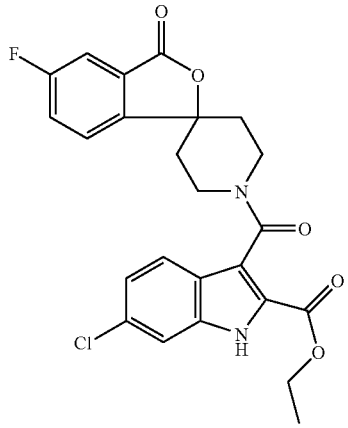

Following the general procedure I as described above, the acylation of 1'-[(6-chloro-1H-indol-3-yl)carbonyl]-5-fluoro-3H-spiro[2-benzofuran-1,4'-piperidin]-3-one (prepared according to example 19) with 6-chloro-1H-indole-2,3-dicarboxylic acid 2-ethyl ester gave the title compound. ES-MS m/e (%): 471.0 (M+H⁺).

c) 6-Chloro-3-[(5-fluoro-3-oxo-1'H,3H-spiro[2-benzofuran-1,4'-piperidin]-1'-yl)carbonyl]-1H-indole-2-carboxylic acid

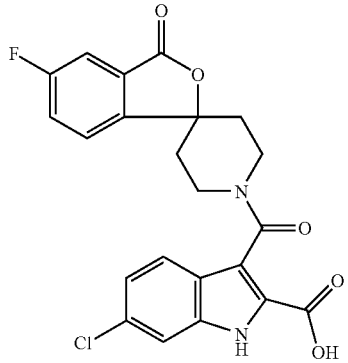

A solution of the ethyl 6-chloro-3-[(5-fluoro-3-oxo-1'H,3H-spiro[2-benzofuran-1,4'-piperidin]-1'-yl)carbonyl]-1H-indole-2-carboxylate in EtOH was treated with 2 eq. of aq. 1N LiOH at 80° C. for 12 h, then concentrated and dissolved in 1N HCl and extracted with dichloromethane. Evaporation of the solvent gave the title compound in 72% yield.

d) 6-Chloro-N-(2-chloroethyl)-3-(5-fluoro-3-oxo-1'H,3H-spiro[2-benzofuran-1,4'-piperidin]-1'-yl)carbonyl]-1H-indole-2-carboxamide

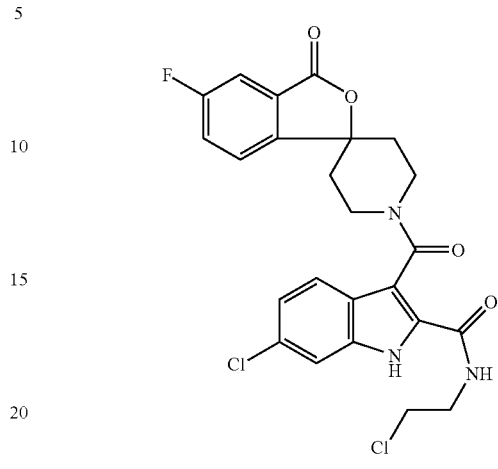

To a stirred solution of 6-chloro-3-[(5-fluoro-3-oxo-1'H,3H-spiro[2-benzofuran-1,4'-piperidin]-1'-yl)carbonyl]-1H-indole-2-carboxylic acid in dichloromethane were added EDC, HOBt, NEt₃ and 2-chloroethylamine hydrochloride. The reaction mixture was stirred at room temperature for 2 days. The reaction mixture was poured onto water and extracted with dichloromethane. The combined organic phases were dried over Na₂SO₄ and the solvent was evaporated. Column chromatography (ethyl acetate/hexane 1:1) gave the desired compound in 59% yield. MS m/e (%): 504.0 (M+H⁺).

e) 1'-[(7-Chloro-1-oxo-1,2,3,4-tetrahydropyrazino[1,2-a]indol-10-yl)carbonyl]-5-fluoro-3H-spiro[2-benzofuran-1,4'-piperidin]-3-one

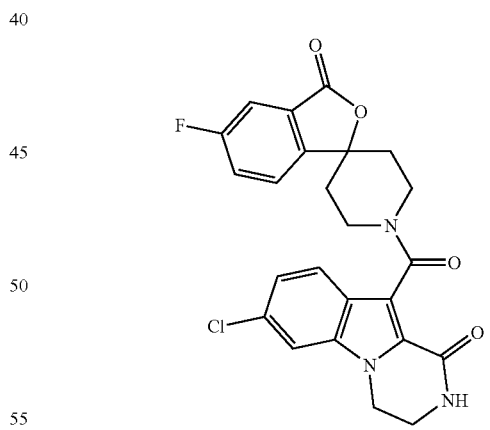

A solution of the 6-chloro-N-(2-chloroethyl)-3-[(5-fluoro-3-oxo-1'H,3H-spiro[2-benzofuran-1,4'-piperidin]-1'-yl)carbonyl]-1H-indole-2-carboxamide in dry DMF was treated with NaH (1 eq) and stirred for 1 h at room temperature, then treated with a further portion of NaH (1 eq) and stirred for 2 h at room temperature. Dilution with water and extraction with EtOAc followed by washing with aq. NH₄Cl gave the crude product which was purified by silica gel chromatography (dichloromethane/MeOH 98:2) to give 42% yield of the desired product.

ES-MS m/e (%): 468.3 (M+H⁺).

Example 177

1'-({1-[(4-Benzylmorpholin-2-yl)methyl]-6-chloro-1H-indol-3-yl}carbonyl)-5-fluoro-3H-spiro[2-benzofuran-1,4'-piperidin]-3-one

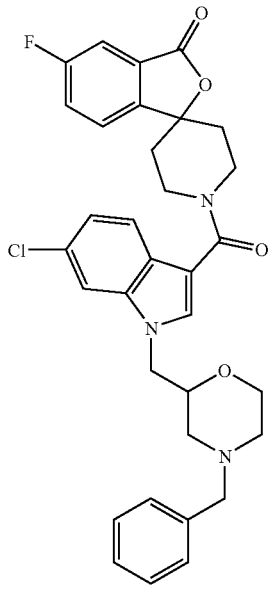

Following the general procedure III as described above, the alkylation of 1'-[(6-chloro-1H-indol-3-yl)carbonyl]-5-fluoro-3H-spiro[2-benzofuran-1,4'-piperidin]-3-one (prepared according to example 19 above) with commercially available 4-benzyl-2-(chloromethyl)morpholine gave the title compound.

ES-MS m/e (%): 588.2(M+H$^+$).

Example 178

1'-({6-Chloro-1-[(1,4-dibenzylpiperazin-2-yl)methyl]-1H-indol-3-yl}carbonyl)-5-fluoro-3H-spiro[2-benzofuran-1,4'-piperidin]-3-one

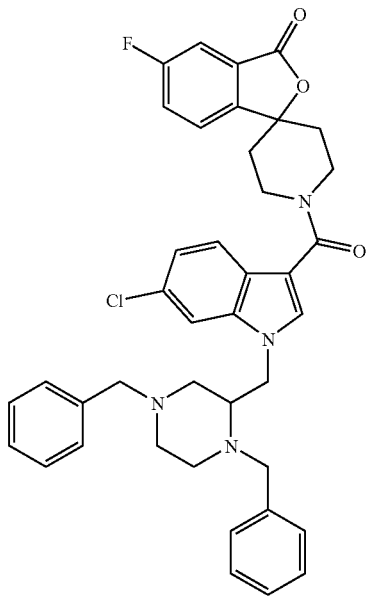

Following the general procedure III as described above, the alkylation of 1'-[(6-chloro-1H-indol-3-yl)carbonyl]-5-fluoro-3H-spiro[2-benzofuran-1,4'-piperidin]-3-one (prepared according to example 19) with 1,4-dibenzyl-2-chloromethyl-piperazine described in Journal of Medicinal Chemistry 1999, 42(9), 1587-1603) gave the title compound.

ES-MS m/e (%): 677.3(M+H$^+$).

Example 179

1'-({6-Chloro-1-[(5-methylisoxazol-3-yl)methyl]-1H-indol-3-yl}carbonyl)-5-fluoro-3H-spiro[2-benzofuran-1,4'-piperidin]-3-one

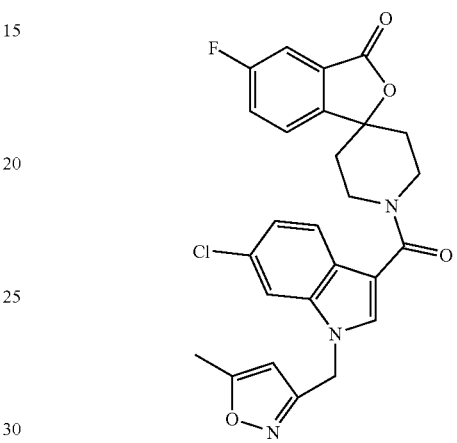

Following the general procedure III as described above, the alkylation of 1'-[(6-chloro-1H-indol-3-yl)carbonyl]-5-fluoro-3H-spiro[2-benzofuran-1,4'-piperidin]-3-one (prepared according to example 19) with methanesulfonic acid 5-methyl-isoxazol-3-ylmethyl ester (described in WO 2004092172) gave the title compound.

ES-MS m/e (%): 494.1(M+H$^+$).

Example 180

1'-{[6-Chloro-1-(pyridin-2-ylmethyl)-1H-indol-3-yl]carbonyl}-3H-spiro[2-benzofuran-1,4'-piperidin]-3-one

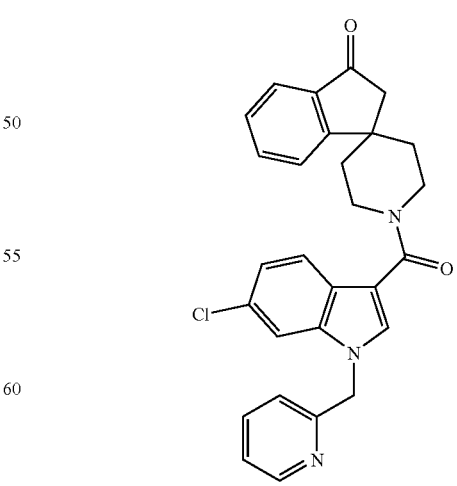

Following the general procedure III as described above, the alkylation of 1'-[(6-chloro-1H-indol-3-yl)carbonyl]-3H-spiro[2-benzofuran-1,4'-piperidin]-3-one (prepared according to example 16 above) with methanesulfonic acid pyridin-2-ylmethyl ester (described in WO 9955318) gave the title compound.

ES-MS m/e (%): 472.1(M+H+).

Example 181

6-Chloro-3-[(5-fluoro-3-oxo-1'H,3H-spiro[2-benzofuran-1,4'-piperidin]-1'-yl)carbonyl]-N-methyl-1H-indole-2-carboxamide

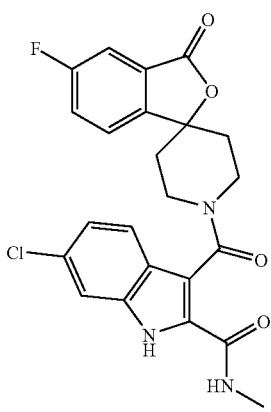

A suspension of the 6-chloro-3-[(5-fluoro-3-oxo-1'H,3H-spiro[2-benzofuran-1,4'-piperidin]-1'-yl)carbonyl]-1H-indole-2-carboxylic acid in dichloromethane was treated with EDC (1.2 eq), HOBt (1.2 eq) and Et₃N (1.2 eq) and the solution stirred at room temperature for 15 min. Methylamine (1 eq) was then added and the reaction mixture stirred at room temperature for 16 h. Purification by preparative HPLC yielded the desired product.

ES-MS m/e (%): 456.1(M+H+).

Example 182

1'-({6-Chloro-1-[(5-cyclopropyl-2-methyl-1,3-oxazol-4-yl)methyl]-1H-indol-3-yl}carbonyl)-5-fluoro-3H-spiro[2-benzofuran-1,4'-piperidin]-3-one a) 2-Acetylamino-2-cyclopropanecarbonyl-malonic acid diethyl ester

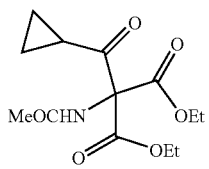

To a solution of 6 eq KO$_t$-Bu in THF at room temperature was added 6 eq 2-acetylamino-malonic acid diethyl ester and after 5 min 1 eq cyclopropane-carbonylchloride. After 15 min, the mixture was concentrated and partitioned between EtOAc and H₂O. The organic layer was concentrated to give the desired product in 60% yield.

ES-MS m/e (%): 286.2 (M+H+).

b) 5-Cyclopropyl-2-methyl-oxazole-4-carboxylic Acid Ethyl Ester

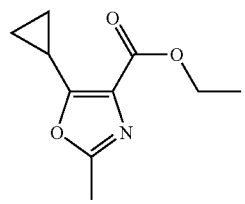

2-Acetylamino-2-cyclopropanecarbonyl-malonic acid diethyl ester in DMSO was treated with 2 eq H₂O and stirred at room temperature for 6 h then extracted with Et₂O to give after concentration the title compound in 34% yield.

c) (5-Cyclopropyl-2-methyl-oxazol-4-yl)-methanol

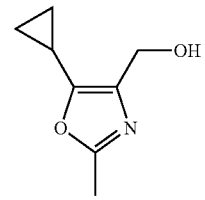

A solution of 5-cyclopropyl-2-methyl-oxazole-4-carboxylic acid ethyl ester in Et₂O at 0° C. was treated sequentially with (2×2.3 eq) LiBH₄ and stirred for 1 h. 10 eq of MeOH were then added and the solution stirred for 4 h at room temperature. Sequential addition of aq NH₄Cl (H₂ evolution) and then Na₂CO₃/NaCl gave a mixture which was extracted with EtOAc to give after concentration the title compound in 16% yield.

ES-MS m/e (%): 154.1 (M+H+).

d) 1'-({6-Chloro-1-[(5-cyclopropyl-2-methyl-1,3-oxazol-4-yl)methyl]-1H-indol-3-yl}carbonyl)-5-fluoro-3H-spiro[2-benzofuran-1,4'-piperidin]-3-one

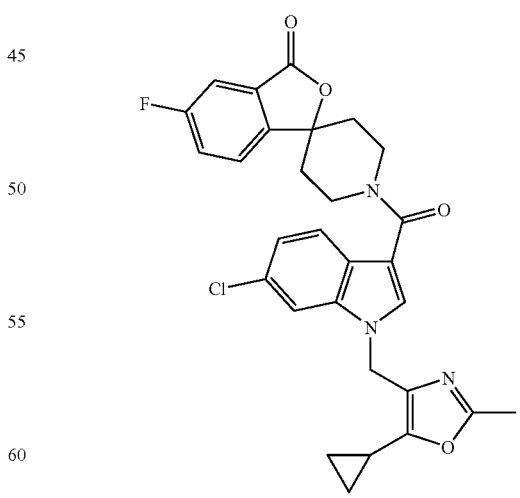

Following the general procedure III as described above, the alkylation of 1'-[(6-chloro-1H-indol-3-yl)carbonyl]-5-fluoro-3H-spiro[2-benzofuran-1,4'-piperidin]-3-one (prepared according to example 19) with methanesulfonic acid 5-cyclopropyl-2-methyl-oxazol-4-ylmethyl ester (prepared by mesylation of (5-cyclopropyl-2-methyl-oxazol-4-yl)-methanol) gave the title compound. ES-MS m/e (%): 534.2 (M+H⁺).

Example 183

1'-({6-Chloro-1-[(1-methyl-1H-imidazol-5-yl)methyl]-1H-indol-3-yl}carbonyl)-5-fluoro-3H-spiro[2-benzofuran-1,4'-piperidin]-3-one

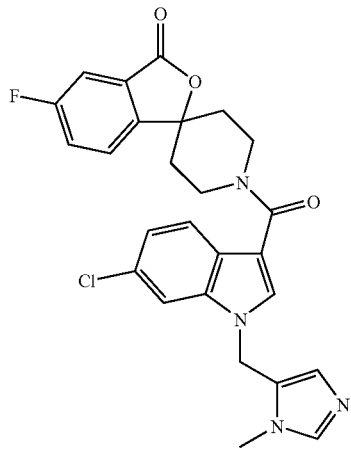

Following the general procedure III as described above, the alkylation of 1'-[(6-chloro-1H-indol-3-yl)carbonyl]-5-fluoro-3H-spiro[2-benzofuran-1,4'-piperidin]-3-one (prepared according to example 19) with methanesulfonic acid 3-methyl-3H-imidazol-4-ylmethyl ester (prepared by mesylation of the commercially available (3-methyl-3H-imidazol-4-yl)-methanol) gave the title compound. ES-MS m/e (%): 493.1(M+H⁺).

Example 184

1'-({6-Chloro-1-[(3-methylisoxazol-5-yl)methyl]-1H-indol-3-yl}carbonyl)-5-fluoro-3H-spiro[2-benzofuran-1,4'-piperidin]-3-one

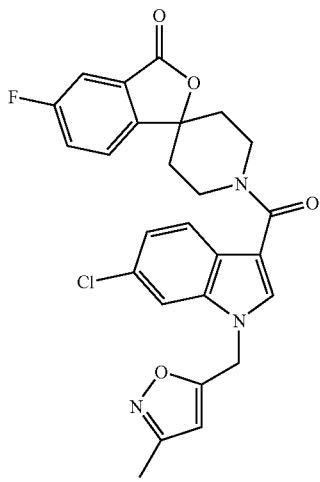

Following the general procedure III as described above, the alkylation of 1'-[(6-chloro-1H-indol-3-yl)carbonyl]-5-fluoro-3H-spiro[2-benzofuran-1,4'-piperidin]-3-one (prepared according to example 19) with methanesulfonic acid 3-methyl-isoxazol-5-ylmethyl ester (described in Heterocycles, 23(3), 571-83; 1985) gave the title compound. ES-MS m/e (%): 494.1(M+H⁺).

Example 185

1'-({6-Chloro-1-[(1,5-dimethyl-1H-pyrazol-3-yl)methyl]-1H-indol-3-yl}carbonyl)-5-fluoro-3H-spiro[2-benzofuran-1,4'-piperidin]-3-one

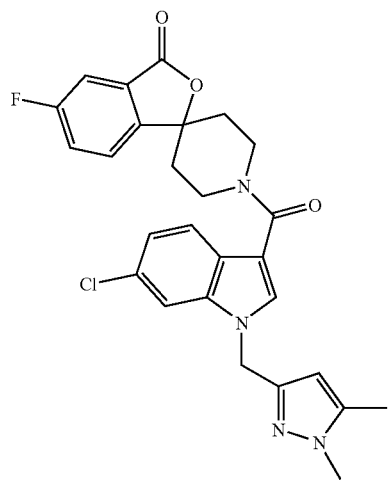

Following the general procedure III as described above, the alkylation of 1'-[(6-chloro-1H-indol-3-yl)carbonyl]-5-fluoro-3H-spiro[2-benzofuran-1,4'-piperidin]-3-one (prepared according to example 19) with methanesulfonic acid 1,5-dimethyl-1H-pyrazol-3-ylmethyl ester (prepared by mesylation of commercially available methanesulfonic acid 1,5-dimethyl-1H-pyrazol-3-ylmethyl ester) gave the title compound. ES-MS m/e (%): 507.2(M+H⁺).

Example 186

1'-({6-Chloro-1-[(3,5-dimethylisoxazol-4-yl)methyl]-1H-indol-3-yl}carbonyl)-5-fluoro-3H-spiro[2-benzofuran-1,4'-piperidin]-3-one

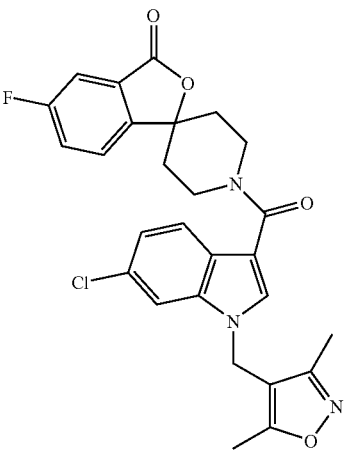

Following the general procedure III as described above, the alkylation of 1'-[(6-chloro-1H-indol-3-yl)carbonyl]-5-fluoro-3H-spiro[2-benzofuran-1,4'-piperidin]-3-one (prepared according to example 19 above) with methanesulfonic acid 3,5-dimethyl-isoxazol-4-ylmethyl ester (prepared by mesylation of the commercially available 1,5-dimethyl-1H-pyrazol-3-yl)-methanol) gave the title compound. ES-MS m/e (%): 508.2(M+H$^+$).

Example 187

1'-({6-Chloro-1-[(2,5-dimethyl-1,3-oxazol-4-yl)methyl]-1H-indol-3-yl}carbonyl)-5-fluoro-3H-spiro[2-benzofuran-1,4'-piperidin]-3-one

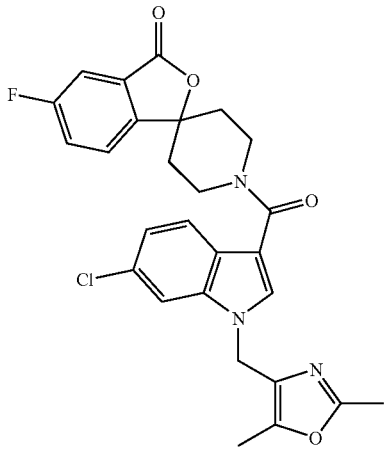

Following the general procedure III as described above, the alkylation of 1'-[(6-chloro-1H-indol-3-yl)carbonyl]-5-fluoro-3H-spiro[2-benzofuran-1,4'-piperidin]-3-one (prepared according to example 19 above) with methanesulfonic acid 2,5-dimethyl-oxazol-4-ylmethyl ester (prepared by mesylation of (2,5-dimethyl-oxazol-4-yl)-methanol, described in Organic Letters (1999), 1(1), 87-90) gave the title compound.
ES-MS m/e (%): 508.1(M+H$^+$).

Example 188

1'-({6-Chloro-1-[(3-fluorooxetan-3-yl)methyl]-1H-indol-3-yl}carbonyl)-5-fluoro-3H-spiro[2-benzofuran-1,4'-piperidin]-3-one

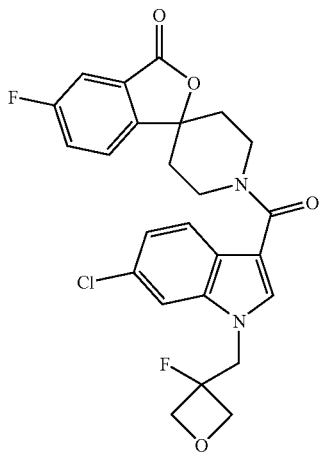

Following the general procedure III as described above, the alkylation of 1'-[(6-chloro-1H-indol-3-yl)carbonyl]-5-fluoro-3H-spiro[2-benzofuran-1,4'-piperidin]-3-one (prepared according to example 19) with 3-bromomethyl-3-fluoro-oxetane (described in US2005215599) gave the title compound. ES-MS m/e (%): 487.1(M+H$^+$).

Example 189

1'-({6-Chloro-1-[(3-fluorooxetan-3-yl)methyl]-1H-indol-3-yl}carbonyl)-3H-spiro[2-benzofuran-1,4'-piperidin]-3-one

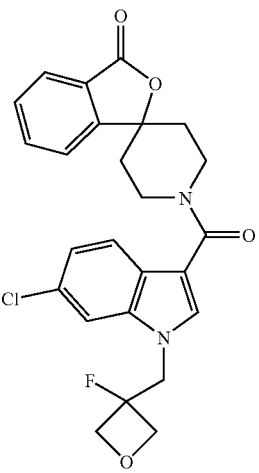

Following the general procedure III as described above, the alkylation of 1'-[(6-chloro-1H-indol-3-yl)carbonyl]-3H-spiro[2-benzofuran-1,4'-piperidin]-3-one (prepared according to example 16 above) with 3-bromomethyl-3-fluoro-oxetane (described in US2005215599) gave the title compound. ES-MS m/e (%): 469.2(M+H$^+$).

Example 190

1'-[(6-Chloro-1-{[1-(methoxymethyl)cyclopropyl]methyl}-1H-indol-3-yl)carbonyl]-5-fluoro-3H-spiro[2-benzofuran-1,4'-piperidin]-3-one

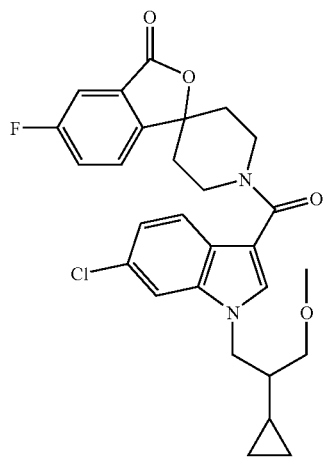

Following the general procedure III as described above, the alkylation of 1'-[(6-chloro-1H-indol-3-yl)carbonyl]-5-fluoro-3H-spiro[2-benzofuran-1,4'-piperidin]-3-one (prepared according to example 19) with 1-bromomethyl-1-methoxymethyl-cyclopropane (described in WO 2001032633) gave the title compound.
ES-MS m/e (%): 497.5(M+H⁺).

Example 191

[1-({6-Chloro-3-[(5-fluoro-3-oxo-1'H,3H-spiro[2-benzofuran-1,4'-piperidin]-1'-yl)carbonyl]-1H-indol-1-yl}methyl)cyclopropyl]acetonitrile

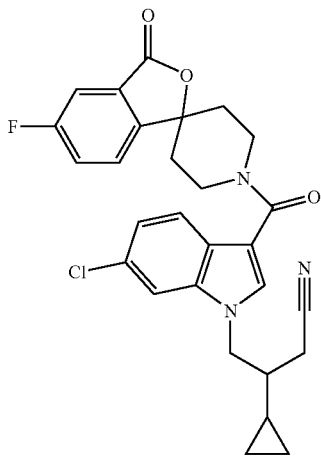

Following the general procedure III as described above, the alkylation of 1'-[(6-chloro-1H-indol-3-yl)carbonyl]-5-fluoro-3H-spiro[2-benzofuran-1,4'-piperidin]-3-one (prepared according to example 19) with 1-bromomethyl-cyclopropanecarbonitrile (described in EP 148004) gave the title compound. ES-MS m/e (%): 492.5(M+H⁺).

Example 192

1'-[(6-Chloro-1-{[1-(methoxymethyl)cyclopropyl]methyl}-1H-indol-3-yl)carbonyl]-3H-spiro[2-benzofuran-1,4'-piperidin]-3-one

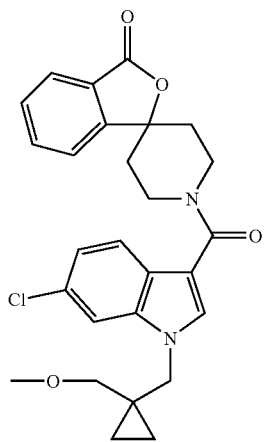

Following the general procedure III as described above, the alkylation of 1'-[(6-chloro-1H-indol-3-yl)carbonyl]-3H-spiro[2-benzofuran-1,4'-piperidin]-3-one (prepared according to example 16 above) with 1-bromomethyl-1-methoxymethyl-cyclopropane (prepared as described in WO 2001032633) gave the title compound.
ES-MS m/e (%): 479.5(M+H⁺).

Example 193

[1-({6-Chloro-3-[(3-oxo-1'H,3H-spiro[2-benzofuran-1,4'-piperidin]-1'-yl)carbonyl]-1H-indol-1-yl}methyl)cyclopropyl]acetonitrile

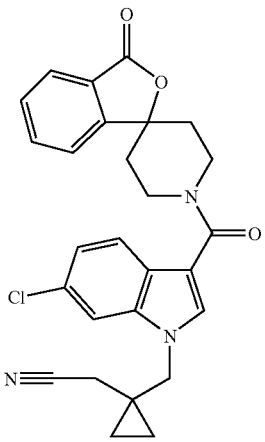

Following the general procedure III as described above, the alkylation of 1'-[(6-chloro-1H-indol-3-yl)carbonyl]-3H-spiro[2-benzofuran-1,4'-piperidin]-3-one (prepared according to example 16) with 1-bromomethyl-1-methoxymethyl-cyclopropane (prepared by WO 2001032633) gave the title compound. ES-MS m/e (%): 474.5(M+H⁺).

Example 194

6-Chloro-3-[(5-fluoro-3-oxo-1'H,3H-spiro[2-benzofuran-1,4'-piperidin]-1'-yl)carbonyl]-N-[2-(methylamino)ethyl]-1H-indole-2-carboxamide hydrochloride

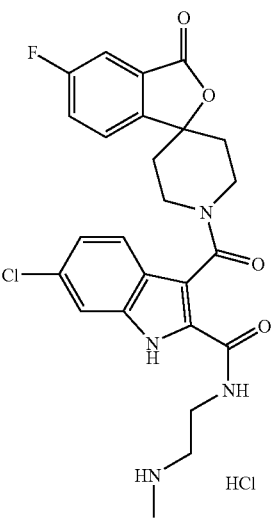

A solution of tert-butyl {2-[({6-chloro-3-[(5-fluoro-3-oxo-1'H,3H-spiro[2-benzofuran-1,4'-piperidin]-1'-yl)carbonyl]-1H-indol-2-yl}carbonyl)amino]ethyl}methylcarbamate was treated with 4 eq of HCl in dioxane and stirred at room temperature for 3 h then treated with a further portion of 4 eq of HCl in dioxane. The solution was stirred at room temperature for 16 h and evaporated to give the product in 58% yield.
ES-MS m/e (%): 511.2(M+H⁺).

Example 195

1'-({6-Chloro-1-[2-(tetrahydro-2H-pyran-4-yl)ethyl]-1H-indol-3-yl}carbonyl)-5-fluoro-3H-spiro[2-benzofuran-1,4'-piperidin]-3-one hydrochloride

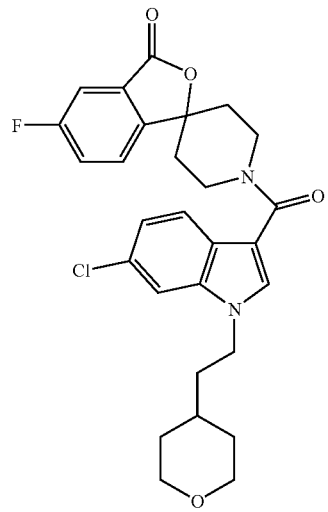

Following the general procedure III as described above, the alkylation of 1'-[(6-chloro-1H-indol-3-yl)carbonyl]-5-fluoro-3H-spiro[2-benzofuran-1,4'-piperidin]-3-one (prepared according to example 19) with 4-(2-bromo-ethyl)-tetrahydro-pyran (described in US 2004220214) gave the title compound. ES-MS m/e (%): 511.2 (M+H$^+$).

Example 196

1'-({6-Chloro-1-[2-(tetrahydro-2H-pyran-4-yl)ethyl]-1H-indol-3-yl}carbonyl)-3H-spiro[2-benzofuran-1,4'-piperidin]-3-one

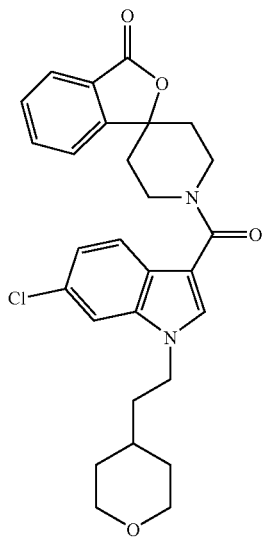

Following the general procedure III as described above, the alkylation of 1'-[(6-chloro-1H-indol-3-yl)carbonyl]-3H-spiro[2-benzofuran-1,4'-piperidin]-3-one (prepared according to example 16) with 4-(2-bromo-ethyl)-tetrahydro-pyran (described in US 2004220214) gave the title compound. ES-MS m/e (%): 493.2 (M+H$^+$).

Example 197 tert-Butyl 2-({6-chloro-3-[(3-oxo-1'H,3H-spiro[2-benzofuran-1,4'-piperidin]-1'-yl)carbonyl]-1H-indol-1-yl}methyl)morpholine-4-carboxylate

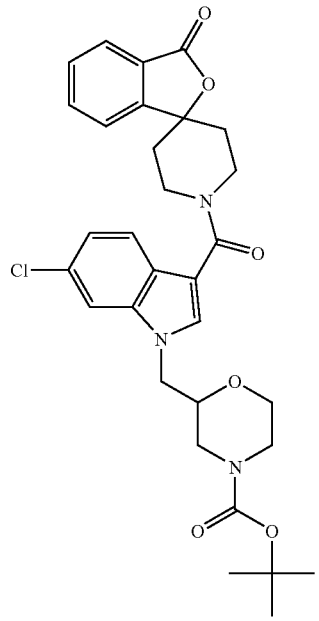

Following the general procedure III as described above, the alkylation of 1'-[(6-chloro-1H-indol-3-yl)carbonyl]-3H-spiro[2-benzofuran-1,4'-piperidin]-3-one (prepared according to example 16) with 2-chloromethyl-morpholine-4-carboxylic acid tert-butyl ester (described in WO 2006020415) gave the title compound. ES-MS m/e (%): 580.0(M+H$^+$).

Example 198

1'-{[6-Chloro-1-(morpholin-2-ylmethyl)-1H-indol-3-yl]carbonyl}-3H-spiro[2-benzofuran-1,4'-piperidin]-3-one hydrochloride

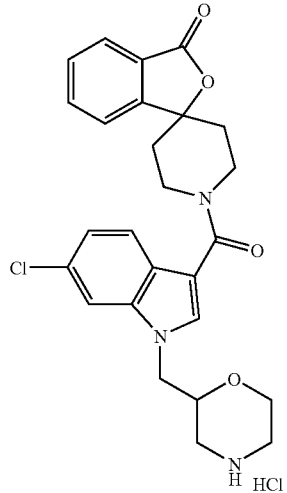

tert-Butyl 2-({6-chloro-3-[(3-oxo-1'H,3H-spiro[2-benzofuran-1,4'-piperidin]-1'-yl)carbonyl]-1H-indol-1-yl}methyl) morpholine-4-carboxylate was dissolved in a solution of HCl (5 eq) in dioxane and stirred at room temperature for 5 h. A further portion of HCl (5 eq) in dioxane was added and the solution stirred for an additional 5 h at room temperature. Evaporation gave the desired product in 96% yield. ES-MS m/e (%): 480.2 (M+H$^+$).

Example 199 tert-Butyl 2-({6-chloro-3-[(5-fluoro-3-oxo-1'H,3H-spiro[2-benzofuran-1,4'-piperidin]-1'-yl)carbonyl]-1H-indol-1-yl}methyl)morpholine-4-carboxylate

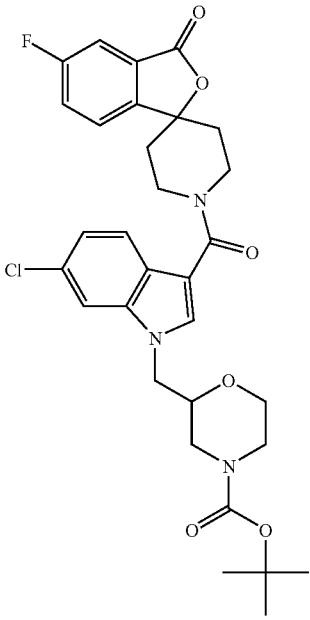

Following the general procedure III as described above, the alkylation of 1'-[(6-chloro-1H-indol-3-yl)carbonyl]-5-fluoro-3H-spiro[2-benzofuran-1,4'-piperidin]-3-one (prepared according to example 19) with 2-chloromethyl-morpholine-4-carboxylic acid tert-butyl ester (described in WO 2006020415) gave the title compound.
ES-MS m/e (%): 598.2(M+H$^+$).

Example 200

1'-{[6-Chloro-1-(morpholin-2-ylmethyl)-1H-indol-3-yl]carbonyl}-5-fluoro-3H-spiro[2-benzofuran-1,4'-piperidin]-3-one dihydrochloride

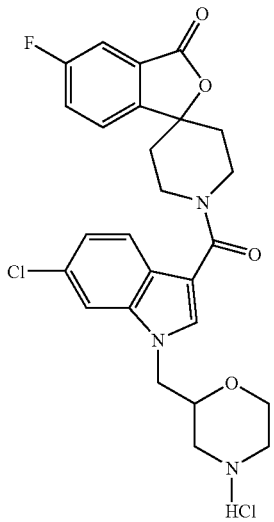

tert-Butyl 2-({6-chloro-3-[(5-fluoro-3-oxo-1'H,3H-spiro[2-benzofuran-1,4'-piperidin]-1'-yl)carbonyl]-1H-indol-1-yl}methyl)morpholine-4-carboxylate was dissolved in a solution of HCl (5 eq) in dioxane and stirred at room temperature for 5 h. A further portion of HCl (5 eq) in dioxane was added and the solution stirred for an additional 5 h at room temperature. Evaporation gave the desired product in quantitative yield. ES-MS m/e (%): 498.1 (M+H$^+$).

Example 201

1'-{[1-(3,5-Difluorobenzyl)-1H-indol-3-yl]carbonyl}-5-fluoro-3H-spiro[2-benzofuran-1,4'-piperidin]-3-one

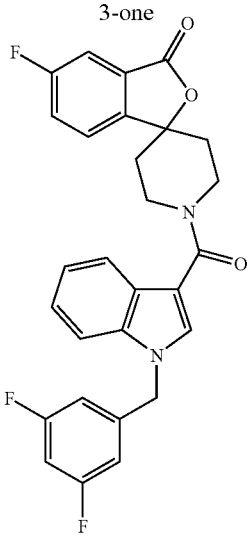

Following the general procedure III as described above, the alkylation of 1'-[(6-chloro-1H-indol-3-yl)carbonyl]-5-fluoro-3H-spiro[2-benzofuran-1,4'-piperidin]-3-one (prepared according to example 19) with commercially available 3,5-difluorobenzyl chloride gave the title compound. ES-MS m/e (%): 491.5(M+H$^+$).

Example 202

1'-{[1-(3,5-Difluorobenzyl)-1H-indol-3-yl]carbonyl}-3H-spiro[2-benzofuran-1,4'-piperidin]-3-one

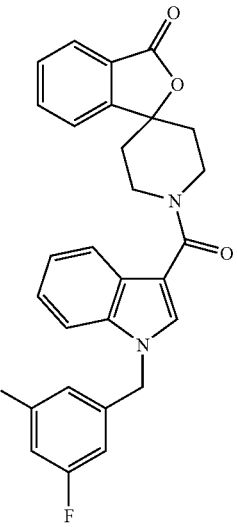

Following the general procedure III as described above, the alkylation of 1'-[(6-chloro-1H-indol-3-yl)carbonyl]-3H- spiro[2-benzofuran-1,4'-piperidin]-3-one (prepared according to example 16) with commercially available 3,5-difluorobenzyl chloride gave the title compound.
ES-MS m/e (%): 473.5(M+H⁺).

Example 203

N,N-Diethyl-2-{3-[(3-oxo-1'H,3H-spiro[2-benzofuran-1,4'-piperidin]-1'-yl)carbonyl]-1H-indol-1-yl}acetamide

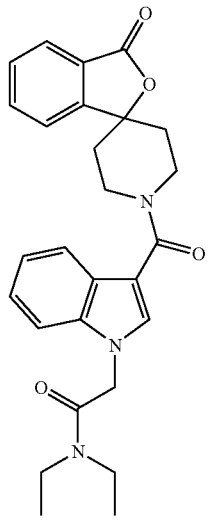

Following the general procedure III as described above, the alkylation of 1'-[(6-chloro-1H-indol-3-yl)carbonyl]-3H-spiro[2-benzofuran-1,4'-piperidin]-3-one (prepared according to example 16) with commercially available 2-chloro-N,N-diethyl-acetamide gave the title compound. ES-MS m/e (%): 460.6(M+H⁺).

Examples of Compounds of Formula (I-d)

Example 204

1'-{[6-Chloro-1-(2-oxo-2-piperidin-1-ylethyl)-1H-indol-3-yl]carbonyl}-3H-spiro[2-benzofuran-1,4'-piperidine]

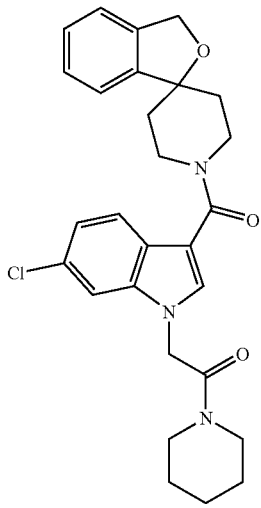

Following the general procedure V as described hereinabove, the alkylation of 1'-[(6-chloro-1H-indol-3-yl)carbo-nyl]-3H-spiro[2-benzofuran-1,4'-piperidine] (the preparation of which have been described in example 69) with commercially available 2-chloro-1-piperidin-1-yl-ethanone as electrophile, the title compound was obtained as a white powder.
ES-MS m/e (%): 492.1 (M+H⁺).

Example 205

1'-{[6-Chloro-1-(2-morpholin-4-yl-2-oxoethyl)-1H-indol-3-yl]carbonyl}-3H-spiro[2-benzofuran-1,4'-piperidine]

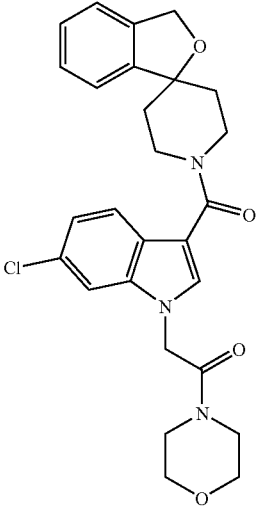

Following the general procedure V as described hereinabove, the alkylation of 1'-[(6-chloro-1H-indol-3-yl)carbo-nyl]-3H-spiro[2-benzofuran-1,4'-piperidine] (the preparation of which have been described in example 69) with commercially available 2-Chloro-1-morpholin-4-yl-etha-none as electrophile, the title compound was obtained as a white powder.
ES-MS m/e (%): 494.1 (M+H⁺).

Example 206

2-[6-Chloro-3-(1'H,3H-spiro[2-benzofuran-1,4'-piperidin]-1'-ylcarbonyl)-1H-indol-1-yl]-N,N-dimethylacetamide

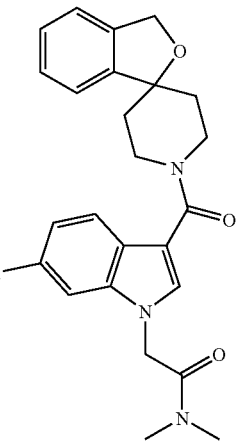

Following the general procedure V as described hereinabove, the alkylation of 1'-[(6-chloro-1H-indol-3-yl)carbonyl]-3H-spiro[2-benzofuran-1,4'-piperidine] (the preparation of which have been described in example 69) with commercially available 2-chloro-N,N-dimethyl-acetamide as electrophile, the title compound was obtained as a white powder.

ES-MS m/e (%): 452.0 (M+H⁺).

Example 207

2-[6-Chloro-3-(1'H,3H-spiro[2-benzofuran-1,4'-piperidin]-1'-ylcarbonyl)-1H-indol-1-yl]-N,N-diethylacetamide

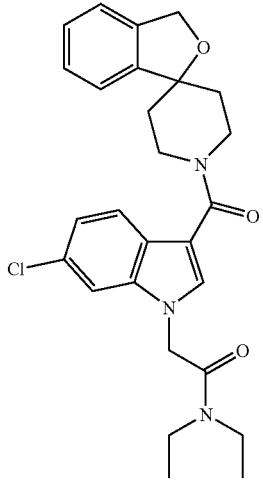

Following the general procedure V as described hereinabove, the alkylation of 1'-[(6-chloro-1H-indol-3-yl)carbonyl]-3H-spiro[2-benzofuran-1,4'-piperidine] (the preparation of which have been described in example 69) with commercially available 2-chloro-N,N-diethyl-acetamide as electrophile, the title compound was obtained as a white powder.

ES-MS m/e (%): 480.1 (M+H⁺).

Example 208

1'-{[6-Chloro-1-(piperidin-1-ylcarbonyl)-1H-indol-3-yl]carbonyl}-3H-spiro[2-benzofuran-1,4'-piperidine]

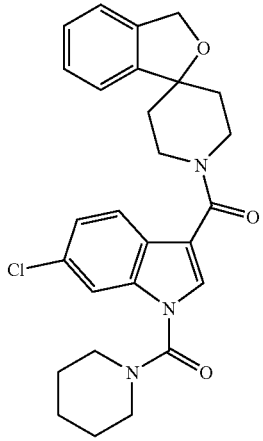

Following the general procedure V as described hereinabove, the alkylation of 1'-[(6-chloro-1H-indol-3-yl)carbonyl]-3H-spiro[2-benzofuran-1,4'-piperidine] (the preparation of which have been described in example 69) with commercially available piperidine-1-carbonyl chloride as electrophile, the title compound was obtained as a white powder.

ES-MS m/e (%): 478.0 (M+H⁺).

Example 209 tert-Butyl[6-chloro-3-(1'H,3H-spiro[2-benzofuran-1,4'-piperidin]-1'-ylcarbonyl)-1H-indol-1-yl]acetate

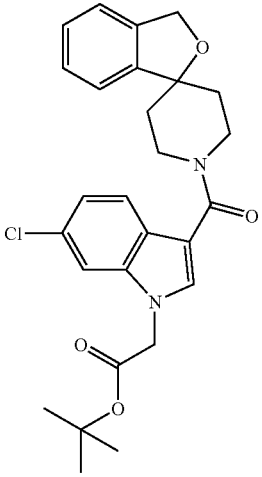

Following the general procedure V as described hereinabove, the alkylation of 1'-[(6-chloro-1H-indol-3-yl)carbonyl]-3H-spiro[2-benzofuran-1,4'-piperidine] (the preparation of which have been described in example 69) with commercially available chloro-acetic acid tert-butyl ester as electrophile, the title compound was obtained as a white solid.

ES-MS m/e (%): 481.3 (M+H⁺).

Example 210

2-[6-Chloro-3-(1'H,3H-spiro[2-benzofuran-1,4'-piperidin]-1'-ylcarbonyl)-1H-indol-1-yl]-N,N-dimethylethanamine

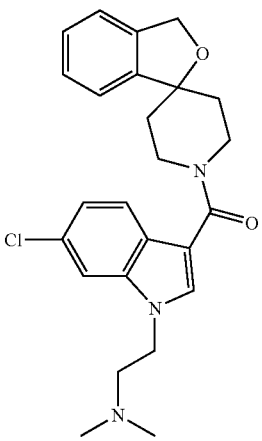

Following the general procedure V as described hereinabove, the alkylation of 1'-[(6-chloro-1H-indol-3-yl)carbonyl]-3H-spiro[2-benzofuran-1,4'-piperidine] (the preparation of which have been described in example 69) with commercially available (2-chloro-ethyl)-dimethyl-amine as electrophile, the title compound was obtained as a white solid.

ES-MS m/e (%): 438.4 (M+H⁺).

Example 211

1'-{[6-Chloro-1-(2-oxo-2-piperazin-1-ylethyl)-1H-indol-3-yl]carbonyl}-3H-spiro[2-benzofuran-1,4'-piperidine]

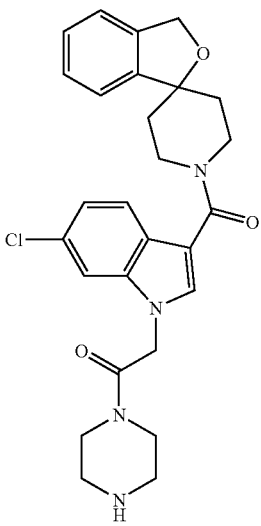

Following the general procedure V as described hereinabove, the alkylation of 1'-[(6-chloro-1H-indol-3-yl)carbonyl]-3H-spiro[2-benzofuran-1,4'-piperidine] (the preparation of which have been described in example 69) with commercially available 4-(2-chloro-acetyl)-piperazine-1-carboxylic acid tert-butyl ester as electrophile, the title compound was obtained as a white solid after removal of the Boc protecting group under standard conditions (TFA/dichloromethane, room temperature).

ES-MS m/e (%): 493.1 (M+H$^+$).

Example 212

1'-({6-Chloro-1-[2-(4-methylpiperazin-1-yl)-2-oxo-ethyl]-1H-indol-3-yl}carbonyl)-3H-spiro[2-benzofuran-1,4'-piperidine]

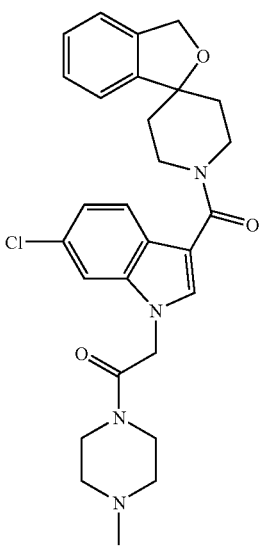

Following the general procedure V as described hereinabove, the alkylation of 1'-[(6-chloro-1H-indol-3-yl)carbonyl]-3H-spiro[2-benzofuran-1,4'-piperidine] (the preparation of which have been described in example 69) with commercially available 2-chloro-1-(4-methyl-piperazin-1-yl)-ethanone as electrophile, the title compound was obtained as a white solid.

ES-MS m/e (%): 507.4 (M+H$^+$).

Example 213

2-[6-Chloro-5-methyl-3-(1'H,3H-spiro[2-benzofuran-1,4'-piperidin]-1'-ylcarbonyl)-1H-indol-1-yl]-N,N-dimethylacetamide

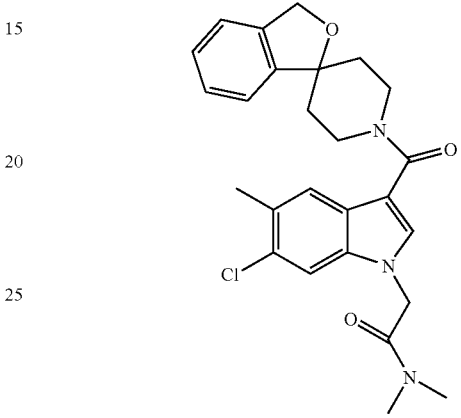

Amide coupling according to general procedure I described hereinabove:
Amine: Spiro[isobenzofuran-1(3H), 4'-piperidine] pepared as described in *J. Org. Chem.* 1976, 41, 2628,
Acid: 6-Chloro-1-dimethylcarbamoylmethyl-5-methyl-1H-indole-3-carboxylic acid,
ES-MS m/e (%): 466.3 (M+H$^+$).

Example 214

1'-{[6-Chloro-1-(3-fluorobenzoyl)-1H-indol-3-yl]carbonyl}-3H-spiro[2-benzofuran-1,4'-piperidine

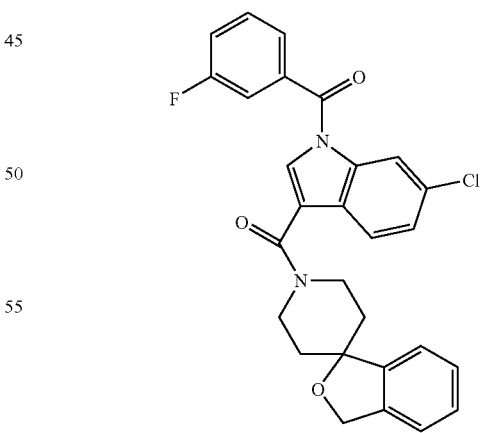

Following the general procedure VII as described above, the acylation of 1'-[(6-chloro-1H-indol-3-yl)carbonyl]-3H-spiro[2-benzofuran-1,4'-piperidine] (prepared according to example 69) with commercially available 3-fluorobenzoyl chloride gave the title compound.

ES-MS m/e (%): 489.4(M+H$^+$).

Example 215

1'-{[6-Chloro-1-(2-fluorobenzoyl)-1H-indol-3-yl]carbonyl}-3H-spiro[2-benzofuran-1,4'-piperidine

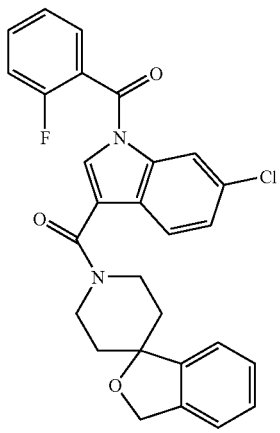

Following the general procedure VII as described above, the acylation of 1'-[(6-chloro-1H-indol-3-yl)carbonyl]-3H-spiro[2-benzofuran-1,4'-piperidine] (prepared according to example 69) with commercially available 2-fluorobenzoyl chloride gave the title compound.

ES-MS m/e (%): 489.4(M+H$^+$).

Example 216

1'-{[6-Chloro-1-(3,5-difluorobenzoyl)-1H-indol-3-yl]carbonyl}-3H-spiro[2-benzofuran-1,4'-piperidine

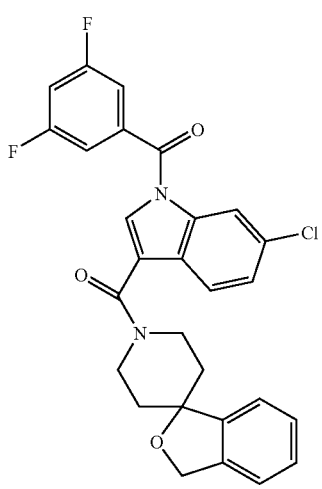

Following the general procedure VII as described above, the acylation of 1'-[(6-chloro-1H-indol-3-yl)carbonyl]-3H-spiro[2-benzofuran-1,4'-piperidine] (prepared according to example 69) with commercially available 3,5-difluorobenzoyl chloride gave the title compound.

ES-MS m/e (%): 507.4(M+H$^+$).

Example 217

1'-{[6-Chloro-1-(2,3-difluorobenzoyl)-1H-indol-3-yl]carbonyl}-3H-spiro[2-benzofuran-1,4'-piperidine

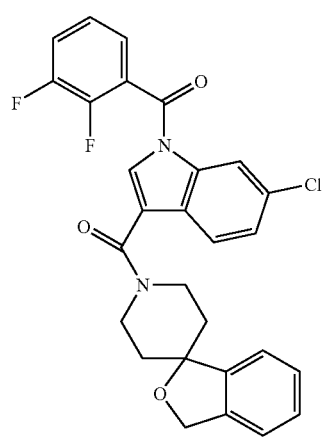

Following the general procedure VII as described above, the acylation of 1'-[(6-chloro-1H-indol-3-yl)carbonyl]-3H-spiro[2-benzofuran-1,4'-piperidine] (prepared according to example 69) with commercially available 2,3-difluorobenzoyl chloride gave the title compound.

ES-MS m/e (%): 507.4(M+H$^+$).

Example 218

1'-({6-Chloro-1-[(3,5-difluorophenyl)sulfonyl]-1H-indol-3-yl}carbonyl)-3H-spiro[2-benzofuran-1,4'-piperidine

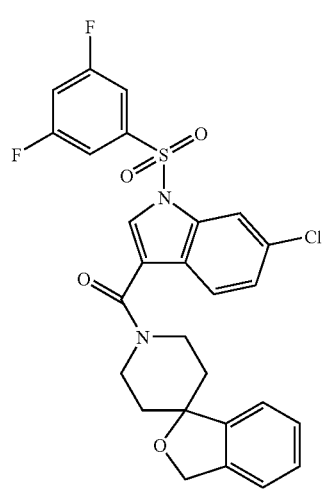

Following the general procedure VII as described above, the sulphonylation of 1'-[(5-chloro-1H-indol-3-yl)carbonyl]-3H-spiro[2-benzofuran-1,4'-piperidine] (prepared according to example 69) with commercially available 3,5-difluorobenzenesulfonyl chloride gave the title compound.

ES-MS m/e (%): 543.3(M+H$^+$).

Example 219

1'-{[6-Chloro-1-(3,5-difluorobenzyl)-1H-indol-3-yl]carbonyl}-3H-spiro[2-benzofuran-1,4'-piperidine

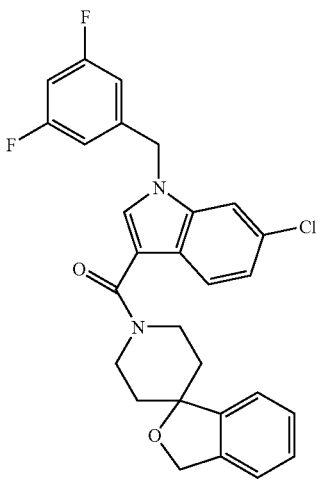

Following the general procedure III as described above, the alkylation of 1'-[(6-chloro-1H-indol-3-yl)carbonyl]-3H-spiro[2-benzofuran-1,4'-piperidine] (prepared according to example 69) with commercially available 3,5-difluorobenzyl chloride gave the title compound.

ES-MS m/e (%): 493.4(M+H$^+$).

Example 220

1'-{[6-Chloro-1-(3-fluorobenzyl)-1H-indol-3-yl]carbonyl}-3H-spiro[2-benzofuran-1,4'-piperidine

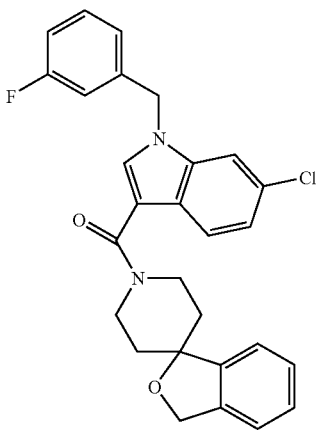

Following the general procedure III as described above, the alkylation of 1'-[(6-chloro-1H-indol-3-yl)carbonyl]-3H-spiro[2-benzofuran-1,4'-piperidine] (prepared according to example 69) with commercially available 3-fluorobenzyl chloride gave the title compound.

ES-MS m/e (%): 475.4(M+H$^+$).

Example 221

1'-{[1-(Biphenyl-3-ylcarbonyl)-6-chloro-1H-indol-3-yl]carbonyl}-3H-spiro[2-benzofuran-1,4'-piperidine

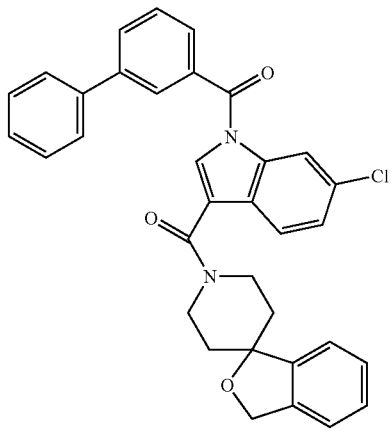

Following the general procedure VII as described above, the acylation of 1'-[(6-chloro-1H-indol-3-yl)carbonyl]-3H-spiro[2-benzofuran-1,4'-piperidine] (prepared according to example 69) with commercially available biphenyl-3-carbonyl chloride gave the title compound.

ES-MS m/e (%): 547.4(M+H$^+$).

Example 222

1'-{[6-Chloro-1-(3,5-difluorophenyl)-1H-indol-3-yl]carbonyl}-3H-spiro[2-benzofuran-1,4'-piperidine

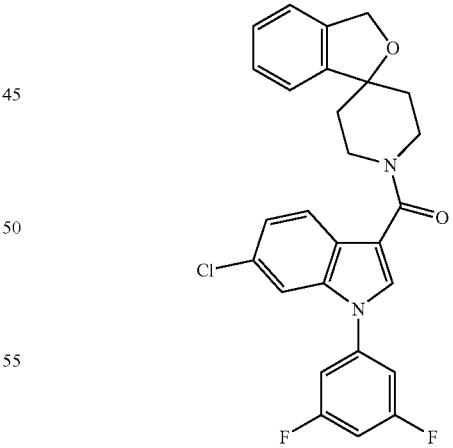

Following the general procedure VI as described above, the arylation of 1'-[(6-chloro-1H-indol-3-yl)carbonyl]-3H-spiro[2-benzofuran-1,4'-piperidine] (prepared according to example 69) with commercially available 3,5-difluorophenylboronic acid gave the title compound.

ES-MS m/e (%): 478.9(M+H$^+$).

1'-{[6-Chloro-1-(3-fluorophenyl)-1H-indol-3-yl]carbonyl}-3H-spiro[2-benzofuran-1,4'-piperidine

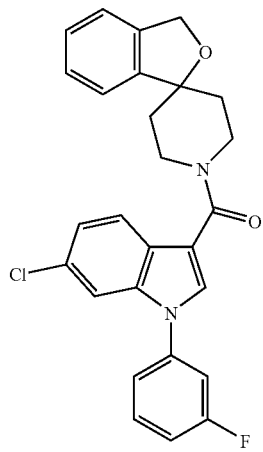

Following the general procedure VI as described above, the arylation of 1'-[(6-chloro-1H-indol-3-yl)carbonyl]-3H-spiro[2-benzofuran-1,4'-piperidine] (prepared according to example 69) with commercially available 3-fluorophenylboronic acid gave the title compound.

ES-MS m/e (%): 461.1(M+H$^+$).

Example 224

2-[6-Chloro-3-(1'H,3H-spiro[2-benzofuran-1,4'-piperidin]-1'-ylcarbonyl)-1H-indol-1-yl]-1-(2-fluorophenyl)ethanone

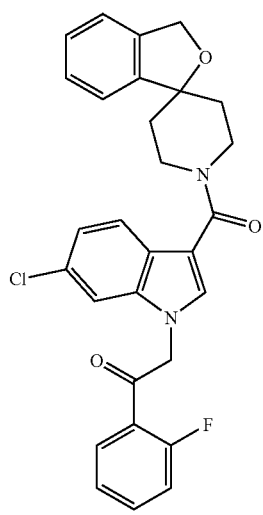

Following the general procedure III as described above, the alkylation of 1'-[(6-chloro-1H-indol-3-yl)carbonyl]-3H-spiro[2-benzofuran-1,4'-piperidine] (prepared according to example 69) with commercially available 2-bromo-1-(2-fluoro-phenyl)-ethanonegave the title compound. ES-MS m/e (%): 503.4(M+H$^+$).

Example 225

1'-[(1-Biphenyl-2-yl-6-chloro-1H-indol-3-yl)carbonyl]-3H-spiro[2-benzofuran-1,4'-piperidine

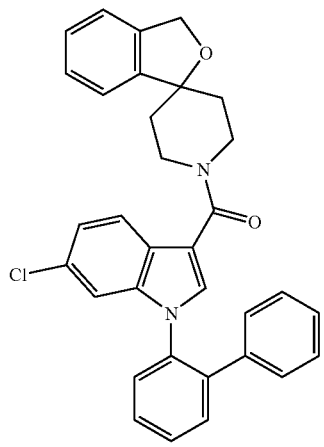

Following the general procedure VI as described above, the arylation of 1'-[(6-chloro-1H-indol-3-yl)carbonyl]-3H-spiro[2-benzofuran-1,4'-piperidine] (prepared according to example 69) with commercially available 2-biphenylboronic acid gave the title compound.

ES-MS m/e (%): 519.3(M+H$^+$).

Example 226

1'-[(1-Biphenyl-2-yl-6-chloro-1H-indol-3-yl)carbonyl]-3H-spiro[2-benzofuran-1,4'-piperidine

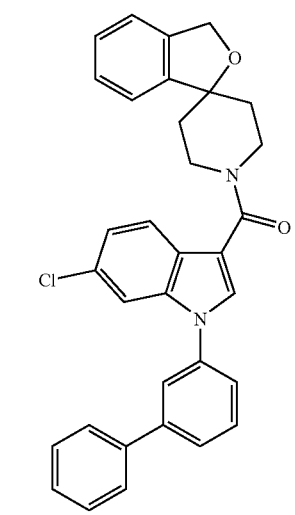

Following the general procedure VI as described above, the arylation of 1'-[(6-chloro-1H-indol-3-yl)carbonyl]-3H-spiro[2-benzofuran-1,4'-piperidine] (prepared according to example 69) with commercially available 3-biphenylboronic acid gave the title compound.

ES-MS m/e (%): 519.3(M+H$^+$).

Example 227

1'-[(6-Chloro-1-pyridin-2-yl-1H-indol-3-yl)carbonyl]-3H-spiro[2-benzofuran-1,4'-piperidine]

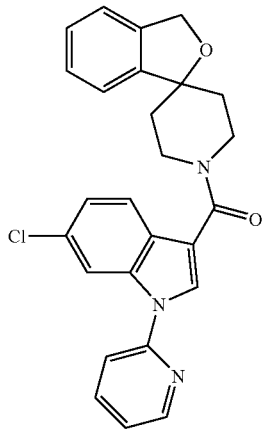

To a solution of 1'-[(6-chloro-1H-indol-3-yl)carbonyl]-3H-spiro[2-benzofuran-1,4'-piperidine] (prepared according to example 69) in dry DMF was added NaH (1 eq) and the reaction mixture stirred at room temperature for 30 min and then treated with 2-fluoropyridine (1.5 eq) and heated at 140° C. under microwave irradiation for 15 min. Purification by preparative HPLC gave the desired product in 24% yield.

ES-MS m/e (%): 444.1(M+H+).

Example 228

1'-{[6-Chloro-1-(pyridin-4-ylmethyl)-1H-indol-3-yl]carbonyl}-3H-spiro[2-benzofuran-1,4'-piperidine]

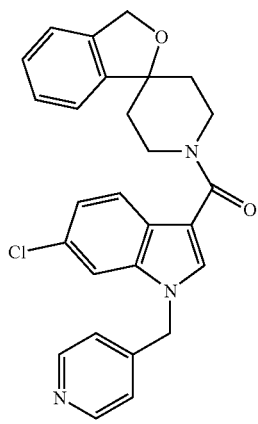

Following the general procedure III as described above, the alkylation of 1'-[(6-chloro-1H-indol-3-yl)carbonyl]-3H-spiro[2-benzofuran-1,4'-piperidine] (prepared according to example 69) with commercially available 4-bromomethylpyridine gave the title compound.

ES-MS m/e (%): 458.4(M+H+).

Example 229

2-[6-Chloro-3-(1'H,3H-spiro[2-benzofuran-1,4'-piperidin]-1'-ylcarbonyl)-1H-indol-1-yl]-1-pyridin-2-ylethanone

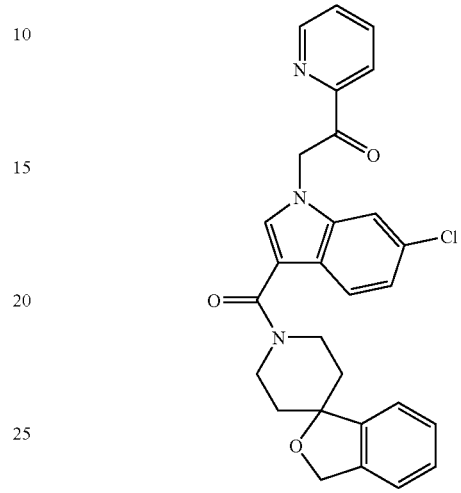

Following the general procedure III as described above, the alkylation of 1'-[(6-chloro-1H-indol-3-yl)carbonyl]-3H-spiro[2-benzofuran-1,4'-piperidine] (prepared according to example 69 above) with commercially available 2-bromo-1-pyridin-2-ylethanone gave the title compound. ES-MS m/e (%): 486.4(M+H+).

Example 230

1'-{[6-Chloro-1-(pyridin-3-ylmethyl)-1H-indol-3-yl]carbonyl}-3H-spiro[2-benzofuran-1,4'-piperidine]

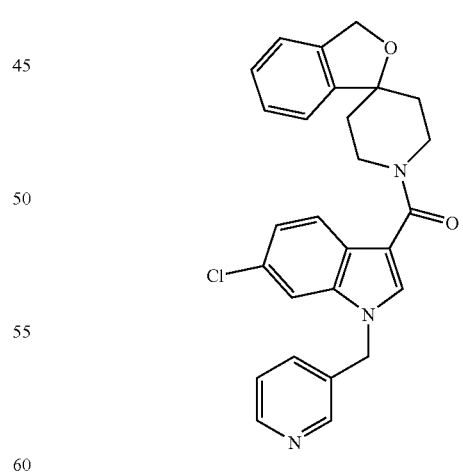

Following the general procedure III as described above, the alkylation of 1'-[(6-chloro-1H-indol-3-yl)carbonyl]-3H-spiro[2-benzofuran-1,4'-piperidine] (prepared according to example 69) with commercially available 3-bromomethylpyridine gave the title compound.

ES-MS m/e (%): 458.4(M+H+).

Example 231

1'-{[6-Chloro-1-(pyridin-2-ylmethyl)-1H-indol-3-yl]carbonyl}-3H-spiro[2-benzofuran-1,4'-piperidine]

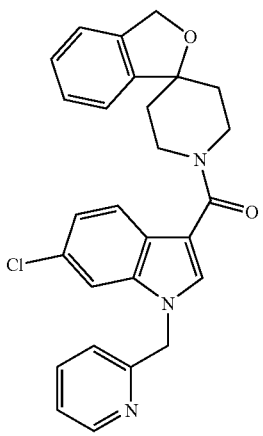

Following the general procedure III as described above, the alkylation of 1'-[(6-chloro-1H-indol-3-yl)carbonyl]-3H-spiro[2-benzofuran-1,4'-piperidine] (prepared according to example 69) with methanesulfonic acid pyridin-2-ylmethyl ester (described in WO 9955318) gave the title compound. ES-MS m/e (%): 458.3(M+H$^+$).

Example 232

1'-({1-[(4-Benzylmorpholin-2-yl)methyl]-6-chloro-1H-indol-3-yl}carbonyl)-3H-spiro[2-benzofuran-1,4'-piperidine]

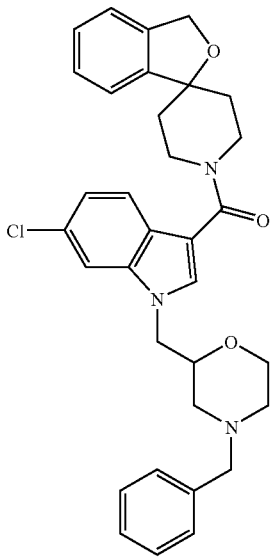

Following the general procedure III as described above, the alkylation of 1'-[(6-chloro-1H-indol-3-yl)carbonyl]-3H-spiro[2-benzofuran-1,4'-piperidine] (prepared according to example 69) with commercially available 4-benzyl-2-(chloromethyl)morpholine gave the title compound. ES-MS m/e (%): 556.3(M+H$^+$).

Example 233

1'-({6-Chloro-1-[(1,4-dibenzylpiperazin-2-yl)methyl]-1H-indol-3-yl}carbonyl)-3H-spiro[2-benzofuran-1,4'-piperidine]

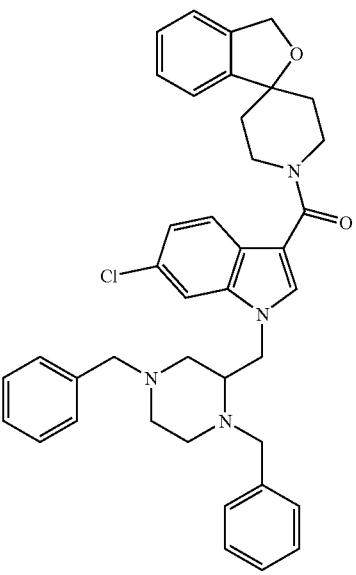

Following the general procedure III as described above, the alkylation of 1'-[(6-chloro-1H-indol-3-yl)carbonyl]-3H-spiro[2-benzofuran-1,4'-piperidine] (prepared according to example 69 above) with 1,4-dibenzyl-2-chloromethyl-piperazine (described in Journal of Medicinal Chemistry (1999), 42(9), 1587-1603) gave the title compound.
ES-MS m/e (%): 645.3(M+H$^+$).

Example 234

1'-{[6-Chloro-1-(pyrazin-2-ylmethyl)-1H-indol-3-yl]carbonyl}-3H-spiro[2-benzofuran-1,4'-piperidine]

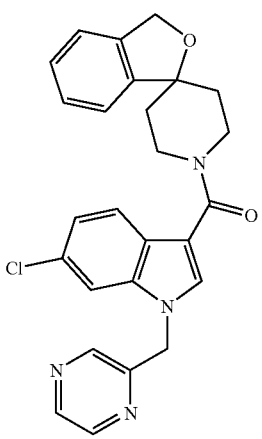

Following the general procedure III as described above, the alkylation of 1'-[(6-chloro-1H-indol-3-yl)carbonyl]-3H-spiro[2-benzofuran-1,4'-piperidine] (prepared according to example 69 above) with methanesulfonic acid pyrazin-2-ylmethyl ester (preparation described in WO 2002064574) gave the title compound. ES-MS m/e (%): 459.3(M+H⁺).

Example 235

1'-{[6-Chloro-1-(pyrimidin-5-ylmethyl)-1H-indol-3-yl]carbonyl}-3H-spiro[2-benzofuran-1,4'-piperidine

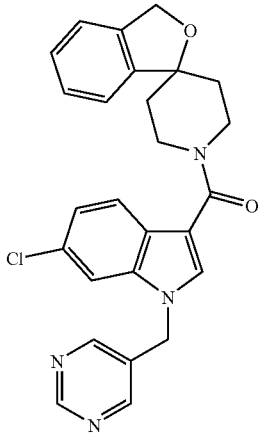

Following the general procedure III as described above, the alkylation of 1'-[(6-chloro-1H-indol-3-yl)carbonyl]-3H-spiro[2-benzofuran-1,4'-piperidine] (prepared according to example 69) with methanesulfonic acid pyrimidin-5-ylmethyl ester (preparation described herein) gave the title compound. ES-MS m/e (%): 459.3(M+H⁺).

Example 236

1'-({6-Chloro-1-[(5-methylisoxazol-3-yl)methyl]-1H-indol-3-yl}carbonyl)-3H-spiro[2-benzofuran-1,4'-piperidine]

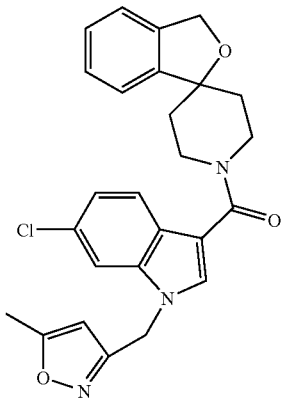

Following the general procedure III as described above, the alkylation of 1'-[(6-chloro-1H-indol-3-yl)carbonyl]-3H-spiro[2-benzofuran-1,4'-piperidine] (prepared according to example 69) with methanesulfonic acid 5-methyl-isoxazol-3-ylmethyl ester (described in WO 2004092172) gave the title compound. ES-MS m/e (%): 462.2(M+H⁺).

Example 237

1'-({6-Chloro-1-[(5-cyclopropyl-2-methyl-1,3-oxazol-4-yl)methyl]-1H-indol-3-yl}carbonyl)-3H-spiro[2-benzofuran-1,4'-piperidine

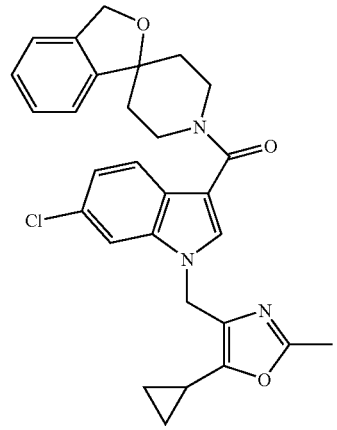

Following the general procedure III as described above, the alkylation of 1'-[(6-chloro-1H-indol-3-yl)carbonyl]-3H-spiro[2-benzofuran-1,4'-piperidine] (prepared according to example 69 above) with methanesulfonic acid 5-cyclopropyl-2-methyl-oxazol-4-ylmethyl ester (prepared herein) gave the title compound. ES-MS m/e (%): 502.2(M+H⁺).

Example 238

1'-({6-Chloro-1-[(1-methyl-1H-imidazol-5-yl)methyl]-1H-indol-3-yl}carbonyl)-3H-spiro[2-benzofuran-1,4'-piperidine

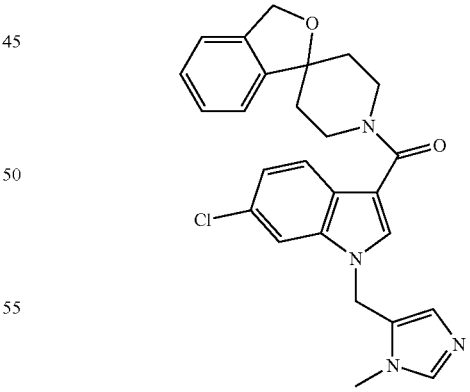

Following the general procedure III as described above, the alkylation of 1'-[(6-chloro-1H-indol-3-yl)carbonyl]-3H-spiro[2-benzofuran-1,4'-piperidine] (prepared according to example 69) with methanesulfonic acid 3-methyl-3H-imidazol-4-ylmethyl ester (prepared by mesylation of the commercially available (3-methyl-3H-imidazol-4-yl)-methanol) gave the title compound. ES-MS m/e (%): 461.2(M+H⁺).

Example 239

1'-({6-Chloro-1-[(3-methylisoxazol-5-yl)methyl]-1H-indol-3-yl}carbonyl)-3H-spiro[2-benzofuran-1,4'-piperidine]

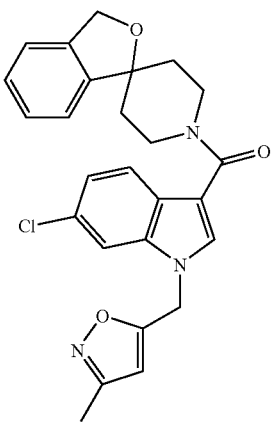

Following the general procedure III as described above, the alkylation of 1'-[(6-chloro-1H-indol-3-yl)carbonyl]-3H-spiro[2-benzofuran-1,4'-piperidine] (prepared according to example 69) with methanesulfonic acid 3-methyl-isoxazol-5-ylmethyl ester (described in Heterocycles, 23(3), 571-83; 1985) gave the title compound. ES-MS m/e (%): 462.2(M+H$^+$).

Example 240

1'-({6-Chloro-1-[(1,5-dimethyl-1H-pyrazol-3-yl)methyl]-1H-indol-3-yl}carbonyl)-3H-spiro[2-benzofuran-1,4'-piperidine

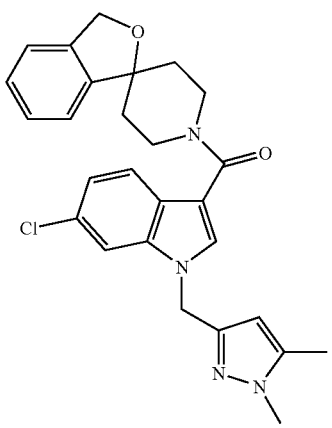

Following the general procedure III as described above, the alkylation of 1'-[(6-chloro-1H-indol-3-yl)carbonyl]-3H-spiro[2-benzofuran-1,4'-piperidine] (prepared according to example 69) with methanesulfonic acid 1,5-dimethyl-1H-pyrazol-3-ylmethyl ester (prepared by mesylation of commercially available methanesulfonic acid 1,5-dimethyl-1H-pyrazol-3-ylmethyl ester) gave the title compound. ES-MS m/e (%): 475.2(M+H$^+$).

Example 241

1'-({6-Chloro-1-[(3,5-dimethylisoxazol-4-yl)methyl]-1H-indol-3-yl}carbonyl)-3H-spiro[2-benzofuran-1,4'-piperidine

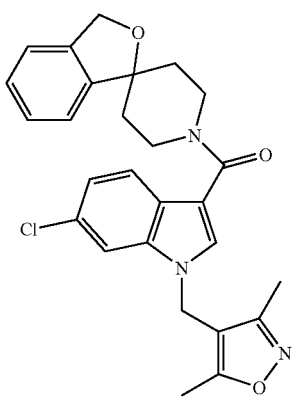

Following the general procedure III as described above, the alkylation of 1'-[(6-chloro-1H-indol-3-yl)carbonyl]-3H-spiro[2-benzofuran-1,4'-piperidine] (prepared according to example 69) with methanesulfonic acid 3,5-dimethyl-isoxazol-4-ylmethyl ester (prepared by mesylation of the commercially available 1,5-dimethyl-1H-pyrazol-3-yl)-methanol) gave the title compound. ES-MS m/e (%): 476.2(M+H$^+$).

Example 242

1'-({6-Chloro-1-[(2,5-dimethyl-1,3-oxazol-4-yl)methyl]-1H-indol-3-yl}carbonyl)-3H-spiro[2-benzofuran-1,4'-piperidine

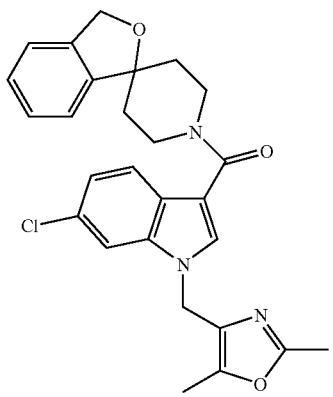

Following the general procedure III as described above, the alkylation of 1'-[(6-chloro-1H-indol-3-yl)carbonyl]-3H-spiro[2-benzofuran-1,4'-piperidine] (prepared according to example 69) with methanesulfonic acid 2,5-dimethyl-oxazol-4-ylmethyl ester (prepared by mesylation of (2,5-dimethyl-oxazol-4-yl)-methanol, described in Organic Letters 1999, 1(1), 87-90) gave the title compound. ES-MS m/e (%): 476.2(M+H$^+$).

Example 243

1'-({6-Chloro-1-[(3-fluorooxetan-3-yl)methyl]-1H-indol-3-yl}carbonyl)-3H-spiro[2-benzofuran-1,4'-piperidine]

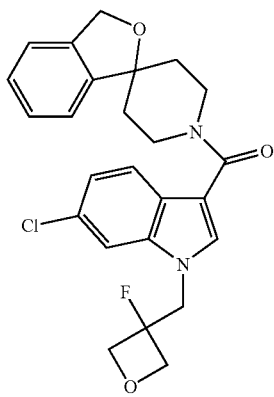

Following the general procedure III as described above, the alkylation of 1'-[(6-chloro-1H-indol-3-yl)carbonyl]-3H-spiro[2-benzofuran-1,4'-piperidine] (prepared according to example 69) with 3-bromomethyl-3-fluoro-oxetane (described in US2005215599) gave the title compound. ES-MS m/e (%): 455.2(M+H$^+$).

Example 244

1'-[(6-Chloro-1-{[1-(methoxymethyl)cyclopropyl]methyl}-1H-indol-3-yl)carbonyl]-3H-spiro[2-benzofuran-1,4'-piperidine]

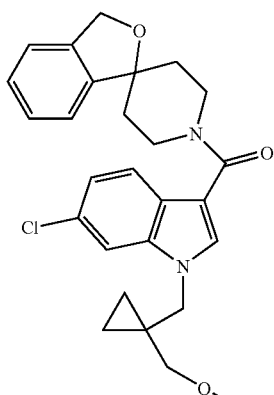

Following the general procedure III as described above, the alkylation of 1'-[(6-chloro-1H-indol-3-yl)carbonyl]-3H-spiro[2-benzofuran-1,4'-piperidine] (prepared according to example 69) with 1-bromomethyl-1-methoxymethyl-cyclopropane (described in WO 2001032633) gave the title compound. ES-MS m/e (%): 465.5(M+H$^+$).

Example 245

(1-{[6-Chloro-3-(1'H,3H-spiro[2-benzofuran-1,4'-piperidin]-1'-ylcarbonyl)-1H-indol-1-yl]methyl}cyclopropyl)acetonitrile

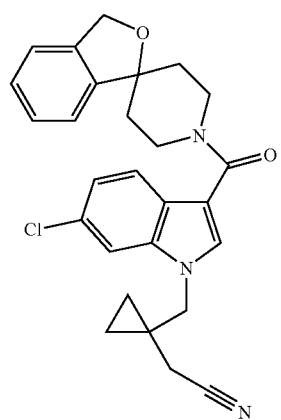

Following the general procedure III as described above, the alkylation of 1'-[(6-chloro-1H-indol-3-yl)carbonyl]-3H-spiro[2-benzofuran-1,4'-piperidine] (prepared according to example 69) with 1-bromomethyl-cyclopropanecarbonitrile (described in EP 148004) gave the title compound. ES-MS m/e (%): 460.5(M+H$^+$).

Example 246

1'-({6-Chloro-1-[2-(tetrahydro-2H-pyran-4-yl)ethyl]-1H-indol-3-yl}carbonyl)-3H-spiro[2-benzofuran-1,4'-piperidine]

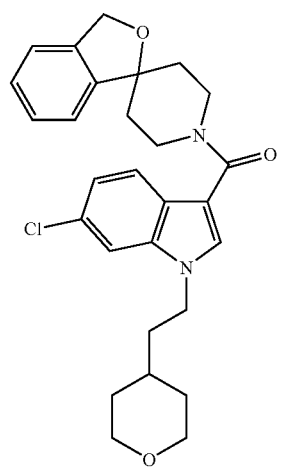

Following the general procedure III as described above, the alkylation of 1'-[(6-chloro-1H-indol-3-yl)carbonyl]-3H-spiro[2-benzofuran-1,4'-piperidine] (prepared according to example 69) with 4-(2-bromo-ethyl)-tetrahydro-pyran (described in US 2004220214) gave the title compound. ES-MS m/e (%): 479.5(M+H$^+$).

Example 247 tert-Butyl 2-{[6-chloro-3-(1'H,3H-spiro[2-benzofuran-1,4'-piperidin]-1'-ylcarbonyl)-1H-indol-1-yl]methyl}morpholine-4-carboxylate

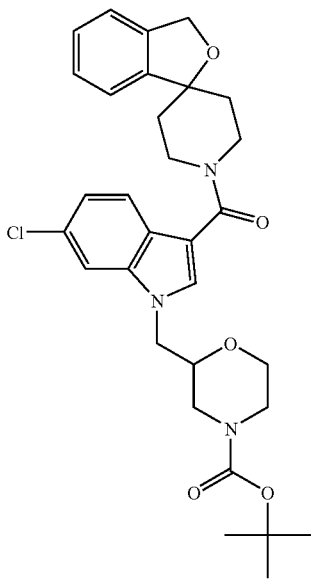

Following the general procedure III as described above, the alkylation of 1'-[(6-chloro-1H-indol-3-yl)carbonyl]-3H-spiro[2-benzofuran-1,4'-piperidine] (prepared according to example 69) with 2-chloromethyl-morpholine-4-carboxylic acid tert-butyl ester (described in WO 2006020415) gave the title compound. ES-MS m/e (%): 566.3(M+H⁺).

Example 248

1'-{[6-Chloro-1-(morpholin-2-ylmethyl)-1H-indol-3-yl]carbonyl}-3H-spiro[2-benzofuran-1,4'-piperidine] hydrochloride

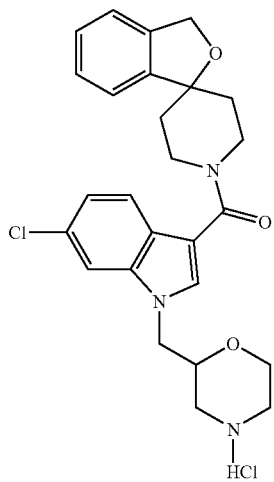

tert-Butyl 2-{[6-chloro-3-(1'H,3H-spiro[2-benzofuran-1,4'-piperidin]-1'-ylcarbonyl)-1H-indol-1-yl]methyl}morpholine-4-carboxylate (prepared in example 247 above) was dissolved in a solution of HCl (5 eq) in dioxane and stirred at room temperature for 5 h. A further portion of HCl (5 eq) in dioxane was added and the solution stirred for an additional 5 h at room temperature. Evaporation gave the desired product in quantitative yield. ES-MS m/e (%): 466.2 (M+H⁺).

Example 249

2-[6-Chloro-3-(1'H,3H-spiro[2-benzofuran-1,4'-piperidin]-1'-ylcarbonyl)-1H-indol-1-yl]-N-[2-(dimethylamino)ethyl]acetamide

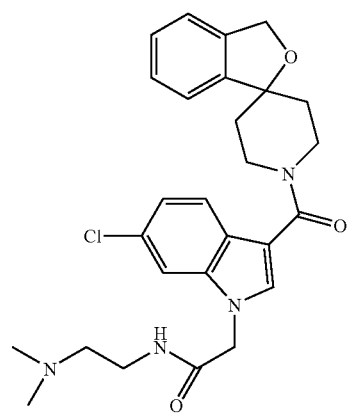

A solution of [6-chloro-3-(1'H,3H-spiro[2-benzofuran-1,4'-piperidin]-1'-ylcarbonyl)-1H-indol-1-yl]acetic acid (prepared by treatment of the sodium salt of 1'-[(6-chloro-1H-indol-3-yl)carbonyl]-3H-spiro[2-benzofuran-1,4'-piperidine] with bromoacetic acid at room temperature in DMF), EDC (1 eq), HOBt (1 eq) and Et₃N (1 eq) were stirred together at room temperature in DMF for 15 min. N,N-Dimethyl-ethane-1,2-diamine (1 eq) was added and the solution stirred at room temperature for 16 h. Purification by prep. HPLC gave 37% of product.

ES-MS m/e (%): 495.6(M+H⁺).

Example 250

2-[6-Chloro-3-(1'H,3H-spiro[2-benzofuran-1,4'-piperidin]-1'-ylcarbonyl)-1H-indol-1-yl]acetamide

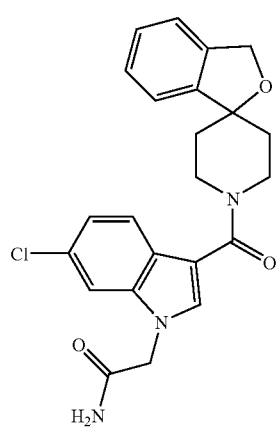

A solution of [6-chloro-3-(1'H,3H-spiro[2-benzofuran-1,4'-piperidin]-1'-ylcarbonyl)-1H-indol-1-yl]acetic acid (prepared as for 2-[6-chloro-3-(1'H,3H-spiro[2-benzofuran-1,4'-piperidin]-1'-ylcarbonyl)-1H-indol-1-yl]-N-[2-(dimethylamino)ethyl]acetamide), O-(7-azabenzotriazol-1-yl)-N,N,N',N'-tetramethyluronium hexafluorophosphate (1.05 eq) and Et₃N (1.05 eq) were stirred together at room temperature in dry DMF for 15 min. A solution of ammonia (5 eq) in dioxane was added and the solution stirred at room temperature for 16 h. Purification by prep. HPLC gave 31% of product. ES-MS m/e (%): 424.3(M+H⁺).

Example 251

2-[6-Chloro-3-(1'H,3H-spiro[2-benzofuran-1,4'-piperidin]-1'-ylcarbonyl)-1H-indol-1-yl]-N-[2-(methylamino)ethyl]acetamide

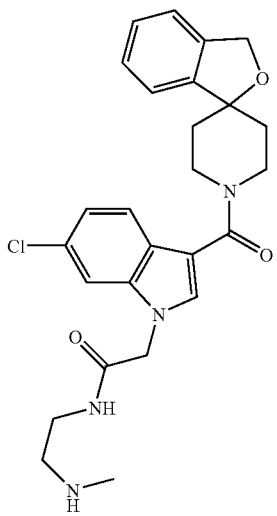

A solution of [6-chloro-3-(1'H,3H-spiro[2-benzofuran-1,4'-piperidin]-1'-ylcarbonyl)-1H-indol-1-yl]acetic acid (prepared by treatment of the sodium salt of 1'-[(6-chloro-1H-indol-3-yl)carbonyl]-3H-spiro[2-benzofuran-1,4'-piperidine] with bromoacetic acid at room temperature in DMF), O-(7-azabenzotriazol-1-yl)-N,N,N',N'-tetramethyluronium hexafluorophosphate (1.05 eq) and Et₃N (1.05 eq) were stirred together at room temperature in dry DMF for 15 min. Commercially available N-(2-aminoethyl)-N-methylcarbamic acid tert-butyl ester (1.5 eq) was added and the solution stirred at room temperature for 2 h, then a solution of HCl (15 eq) in dioxane was added and the solution stirred for 2 h. Evaporation and purification by prep. HPLC gave 37% of product. ES-MS m/e (%): 481.3(M+H⁺).

Example 252

N-(2-Aminoethyl)-2-[6-chloro-3-(1'H,3H-spiro[2-benzofuran-1,4'-piperidin]-1'-ylcarbonyl)-1H-indol-1-yl]acetamide

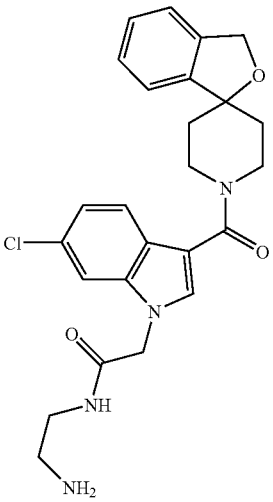

A solution of [6-chloro-3-(1'H,3H-spiro[2-benzofuran-1,4'-piperidin]-1'-ylcarbonyl)-1H-indol-1-yl]acetic acid (prepared by treatment of the sodium salt of 1'-[(6-chloro-1H-indol-3-yl)carbonyl]-3H-spiro[2-benzofuran-1,4'-piperidine] with bromoacetic acid at room temperature in DMF), O-(7-azabenzotriazol-1-yl)-N,N,N',N'-tetramethyluronium hexafluorophosphate (1.05 eq) and Et₃N (1.05 eq) were stirred together at room temperature in dry DMF for 15 min. Commercially available N-(tert-Butoxycarbonyl)-1,2-diaminoethane (1.5 eq) was added and the solution stirred at room temperature for 2 h, then a solution of HCl (15 eq) in dioxane was added and the solution stirred for 2 h. Evaporation and purification by prep. HPLC gave 39% of product. ES-MS m/e (%): 467.4(M+H⁺).

Example 253

2-[6-Chloro-3-(1'H,3H-spiro[2-benzofuran-1,4'-piperidin]-1'-ylcarbonyl)-1H-indol-1-yl]ethanamine

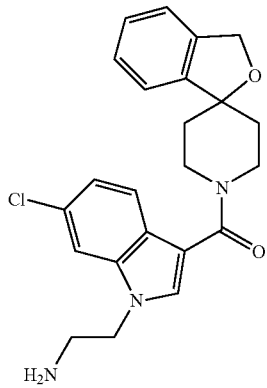

Following the general procedure III as described above, the alkylation of 1'-[(6-chloro-1H-indol-3-yl)carbonyl]-3H-spiro[2-benzofuran-1,4'-piperidine] (prepared according to example 69 above) with commercially available 2-chloro-ethylamine gave the title compound in 11% yield. ES-MS m/e (%): 410.2(M+H⁺).

Example 254

2-[6-Chloro-3-(1'H,3H-spiro[2-benzofuran-1,4'-piperidin]-1'-ylcarbonyl)-1H-indol-1-yl]-N-methylethanamine

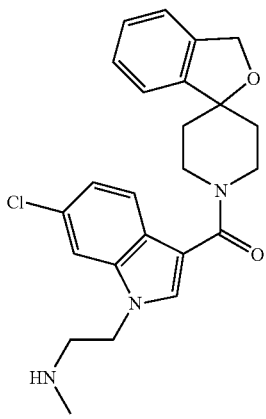

Following the general procedure III as described above, the alkylation of 1'-[(6-chloro-1H-indol-3-yl)carbonyl]-3H-spiro[2-benzofuran-1,4'-piperidine] (prepared according to example 69) with commercially available (2-chloro-ethyl)-methyl-amine gave the title compound in 42% yield. ES-MS m/e (%): 424.2(M+H⁺).

Example 255

2-[6-Chloro-3-(1'H,3H-spiro[2-benzofuran-1,4'-piperidin]-1'-ylcarbonyl)-1H-indol-1-yl]-N-methylacetamide

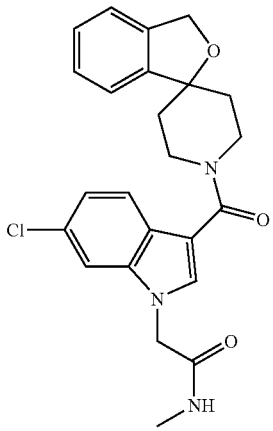

Following the general procedure III as described above, the alkylation of 1'-[(6-chloro-1H-indol-3-yl)carbonyl]-3H-spiro[2-benzofuran-1,4'-piperidine] (prepared according to example 69) with commercially available 2-chloro-N-methyl-acetamide gave the title compound in 19% yield. ES-MS m/e (%): 438.2(M+H⁺).

Example 256

1'-{[6-Chloro-1-(2-morpholin-4-ylethyl)-1H-indol-3-yl]carbonyl}-3H-spiro[2-benzofuran-1,4'-piperidine]

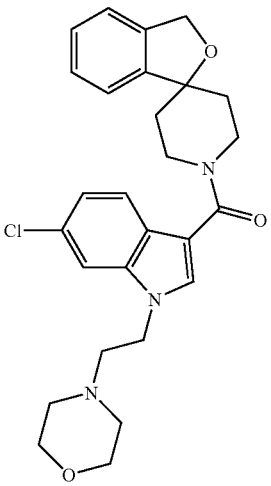

Following the general procedure III as described above, the alkylation of 1'-[(6-chloro-1H-indol-3-yl)carbonyl]-3H-spiro[2-benzofuran-1,4'-piperidine] (prepared according to example 69) with commercially available 4-(2-chloro-ethyl)-morpholine gave the title compound in 50% yield. ES-MS m/e (%): 480.5(M+H⁺).

Example 257

1'-{[6-Chloro-1-(3-morpholin-4-ylpropyl)-1H-indol-3-yl]carbonyl}-3H-spiro[2-benzofuran-1,4'-piperidine]

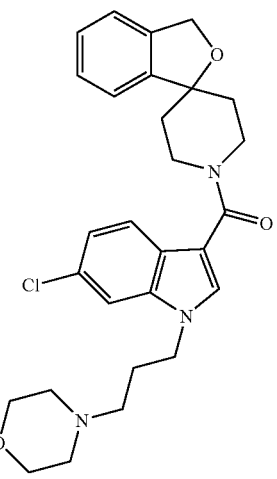

Following the general procedure III as described above, the alkylation of 1'-[(6-chloro-1H-indol-3-yl)carbonyl]-3H-spiro[2-benzofuran-1,4'-piperidine] (prepared according to example 69) with commercially available 4-(3-chloro-propyl)-morpholine gave the title compound in 52% yield. ES-MS m/e (%): 494.6(M+H⁺).

Example 258

1'-{[6-Chloro-1-(oxiran-2-ylmethyl)-1H-indol-3-yl]carbonyl}-3H-spiro[2-benzofuran-1,4'-piperidine]

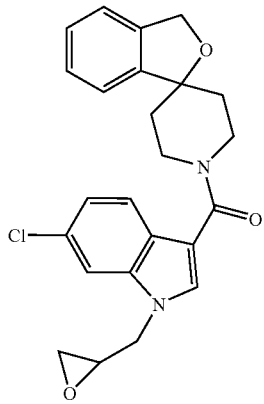

Following the general procedure III as described above, the alkylation of 1'-[(6-chloro-1H-indol-3-yl)carbonyl]-3H-spiro[2-benzofuran-1,4'-piperidine] (prepared according to example 69) with commercially available 2-bromomethyloxirane gave the title compound in 47% yield. ES-MS m/e (%): 423.4(M+H$^+$).

Example 259

2-[6-Chloro-3-(1'H,3H-spiro[2-benzofuran-1,4'-piperidin]-1'-ylcarbonyl)-1H-indol-1-yl]ethanol

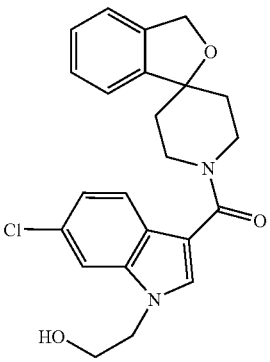

Following the general procedure III as described above, the alkylation of 1'-[(6-chloro-1H-indol-3-yl)carbonyl]-3H-spiro[2-benzofuran-1,4'-piperidine] (prepared according to example 69) with commercially available 2-chloro-ethanol gave the title compound in 47% yield.
ES-MS m/e (%): 411.4(M+H$^+$).

Example 260

1'-({6-Chloro-1-[(2-methylpyridin-4-yl)methyl]-1H-indol-3-yl}carbonyl)-3H-spiro[2-benzofuran-1,4'-piperidine]

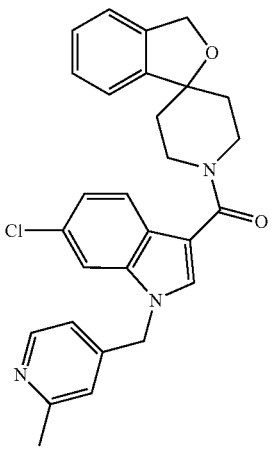

Following the general procedure III as described above, the alkylation of 1'-[(6-chloro-1H-indol-3-yl)carbonyl]-3H-spiro[2-benzofuran-1,4'-piperidine] (prepared according to example 69) with 4-chloromethyl-2-methyl-pyridine (described in WO 2006023707) gave the title compound in 56% yield. ES-MS m/e (%): 472.2(M+H$^+$).

Example 261

1'-({6-Chloro-1-[(3S)-piperidin-3-ylmethyl]-1H-indol-3-yl}carbonyl)-3H-spiro[2-benzofuran-1,4'-piperidine]

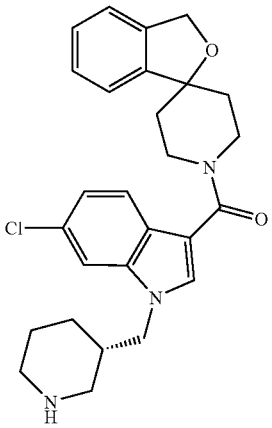

A solution of the 1'-[(6-chloro-1H-indol-3-yl)carbonyl]-3H-spiro[2-benzofuran-1,4'-piperidine] (prepared according to example 69) in dry DMF was treated with NaH (1.1 eq) and stirred for 10 min at room temperature, then treated with (S)-3-methanesulfonyloxymethyl-piperidine-1-carboxylic acid tert-butyl ester (1.1 eq) (JP 2001278872) and stirred at room temperature for 16 h then 70° for 4 h. Concentration and treatment with excess HCl in dioxane gave after purification by preparative HPLC the desired product in 39% yield.

ES-MS m/e (%): 464.2(M+H+).

Example 262

2-[6-Chloro-3-(1'H,3H-spiro[2-benzofuran-1,4'-piperidin]-1'-ylcarbonyl)-1H-indol-1-yl]-N-hydroxyethanamine

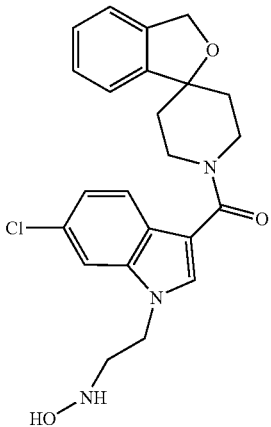

A solution of the [6-chloro-3-(1'H,3H-spiro[2-benzofuran-1,4'-piperidin]-1'-ylcarbonyl)-1H-indol-1-yl]acetaldehyde in MeOH was treated with KOAc (1.5 eq) and hydroxylamine hydrochloride (1.2 eq) and stirred for 1 h at room temperature, then treated with NaCNBH₃ (1.1 eq) and stirred at room temperature for 5 h. Concentration and purification by preparative HPLC the desired product in 19% yield. ES-MS m/e (%): 426.1(M+H+).

Example 263

1'-{[6-Chloro-1-(tetrahydro-2H-pyran-4-ylmethyl)-1H-indol-3-yl]carbonyl}-3H-spiro[2-benzofuran-1,4'-piperidine]

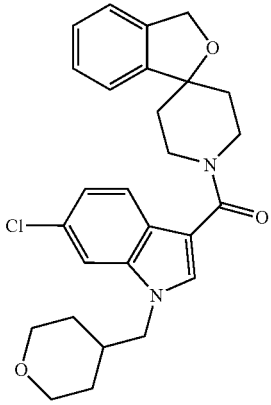

Following the general procedure III as described above, the alkylation of 1'-[(6-chloro-1H-indol-3-yl)carbonyl]-3H-spiro[2-benzofuran-1,4'-piperidine] (prepared according to example 69) with commercially available methanesulfonic acid 2-(tetrahydro-pyran-4-yl)-ethylester (described in US 2004220214) gave the title compound in 55% yield. ES-MS m/e (%): 465.2(M+H+).

Example 264

1'-({6-Chloro-1-[(1-methylpyrrolidin-3-yl)methyl]-1H-indol-3-yl}carbonyl)-3H-spiro[2-benzofuran-1,4'-piperidine]

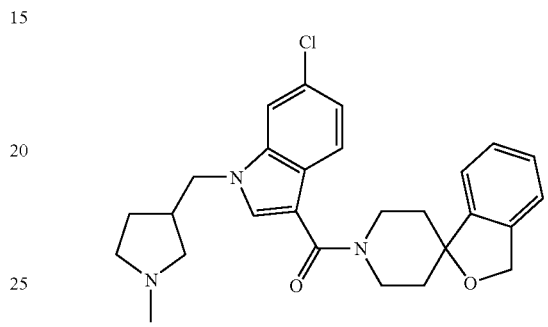

A solution of 1'-{[6-chloro-1-(pyrrolidin-3-ylmethyl)-1H-indol-3-yl]carbonyl}-3H-spiro[2-benzofuran-1,4'-piperidine] in MeOH was treated with aq. H₂CO (1.5 eq), AcOH (1.1 eq) and stirred for 15 min at room temperature, then treated with NaCNBH₃ (1.1 eq) and stirred at room temperature for 1 h. Concentration and purification by preparative HPLC gave the desired product. ES-MS m/e (%): 464.2(M+H+).

Example 265

1'-[(6-Chloro-1-{[(3S)-1-methylpiperidin-3-yl]methyl}-1H-indol-3-yl)carbonyl]-3H-spiro[2-benzofuran-1,4'-piperidine]

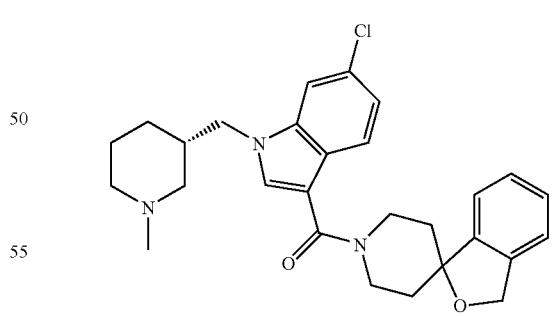

A solution of 1'-({6-chloro-1-[(3S)-piperidin-3-ylmethyl]-1H-indol-3-yl}carbonyl)-3H-spiro[2-benzofuran-1,4'-piperidine] in MeOH was treated with aq. H₂CO (1.5 eq), AcOH (1.1 eq) and stirred for 15 min at room temperature, then treated with NaCNBH₃ (1.1 eq) and stirred at room temperature for 1 h. Concentration and purification by preparative HPLC the desired product. ES-MS m/e (%): 478.2(M+H+).

Example 266

1'-{[6-Chloro-1-(pyrrolidin-3-ylmethyl)-1H-indol-3-yl]carbonyl}-3H-spiro[2-benzofuran-1,4'-piperidine]

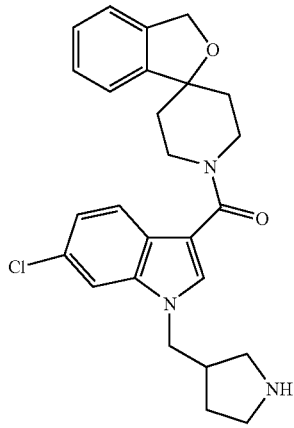

Following the general procedure III as described above, the alkylation of 1'-[(6-chloro-1H-indol-3-yl)carbonyl]-3H-spiro[2-benzofuran-1,4'-piperidine] (prepared according to example 69) with methanesulfonic acid pyrrolidin-3-ylmethyl ester (described in WO 9742189) gave the title compound. ES-MS m/e (%): 450.2(M+H$^+$).

Example 267

1'-({6-Chloro-1-[(2S)-pyrrolidin-2-ylmethyl]-1H-indol-3-yl}carbonyl)-3H-spiro[2-benzofuran-1,4'-piperidine

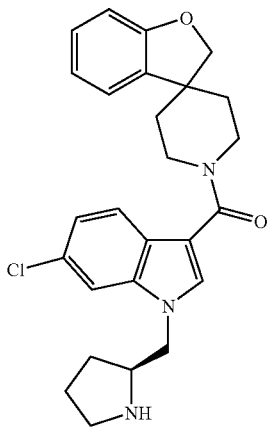

Following the general procedure III as described above, the alkylation of 1'-[(6-chloro-1H-indol-3-yl)carbonyl]-3H-spiro[2-benzofuran-1,4'-piperidine] (prepared according to example 69) with methanesulfonic acid (S)-1-pyrrolidin-2-ylmethyl ester (described in Tetrahedron: Asymmetry (1997), 8(13), 2209-2213) gave the title compound.
ES-MS m/e (%): 450.2(M+H$^+$).

Example 268

1'-[(6-Chloro-1-{[(2S)-1-methylpyrrolidin-2-yl]methyl}-1H-indol-3-yl)carbonyl]-3H-spiro[2-benzofuran-1,4'-piperidine

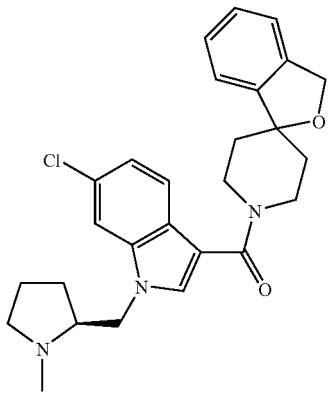

1'-({6-Chloro-1-[(2S)-pyrrolidin-2-ylmethyl]-1H-indol-3-yl}carbonyl)-3H-spiro[2-benzofuran-1,4'-piperidine was treated with a 37% aq. formaldehyde (1.05 eq.), acetic acid (1.05 eq.) and soduim cyanoborohydride (1.0 eq.) in MeOH at room temperature for 2 h to give after purification by preparative HPLC the title compound. ES-MS m/e (%): 464.2(M+H$^+$).

Example 269

1'-[(6-Chloro-1-{[(2R)-1-methylpyrrolidin-2-yl]methyl}-1H-indol-3-yl)carbonyl]-3H-spiro[2-benzofuran-1,4'-piperidine

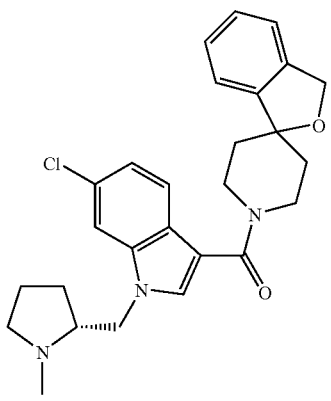

1'-({6-Chloro-1-[(2R)-pyrrolidin-2-ylmethyl]-1H-indol-3-yl}carbonyl)-3H-spiro[2-benzofuran-1,4'-piperidine (prepared according to the procedure described above for the preparation of 1'-({6-chloro-1-[(2S)-pyrrolidin-2-ylmethyl]-1H-indol-3-yl}carbonyl)-3H-spiro[2-benzofuran-1,4'-piperidine using methanesulfonic acid (R)-1-pyrrolidin-2-ylmethyl ester instead of methanesulfonic acid (S)-1-pyrrolidin-2-ylmethyl ester) was treated with a 37% aq. formaldehyde (1.05 eq.), acetic acid (1.05 eq.) and soduim cyanoborohydride (1.0 eq.) in MeOH at room temperature for 2 h to give after purification by prep. HPLC the title compound.
ES-MS m/e (%): 464.2(M+H$^+$).

Example 270

N-{2-[6-Chloro-3-(1'H,3H-spiro[2-benzofuran-1,4'-piperidin]-1'-ylcarbonyl)-1H-indol-1-yl]ethyl}acetamide

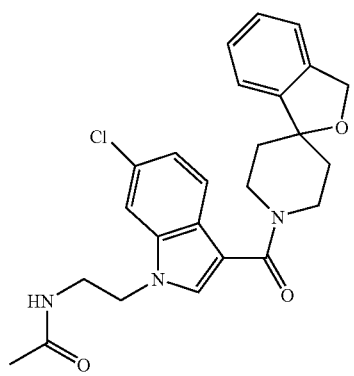

2-[6-Chloro-3-(1'H,3H-spiro[2-benzofuran-1,4'-piperidin]-1'-ylcarbonyl)-1H-indol-1-yl]ethanamine was treated with acetylchloride (1.05 eq) and triethylamine (1.05 eq) in dichloromethane under argon at room temperature for 2 h to give after purification by prep. HPLC the title compound.
ES-MS m/e (%): 452.2(M+H$^+$).

Example 271

N-{2-[6-Chloro-3-(1'H,3H-spiro[2-benzofuran-1,4'-piperidin]-1'-ylcarbonyl)-1H-indol-1-yl]ethyl}methanesulfonamide

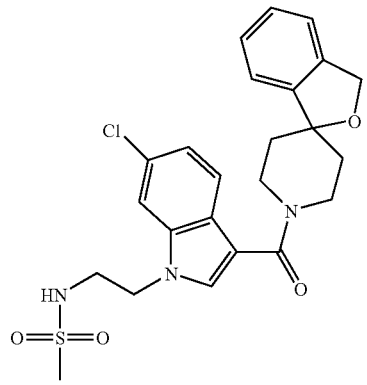

2-[6-Chloro-3-(1'H,3H-spiro[2-benzofuran-1,4'-piperidin]-1'-ylcarbonyl)-1H-indol-1-yl]ethanamine was treated with mesylchloride (1.05 eq) and triethylamine (1.05 eq) in dichloromethane under argon at room temperature to give after purification by prep. HPLC the title compound. ES-MS m/e (%): 488.1(M+H$^+$).

Example 272

N-{2-[6-Chloro-3-(1'H,3H-spiro[2-benzofuran-1,4'-piperidin]-1'-ylcarbonyl)-1H-indol-1-yl]ethyl}-N-methylacetamide

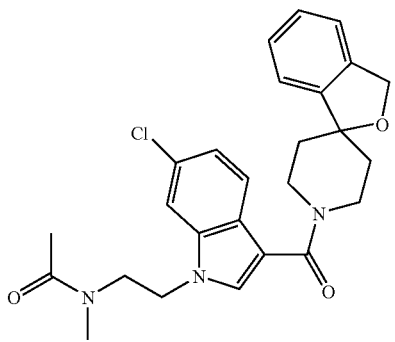

N-{2-[6-Chloro-3-(1'H,3H-spiro[2-benzofuran-1,4'-piperidin]-1'-ylcarbonyl)-1H-indol-1-yl]ethyl}acetamide was treated with NaH (1.05 eq), MeI (1.05 eq) in dry DMF under argon at room temperature for 2 h to give after purification by prep. HPLC the title compound.
ES-MS m/e (%): 466.2(M+H$^+$).

Example 273

N-{2-[6-Chloro-3-(1'H,3H-spiro[2-benzofuran-1,4'-piperidin]-1'-ylcarbonyl)-1H-indol-1-yl]ethyl}-N-methylmethanesulfonamide

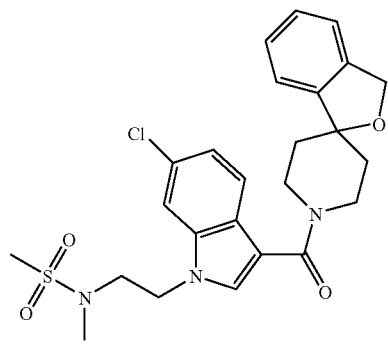

N-{2-[6-Chloro-3-(1'H,3H-spiro[2-benzofuran-1,4'-piperidin]-1'-ylcarbonyl)-1H-indol-1-yl]ethyl}methanesulfonamide was treated with NaH (1.05 eq), MeI (1.05 eq) in dry DMF under argon at room temperature for 2 h to give after purification by prep. HPLC the title compound.
ES-MS m/e (%): 502.1(M+H$^+$).

Example 274 tert-Butyl 10-(1'H,3H-spiro[2-benzofuran-1,4'-piperidin]-1'-ylcarbonyl)-3,4-dihydropyrazino[1,2-a]indole-2(1H)-carboxylate a) 10-(2,2,2-Trifluoro-acetyl)-3,4-dihydro-1H-pyrazino[1,2-a]indole-2-carboxylic acid tert-butyl ester

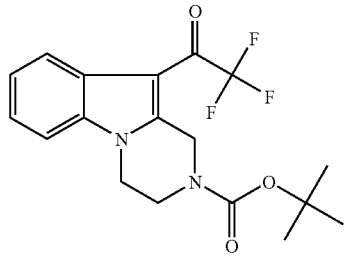

To a stirred solution of 0.21 ml (1.5 mmol) trifluoroacetic anhydride in 7 ml 1,2-dichloroethane was added at 0° C. a solution of 0.37 g (1.4 mmol) 3,4-dihydro-1H-pyrazino[1,2-a]indole-2-carboxylic acid tert-butyl ester and a solution of 0.23 ml (1.63 mmol) triethylamine in 3 ml 1,2-dichloroethane. After stirring for 30 min the reaction mixture was quenched with saturated aqueous sodium hydrogen carbonate solution and extracted with dichloromethane (2×100 ml). The combined organic layers were dried over sodium sulfate, concentrated in vacuo and purified by flash chromatography (n-heptane/ethyl acetate) to give the title compound (0.288 g, 58%) as a light yellow solid.

MS m/e (%): 369 (M+H$^+$, 27).

b) 3,4-Dihydro-1H-pyrazino[1,2-a]indole-2,10-dicarboxylic acid 2-tert-butyl ester

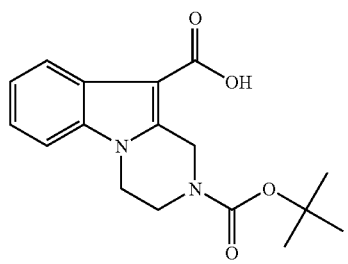

To a solution of 0.29 g (0.77 mmol) 10-(2,2,2-trifluoro-acetyl)-3,4-dihydro-1H-pyrazino[1,2-a]indole-2-carboxylic acid tert-butyl ester in 7 ml N,N-dimethylformamide were subsequently added 0.22 g (4.6 mmol) sodium hydride (50% in oil) and a solution of 0.070 ml (3.9 mmol) water in 1 ml N,N-dimethylformamide at room temperature. The reaction mixture was diluted with tert-butyl methyl ether after 2 h and extracted with 1 M sodium hydroxide solution (2×30 ml). The combined aqueous layers were acidified (pH 1-2) with 2 M hydrochloric acid at 0° C. and extracted with tert-butyl methyl ether (3×50 ml). The combined organic layers were dried over sodium sulfate and concentrated in vacuo to give the title compound (0.21 g, 86%) as a light brown solid.

MS m/e (%): 315 (M−H$^+$, 100).

c) tert-Butyl 10-(1'H,3H-spiro[2-benzofuran-1,4'-piperidin]-1'-ylcarbonyl)-3,4-dihydropyrazino[1,2-a]indole-2(1H)-carboxylate

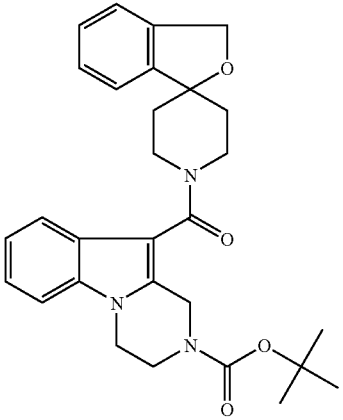

To a solution of 0.10 g (0.32 mmol) 3,4-dihydro-1H-pyrazino[1,2-a]indole-2,10-dicarboxylic acid 2-tert-butyl ester, 0.066 g (0.35 mmol) spiro[isobenzofuran-1(3H), 4'-piperidine] and 0.051 g (0.38 mmol) 1-hydroxybenzotriazole in 3.5 ml N,N-dimethylformamide were added 0.073 g (0.38 mmol) N-(3-dimethylaminopropyl)-N'-ethylcarbodiimide hydrochloride at room temperature. After stirring for 3 h the reaction mixture was diluted with saturated aqueous ammonium chloride solution and extracted with tert-butyl methyl ether (2×50 ml). The combined organic layers were washed with 1 M sodium hydroxide solution (1×30 ml) and water (1×30 ml), dried over sodium sulfate, concentrated in vacuo and purified by flash-chromatography (aminopropyl-modified silica gel, n-heptane/ethyl acetate) to give the title compound (0.097 g, 63%) as a light yellow solid.

MS m/e (%): 488 (M+H$^+$, 81).

Example 275

1'-(1,2,3,4-Tetrahydropyrazino[1,2-a]indol-10-ylcarbonyl)-3H-spiro[2-benzofuran-1,4'-piperidine]hydrochloride

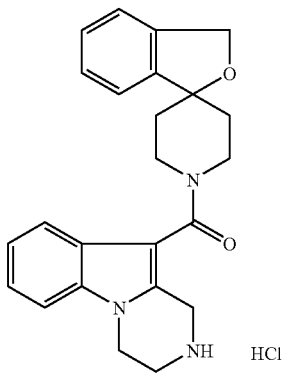

A mixture of 0.095 g (0.19 mmol) tert-butyl 10-(1'H,3H-spiro[2-benzofuran-1,4'-piperidin]-1'-ylcarbonyl)-3,4-dihydropyrazino[1,2-a]indole-2(1H)-carboxylate and 1.56 ml of a 1.25 M solution of hydrochloric acid (1.95 mmol) in methanol was stirred for 15 min at 50° C. The reaction mixture was concentrated in vacuo to give the title compound (0.084 g, 100%) as a light yellow solid. MS m/e (%): 388 (M+H⁺, 100).

Example 276

1'-[(2-Methyl-1,2,3,4-tetrahydropyrazino[1,2-a]indol-10-yl)carbonyl]-3H-spiro[2-benzofuran-1,4'-piperidine]

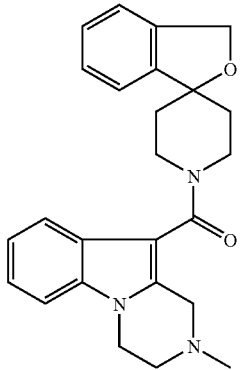

A solution of 0.050 g (0.12 mmol) 1'-(1,2,3,4-tetrahydropyrazino[1,2-a]indol-10-ylcarbonyl)-3H-spiro[2-benzofuran-1,4'-piperidine]hydrochloride, 0.033 ml (0.24 mmol) triethylamine and 0.028 g (0.94 mmol) paraformaldehyde in 2 ml methanol was heated at reflux for 1 h. The reaction mixture was cooled to 0° C. on an ice-water bath and treated with 0.011 g (0.18 mmol) sodium cyanoborohydride. After completed addition the mixture was allowed to warm to room temperature and stirred for 2 h. Quenching with water and dilution with 2 M aqueous sodium carbonate solution was followed by extraction with dichloromethane (2×50 ml). The combined organic layers were dried over sodium sulfate, concentrated in vacuo and purified by flash-chromatography (aminopropyl-modified silica gel, n-heptane/ethyl acetate) to give the title compound (0.036 g, 76%) as an off-white solid.

MS m/e (%): 402 (M+H⁺, 100).

Example 277

1'-[(6-Chloro-2-methyl-1H-indol-3-yl)carbonyl]-3H-spiro[2-benzofuran-1,4'-piperidine]

a) (6-Chloro-1H-indol-2-yl)-methanol

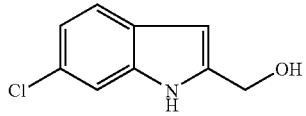

To a solution of 2.00 g (8.94 mmol) 6-chlorindole-2-carboxylic acid ethyl ester in 50 ml diethyl ether were added 0.475 g (12.5 mmol) lithium aluminum hydride at 0° C. The reaction mixture was heated at reflux for 45 min and quenched by consecutive addition of 10 ml water, 10 ml aqueous 2 M sodium hydroxide solution and 10 ml water at 0° C. The aqueous layer was extracted with tert-butyl methyl ether (3×100 ml). The combined organic layers were dried over sodium sulfate and concentrated in vacuo to give the crude title compound (1.64 g; 100%) as a white solid. MS m/e (%): 180 (M−H⁺, 100).

b) 6-Chloro-2-methyl-1H-indole

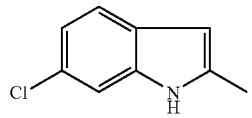

A solution of 1.60 g (8.81 mmol) (6-chloro-1H-indol-2-yl)-methanol in 5 ml 1,2-dichloroethane was added to a mixture of 80.0 ml trifluoroacetic acid and 32.0 ml triethylsilane at 65° C. After 5 min, the reaction mixture was cooled to room temperature and quenched with water. The pH was adjusted to 14 by the addition of aqueous sodium hydroxide solution (32%). The aqueous layer was extracted with tert-butyl methyl ether (3×200 ml). The combined organic layers were dried over sodium sulfate and concentrated in vacuo. The residue was purified by flash-chromatography (aminopropyl-modified silica gel, n-heptane/ethyl acetate) to give the title compound (0.39 g; 27%) as a white solid.

MS m/e (%): 164 (M−H⁺, 100).

c) 1-(6-Chloro-2-methyl-1H-indol-3-yl)-2,2,2-trifluoro-ethanone

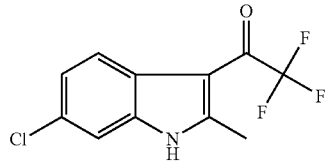

To a solution of 0.38 g (2.3 mmol) 6-chloro-2-methyl-1H-indole in 20 ml 1,2-dichloroethane at 0° C. were added 0.35 ml (2.5 mmol) trifluoroacetic anhydride. The reaction mixture was quenched with aqueous 2 M sodium carbonate solution after 30 min and extracted with dichloromethane (3×100 ml). The combined organic layers were dried over sodium sulfate and concentrated in vacuo to give the title compound (0.57 g; 95%) as an off-white solid.

MS m/e (%): 260 (M−H⁺, 100).

d) 6-Chloro-2-methyl-1H-indole-3-carboxylic acid

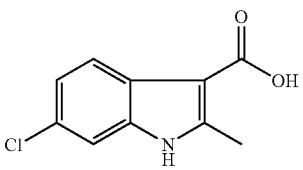

A solution of 0.57 g (2.2 mmol) 1-(6-chloro-2-methyl-1H-indol-3-yl)-2,2,2-trifluoro-ethanone in 21.7 ml (86.8 mmol) aqueous 4 M sodium hydroxide solution was heated at reflux for 45 min. After cooling to room temperature the reaction mixture was diluted with water and extracted with tert-butyl methyl ether (2×50 ml). The aqueous layer was cooled to 0-5° C., acidified (pH 1-2) with concentrated aqueous hydrochloric acid solution and extracted with ethyl acetate (3×100 ml). The combined ethyl acetate layers were dried over sodium sulfate and concentrated in vacuo to give the title compound (0.14 g, 31%) as an off-white solid.

MS m/e (%): 208 (M−H⁺, 100).

e) 1'-[(6-Chloro-2-methyl-1H-indol-3-yl)carbonyl]-3H-spiro[2-benzofuran-1,4'-piperidine]

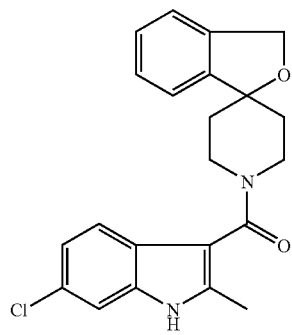

To a solution of 0.040 g (0.19 mmol) 6-chloro-2-methyl-1H-indole-3-carboxylic acid, 0.069 ml (0.40 mmol) N,N-diisopropylethylamine and 0.061 g (0.19 mmol) 2-(1H-benzotriazole-1-yl)-1,1,3,3-tetramethyluronium tetrafluoroborate in 1 ml dry N,N-dimethylformamide were added 0.036 g (0.19 mmol) spiro[isobenzofuran-1(3H), 4'-piperidine] at room temperature. After stirring for 1 h the reaction mixture was quenched with 0.5 M aqueous sodium hydroxide solution (20 ml) and extracted with ethyl acetate (2×30 ml). The combined organic layers were washed with water (2×30 ml) and brine (1×30 ml), dried over sodium sulfate and concentrated in vacuo. The residue was purified by flash chromatography (n-heptane/ethyl acetate) to give the title compound (0.036 g, 49%) as a white solid.
MS m/e (%): 379 (M–H$^+$, 100).

Example 278

1'-({1-[3,5-Bis(trifluoromethyl)benzyl]-6-chloro-2-methyl-1H-indol-3-yl}carbonyl)-3H-spiro[2-benzofuran-1,4'-piperidine]

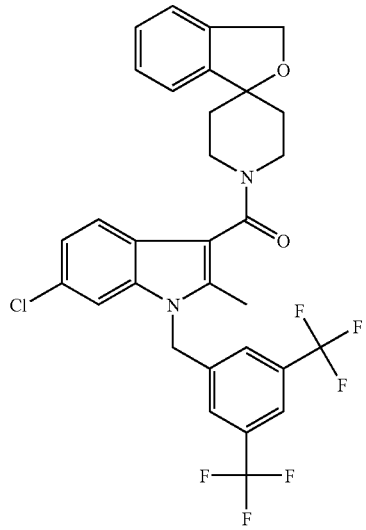

To a solution of 0.031 g (0.080 mmol) 1'-[(6-chloro-2-methyl-1H-indol-3-yl)carbonyl]-3H-spiro[2-benzofuran-1, 4'-piperidine] (5) in 1 ml dry N,N-dimethylformamide were added 0.004 g (0.08 mmol) sodium hydride (50% in oil). After stirring for 20 min 0.015 ml (0.08 mmol) 3,5-bis (trifluoromethyl)benzyl bromide were added. After stirring for 16 h the reaction mixture was quenched with water and extracted with ethyl acetate (2×50 ml). The combined organic layers were washed with water (2×30 ml) and brine (1×30), dried over sodium sulfate and concentrated in vacuo. The residue was purified by flash chromatography (n-heptane/ethyl acetate) to give the title compound (0.020 g; 41%) as a white solid. MS m/e (%): 607 (M+H$^+$, 100).

Examples of Compounds of Formula (I-f)

Example 279

5-Bromo-1'-(1H-indol-3-ylcarbonyl)spiro[indole-3, 4'-piperidin]-2(1H)-one a) 5-Bromo-1,2-dihydro-2-oxospiro[3H-indole-3,4'-piperidine]-1'methyl

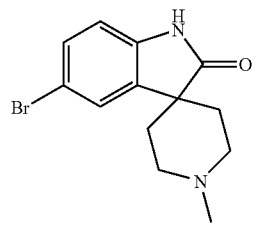

A solution of 1,2-benzo-8-methyl-3,8-diazaspiro[4,5]decane-4-one (described in Organic Preparations and Procedures International (1995), 27(6), 691-4)(6.3 g, 29.1 mmol) in CH$_3$CN (100 ml) and MeOH (5 ml) was cooled to −5° C. and NBS (7.8 g, 44 mmol) was slowly added with stirring. The reaction mixture was stirred for 3.5 h at 0° C. Solvent was removed by vacuo. The residue was purified by silica gel chromatography (2-20% MeOH/dichloromethane) to give 6 g of a solid. The solid compound was dissolved in ethyl acetate (600 ml) and washed with saturated aqueous NaHCO$_3$ solution, dried (Na$_2$SO$_4$). Evaporation of the solvent in vacuo gave 4.2 g (47%) of the desired product.
$^1$HNMR (CD$_3$OD, 400 MHz) d 7.51(d, J=1.8 Hz, 1H), 7.35(dd, J=1.9 and 8.2 Hz, 1H), 6.81(d, J=8.2 Hz, 1H), 2.93(m, 2H), 2.67(m, 2H), 2.41(s, 3H), 1.86(m, 4H).

b) 5-Bromo-1,2-dihydro-2-oxospiro[3H-indole-3,4'-piperidine]-1'-cyano

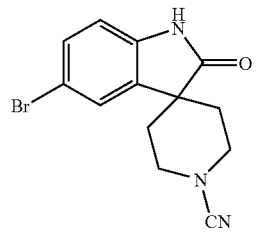

5-Bromo-1,2-dihydro-2-oxospiro[3H-indole-3,4'-piperidine]-1'-methyl (4.6 g, 15.6 mmol) was dissolved in chloroform (700 ml) and treated with CNBr (22 g, 209.5 mmol)

at room temperature. The mixture was heated to reflux for 24 h. The reaction mixture was cooled, diluted with methylene chloride (300 ml) and washed with 10% aqueous K$_2$CO$_3$ solution (2×100 ml). After the mixture was dried (Na$_2$SO$_4$) and concentrated, the residue was purified by silica gel chromatography (0-5% MeOH/dichloromethane) to give the desired product as a solid (3.9 g, 82%). $^1$HNMR (CDCl$_3$, 400 MHz) δ 7.52 (d, J=1.8 Hz, 1H), 7.37(dd, J=1.8 and 8.2 Hz, 1H), 6.82 (d, J=8.2 Hz, 1H), 3.83(m, 2H), 3.41(m, 2H), 2.00(m, 2H), 1.86(m, 2H).

c) 5-Bromospiro[indole-3,4'-piperidin]-2(1H)-one

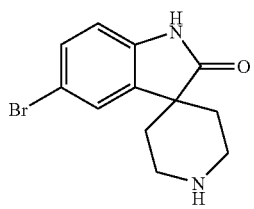

5-Bromo-1,2-dihydro-2-oxospiro[3H-indole-3,4'-piperidine]-1'-cyano (3.3 g, 10.8 mmol) was suspended in ethylene glycol (10 ml). The mixture was treated in NaOH (1.8 g, 45 mmol) and heated to 130° C. for 15 min. It was diluted with methylene chloride (500 ml) and washed with 10% aqueous K$_2$CO$_3$ (2×100 m). The organic layer was dried (Na$_2$SO$_4$) and concentrated and residue purified by silica gel chromatography (30% MeOH/dichloromethane) to give the desired product as a light ceramic white solid (1.8 g, 60%).

Mp 256-258° C. $^1$HNMR (DMSO-d$_6$, 400 MHz) δ 10.6 (br s, 1H, NH), 7.57(d, J=1.84 Hz, 1H), 7.36(d, J=8.2 Hz, 1H), 6.79(d, J=8.2 Hz, 1H), 4.05 (br s, 1H, NH), 3.06(m, 2H), 2.84(m, 2H), 1.64(m, 2H), 1.55(m, 2H), $^{13}$C NMR (DMSO-d$_6$, 100 MHz) δ 180.93, 140.64, 137.98, 130.42, 126.75, 113.20, 111.45, 46.24, 40.92, 32.94. Anal. Calcd for C$_{12}$H$_{13}$BrN$_2$O: C, 51.26; H, 4.66; N, 9.9. Found: C, 50.87; H, 4.91; N, 9.67.

d) 5-Bromo-1'-(1H-indol-3-ylcarbonyl)spiro[indole-3,4'-piperidin]-2(1H)-one

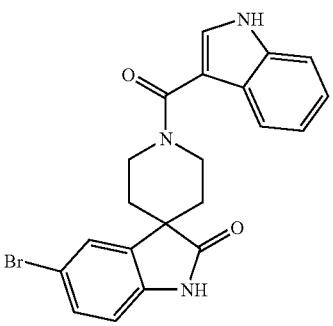

Following the general procedure I as described above, the acylation of 5-bromospiro[indole-3,4'-piperidin]-2(1H)-one with 1H-indole-3-carboxylic acid (commercially available), gave the title compound. ES-MS m/e (%): 424.3(M+H$^+$).

Example 280

5-Bromo-1'-[(6-chloro-1H-indol-3-yl)carbonyl]spiro[indole-3,4'-piperidin]-2(1H)-one

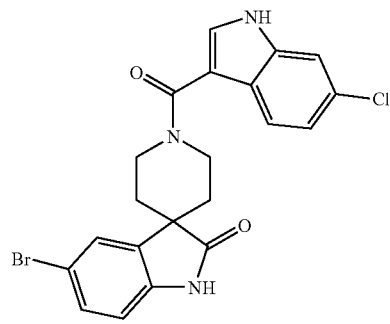

Following the general procedure I as described above, the acylation of 5-bromospiro[indole-3,4'-piperidin]-2(1H)-one with 6-chloro-1H-indole-3-carboxylic acid (preparation described in example 5 above), gave the title compound. ES-MS m/e (%): 458.3(M+H$^+$).

Example of Compounds of Formula (I-g)

Example 281

(1R,3'R,5'S)-1'-[(1-Benzyl-2-methyl-1H-indol-3-yl)carbonyl]-3',5'-dimethyl-3H-spiro[2-benzofuran-1,4'-piperidin]-3-one

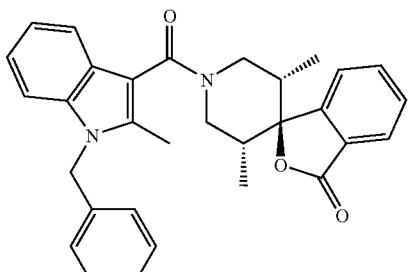

Following the general procedure I as described above, the acylation of (1R,3'R,5'S)-1'-[(6-chloro-1H-indol-3-yl)carbonyl]-3',5'-dimethyl-3H-spiro[2-benzofuran-1,4'-piperidin]-3-one (described in WO 9929696) with 1-benzyl-2-methyl-1H-indole-3-carboxylic acid (preparation described in example 1), gave the title compound. ES-MS m/e (%): 479.6(M+H$^+$).

Examples of Compounds of Formula (I-h)

Example 282

1'-[(6-Chloro-1H-indol-3-yl)carbonyl]spiro[isoindole-1,4'-piperidin]-3 (2H)-one a) Bis-(2-chloro-ethyl)-carbamic acid tert-butyl ester

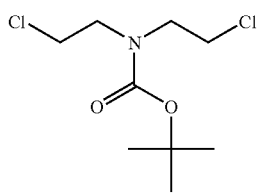

To a solution of 10.0 g (56.0 mmol) bis(2-chloroethyl) amine hydrochloride and 14.7 g (67.2 mmol) di-tert-butyl dicarbonate in 60 ml dichloromethane were added dropwise 9.37 ml (67.2 mmol) triethylamine at room temperature. After stirring for 4 h the solvent was evaporated. The residual oil was redissolved in 300 ml tert-butyl methyl ether and washed with saturated aqueous ammonium chloride solution (1×100 ml) and water (1×100 ml). The combined aqueous layers were extracted with tert-butyl methyl ether (1×200 ml). The combined organic layers were dried over sodium sulfate, concentrated in vacuo and purified by flash chromatography (n-heptane/ethyl acetate) to give the title compound (9.6 g, 71%) as a colourless oil. MS m/e (%): 186 (M-$C_4H_8$+H$^+$, 100).

b) 4-(2-Bromo-phenyl)-4-cyano-piperidine-1-carboxylic acid tert-butyl ester

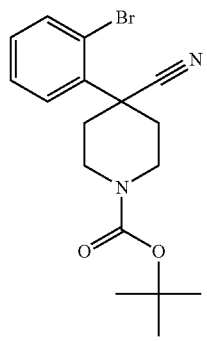

A mixture of 4.50 g (23.0 mmol) 3-bromophenylacetonitrile and 0.78 g (2.3 mmol) tetrabutylammonium hydrogensulfate in 27 ml tetrahydrofuran and 45 ml of a 50% aqueous sodium hydroxide solution was heated at reflux for 10 min. Thereafter 6.11 g (25.3 mmol) bis-(2-chloro-ethyl)-carbamic acid tert-butyl ester were added at room temperature. The reaction mixture was heated at reflux for 4 h. Cooling to room temperature was followed by dilution with 60 ml water and extraction with tert-butyl methyl ether (3×100 ml). The combined organic layers were washed with brine (1×100 ml), dried over sodium sulfate and concentrated in vacuo. The residual crude product was purified by flash chromatography (n-heptane/ethyl acetate) to give the title compound (6.72 g, 80%) as a pale yellow oil. MS m/e (%): 265, 267 (M-BOC+H$^+$, 82, 100).

c) 4-(2-Bromo-phenyl)-piperidine-1,4-dicarboxylic acid mono-tert-butyl ester

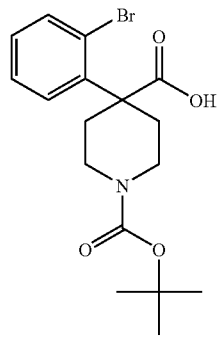

A mixture of 5.7 g (15.6 mmol) 4-(2-bromo-phenyl)-4-cyano-piperidine-1-carboxylic acid tert-butyl ester and 235 ml (936 mmol) of a 4 M aqueous hydrochloric acid solution was heated at reflux for 96 h. After cooling to room temperature the reaction mixture was basified with 93.90 ml (1014 mmol) of a 10.8 M aqueous sodium hydroxide solution and diluted with 200 ml 1,4-dioxane. A solution of 5.11 g (23.4 mmol) di-tert-butyl dicarbonate in 50 ml 1,4-dioxane was added quickly at 0° C. After stirring for 2 h the reaction mixture was extracted with tert-butyl methyl ether (2×100 ml). The combined organic layers were washed with 1 M sodium hydroxide solution (1×100 ml). The combined aqueous layers were cooled by the addition of 100 g ice, acidified (pH 1-2) with ice-cold 2 M aqueous hydrochloric acid solution and extracted with ethyl acetate (3×150 ml). The combined ethyl acetate layers were dried over sodium sulfate and concentrated in vacuo to give the title compound (5.51 g, 92%) as a light yellow solid.
MS m/e (%): 382, 384 (M+H$^+$, 90, 100).

d) 4-Azidocarbonyl-4-(2-bromo-phenyl)-piperidine-1-carboxylic acid tert-butyl ester

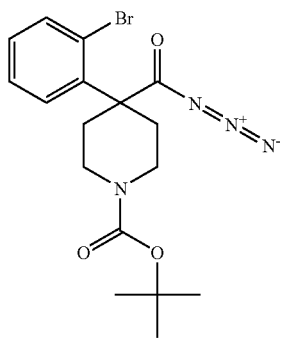

To a solution of 2.00 g (5.20 mmol) 4-(2-bromo-phenyl)-piperidine-1,4-dicarboxylic acid mono-tert-butyl ester in 26 ml dichloromethane were added 0.76 ml (5.73 mmol) 1-chloro-N,N,2-trimethylpropenylamine at room temperature. After stirring for 45 min the reaction mixture was concentrated in vacuo. The residual oil was redissolved in 26 ml dry N,N-dimethylformamide and treated with 0.51 g (7.8 mmol) sodium azide. After stirring for 1 h the reaction mixture was diluted with 200 ml tert-butyl methyl ether and washed with 0.5 M aqueous sodium carbonate solution (2×50 ml). The combined aqueous layers were extracted with tert-butyl methyl ether (2×100 ml). The combined organic layers were washed with water (1×50 ml) and brine (1×50 ml), dried over sodium sulfate and concentrated in vacuo to give the crude title compound (1.76 g, 83%) as a light yellow solid.

e) tert-Butyl 3-oxo-2,3-dihydro-1'H-spiro[isoindole-1,4'-piperidine]-1'-carboxylate

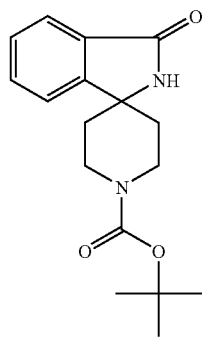

A solution of 1.60 g (3.91 mmol) 4-azidocarbonyl-4-(2-bromo-phenyl)-piperidine-1-carboxylic acid tert-butyl ester in 40 ml toluene was stirred at 90° C. for 1 h. The reaction mixture was concentrated in vacuo and the residue was redissolved in 40 ml dry tetrahydrofuran. Cooling of the solution to −100° C. was followed by slow dropwise additon of 4.6 ml (7.8 mmol) of a 1.7 M solution of tert-butyl lithium in pentane. The cooling bath was removed after 10 min and the reaction mixture was allowed to warm to 0° C. After quenching with 5 ml saturated aqueous ammonium chloride solution the mixture was extracted with tert-butyl methyl ether (3×50 ml). The combined organic layers were washed with brine (1×50 ml), dried over sodium sulfate and concentrated in vacuo to give the title compound (1.15 g, 97%) as a light yellow solid.

MS m/e (%): 247 (M-C$_4$H$_8$+H$^+$, 100).

f) Spiro [isoindole-1,4'-piperidin]-3(2H)-one

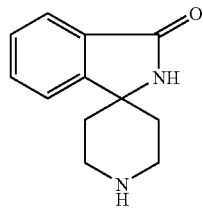

To a solution of 0.10 g (0.33 mmol) tert-butyl 3-oxo-2,3-dihydro-1'H-spiro[isoindole-1,4'-piperidine]-1'-carboxylate in 3.3 ml dichloromethane were added 0.25 ml (3.3 mmol) trifluoroacetic acid at room temperature. After stirring for 4 h the reaction mixture was diluted with 20 ml aqueous 1 M sodium hydroxide solution (20 ml) and extracted with ethyl acetate (3×50 ml). The combined organic layers were dried over sodium sulfate and concentrated in vacuo to give the crude title compound (0.095 g) as a light yellow solid.

MS m/e (%): 203 (M+H$^+$, 100).

g) 1'-[(6-Chloro-1H-indol-3-yl)carbonyl]spiro[isoindole-1,4'-piperidin]-3(2H)-one

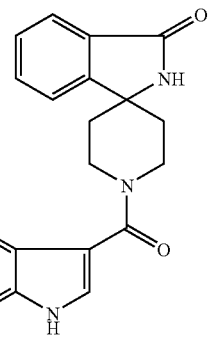

To a solution of 0.060 g (0.31 mmol) 6-chloro-1H-indole-3-carboxylic acid in 3 ml dichloromethane were added 0.045 ml (0.38 mmol) 1-chloro-N,N,2-trimethyl-propenylamine at room temperature. After stirring for 1 h the reaction mixture was concentrated in vacuo. The residue was redissolved in 2 ml dry N,N-dimethylformamide. A solution of 0.062 g (0.31 mmol) spiro[isoindole-1,4'-piperidin]-3(2H)-one and 0.064 ml (0.46 mmol) triethylamine in 1 ml dry N,N-dimethylformamide was added at room temperature. After stirring for 2 h the reaction mixture was quenched with 1 M aqueous sodium hydroxide solution (30 ml) and extracted with ethyl acetate (3×50 ml). The combined organic layers were washed with water (2×30 ml), 0.5 M aqueous hydrochloric acid solution (1×30 ml) and brine (1×30 ml), dried over sodium sulfate and concentrated in vacuo. The crude product was triturated in warm diethyl ether, filtrated and dried in vacuo to give the title compound (0.031 g, 22%) as light brown solid with a purity of approx. 80% by LC-.MS.

MS m/e (%): 378 (M−H$^+$, 100).

Example 283

2-{6-Chloro-3-[(3-oxo-2,3-dihydro-1'H-spiro[isoindole-1,4'-piperidin]-1'-yl)carbonyl]-1H-indol-1-yl}-N-methylacetamide

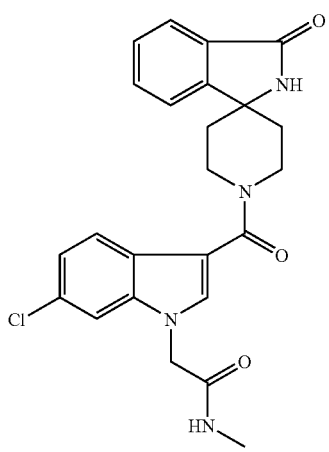

To a solution of 0.35 g (0.13 mmol) 6-chloro-1-methyl-carbamoylmethyl-1H-indole-3-carboxylic acid, 0.025 ml (0.14 mmol) N,N-diisopropylethylamine and 0.055 g (0.14 mmol) O-(7-azabenzotriazol-1-yl)-N,N,N',N'-tetramethyluronium hexafluorophosphate in 2 ml dry N,N-dimethylformamide were added 0.029 g (0.14 mmol) spiro[isoindole-1,4'-piperidin]-3(2H)-one at room temperature. After stirring for 2 h the reaction mixture was quenched with 0.5 M aqueous sodium hydroxide solution (20 ml) and extracted with ethyl acetate (2×30 ml). The combined organic layers were washed with water (2×30 ml) and brine (1×30 ml), dried over sodium sulfate and concentrated in vacuo. The residue was purified by flash chromatography (aminopropyl-modified silica gel, dichloromethane/methanol) to give the title compound (0.026 g, 44%) as a white solid. MS m/e (%): 451 (M+H+, 100).

Example 284

1'-[(6-Chloro-1H-indol-3-yl)carbonyl]-2,3-dihydrospiro[isoindole-1,4'-piperidine]

a) tert-Butyl 2,3-dihydro-1'H-spiro[isoindole-1,4'-piperidine]-1'-carboxylate

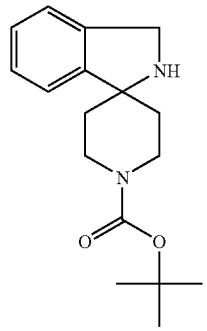

To a solution of 0.20 g (0.66 mmol) tert-butyl 3-oxo-2,3-dihydro-1'H-spiro[isoindole-1,4'-piperidine]-1'-carboxylate in 6.6 ml toluene were added 0.33 ml (0.66 mmol) of a 2 M solution of borane dimethylsulfide complex in tetrahydrofuran. After stirring at reflux for 5 h the mixture was cooled to room temperature, treated with 1.5 ml of methanol and reheated to reflux for 15 min. The reaction mixture was then concentrated in vacuo to give the crude title compound (0.23 g, 84.%) as a light yellow solid with a purity of 70% by LC-MS.

MS m/e (%): 289 (M+H+, 83).

b) 2,3-Dihydrospiro[isoindole-1,4'-piperidine]dihydrochloride

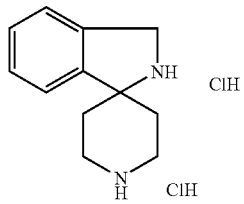

A solution of 0.16 g (0.56 mmol) tert-butyl 2,3-dihydro-1'H-spiro[isoindole-1,4'-piperidine]-1'-carboxylate in 4.5 ml (5.6 mmol) of a 1.25 M solution of hydrochloric acid in methanol was stirred at 50° C. for 30 min. The reaction mixture was concentrated in vacuo. The residue was triturated in hot tetrahydrofuran, filtrated and dried in vacuo to give the title compound (0.15 g, 100%) as a light yellow solid. MS m/e (%): 189 (M+H+, 100).

c) 1'-[(6-Chloro-1H-indol-3-yl)carbonyl]-2,3-dihydrospiro[isoindole-1,4'-piperidine]

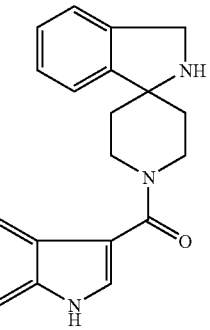

To a solution of 0.10 g (0.51 mmol) 6-chloro-1H-indole-3-carboxylic acid in 5 ml dichloromethane were added 0.074 ml (0.56 mmol) 1-chloro-N,N,2-trimethyl-propenylamine at room temperature. The reaction mixture was concentrated in vacuo after 1 h. The residue was redissolved in 2 ml dry N,N-dimethylformamide. A suspension of 0.147 g (0.56 mmol) 2,3-dihydrospiro[isoindole-1,4'-piperidine]dihydrochloride and 0.285 ml (2.04 mmol) triethylamine in 2 ml dry N,N-dimethylformamide was added at room temperature. After stirring for 16 h the reaction mixture was quenched with 1 M aqueous sodium hydroxide solution (30 ml) and extracted with ethyl acetate (3×50 ml). The combined organic layers were washed with water (2×30 ml) and brine (1×30 ml), dried over sodium sulfate and concentrated in vacuo. The residue was purified by flash chromatography (dichloromethane/methanol) to give the title compound (0.045 g; 24%) as an off-white solid. MS m/e (%): 366 (M+H+, 100).

Example 285

1'-[(6-Chloro-1H-indol-3-yl)carbonyl]-2-methyl-2,3-dihydrospiro[isoindole-1,4'-piperidine]

a) tert-Butyl 2-methyl-3-oxo-2,3-dihydro-1'H-spiro[isoindole-1,4'-piperidine]-1'-carboxylate

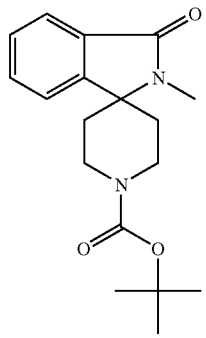

To a solution of 0.310 g (1.03 mmol) spiro[isoindole-1,4'-piperidin]-3(2H)-one-1-carboxylic acid tert-butyl ester in 10 ml N,N-dimethylformamide were added 0.054 g (1.1 mmol) sodium hydride (50% in oil) at room temperature. After stirring for 30 min 0.067 ml (1.1 mmol) iodomethane were added. The reaction mixture was quenched with water after 1 h and extracted with tert-butyl methyl ether (2×100). The combined organic layers were washed with water (2×50 ml) and brine (1×50 ml), dried over sodium sulfate and concentrated in vacuo to give the title compound (0.32 g, 99%) as light yellow solid. MS m/e (%): 317 (M+H$^+$, 21).

b) tert-Butyl 2-methyl-2,3-dihydro-1′H-spiro[isoindole-1,4′-piperidine]-1′-carboxylate

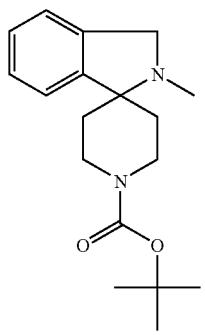

To a solution of 0.10 g (0.32 mmol) tert-butyl 2-methyl-3-oxo-2,3-dihydro-1′H-spiro[isoindole-1,4′-piperidine]-1′-carboxylate in 3.2 ml toluene were added 0.16 ml (0.32 mmol) of a 2 M solution of borane dimethylsulfide complex in tetrahydrofuran. After heating at reflux for 4 h the reaction mixture was cooled to room temperature, quenched with 1.5 ml of methanol and reheated to reflux for 15 min. The reaction mixture was concentrated in vacuo and the residue was purified by flash chromatography (n-heptane/ethyl) to give the title compound (0.057 g, 60%) as a light yellow solid.

MS m/e (%): 303 (M+H$^+$, 100).

c) 2-Methyl-2,3-dihydrospiro[isoindole-1,4′-piperidine]

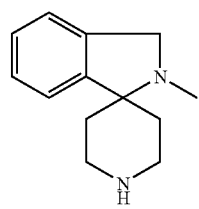

A solution of 0.057 g (0.33 mmol) tert-butyl 2-methyl-2,3-dihydro-1′H-spiro[isoindole-1,4′-piperidine]-1′-carboxylate in 1.32 ml (1.65 mmol) of a 1.25 M solution of hydrochloric acid in methanol was stirred at 50° C. for 15 min. The reaction mixture was concentrated in vacuo. The residue was dissolved in 2 M aqueous sodium hydroxide solution and extracted with dichloromethane (3×50 ml). The combined organic layers were dried over sodium sulfate and concentrated in vacuo to give the crude title compound (0.041 g) as a pale yellow amorphous solid. MS m/e (%): 203 (M+H$^+$, 100).

d) 1′-[(6-Chloro-1H-indol-3-yl)carbonyl]-2-methyl-2,3-dihydrospiro[isoindole-1,4′-piperidine]

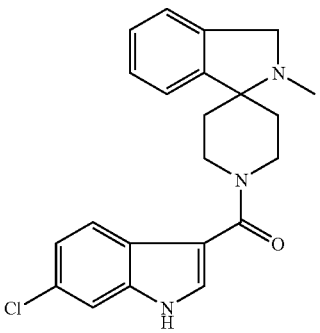

To a solution of 0.040 g (0.20 mmol) 6-chloro-1H-indole-3-carboxylic acid in 3 ml dichloromethane were added 0.03 ml (0.22 mmol) 1-chloro-N,N,2-trimethyl-propenylamine at room temperature. After stirring for 1 h the reaction mixture was concentrated in vacuo. The residue was redissolved in 2 ml dry N,N-dimethylformamide. A solution of 0.041 g (0.20 mmol) 2-methyl-2,3-dihydrospiro[isoindole-1,4′-piperidine] and 0.043 ml (0.31 mmol) triethylamine in 1 ml dry N,N-dimethylformamide was added at room temperature. After stirring for 2 h the reaction mixture was quenched with 1 M aqueous sodium hydroxide solution (30 ml) and extracted with ethyl acetate (3×50 ml). The combined organic layers were washed with water (2×30 ml) and brine (1×30 ml), dried over sodium sulfate and concentrated in vacuo. The residue was purified by flash chromatography (n-heptane/ethyl acetate) to give the title compound (0.022 g, 23%) as an off-white solid with a purity of approx. 83% by LC-MS.

MS m/e (%): 380 (M+H$^+$, 100).

The invention claimed is:

1. A compound of formula (I)

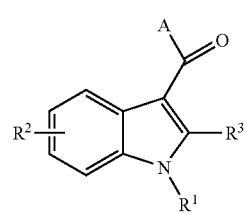

wherein

A is selected from the group consisting of (a), (b), (c), (d), (e), (f), (g) and (h):

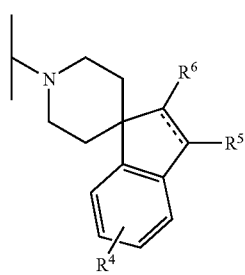

(b)
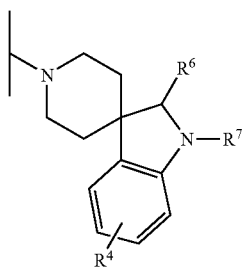

(c)
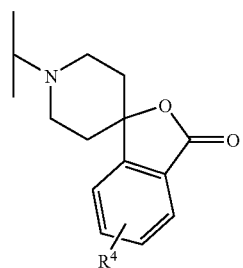

(d)
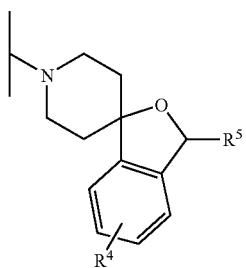

(e)
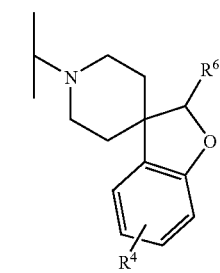

(f)
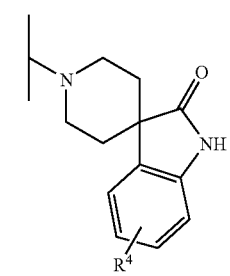

(g)
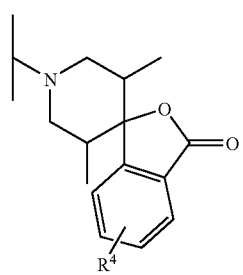

(h)
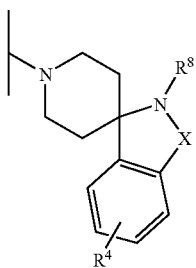

wherein in (a) the dotted line is an optional double bond;

$R^1$ is H,
  $C_{1-6}$-alkyl optionally substituted by CN,
  aryl, 5 or 6 membered heteroaryl or sulfonylaryl, each of which is optionally substituted by one or more B,
  —$(CH_2)_m$—$R^a$ wherein $R^a$ is:
    CN,
    $OR^i$,
    $NR^iR^{ii}$, or
    $C_{3-6}$-cycloalkyl, 3 to 7 membered-heterocycloalkyl, aryl, or 5 or 6 membered heteroaryl, each of which is optionally substituted by one or more B,
  or —$(CH_2)_n$—(CO)—$R^b$ or —$(CH_2)_n$—$(SO_2)$—$R^b$, wherein $R^b$ is:
    $C_{1-6}$-alkyl,
    $C_{1-6}$-alkoxy,
    $C_{3-6}$-cycloalkyl,
    —$(CH_2)_m$—$NR^{iii}R^{iv}$,
    $NR^iR^{ii}$, or
    $C_{3-6}$-cycloalkyl, 4 to 7 membered-heterocycloalkyl, aryl, or 5 or 6 membered heteroaryl, each of which is optionally substituted by one or more B,
  or $R^1$ and $R^3$ together with the indole ring to which they are attached form a 5 or 6 membered heterocycloalkyl which is optionally substituted by =O, C(O)O—$C_{1-6}$-alkyl or $C_{1-6}$-alkyl;

there is one or more $R^2$, wherein each $R^2$ is the same or different, $R^2$ is one or more H, OH, halo, CN, nitro, $C_{1-6}$-alkyl optionally substituted by —$NR^{iii}R^{iv}$, $C_{1-6}$-alkoxy, —O—$CH_2$—$C_{2-6}$-alkenyl, or benzyloxy,
  or two $R^2$ together with the indole ring to which they are attached form an oxo or dioxo bridge;

$R^3$ is H,
  halo,
  —(CO)—$R^c$, wherein $R^c$ is:
    $C_{1-6}$-alkyl,
    —$(CH_2)_n$—$NR^iR^{ii}$,
    —$(CH_2)_n$—$NR^{iii}R^{iv}$, or
    5 or 6 membered heterocycloalkyl optionally substituted by $C_{1-6}$-alkyl,
  or $C_{1-6}$-alkyl or aryl, each of which is optionally substituted by
    halo,
    —O(CO)—$C_{1-6}$-alkyl, or
    —NH(CO)$R^d$, wherein $R^d$ is $C_{1-6}$-alkyl optionally substituted by halo or nitro, or $R^d$ is aryl or a 5 or 6 membered heteroaryl, each of which is optionally substituted by halo, nitro, $C_{1-6}$-alkyl or $C_{1-6}$-haloalkyl;

there is one or more $R^4$, wherein each $R^4$ is the same or different, $R^4$ is one or more H, halo, $C_{1-6}$-alkyl or $C_{1-6}$-alkoxy optionally substituted by OH, or two $R^4$ together with the phenyl ring to which they are attached form an oxo or dioxo bridge;

$R^5$ is H, $C_{1-6}$-alkyl or aryl;

$R^6$ is H or $C_{1-6}$-alkyl;

$R^7$ is H or —$SO_2$—$R^e$ wherein $R^e$ is $C_{1-6}$-alkyl or aryl;

$R^8$ is H or $C_{1-6}$-alkyl;

X is $CH_2$ or $C=O$;

B is halo,
  CN,
  $NR^iR^{ii}$,
  $C_{1-6}$-alkyl optionally substituted by CN, halo or $C_{1-6}$-alkoxy,
  $C_{1-6}$-alkoxy,
  $C_{1-6}$-haloalkoxy,
  $C_{3-6}$-cycloalkyl,
  —C(O)O—$C_{1-6}$-alkyl,
  —C(O)$NR^iR^{ii}$,
  —C(O)—$C_{1-6}$-alkyl,
  —$S(O)_2$—$C_{1-6}$-alkyl, or
  —$S(O)_2$—$NR^iR^{ii}$, $(CR^{iii}R^{iv})_n$-phenyl, or $(CR^{iii}R^{iv})_n$-5 or 6 membered heteroaryl wherein the phenyl or 5 or 6 membered heteroaryl moiety is optionally substituted by one or more substituent(s) selected from the group consisting of:
    halo,
    CN,
    $NR^iR^{ii}$,
    $C_{1-6}$-alkyl optionally substituted by CN, halo or $C_{1-6}$-alkoxy,
    $C_{1-6}$-alkoxy,
    $C_{1-6}$-haloalkoxy,
    $C_{3-6}$-cycloalkyl,
    —C(O)O—$C_{1-6}$-alkyl,
    —C(O)—$NR^iR^{ii}$,
    —C(O)—$C_{1-6}$-alkyl,
    —$S(O)_2$—$C_{1-6}$-alkyl, and
    —$S(O)_2$—$NR^iR^{ii}$;

$R^i$ and $R^{ii}$ are each independently H, $C_{1-6}$-alkyl, $C_{1-6}$-alkyl-$NR^{iii}R^{iv}$, —(CO)O—$C_{1-6}$-alkyl, —C(O)—$NR^{iii}R^{iv}$, —C(O)—$C_{1-6}$-alkyl, —$S(O)_2$—$C_{1-6}$-alkyl, —$S(O)_2$—$NR^{iii}R^{iv}$ or OH;

$R^{iii}$ and $R^{iv}$ are each independently H or $C_{1-6}$-alkyl;

m is 1 to 6; and n is 0 to 4;

or a pharmaceutically acceptable salt thereof.

2. A compound of claim 1, wherein

A is selected from the group consisting of (a), (b), (c), (d), (e), (f), (g) and (h) and wherein $R^1$ is H,
  $C_{1-6}$-alkyl optionally substituted by CN,
  aryl, 5 or 6 membered heteroaryl or sulfonylaryl, each of which is optionally substituted by one or more B,
  —$(CH_2)_m$—$R^a$ wherein $R^a$ is:
    $OR^i$,
    CN,
    $NR^iR^{ii}$, or
    $C_{3-6}$-cycloalkyl, 3 to 7 membered-heterocycloalkyl, aryl or 5 or 6 membered heteroaryl, each of which is optionally substituted by one or more B,
  or —$(CH_2)_n$—(CO)—$R^b$ or —$(CH_2)_n$—$(SO_2)$—$R^b$, wherein $R^b$ is:
    $C_{1-6}$-alkoxy,
    $NR^iR^{ii}$,
    4 to 7 membered-heterocycloalkyl, aryl, or 5 or 6 membered heteroaryl, each of which is optionally substituted by one or more B, or $R^1$ and $R^3$ together with the indole ring to which they are attached form a 5 or 6 membered heterocycloalkyl which is optionally substituted by =O, C(O)O—$C_{1-6}$-alkyl or $C_{1-6}$-alkyl;

there is one or more $R^2$, wherein each $R^2$ is the same or different, $R^2$ is one or more H, OH, halo, $C_{1-6}$-alkyl optionally substituted by —$NR^{iii}R^{iv}$, or $C_{1-6}$-alkoxy;

$R^3$ is H,
  halo
  —(CO)—$R^c$, wherein $R^c$ is:
    $C_{1-6}$-alkyl
    —$(CH_2)_n$—$NR^iR^{ii}$,
    —$(CH_2)_n$—$NR^{iii}R^{iv}$, or
    5 or 6 membered heterocycloalkyl optionally substituted by $C_{1-6}$-alkyl,
  or $C_{1-6}$-alkyl or aryl, each of which is optionally substituted by halo, there is one or more $R^4$, wherein each $R^4$ is the same or different, $R^4$ is is one or more H, halo, or $C_{1-6}$-alkoxy optionally substituted by OH, or two $R^4$ together with the phenyl ring to which they are attached form an oxo or dioxo bridge;

$R^5$ is H or aryl;

$R^6$ is H;

$R^7$ is H or —$SO_2$—$R^e$ wherein $R^e$ is $C_{1-6}$-alkyl or aryl;

$R^8$ is H or $C_{1-6}$-alkyl;

X is $CH_2$ or $C=O$;

B is halo,
  CN,
  $NH_2$,
  $C_{1-6}$-alkyl optionally substituted by CN or $C_{1-6}$-alkoxy,
  $C_{1-6}$-alkoxy,
  $C_{1-6}$-haloalkoxy,
  $C_{3-6}$-cycloalkyl,
  —C(O)O—$C_{1-6}$-alkyl,
  —$(CR^{iii}R^{iv})_n$-phenyl, wherein the phenyl is optionally substituted by one or more substituent(s) selected from the group consisting of:
    halo,
    $C_{1-6}$-alkyl optionally substituted by CN or halo, and
    $C_{1-6}$-alkoxy;

$R^i$ and $R^{ii}$ are each independently H, $C_{1-6}$-alkyl, $C_{1-6}$-alkyl-$NR^{iii}R^{iv}$, —(CO)O—$C_{1-6}$-alkyl, —C(O)—$NR^{iii}R^{iv}$, —C(O)—$C_{1-6}$-alkyl, —$S(O)_2$—$C_{1-6}$-alkyl, —$S(O)_2$—$NR^{iii}R^{iv}$ or OH;

$R^{iii}$ and $R^{iv}$ are each independently H or $C_{1-6}$-alkyl;

m is 1 to 6; and n is 0 to 4;

or a pharmaceutically acceptable salt thereof.

3. A compound of claim 1, wherein A is selected from the group consisting of (a), (b), (c), (d) and (e); and $R^1$ is H,
  $C_{1-6}$-alkyl optionally substituted by CN,
  aryl, 5 or 6 membered heteroaryl or sulfonylaryl, each of which is optionally substituted by one or more B, —$(CH_2)_m$—$R^a$ wherein $R^a$ is:
CN,
$OR^i$,
$NR^iR^{ii}$, or
$C_{3-6}$-cycloalkyl, 4 to 7 membered-heterocycloalkyl, aryl, or 5 or 6 membered heteroaryl, each of which is optionally substituted by one or more B,
or —$(CH_2)_n$—(CO)—$R^b$ or —$(CH_2)_n$—$(SO_2)$—$R^b$, wherein $R^b$ is:
$C_{1-6}$-alkyl,
$C_{1-6}$-alkoxy,
$C_{3-6}$-cycloalkyl,
—$(CH_2)_m$—$NR^{iii}R^{iv}$,
$NR^iR^{ii}$, or
$C_{3-6}$-cycloalkyl, 4 to 7 membered-heterocycloalkyl, aryl, or 5 or 6 membered heteroaryl, each of which is optionally substituted by one or more B,
or $R^1$ and $R^3$ together with the indole ring to which they are attached form a 5 or 6 membered heterocycloalkyl which is optionally substituted by (CO);
there is one or more $R^2$, wherein each $R^2$ is the same or different,
$R^2$ is one or more H, OH, halo, CN, nitro, $C_{1-6}$-alkyl optionally substituted by —$NR^{iii}R^{iv}$, $C_{1-6}$-alkoxy, —O—$CH_2$—$C_{2-6}$-alkenyl, or benzyloxy,
or two $R^2$ together with the indole ring to which they are attached form an oxo or dioxo bridge;
$R^3$ is H,
halo,
—(CO)—$R^c$, wherein $R^c$ is:
$C_{1-6}$-alkyl,
—$(CH_2)_n$—$NR^iR^{ii}$,
—$(CH_2)_n$—$NR^{iii}R^{iv}$, or
5 or 6 membered heterocycloalkyl optionally substituted by $C_{1-6}$-alkyl,
or $C_{1-6}$-alkyl or aryl, each of which is optionally substituted by
halo,
—O(CO)—$C_{1-6}$-alkyl,
or —NH(CO)$R^d$, wherein $R^d$ is $C_{1-6}$-alkyl optionally substituted by halo or nitro, or $R^d$ is aryl or a 5 or 6 membered heteroaryl, each of which is optionally substituted by halo, nitro, $C_{1-6}$-alkyl or $C_{1-6}$-haloalkyl;
there is one or more $R^4$, wherein each $R^4$ is the same or different,
$R^4$ is one or more H, halo, $C_{1-6}$-alkyl or $C_{1-6}$-alkoxy or two $R^4$ together with the phenyl ring to which they are attached form an oxo or dioxo bridge;
$R^5$ is H, $C_{1-6}$-alkyl or aryl;
$R^6$ is H or $C_{1-6}$-alkyl;
$R^7$ is H or —$SO_2$—$R^e$ wherein $R^e$ is $C_{1-6}$-alkyl or aryl;
B is halo,
CN,
$NR^iR^{ii}$,
$C_{1-6}$-alkyl optionally substituted by CN, halo or $C_{1-6}$-alkoxy,
$C_{1-6}$-alkoxy,
$C_{1-6}$-haloalkoxy,
$C_{3-6}$-cycloalkyl,
—C(O)O—$C_{1-6}$-alkyl,
—C(O)$NR^iR^{ii}$,
—C(O)—$C_{1-6}$-alkyl,
—$S(O)_2$—$C_{1-6}$-alkyl,
—$S(O)_2$—$NR^iR^{ii}$, or
$(CR^{iii}R^{iv})_n$-phenyl, or $(CR^{iii}R^{iv})_n$-5 or 6 membered heteroaryl wherein the phenyl or 5 or 6 membered heteroaryl moiety is optionally substituted by one or more substituent(s) selected from the group consisting of:
halo,
CN, $NR^iR^{ii}$,
$C_{1-6}$-alkyl optionally substituted by CN or $C_{1-6}$-alkoxy,
$C_{1-6}$-alkoxy,
$C_{1-6}$-haloalkoxy,
$C_{3-6}$-cycloalkyl,
—C(O)O—$C_{1-6}$-alkyl,
—C(O)—$NR^iR^{ii}$,
—C(O)—$C_{1-6}$-alkyl,
—$S(O)_2$—$C_{1-6}$-alkyl, or
—$S(O)_2$—$NR^iR^{ii}$;
$R^i$ and $R^{ii}$ are each independently H, $C_{1-6}$-alkyl, $C_{1-6}$-alkyl-$NR^{iii}R^{iv}$, —(CO)O—$C_{1-6}$-alkyl, —C(O)—$NR^{iii}R^{iv}$, —C(O)—$C_{1-6}$-alkyl, —$S(O)_2$—$C_{1-6}$-alkyl or —$S(O)_2$—$NR^{iii}R^{iv}$;
$R^{iii}$ and $R^{iv}$ are each independently H or $C_{1-6}$-alkyl;
m is 1 to 6; and
n is 0 to 4;
or a pharmaceutically acceptable salt thereof.

4. A compound of claim 1,
wherein A is selected from the group consisting of (a), (b), (c), (d) and (e); and
$R^1$ is H,
$C_{1-6}$-alkyl optionally substituted by CN,
aryl,
5 or 6 membered heteroaryl,
sulfonylaryl,
—$(CH_2)_m$—$R^a$ wherein $R^a$ is $C_{3-6}$-cycloalkyl, 5 or 6 membered-heterocycloalkyl, aryl, or 5 or 6 membered heteroaryl, each of which is optionally substituted by one or more substituents selected from the group consisting of:
halo, CN, $C_{1-6}$-alkyl, $C_{1-6}$-alkoxy, $C_{1-6}$-haloalkoxy, —C(O)O—$C_{1-6}$-alkyl and phenyl each of which is optionally substituted by halo, $C_{1-6}$-alkyl, $C_{1-6}$-haloalkyl or $C_{1-6}$-alkoxy,
—$(CH_2)_m$—NR'R", or
—$(CH_2)_n$—(CO)—$R^b$, wherein $R^b$ is aryl or 5 or 6 membered-heterocycloalkyl;
there is one or more $R^2$, wherein each $R^2$ is the same or different,
$R^2$ is one or more H, halo, CN, nitro, $C_{1-6}$-alkyl, $C_{1-6}$-alkoxy, —O—$CH_2$—$C_{2-6}$-alkenyl, or benzyloxy,
or two $R^2$ together with the indole ring to which they are attached form an oxo or dioxo bridge;
$R^3$ is H,
halo,
—(CO)—$R^c$, wherein $R^c$ is $C_{1-6}$-alkyl, 5 or 6 membered heterocycloalkyl optionally substituted by $C_{1-6}$-alkyl, or $R^c$ is —$(CH_2)_n$—NR'R", or
$C_{1-6}$-alkyl or aryl, each of which is optionally substituted by:
—O(CO)—$C_{1-6}$-alkyl,
or —NH(CO)$R^d$, wherein $R^d$ is $C_{1-6}$-alkyl optionally substituted by halo or nitro, or $R^d$ is aryl or a 5 or 6 membered heteroaryl, each of which is optionally substituted by halo, nitro, $C_{1-6}$-alkyl or $C_{1-6}$-haloalkyl;
there is one or more $R^4$, wherein each $R^4$ is the same or different,
$R^4$ is one or more H, halo, $C_{1-6}$-alkyl or $C_{1-6}$-alkoxy or two $R^4$ together with the phenyl ring to which they are attached form an oxo or dioxo bridge;

$R^5$ is H, $C_{1-6}$-alkyl or aryl;
$R^6$ is H or $C_{1-6}$-alkyl;
$R^7$ is H or —$SO_2$—$R^e$ wherein $R^e$ is $C_{1-6}$-alkyl or aryl;
R' and R" are each independently selected from H, $C_{1-6}$-alkyl and —(CO)O—$C_{1-6}$-alkyl;
m is 1 to 6; and
n is 0 to 4;
or a pharmaceutically acceptable salt thereof.

5. The compound of claim 1 having formula (I-a):

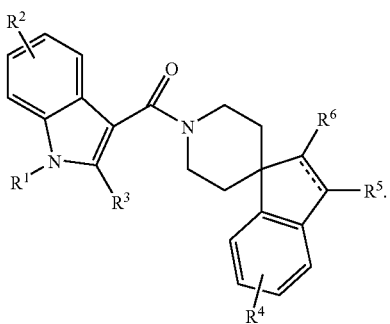

(I-a)

6. The compound of claim 5, wherein:
the dotted line is an optional double bond;
$R^1$ is H,
$C_{1-6}$-alkyl optionally substituted by CN, sulfonylaryl,
—$(CH_2)_m$—$R^a$ wherein $R^a$ is:
$OR^i$,
CN,
$NR^iR^{ii}$, or
$C_{3-6}$-cycloalkyl, 3 to 6 membered-heterocycloalkyl, aryl or 5 or 6 membered heteroaryl, each of which is optionally substituted by one or more B,
or —$(CH_2)_n$—(CO)—$R^b$, wherein $R^b$ is:
$C_{1-6}$-alkoxy,
$NR^iR^{ii}$, or
6 membered-heterocycloalkyl, aryl, or 5 or 6 membered heteroaryl, each of which is optionally substituted by one or more B;
there is one or more $R^2$, wherein each $R^2$ is the same or different,
$R^2$ is one or more H, halo, or $C_{1-6}$-alkyl;
$R^3$ is H,
$C_{1-6}$-alkyl,
or —(CO)—$R^c$, wherein $R^c$ is:
$C_{1-6}$-alkyl or
—$(CH_2)_n$—$NR^iR^{ii}$,
there is one or more $R^4$, wherein each $R^4$ is the same or different,
$R^4$ is one or more H, halo, or $C_{1-6}$-alkoxy optionally substituted by OH, or two $R^4$ together with the phenyl ring to which they are attached form an oxo or dioxo bridge;
$R^5$ is H;
$R^6$ is H;
B is halo,
CN,
$C_{1-6}$-alkyl optionally substituted by CN or $C_{1-6}$-alkoxy,
$C_{1-6}$-alkoxy,
$C_{1-6}$-haloalkoxy,
$C_{3-6}$-cycloalkyl,
—C(O)O—$C_{1-6}$-alkyl, —$(CR^{iii}R^{iv})_n$-phenyl, wherein the phenyl is optionally substituted by one or more substituent(s) selected from the group consisting of:
halo, $C_{1-6}$-alkyl optionally substituted by CN or halo, and $C_{1-6}$-alkoxy;
$R^i$ and $R^{ii}$ are each independently H, $C_{1-6}$-alkyl, $C_{1-6}$-alkyl-$NR^{iii}R^{iv}$, —C(O)—$C_{1-6}$-alkyl, —$S(O)_2$—$C_{1-6}$-alkyl or OH;
$R^{iii}$ and $R^{iv}$ are each independently H or $C_{1-6}$-alkyl;
m is 1 to 6; and
n is 0 to 4;
or a pharmaceutically acceptable salt thereof.

7. The compound of claim 5, wherein:
the dotted line is an optional double bond;
$R^1$ is H, or
—$(CH_2)_m$—$R^a$ wherein $R^a$ is aryl which is optionally substituted by one or more substituents selected from the group consisting of:
halo, CN, $C_{1-6}$-alkyl, $C_{1-6}$-alkoxy, $C_{1-6}$-haloalkoxy, —C(O)O—$C_{1-6}$-alkyl, and phenyl which is optionally substituted by halo, $C_{1-6}$-alkyl, $C_{1-6}$-haloalkyl or $C_{1-6}$-alkoxy;
$R^2$ is H or halo;
$R^3$ is H or $C_{1-6}$-alkyl;
$R^4$, $R^5$ and $R^6$ are H; and
m is 1 to 6;
or a pharmaceutically acceptable salt thereof.

8. The compound of claim 5, wherein the compound is selected from the group consisting of:
1'-[(1-benzyl-2-methyl-1H-indol-3-yl)carbonyl]spiro[indene-1,4'-piperidine];
1'-[(1-benzyl-2-methyl-1H-indol-3-yl)carbonyl]-2,3-dihydrospiro[indene-1,4'-piperidine];
1'-[(1-benzyl-1H-indol-3-yl)carbonyl]spiro[indene-1,4'-piperidine];
1'-[(2-methyl-1H-indol-3-yl)carbonyl]spiro[indene-1,4'-piperidine];
1'-[(6-chloro-1H-indol-3-yl)carbonyl]spiro[indene-1,4'-piperidine]; and
1'-[(6-chloro-1H-indol-3-yl)carbonyl]-2,3-dihydrospiro[indene-1,4'-piperidine].

9. The compound of claim 1 having formula (I-b):

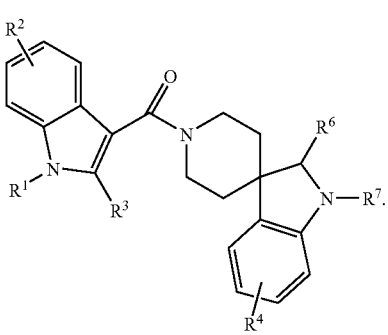

(I-b)

10. The compound of claim 9, wherein
$R^1$ is H,
$C_{1-6}$-alkyl optionally substituted by CN, sulfonylaryl, —(CH₂)ₘ—Rᵃ wherein Rᵃ is:
  ORⁱ,
  CN,
  NRⁱRⁱⁱ, or
  $C_{3-6}$-cycloalkyl, 3 to 6 membered-heterocycloalkyl, aryl or 5 or 6 membered heteroaryl, each of which is optionally substituted by one or more B,
or —(CH₂)ₙ—(CO)—Rᵇ, wherein Rᵇ is:
  $C_{1-6}$-alkoxy,
  NRⁱRⁱⁱ, or
  5 or 6 membered-heterocycloalkyl, aryl, or 5 or 6 membered heteroaryl, each of which is optionally substituted by one or more B;
there is one or more R², wherein each R² is the same or different,
R² is one or more H, halo, or $C_{1-6}$-alkyl;
R³ is H,
  $C_{1-6}$-alkyl,
  or —(CO)—Rᶜ, wherein Rᶜ is:
    $C_{1-6}$-alkyl or
    —(CH₂)ₙ—NRⁱRⁱⁱ,
there is one or more R⁴, wherein each R⁴ is the same or different,
R⁴ is one or more H, halo, or $C_{1-6}$-alkoxy optionally substituted by OH, or two R⁴ together with the phenyl ring to which they are attached form an oxo or dioxo bridge;
R⁶ is H;
R⁷ is H or —SO₂—Rᵉ wherein Rᵉ is $C_{1-6}$-alkyl or aryl;
B is halo,
  CN,
  $C_{1-6}$-alkyl optionally substituted by CN or $C_{1-6}$-alkoxy,
  $C_{1-6}$-alkoxy,
  $C_{1-6}$-haloalkoxy,
  $C_{3-6}$-cycloalkyl,
  —C(O)O—$C_{1-6}$-alkyl, or
  —(CRⁱⁱⁱRⁱᵛ)ₙ-phenyl, wherein the phenyl is optionally substituted by one or more substituent(s) selected from the group consisting of:
    halo, $C_{1-6}$-alkyl optionally substituted by CN or halo, and $C_{1-6}$-alkoxy;
Rⁱ and Rⁱⁱ are each independently H, $C_{1-6}$-alkyl, $C_{1-6}$-alkyl-NRⁱⁱⁱRⁱᵛ, —C(O)—$C_{1-6}$-alkyl, —S(O)₂—$C_{1-6}$-alkyl or OH;
Rⁱⁱⁱ and Rⁱᵛ are each independently H or $C_{1-6}$-alkyl;
m is 1 to 6; and
n is 0 to 4;
or a pharmaceutically acceptable salt thereof.
11. The compound of claim 9, wherein:
R¹ is H,
  —(CH₂)ₘ—Rᵃ wherein Rᵃ is aryl, or 5 or 6 membered heteroaryl, each of which is optionally substituted by one or more subsituents selected from the group consisting of:
    halo, CN, $C_{1-6}$-alkyl, $C_{1-6}$-alkoxy, $C_{1-6}$-haloalkoxy, —C(O)O—$C_{1-6}$-alkyl, and phenyl which is optionally substituted by halo, $C_{1-6}$-haloalkyl or $C_{1-6}$-alkoxy,
  —(CH₂)ₘ—NRⁱRⁱⁱ,
  —(CH₂)ₙ—(CO)—Rᵇ, wherein Rᵇ is aryl or 5 or 6 membered-heterocycloalkyl, each of which is optionally substituted by one or more B,
  or —(CH₂)ₙ—(CO)—Rᵇ wherein Rᵇ is NRⁱRⁱⁱ,
R² is H or halo;
R³ is H or $C_{1-6}$-alkyl;
R⁴ is H or halo;

R⁶ is H;
R⁷ is H or —SO₂—Rᵉ wherein Rᵉ is $C_{1-6}$-alkyl or aryl;
B is halo,
  NH₂,
  $C_{1-6}$-alkyl optionally substituted by CN or $C_{1-6}$-alkoxy,
  $C_{1-6}$-alkoxy,
  $C_{1-6}$-haloalkoxy,
  $C_{3-6}$-cycloalkyl,
  —C(O)O—$C_{1-6}$-alkyl, or
  —(CRⁱⁱⁱRⁱᵛ)ₙ-phenyl, wherein the phenyl is optionally substituted by one or more substituent(s) selected from the group consisting of:
    halo, $C_{1-6}$-alkyl optionally substituted by CN or halo, and $C_{1-6}$-alkoxy;
Rⁱ and Rⁱⁱ are each independently selected from H or $C_{1-6}$-alkyl;
m is 1 to 6; and
n is 0 to 4;
or a pharmaceutically acceptable salt thereof.
12. The compound of claim 9, wherein the compound is selected from the group consisting of:
  1'-[(1-benzyl-2-methyl-1H-indol-3-yl)carbonyl]-1-(methylsulfonyl)-1,2-dihydrospiro[indole-3,4'-piperidine];
  1'-{[6-chloro-1-(3-fluorobenzoyl)-1H-indol-3-yl]carbonyl}-1,2-dihydrospiro[indole-3,4'-piperidine];
  1'-{[6-chloro-1-(2-fluorobenzoyl)-1H-indol-3-yl]carbonyl}-1,2-dihydrospiro[indole-3,4'-piperidine];
  1'-{[6-chloro-1-(3,5-difluorobenzoyl)-1H-indol-3-yl]carbonyl}-1,2-dihydrospiro[indole-3,4'-piperidine];
  1'-{[6-chloro-1-(2,3-difluorobenzoyl)-1H-indol-3-yl]carbonyl}-1,2-dihydrospiro[indole-3,4'-piperidine];
  1'-({6-chloro-1-[(3,5-difluorophenyl)sulfonyl]-1H-indol-3-yl}carbonyl)-1,2-dihydrospiro[indole-3,4'-piperidine];
  2-[6-chloro-3-(1,2-dihydro-1'H-spiro[indole-3,4'-piperidin]-1'-ylcarbonyl)-1H-indol-1-yl]-1-(3,5-difluorophenyl)ethanone;
  2-[6-chloro-3-(1,2-dihydro-1'H-spiro[indole-3,4'-piperidin]-1'-ylcarbonyl)-1H-indol-1-yl]-1-(3,4-difluorophenyl)ethanone;
  2-[6-chloro-3-(1,2-dihydro-1'H-spiro[indole-3,4'-piperidin]-1'-ylcarbonyl)-1H-indol-1-yl]-1-(2-fluorophenyl)ethanone;
  2-[6-chloro-3-(1,2-dihydro-1'H-spiro[indole-3,4'-piperidin]-1'-ylcarbonyl)-1H-indol-1-yl]-N,N-diethylethanamine; and
  1'-{[6-chloro-1-(pyridin-2-ylmethyl)-1H-indol-3-yl]carbonyl}-1,2-dihydrospiro[indole-3,4'-piperidine].
13. The compound of claim 1 having formula (I-c):

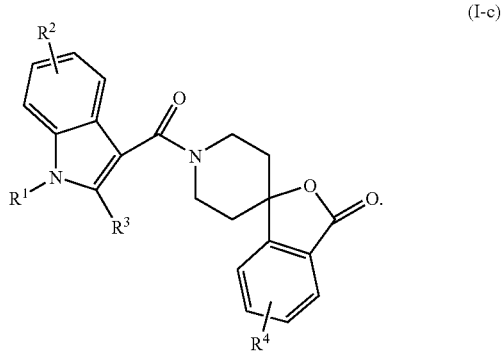

(I-c)

14. The compound of claim 13, wherein

R$^1$ is H,

C$_{1-6}$-alkyl optionally substituted by CN, aryl, 5 or 6 membered heteroaryl or sulfonylaryl, each of which is optionally substituted by one or more B, —(CH$_2$)$_m$—R$^a$ wherein R$^a$ is:

OR$^i$,

CN,

NR$^i$R$^{ii}$, or

C$_{3-6}$-cycloalkyl, 4 to 7 membered-heterocycloalkyl, aryl, or 5 or 6 membered heteroaryl each of which is optionally substituted by one or more B, or —(CH$_2$)$_n$—(CO)—R$^b$ wherein R$^b$ is:

C$_{1-6}$-alkoxy,

NR$^i$R$^{ii}$, or 4 to 7 membered-heterocycloalkyl, aryl, or 5 or 6 membered heteroaryl, each of which is optionally substituted by one or more B, or R$^1$ and R$^3$ together with the indole ring to which they are attached form a 5 or 6 membered heterocycloalkyl which is optionally substituted by =O;

there is one or more R$^2$, wherein each R$^2$ is the same or different,

R$^2$ is one or more H, halo, C$_{1-6}$-alkyl optionally substituted by —NR$^{iii}$R$^{iv}$, or C$_{1-6}$-alkoxy;

R$^3$ is H,

C$_{1-6}$-alkyl, halo, or —(CO)—R$^c$, wherein R$^c$ is:

C$_{1-6}$-alkyl

—(CH$_2$)$_n$—NR$^i$R$^{ii}$,

—(CH$_2$)$_n$—NR$^{iii}$R$^{iv}$, or 5 or 6 membered heterocycloalkyl optionally substituted by C$_{1-6}$-alkyl;

there is one or more R$^4$, wherein each R$^4$ is the same or different,

R$^4$ is one or more H, halo, or C$_{1-6}$-alkoxy optionally substituted by OH, or two R$^4$ together with the phenyl ring to which they are attached form an oxo or dioxo bridge;

B is halo,

NH$_2$,

C$_{1-6}$-alkyl optionally substituted by CN or C$_{1-6}$-alkoxy,

C$_{1-6}$-alkoxy,

C$_{1-6}$-haloalkoxy,

C$_{3-6}$-cycloalkyl,

—C(O)O—C$_{1-6}$-alkyl, or

—(CR$^{iii}$R$^{iv}$)$_n$-phenyl, wherein the phenyl is optionally substituted by one or more substituent(s) selected from the group consisting of:

halo, C$_{1-6}$-alkyl optionally substituted by CN or halo, and C$_{1-6}$-alkoxy;

R$^i$ and R$^{ii}$ are each independently H, C$_{1-6}$-alkyl, C$_{1-6}$-alkyl-NR$^{iii}$R$^{iv}$, —(CO)O—C$_{1-6}$-alkyl, —C(O)—NR$^{iii}$R$^{iv}$, —C(O)—C$_{1-6}$-alkyl, —S(O)$_2$—C$_{1-6}$-alkyl, or —S(O)$_2$—NR$^{iii}$R$^{iv}$;

R$^{iii}$ and R$^{iv}$ are each independently H or C$_{1-6}$-alkyl;

m is 1 to 6; and n is 0 to 4;

or a pharmaceutically acceptable salt thereof.

15. The compound of claim 13, wherein the compound is selected from the group consisting of:

1'-[(1-benzyl-2-methyl-1H-indol-3-yl)carbonyl]-6-chloro-3H-spiro[2-benzofuran-1,4'-piperidin]-3-one;

1'-[(1-benzyl-2-methyl-1H-indol-3-yl)carbonyl]-4-fluoro-3H-spiro[2-benzofuran-1,4'-piperidin]-3-one;

1'-[(1-benzyl-2-methyl-1H-indol-3-yl)carbonyl]-6-methoxy-3H-spiro[2-benzofuran-1,4'-piperidin]-3-one;

1'-[(1-benzyl-2-methyl-1H-indol-3-yl)carbonyl]-5-methoxy-3H-spiro[2-benzofuran-1,4'-piperidin]-3-one;

1'-[(1-benzyl-2-methyl-1H-indol-3-yl)carbonyl]-7-chloro-3H-spiro[2-benzofuran-1,4'-piperidin]-3-one;

1'-[(6-chloro-1H-indol-3-yl)carbonyl]-3H-spiro[2-benzofuran-1,4'-piperidin]-3-one;

1'-[(6-chloro-1H-indol-3-yl)carbonyl]-5-fluoro-3H-spiro[2-benzofuran-1,4'-piperidin]-3-one;

1'-[(1-benzyl-2-methyl-1H-indol-3-yl)carbonyl]-5-fluoro-3H-spiro[2-benzofuran-1,4'-piperidin]-3-one;

6-chloro-3-[(5-fluoro-3-oxo-1'H,3H-spiro[2-benzofuran-1,4'-piperidin]-1'-yl)carbonyl]-N,N-dimethyl-1H-indole-2-carboxamide;

tert-butyl {2-[({6-chloro-3-[(5-fluoro-3-oxo-1'H,3H-spiro[2-benzofuran-1,4'-piperidin]-1'-yl)carbonyl]-1H-indol-2-yl}carbonyl)amino]ethyl}methylcarbamate; and 6-chloro-N,N-diethyl-3-[(5-fluoro-3-oxo-1'H,3H-spiro[2-benzofuran-1,4'-piperidin]-1'-yl)carbonyl]-1H-indole-2-carboxamide.

16. The compound of claim 13, wherein the compound is selected from the group consisting of:

1'-{[6-chloro-2-(piperidin-1-ylcarbonyl)-1H-indol-3-yl]carbonyl}-5-fluoro-3H-spiro[2-benzofuran-1,4'-piperidin]-3-one;

1'-[(1-benzyl-2-methyl-1H-indol-3-yl)carbonyl]-7H-spiro[furo[3,4-f][1,3]benzodioxole-5,4'-piperidin]-7-one;

3-{6-chloro-3-[(3-oxo-1'H,3H-spiro[2-benzofuran-1,4'-piperidin]-1'-yl)carbonyl]-1H-indol-1-yl}propanenitrile;

{6-chloro-3-[(3-oxo-1'H,3H-spiro[2-benzofuran-1,4'-piperidin]-1'-yl)carbonyl]-1H-indol-1-yl}acetonitrile;

1'-[(1-benzyl-2-methyl-1H-indol-3-yl)carbonyl]-6-(2-hydroxyethoxy)-3H-spiro[2-benzofuran-1,4'-piperidin]-3-one;

1'-[(1-benzyl-2-methyl-1H-indol-3-yl)carbonyl]-3H-spiro[2-benzofuran-1,4'-piperidin]-3-one;

1'-{[6-chloro-1-(3,5-difluorophenyl)-1H-indol-3-yl]carbonyl}-3H-spiro[2-benzofuran-1,4'-piperidin]-3-one;

1'-{[6-chloro-1-(3,5-difluorobenzoyl)-1H-indol-3-yl]carbonyl}-3H-spiro[2-benzofuran-1,4'-piperidin]-3-one;

1'-{[6-chloro-1-(3,5-difluorobenzyl)-1H-indol-3-yl]carbonyl}-3H-spiro[2-benzofuran-1,4'-piperidin]-3-one;

1'-{[6-chloro-1-(3-fluorobenzyl)-1H-indol-3-yl]carbonyl}-3H-spiro[2-benzofuran-1,4'-piperidin]-3-one; and 1'-({6-chloro-1-[2-(3-fluorophenyl)-2-oxoethyl]-1H-indol-3-yl}carbonyl)-3H-spiro[2-benzofuran-1,4'-piperidin]-3-one.

17. The compound of claim 13, wherein the compound is selected from the group consisting of:

1'-({6-chloro-1-[2-(2,5-difluorophenyl)-2-oxoethyl]-1H-indol-3-yl}carbonyl)-3H-spiro[2-benzofuran-1,4'-piperidin]-3-one;

1'-{[6-chloro-1-(3,5-difluorobenzyl)-1H-indol-3-yl]carbonyl}-5-fluoro-3H-spiro[2-benzofuran-1,4'-piperidin]-3-one;

1'-{[6-chloro-1-(3-fluorobenzyl)-1H-indol-3-yl]carbonyl}-5-fluoro-3H-spiro[2-benzofuran-1,4'-piperidin]-3-one;

1'-({6-chloro-1-[2-(3-fluorophenyl)-2-oxoethyl]-1H-indol-3-yl}carbonyl)-5-fluoro-3H-spiro[2-benzofuran-1,4'-piperidin]-3-one;

5-bromo-1'-{[6-chloro-1-(3,5-difluorobenzyl)-1H-indol-3-yl]carbonyl}-3H-spiro[2-benzofuran-1,4'-piperidin]-3-one;

5-bromo-1'-{[6-chloro-1-(3-fluorobenzyl)-1H-indol-3-yl]carbonyl}-3H-spiro[2-benzofuran-1,4'-piperidin]-3-one;

5-bromo-1'-({6-chloro-1-[2-(3-fluorophenyl)-2-oxoethyl]-1H-indol-3-yl}carbonyl)-3H-spiro[2-benzofuran-1,4'-piperidin]-3-one;

1'-({6-chloro-1-[2-(2-fluorophenyl)-2-oxoethyl]-1H-indol-3-yl}carbonyl)-3H-spiro[2-benzofuran-1,4'-piperidin]-3-one;

1'-({6-chloro-1-[2-(3,4-difluorophenyl)-2-oxoethyl]-1H-indol-3-yl}carbonyl)-3H-spiro[2-benzofuran-1,4'-piperidin]-3-one; and 1'-{[6-chloro-1-(3-fluorophenyl)-1H-indol-3-yl]carbonyl}-3H-spiro[2-benzofuran-1,4'-piperidin]-3-one.

18. The compound of claim 13, wherein the compound is selected from the group consisting of:

1'-{[6-chloro-1-(2-oxo-2-piperidin-1-ylethyl)-1H-indol-3-yl]carbonyl}-3H-spiro[2-benzofuran-1,4'-piperidin]-3-one;

1'-{[6-chloro-1-(2-morpholin-4-yl-2-oxoethyl)-1H-indol-3-yl]carbonyl}-3H-spiro[2-benzofuran-1,4'-piperidin]-3-one;

2-{6-chloro-3-[(3-oxo-1'H,3H-spiro[2-benzofuran-1,4'-piperidin]-1'-yl)carbonyl]-1H-indol-1-yl}-N,N-dimethylacetamide;

2-{6-chloro-3-[(3-oxo-1'H,3H-spiro[2-benzofuran-1,4'-piperidin]-1'-yl)carbonyl]-1H-indol-1-yl}-N,N-diethylacetamide;

1'-{[6-chloro-1-(piperidin-1-ylcarbonyl)-1H-indol-3-yl]carbonyl}-3H-spiro[2-benzofuran-1,4'-piperidin]-3-one;

tert-butyl {6-chloro-3-[(3-oxo-1'H,3H-spiro[2-benzofuran-1,4'-piperidin]-1'-yl)carbonyl]-1H-indol-1-yl}acetate;

1'-[(6-chloro-1-pyridin-2-yl-1H-indol-3-yl)carbonyl]-3H-spiro[2-benzofuran-1,4'-piperidin]-3-one;

1'-[(6-chloro-1-pyridin-2-yl-1H-indol-3-yl)carbonyl]-5-fluoro-3H-spiro[2-benzofuran-1,4'-piperidin]-3-one;

1'-({6-chloro-1-[(2-methylpyridin-4-yl)methyl]-1H-indol-3-yl}carbonyl)-5-fluoro-3H-spiro[2-benzofuran-1,4'-piperidin]-3-one;

1'-({6-chloro-1-[(6-chloropyridin-3-yl)methyl]-1H-indol-3-yl}carbonyl)-5-fluoro-3H-spiro[2-benzofuran-1,4'-piperidin]-3-one; and 1'-({6-chloro-1-[(3-chloro-6-methylpyridazin-4-yl)methyl]-1H-indol-3-yl}carbonyl)-5-fluoro-3H-spiro[2-benzofuran-1,4'-piperidin]-3-one.

19. The compound of claim 13, wherein the compound is selected from the group consisting of:

1'-{[6-chloro-1-(pyridin-4-ylmethyl)-1H-indol-3-yl]carbonyl}-5-fluoro-3H-spiro[2-benzofuran-1,4'-piperidin]-3-one;

1'-{[6-chloro-1-(2-pyridin-4-ylethyl)-1H-indol-3-yl]carbonyl}-5-fluoro-3H-spiro[2-benzofuran-1,4'-piperidin]-3-one;

1'-{[6-chloro-1-(pyridin-4-ylmethyl)-1H-indol-3-yl]carbonyl}-3H-spiro[2-benzofuran-1,4'-piperidin]-3-one;

1'-{[6-chloro-1-(2-oxo-2-pyridin-2-ylethyl)-1H-indol-3-yl]carbonyl}-5-fluoro-3H-spiro[2-benzofuran-1,4'-piperidin]-3-one;

1'-({6-chloro-1-[2-(5-methyl-2-phenyl-1,3-oxazol-4-yl)-2-oxoethyl]-1H-indol-3-yl}carbonyl)-5-fluoro-3H-spiro[2-benzofuran-1,4'-piperidin]-3-one;

1'-{[6-chloro-1-(pyridin-2-ylmethyl)-1H-indol-3-yl]carbonyl}-5-fluoro-3H-spiro[2-benzofuran-1,4'-piperidin]-3-one;

2-{6-chloro-3-[(5-fluoro-3-oxo-1'H,3H-spiro[2-benzofuran-1,4'-piperidin]-1'-yl)carbonyl]-1H-indol-1-yl}-N,N-dimethylacetamide;

1'-({6-chloro-1-[2-(dimethylamino)ethyl]-1H-indol-3-yl}carbonyl)-5-fluoro-3H-spiro[2-benzofuran-1,4'-piperidin]-3-one;

1'-{[6-chloro-1-(pyridin-3-ylmethyl)-1H-indol-3-yl]carbonyl}-3H-spiro[2-benzofuran-1,4'-piperidin]-3-one;

1'-{[6-chloro-1-(pyrazin-2-ylmethyl)-1H-indol-3-yl]carbonyl}-5-fluoro-3H-spiro[2-benzofuran-1,4'-piperidin]-3-one; and 1'-{[6-chloro-1-(pyrimidin-5-ylmethyl)-1H-indol-3-yl]carbonyl}-5-fluoro-3H-spiro[2-benzofuran-1,4'-piperidin]-3-one.

20. The compound of claim 13, wherein the compound is selected from the group consisting of:

3-{6-chloro-3-[(5-fluoro-3-oxo-1'H,3H-spiro[2-benzofuran-1,4'-piperidin]-1'-yl)carbonyl]-1H-indol-1-yl}propanenitrile;

tert-butyl {6-chloro-3-[(5-fluoro-3-oxo-1'H,3H-spiro[2-benzofuran-1,4'-piperidin]-1'-yl)carbonyl]-1H-indol-1-yl}acetate;

1'-{[6-chloro-1-(2-morpholin-4-yl-2-oxoethyl)-1H-indol-3-yl]carbonyl}-5-fluoro-3H-spiro[2-benzofuran-1,4'-piperidin]-3-one;

1'-({1-[(4-benzylmorpholin-2-yl)methyl]-6-chloro-1H-indol-3-yl}carbonyl)-5-fluoro-3H-spiro[2-benzofuran-1,4'-piperidin]-3-one;

1'-({6-chloro-1-[(5-methylisoxazol-3-yl)methyl]-1H-indol-3-yl}carbonyl)-5-fluoro-3H-spiro[2-benzofuran-1,4'-piperidin]-3-one;

1'-({6-chloro-1-[2-(4-methylpiperazin-1-yl)-2-oxoethyl]-1H-indol-3-yl}carbonyl)-5-fluoro-3H-spiro[2-benzofuran-1,4'-piperidin]-3-one;

1'-{[6-chloro-1-(pyridin-2-ylmethyl)-1H-indol-3-yl]carbonyl}-3H-spiro[2-benzofuran-1,4'-piperidin]-3-one;

1'-({6-chloro-1-[(5-cyclopropyl-2-methyl-1,3-oxazol-4-yl)methyl]-1H-indol-3-yl}carbonyl)-5-fluoro-3H-spiro[2-benzofuran-1,4'-piperidin]-3-one;

1'-({6-chloro-1-[(1-methyl-1H-imidazol-5-yl)methyl]-1H-indol-3-yl}carbonyl)-5-fluoro-3H-spiro[2-benzofuran-1,4'-piperidin]-3-one;

1'-({6-chloro-1-[(3-methylisoxazol-5-yl)methyl]-1H-indol-3-yl}carbonyl)-5-fluoro-3H-spiro[2-benzofuran-1,4'-piperidin]-3-one; and 1'-({6-chloro-1-[(1,5-dimethyl-1H-pyrazol-3-yl)methyl]-1H-indol-3-yl}carbonyl)-5-fluoro-3H-spiro[2-benzofuran-1,4'-piperidin]-3-one.

21. The compound of claim 13, wherein the compound is selected from the group consisting of:
  1'-({6-chloro-1-[(3,5-dimethylisoxazol-4-yl)methyl]-1H-indol-3-yl}carbonyl)-5-fluoro-3H-spiro[2-benzofuran-1,4'-piperidin]-3-one;
  1'-({6-chloro-1-[(2,5-dimethyl-1,3-oxazol-4-yl)methyl]-1H-indol-3-yl}carbonyl)-5-fluoro-3H-spiro[2-benzofuran-1,4'-piperidin]-3-one;
  1'-({6-chloro-1-[(3-fluorooxetan-3-yl)methyl]-1H-indol-3-yl}carbonyl)-5-fluoro-3H-spiro[2-benzofuran-1,4'-piperidin]-3-one;
  1'-({6-chloro-1-[(3-fluorooxetan-3-yl)methyl]-1H-indol-3-yl}carbonyl)-3H-spiro[2-benzofuran-1,4'-piperidin]-3-one;
  1'-[(6-chloro-1-{[1-(methoxymethyl)-cyclopropyl]methyl}-1H-indol-3-yl)carbonyl]-5-fluoro-3H-spiro[2-benzofuran-1,4'-piperidin]-3-one;
  [1-({6-chloro-3-[(5-fluoro-3-oxo-1'H,3H-spiro[2-benzofuran-1,4'-piperidin]-1'-yl)carbonyl]-1H-indol-1-yl}methyl)cyclopropyl]acetonitrile;
  1'-[(6-chloro-1-{[1-(methoxymethyl)-cyclopropyl]methyl}-1H-indol-3-yl)carbonyl]-3H-spiro[2-benzofuran-1,4'-piperidin]-3-one;
  [1-({6-chloro-3-[(3-oxo-1'H,3H-spiro[2-benzofuran-1,4'-piperidin]-1'-yl)carbonyl]-1H-indol-1-yl}methyl)cyclopropyl]acetonitrile;
  1'-({6-chloro-1-[2-(tetrahydro-2H-pyran-4-yl)ethyl]-1H-indol-3-yl}carbonyl)-5-fluoro-3H-spiro[2-benzofuran-1,4'-piperidin]-3-one hydrochloride;
  1'-({6-chloro-1-[2-(tetrahydro-2H-pyran-4-yl)ethyl]-1H-indol-3-yl}carbonyl)-3H-spiro[2-benzofuran-1,4'-piperidin]-3-one; and
  tert-butyl 2-({6-chloro-3-[(5-fluoro-3-oxo-1'H,3H-spiro[2-benzofuran-1,4'-piperidin]-1'-yl)carbonyl]-1H-indol-1-yl}methyl)morpholine-4-carboxylate.

22. The compound of claim 13, wherein the compound is selected from the group consisting of:
  tert-butyl 2-({6-chloro-3-[(3-oxo-1'H,3H-spiro[2-benzofuran-1,4'-piperidin]-1'-yl)carbonyl]-1H-indol-1-yl}methyl)morpholine-4-carboxylate;
  1'-{[6-chloro-1-(morpholin-2-ylmethyl)-1H-indol-3-yl]carbonyl}-5-fluoro-3H-spiro[2-benzofuran-1,4'-piperidin]-3-one dihydrochloride;
  1'-{[6-chloro-1-(morpholin-2-ylmethyl)-1H-indol-3-yl]carbonyl}-3H-spiro[2-benzofuran-1,4'-piperidin]-3-one hydrochloride;
  2-{6-chloro-3-[(5-fluoro-3-oxo-1'H,3H-spiro[2-benzofuran-1,4'-piperidin]-1'-yl)carbonyl]-1H-indol-1-yl}acetamide;
  2-{6-chloro-3-[(5-fluoro-3-oxo-1'H,3H-spiro[2-benzofuran-1,4'-piperidin]-1'-yl)carbonyl]-1H-indol-1-yl}-N-methylacetamide;
  1'-{[6-chloro-1-(2-oxo-2-piperazin-1-ylethyl)-1H-indol-3-yl]carbonyl}-5-fluoro-3H-spiro[2-benzofuran-1,4'-piperidin]-3-one;
  1'-{[1-(3,5-difluorobenzyl)-1H-indol-3-yl]carbonyl}-5-fluoro-3H-spiro[2-benzofuran-1,4'-piperidin]-3-one;
  1'-{[1-(3,5-difluorobenzyl)-1H-indol-3-yl]carbonyl}-3H-spiro[2-benzofuran-1,4'-piperidin]-3-one;
  N,N-diethyl-2-{3-[(3-oxo-1'H,3H-spiro[2-benzofuran-1,4'-piperidin]-1'-yl)carbonyl]-1H-indol-1-yl}acetamide; and
  2-{6-chloro-5-methyl-3-[(3-oxo-1'H,3H-spiro[2-benzofuran-1,4'-piperidin]-1'-yl)carbonyl]-1H-indol-1-yl}-N,N-dimethylacetamide.

23. The compound of claim 1 having formula (I-d):

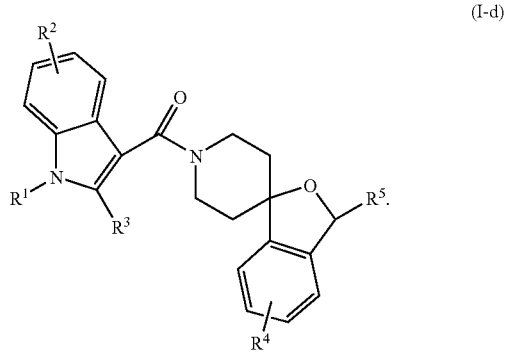

(I-d)

24. The compound of claim 23, wherein
  $R^1$ is H,
    $C_{1-6}$-alkyl optionally substituted by CN,
    aryl, 5 or 6 membered heteroaryl or sulfonylaryl, each of which is optionally substituted by one or more B,
    —$(CH_2)_m$—$R^a$ wherein $R^a$ is:
      $OR^i$,
      CN,
      $NR^iR^{ii}$, or
      $C_{3-6}$-cycloalkyl, 3 to 7 membered-heterocycloalkyl, aryl, or 5 or 6 membered heteroaryl, each of which is optionally substituted by one or more B,
    or —$(CH_2)_n$—(CO)—$R^b$ wherein $R^b$ is:
      $C_{1-6}$-alkoxy,
      $NR^iR^{ii}$, or
      4 to 7 membered-heterocycloalkyl, aryl, or 5 or 6 membered heteroaryl each of which is optionally substituted by one or more B,
  or $R^1$ and $R^3$ together with the indole ring to which they are attached form a 5 or 6 membered heterocycloalkyl which is optionally substituted by C(O)O—$C_{1-6}$-alkyl or $C_{1-6}$-alkyl;
  there is one or more $R^2$, wherein each $R^2$ is the same or different,
  $R^2$ is one or more H, halo, $C_{1-6}$-alkyl, or $C_{1-6}$-alkoxy;
  $R^3$ is H,
    $C_{1-6}$-alkyl,
    or —(CO)—$R^c$, wherein $R^c$ is $C_{1-6}$-alkyl or —$(CH_2)_n$—$NR^iR^{ii}$;
  there is one or more $R^4$, wherein each $R^4$ is the same or different,
  $R^4$ is one or more H, halo, or $C_{1-6}$-alkoxy optionally substituted by OH, or two $R^4$ together with the phenyl ring to which they are attached form an oxo or dioxo bridge;
  $R^5$ is H or aryl;
  B is halo,
    $NH_2$,
    $C_{1-6}$-alkyl optionally substituted by CN or $C_{1-6}$-alkoxy,
    $C_{1-6}$-alkoxy,
    $C_{1-6}$-haloalkoxy,
    $C_{3-6}$-cycloalkyl,
    —C(O)O—$C_{1-6}$-alkyl, or
    —$(CR^{iii}R^{iv})_n$-phenyl, wherein the phenyl is optionally substituted by one or more substituent(s) selected from the group consisting of:
      halo, $C_{1-6}$-alkyl optionally substituted by CN or halo, and $C_{1-6}$-alkoxy;

R$^i$ and R$^{ii}$ are each independently H, C$_{1-6}$-alkyl, C$_{1-6}$-alkyl-NR$^{iii}$R$^{iv}$, —(CO)O—C$_{1-6}$-alkyl, —C(O)—NR$^{iii}$R$^{iv}$, —C(O)—C$_{1-6}$-alkyl, —S(O)$_2$—C$_{1-6}$-alkyl, —S(O)$_2$—NR$^{iii}$R$^{iv}$ or OH;

R$^{iii}$ and R$^{iv}$ are each independently H or C$_{1-6}$-alkyl;

m is 1 to 6; and n is 0 to 4;

or a pharmaceutically acceptable salt thereof.

25. The compound of claim 23, wherein the compound is selected from the group consisting of:

1'-[(1-benzyl-2-methyl-1H-indol-3-yl)carbonyl]-3H-spiro[2-benzofuran-1,4'-piperidine];

1'-[(1-benzyl-2-methyl-1H-indol-3-yl)carbonyl]-6-chloro-3H-spiro[2-benzofuran-1,4'-piperidine];

1'-[(2-methyl-1H-indol-3-yl)carbonyl]-3H-spiro[2-benzofuran-1,4'-piperidine];

1'-[(1-benzoyl-2-methyl-1H-indol-3-yl)carbonyl]-3H-spiro[2-benzofuran-1,4'-piperidine];

1'-{[2-methyl-1-(phenylsulfonyl)-1H-indol-3-yl]carbonyl}-3H-spiro[2-benzofuran-1,4'-piperidine];

1'-{[1-(cyclohexylmethyl)-2-methyl-1H-indol-3-yl]carbonyl}-3H-spiro[2-benzofuran-1,4'-piperidine];

1'-{[1-(3-fluorobenzyl)-2-methyl-1H-indol-3-yl]carbonyl}-3H-spiro[2-benzofuran-1,4'-piperidine];

1'-({2-methyl-1-[2-(trifluoromethoxy)benzyl]-1H-indol-3-yl}carbonyl)-3H-spiro[2-benzofuran-1,4'-piperidine];

1'-{[1-(3,5-dimethylbenzyl)-2-methyl-1H-indol-3-yl]carbonyl}-3H-spiro[2-benzofuran-1,4'-piperidine]; and methyl 4-{[2-methyl-3-(1'H,3H-spiro[2-benzofuran-1,4'-piperidin]-1'-ylcarbonyl)-1H-indol-1-yl]methyl}benzoate.

26. The compound of claim 23, wherein the compound is selected from the group consisting of:

4-{[2-methyl-3-(1'H,3H-spiro[2-benzofuran-1,4'-piperidin]-1'-ylcarbonyl)-1H-indol-1-yl]methyl}benzonitrile;

1'-{[1-(3,5-difluorobenzyl)-2-methyl-1H-indol-3-yl]carbonyl}-3H-spiro[2-benzofuran-1,4'-piperidine];

1'-{[1-(2-chlorobenzyl)-2-methyl-1H-indol-3-yl]carbonyl}-3H-spiro[2-benzofuran-1,4'-piperidine];

1'-{[1-(2-methoxybenzyl)-2-methyl-1H-indol-3-yl]carbonyl}-3H-spiro[2-benzofuran-1,4'-piperidine];

1'-{[1-(4-methoxybenzyl)-2-methyl-1H-indol-3-yl]carbonyl}-3H-spiro[2-benzofuran-1,4'-piperidine];

1'-[(1-{[2-(2-methoxyphenyl)-5-methyl-1,3-oxazol-4-yl]methyl}-2-methyl-1H-indol-3-yl)carbonyl]-3H-spiro[2-benzofuran-1,4'-piperidine];

1'-[(1-benzyl-1H-indol-3-yl)carbonyl]-3H-spiro[2-benzofuran-1,4'-piperidine];

1'-[(6-chloro-1H-indol-3-yl)carbonyl]-3H-spiro[2-benzofuran-1,4'-piperidine];

N,N-dimethyl-2-[3-(1'H,3H-spiro[2-benzofuran-1,4'-piperidin]-1'-ylcarbonyl)-1H-indol-1-yl]ethanamine; and 2-methyl-1-[3-(1'H,3H-spiro[2-benzofuran-1,4'-piperidin]-1'-ylcarbonyl)-1H-indol-2-yl]butan-1-one.

27. The compound of claim 23, wherein the compound is selected from the group consisting of:

[6-chloro-3-(1'H,3H-spiro[2-benzofuran-1,4'-piperidin]-1'-ylcarbonyl)-1H-indol-1-yl]acetonitrile;

1'-{[6-chloro-1-(3-fluorobenzoyl)-1H-indol-3-yl]carbonyl}-3H-spiro[2-benzofuran-1,4'-piperidine];

1'-{[6-chloro-1-(2-fluorobenzoyl)-1H-indol-3-yl]carbonyl}-3H-spiro[2-benzofuran-1,4'-piperidine];

1'-{[6-chloro-1-(3,5-difluorobenzoyl)-1H-indol-3-yl]carbonyl}-3H-spiro[2-benzofuran-1,4'-piperidine];

1'-{[6-chloro-1-(2,3-difluorobenzoyl)-1H-indol-3-yl]carbonyl}-3H-spiro[2-benzofuran-1,4'-piperidine];

1'-{[6-chloro-1-(3,5-difluorobenzyl)-1H-indol-3-yl]carbonyl}-3H-spiro[2-benzofuran-1,4'-piperidine];

1'-{[6-chloro-1-(3-fluorobenzyl)-1H-indol-3-yl]carbonyl}-3H-spiro[2-benzofuran-1,4'-piperidine];

1'-{[6-chloro-1-(2-oxo-2-piperidin-1-ylethyl)-1H-indol-3-yl]carbonyl}-3H-spiro[2-benzofuran-1,4'-piperidine];

1'-{[6-chloro-1-(2-morpholin-4-yl-2-oxoethyl)-1H-indol-3-yl]carbonyl}-3H-spiro[2-benzofuran-1,4'-piperidine]; and 2-[6-chloro-3-(1'H,3H-spiro[2-benzofuran-1,4'-piperidin]-1'-ylcarbonyl)-1H-indol-1-yl]-N,N-dimethylacetamide.

28. The compound of claim 23, wherein the compound is selected from the group consisting of:

2-[6-chloro-3-(1'H,3H-spiro[2-benzofuran-1,4'-piperidin]-1'-ylcarbonyl)-1H-indol-1-yl]-N,N-diethylacetamide;

1'-{[6-chloro-1-(piperidin-1-ylcarbonyl)-1H-indol-3-yl]carbonyl}-3H-spiro[2-benzofuran-1,4'-piperidine];

tert-butyl[6-chloro-3-(1'H,3H-spiro[2-benzofuran-1,4'-piperidin]-1'-ylcarbonyl)-1H-indol-1-yl]acetate;

1'-{[6-chloro-1-(3,5-difluorophenyl)-1H-indol-3-yl]carbonyl}-3H-spiro[2-benzofuran-1,4'-piperidine];

1'-{[6-chloro-1-(3-fluorophenyl)-1H-indol-3-yl]carbonyl}-3H-spiro[2-benzofuran-1,4'-piperidine];

2-[6-chloro-3-(1'H,3H-spiro[2-benzofuran-1,4'-piperidin]-1'-ylcarbonyl)-1H-indol-1-yl]-1-(2-fluorophenyl)ethanone;

1'-[(6-chloro-1-pyridin-2-yl-1H-indol-3-yl)carbonyl]-3H-spiro[2-benzofuran-1,4'-piperidine];

1'-{[6-chloro-1-(pyridin-4-ylmethyl)-1H-indol-3-yl]carbonyl}-3H-spiro[2-benzofuran-1,4'-piperidine];

2-[6-chloro-3-(1'H,3H-spiro[2-benzofuran-1,4'-piperidin]-1'-ylcarbonyl)-1H-indol-1-yl]-1-pyridin-2-ylethanone; and 1'-{[6-chloro-1-(pyridin-3-ylmethyl)-1H-indol-3-yl]carbonyl}-3H-spiro[2-benzofuran-1,4'-piperidine].

29. The compound of claim 23, wherein the compound is selected from the group consisting of:

1'-{[6-chloro-1-(pyridin-2-ylmethyl)-1H-indol-3-yl]carbonyl}-3H-spiro[2-benzofuran-1,4'-piperidine];

1'-{[6-chloro-1-(pyrazin-2-ylmethyl)-1H-indol-3-yl]carbonyl}-3H-spiro[2-benzofuran-1,4'-piperidine];

1'-{[6-chloro-1-(pyrimidin-5-ylmethyl)-1H-indol-3-yl]carbonyl}-3H-spiro[2-benzofuran-1,4'-piperidine];

2-[6-chloro-3-(1'H,3H-spiro[2-benzofuran-1,4'-piperidin]-1'-ylcarbonyl)-1H-indol-1-yl]-N,N-dimethylethanamine;

1'-{[6-chloro-1-(2-oxo-2-piperazin-1-ylethyl)-1H-indol-3-yl]carbonyl}-3H-spiro[2-benzofuran-1,4'-piperidine];

1'-({1-[(4-benzylmorpholin-2-yl)methyl]-6-chloro-1H-indol-3-yl}carbonyl)-3H-spiro[2-benzofuran-1,4'-piperidine];

1'-({6-chloro-1-[(5-methylisoxazol-3-yl)methyl]-1H-indol-3-yl}carbonyl)-3H-spiro[2-benzofuran-1,4'-piperidine];

1'-({6-chloro-1-[2-(4-methylpiperazin-1-yl)-2-oxoethyl]-1H-indol-3-yl}carbonyl)-3H-spiro[2-benzofuran-1,4'-piperidine];

4-(1-{1-[(2-cyclopropyl-4-methylcyclopenta-1,4-dien-1-yl)methyl]-6-methyl-1H-inden-3-yl}vinyl)-2',3'-dihydrospiro[cyclohexane-1,1'-indene]; and 1'-({6-chloro-1-[(1-methyl-1H-imidazol-5-yl)methyl]-1H-indol-3-yl}carbonyl)-3H-spiro[2-benzofuran-1,4'-piperidine].

30. The compound of claim 23, wherein the compound is selected from the group consisting of:

1'-({6-chloro-1-[(3-methylisoxazol-5-yl)methyl]-1H-indol-3-yl}carbonyl)-3H-spiro[2-benzofuran-1,4'-piperidine];

1'-({6-chloro-1-[(1,5-dimethyl-1H-pyrazol-3-yl)methyl]-1H-indol-3-yl}carbonyl)-3H-spiro[2-benzofuran-1,4'-piperidine];

1'-({6-chloro-1-[(3,5-dimethylisoxazol-4-yl)methyl]-1H-indol-3-yl}carbonyl)-3H-spiro[2-benzofuran-1,4'-piperidine];

1'-({6-chloro-1-[(2,5-dimethyl-1,3-oxazol-4-yl)methyl]-1H-indol-3-yl}carbonyl)-3H-spiro[2-benzofuran-1,4'-piperidine];

1'-({6-chloro-1-[(3-fluorooxetan-3-yl)methyl]-1H-indol-3-yl}carbonyl)-3H-spiro[2-benzofuran-1,4'-piperidine];

1'-[(6-chloro-1-{[1-(methoxymethyl)-cyclopropyl]methyl}-1H-indol-3-yl)carbonyl]-3H-spiro[2-benzofuran-1,4'-piperidine];

(1-{[6-chloro-3-(1'H,3H-spiro[2-benzofuran-1,4'-piperidin]-1'-ylcarbonyl)-1H-indol-1-yl]methyl}cyclopropyl)acetonitrile;

1'-({6-chloro-1-[2-(tetrahydro-2H-pyran-4-yl)ethyl]-1H-indol-3-yl}carbonyl)-3H-spiro[2-benzofuran-1,4'-piperidine];

tert-butyl 2-{[6-chloro-3-(1'H,3H-spiro[2-benzofuran-1,4'-piperidin]-1'-ylcarbonyl)-1H-indol-1-yl]methyl}morpholine-4-carboxylate; and 1'-{[6-chloro-1-(morpholin-2-ylmethyl)-1H-indol-3-yl]carbonyl}-3H-spiro[2-benzofuran-1,4'-piperidine]hydrochloride.

31. The compound of claim 23, wherein the compound is selected from the group consisting of:

2-[6-chloro-3-(1'H,3H-spiro[2-benzofuran-1,4'-piperidin]-1'-ylcarbonyl)-1H-indol-1-yl]-N-[2-(dimethylamino)ethyl]acetamide;

2-[6-chloro-5-methyl-3-(1'H,3H-spiro[2-benzofuran-1,4'-piperidin]-1'-ylcarbonyl)-1H-indol-1-yl]-N,N-dimethylacetamide;

2-[6-chloro-3-(1'H,3H-spiro[2-benzofuran-1,4'-piperidin]-1'-ylcarbonyl)-1H-indol-1-yl]acetamide;

2-[6-chloro-3-(1'H,3H-spiro[2-benzofuran-1,4'-piperidin]-1'-ylcarbonyl)-1H-indol-1-yl]-N-[2-(methylamino)ethyl]acetamide;

N-(2-aminoethyl)-2-[6-chloro-3-(1'H,3H-spiro[2-benzofuran-1,4'-piperidin]-1'-ylcarbonyl)-1H-indol-1-yl]acetamide;

2-[6-chloro-3-(1'H,3H-spiro[2-benzofuran-1,4'-piperidin]-1'-ylcarbonyl)-1H-indol-1-yl]ethanamine;

2-[6-chloro-3-(1'H,3H-spiro[2-benzofuran-1,4'-piperidin]-1'-ylcarbonyl)-1H-indol-1-yl]-N-methylethanamine;

2-[6-chloro-3-(1'H,3H-spiro[2-benzofuran-1,4'-piperidin]-1'-ylcarbonyl)-1H-indol-1-yl]-N-methylacetamide;

1'-{[6-chloro-1-(2-morpholin-4-ylethyl)-1H-indol-3-yl]carbonyl}-3H-spiro[2-benzofuran-1,4'-piperidine]; and 1'-{[6-chloro-1-(3-morpholin-4-ylpropyl)-1H-indol-3-yl]carbonyl}-3H-spiro[2-benzofuran -1,4'-piperidine].

32. The compound of claim 23, wherein the compound is selected from the group consisting of:

1'-{[6-chloro-1-(oxiran-2-ylmethyl)-1H-indol-3-yl]carbonyl}-3H-spiro[2-benzofuran-1,4'-piperidine];

2-[6-chloro-3-(1'H,3H-spiro[2-benzofuran-1,4'-piperidin]-1'-ylcarbonyl)-1H-indol-1-yl]ethanol;

1'-({6-chloro-1-[(2-methylpyridin-4-yl)methyl]-1H-indol-3-yl}carbonyl)-3H-spiro[2-benzofuran-1,4'-piperidine];

1'-({6-chloro-1-[(3S)-piperidin-3-ylmethyl]-1H-indol-3-yl}carbonyl)-3H-spiro[2-benzofuran-1,4'-piperidine];

2-[6-chloro-3-(1'H,3H-spiro[2-benzofuran-1,4'-piperidin]-1'-ylcarbonyl)-1H-indol-1-yl]-N-hydroxyethanamine;

1'-{[6-chloro-1-(tetrahydro-2H-pyran-4-ylmethyl)-1H-indol-3-yl]carbonyl}-3H-spiro[2-benzofuran-1,4'-piperidine];

1'-({6-chloro-1-[(1-methylpyrrolidin-3-yl)methyl]-1H-indol-3-yl}carbonyl)-3H-spiro[2-benzofuran-1,4'-piperidine];

1'-[(6-chloro-1-{[(3S)-1-methylpiperidin-3-yl]methyl}-1H-indol-3-yl)carbonyl]-3H-spiro[2-benzofuran-1,4'-piperidine];

1'-{[6-chloro-1-(pyrrolidin-3-ylmethyl)-1H-indol-3-yl]carbonyl}-3H-spiro[2-benzofuran-1,4'-piperidine]; and 1'-({6-chloro-1-[(2S)-pyrrolidin-2-ylmethyl]-1H-indol-3-yl}carbonyl)-3H-spiro[2-benzofuran-1,4'-piperidine].

33. The compound of claim 23, wherein the compound is selected from the group consisting of:

1'-[(6-chloro-2-methyl-1H-indol-3-yl)carbonyl]-3H-spiro[2-benzofuran-1,4'-piperidine];

1'-(1,2,3,4-tetrahydropyrazino[1,2-a]indol-10-ylcarbonyl)-3H-spiro[2-benzofuran-1,4'-piperidine]hydrochloride;

1'-[(2-methyl-1,2,3,4-tetrahydropyrazino[1,2-a]indol-10-yl)carbonyl]-3H-spiro[2-benzofuran-1,4'-piperidine];

1'-[(6-chloro-2-methyl-1H-indol-3-yl)carbonyl]-3H-spiro[2-benzofuran-1,4'-piperidine];

N-[2-[6-chloro-3-(1'H,3H-spiro[2-benzofuran-1,4'-piperidin]-1'-ylcarbonyl)-1H-indol-1-yl]ethyl]acetamide;

N-{2-[6-chloro-3-(1'H,3H-spiro[2-benzofuran-1,4'-piperidin]-1'-ylcarbonyl)-1H-indol-1-yl]ethyl}methanesulfonamide;

N-{2-[6-chloro-3-(1'H,3H-spiro[2-benzofuran-1,4'-piperidin]-1'-ylcarbonyl)-1H-indol-1-yl]ethyl}-N-methylacetamide;

N-{2-[6-chloro-3-(1'H,3H-spiro[2-benzofuran-1,4'-piperidin]-1'-ylcarbonyl)-1H-indol-1-yl]ethyl}-N-methylmethanesulfonamide;

1'-[(6-chloro-1-{[(2S)-1-methylpyrrolidin-2-yl]methyl}-1H-indol-3-yl)carbonyl]-3H-spiro[2-benzofuran-1,4'-piperidine]; and 1'-[(6-chloro-1-{[(2R)-1-methylpyrrolidin-2-yl]methyl}-1H-indol-3-yl)carbonyl]-3H-spiro[2-benzofuran-1,4'-piperidine].

34. The compound of claim 1 having formula (I-e):

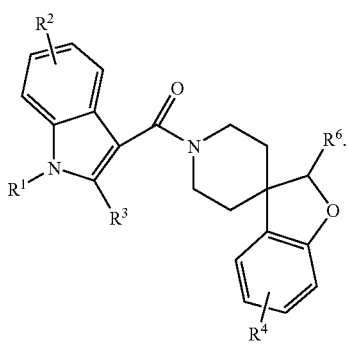

(I-e)

35. The compound of claim 34, wherein
R$^1$ is H,
  C$_{1-6}$-alkyl optionally substituted by CN,
  sulfonylaryl,
  —(CH$_2$)$_m$—R$^a$ wherein R$^a$ is:
    OR$^i$,
    CN,
    NR$^i$R$^{ii}$, and
    C$_{3-6}$-cycloalkyl, 3 to 6 membered-heterocycloalkyl, aryl or 5 or 6 membered heteroaryl, each of which is optionally substituted by one or more B,
  or —(CH$_2$)$_n$—(CO)—R$^b$, wherein R$^b$ is:
    C$_{1-6}$-alkoxy,
    NR$^i$R$^{ii}$, or
    5 or 6 membered-heterocycloalkyl, aryl, or 5 or 6 membered heteroaryl, each of which is optionally substituted by one or more B;
there is one or more R$^2$, wherein each R$^2$ is the same or different,
R$^2$ is one or more H, halo, of C$_{1-6}$-alkyl;
R$^3$ is H,
  C$_{1-6}$-alkyl,
  or —(CO)—R$^c$, wherein R$^c$ is:
    C$_{1-6}$-alkyl or
    —(CH$_2$)$_n$—NR$^i$R$^{ii}$,
there is one or more R$^4$, wherein each R$^4$ is the same or different,
R$^4$ is is one or more H, halo, or C$_{1-6}$-alkoxy optionally substituted by OH, or two R$^4$ together with the phenyl ring to which they are attached form an oxo or dioxo bridge;
R$^6$ is H;
B is halo,
  CN,
  C$_{1-6}$-alkyl optionally substituted by CN or C$_{1-6}$-alkoxy,
  C$_{1-6}$-alkoxy,
  C$_{1-6}$-haloalkoxy,
  C$_{3-6}$-cycloalkyl,
  —C(O)O—C$_{1-6}$-alkyl,
  —(CR$^{iii}$R$^{iv}$)$_n$-phenyl, wherein the phenyl is optionally substituted by one or more substituent(s) selected from the group consisting of:
    halo, C$_{1-6}$-alkyl optionally substituted by CN or halo, and C$_{1-6}$-alkoxy;
R$^i$ and R$^{ii}$ are each independently H, C$_{1-6}$-alkyl, C$_{1-6}$-alkyl-NR$^{iii}$R$^{iv}$, —C(O)—C$_{1-6}$-alkyl, —S(O)$_2$—C$_{1-6}$-alkyl or OH;
R$^{iii}$ and R$^{iv}$ are each independently H or C$_{1-6}$-alkyl;
m is 1 to 6; and
n is 0 to 4;
or a pharmaceutically acceptable salt thereof.

36. The compound of claim 34, wherein
R$^1$ is H
  —(CH$_2$)$_m$—R$^a$ wherein R$^a$ is 5 or 6 membered-heterocycloalkyl, aryl, or 5 or 6 membered heteroaryl,
  —(CH$_2$)$_m$—NR$^i$R$^{ii}$, or
  —(CH$_2$)$_n$—(CO)—R$^b$, wherein R$^b$ is 5 or 6 membered-heterocycloalkyl;
there is one or more R$^2$, wherein each R$^2$ is the same or different,
R$^2$ is one or more H or halo;
R$^3$ is H or C$_{1-6}$-alkyl;
there is one or more R$^4$, wherein each R$^4$ is the same or different,
R$^4$ is one or more H or halo;
R$^6$ is H;
R$^i$ and R$^{ii}$ are each indepdently C$_{1-6}$-alkyl;
m is 1 to 6; and
n is 0 to 4;
or a pharmaceutically acceptable salt thereof.

37. The compound of claim 34, wherein the compound is selected from the group consisting of:
  1'-[(6-chloro-1H-indol-3-yl)carbonyl]spiro[1-benzofuran-3,4'-piperidine];
  1'-[(1-benzyl-2-methyl-1H-indol-3-yl)carbonyl]spiro[1-benzofuran-3,4'-piperidine];
  1'-(1H-indol-3-ylcarbonyl)spiro[1-benzofuran-3,4'-piperidine];
  1'-[(6-chloro-5-fluoro-1H-indol-3-yl)carbonyl]spiro[1-benzofuran-3,4'-piperidine];
  2-[6-chloro-3-(1'H-spiro[1-benzofuran-3,4'-piperidin]-1'-ylcarbonyl)-1H-indol-1-yl]-N,N-dimethylethanamine;
  1'-{[6-chloro-1-(2-pyrrolidin-1-ylethyl)-1H-indol-3-yl]carbonyl}spiro[1-benzofuran-3,4'-piperidine];
  3-[6-chloro-3-(1'H-spiro[1-benzofuran-3,4'-piperidin]-1'-ylcarbonyl)-1H-indol-1-yl]-N,N-dimethylpropan-1-amine;
  1'-{[6-chloro-1-(2-morpholin-4-ylethyl)-1H-indol-3-yl]carbonyl}spiro[1-benzofuran-3,4'-piperidine];
  2-[6-chloro-3-(1'H-spiro[1-benzofuran-3,4'-piperidin]-1'-ylcarbonyl)-1H-indol-1-yl]-N,N-diethylethanamine;
  1'-({6-chloro-1-[2-(1H-pyrrol-1-yl)ethyl]-1H-indol-3-yl}carbonyl)spiro[1-benzofuran-3,4'-piperidine]; and
  1'-{[6-chloro-1-(2-oxo-2-piperidin-1-ylethyl)-1H-indol-3-yl]carbonyl}spiro[1-benzofuran-3,4'-piperidine].

38. The compound of claim 1 having formula (I-f):

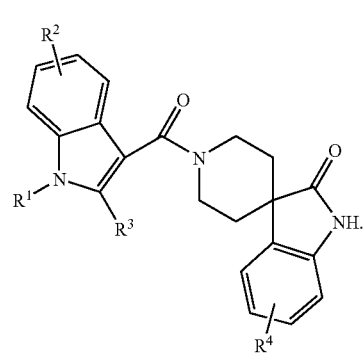

(I-f)

39. The compound of claim 38, wherein
R¹ is H,
  C$_{1-6}$-alkyl optionally substituted by CN,
  sulfonylaryl,
    —(CH$_2$)$_m$—R$^a$ wherein R$^a$ is:
      OR$^i$,
      CN,
      NR$^i$R$^{ii}$, or
      C$_{3-6}$-cycloalkyl, 3 to 6 membered-heterocycloalkyl, aryl or 5 or 6 membered heteroaryl, each of which is optionally substituted by one or more B,
    or —(CH$_2$)$_n$—(CO)—R$^b$, wherein R$^b$ is:
      C$_{1-6}$-alkoxy,
      NR$^i$R$^{ii}$, or
      6 membered-heterocycloalkyl, aryl, or 5 or 6 membered heteroaryl, each of which is optionally substituted by one or more B;
there is one or more R², wherein each R² is the same or different,
R² is one or more H, halo, or C$_{1-6}$-alkyl;
R³ is H,
  C$_{1-6}$-alkyl,
  or —(CO)—R$^c$, wherein R$^c$ is:
    C$_{1-6}$-alkyl or
    —(CH$_2$)$_n$—NR$^i$R$^{ii}$,
there is one or more R⁴, wherein each R⁴ is the same or different,
R⁴ is is one or more H, halo, or C$_{1-6}$-alkoxy optionally substituted by OH, or two R⁴ together with the phenyl ring to which they are attached form an oxo or dioxo bridge;
B is halo,
  CN,
  C$_{1-6}$-alkyl optionally substituted by CN or C$_{1-6}$-alkoxy,
  C$_{1-6}$-alkoxy,
  C$_{1-6}$-haloalkoxy,
  C$_{3-6}$-cycloalkyl,
  —C(O)O—C$_{1-6}$-alkyl,
  —(CR$^{iii}$R$^{iv}$)$_n$-phenyl, wherein the phenyl is optionally substituted by one or more substituent(s) selected from the group consisting of:
    halo, C$_{1-6}$-alkyl optionally substituted by CN or halo, and C$_{1-6}$-alkoxy;
R$^i$ and R$^{ii}$ are each independently H, C$_{1-6}$-alkyl, C$_{1-6}$-alkyl-NR$^{iii}$R$^{iv}$, —C(O)—C$_{1-6}$-alkyl, —S(O)$_2$—C$_{1-6}$-alkyl or OH;
R$^{iii}$ and R$^{iv}$ are each independently H or C$_{1-6}$-alkyl;
m is 1 to 6; and
n is 0 to 4;
or a pharmaceutically acceptable salt thereof.

40. The compound of claim 38, wherein
R¹ is H;
there is one or more R², wherein each R² is the same or different,
R² is one or more H or halo;
R³ is H;
there is one or more R⁴, wherein each R⁴ is the same or different,
R⁴ is one or more H or halo;
or a pharmaceutically acceptable salt thereof.

41. The compound of claims 38, wherein the compound is selected from the group consisting of
5-bromo-1'-(1H-indol-3-ylcarbonyl)spiro[indole-3,4'-piperidin]-2(1H)-one; and
5-bromo-1'-[(6-chloro-1H-indol-3-yl)carbonyl]spiro[indole-3,4'-piperidin]-2(1H)-one.

42. The compound of claim 1 having formula I-g:

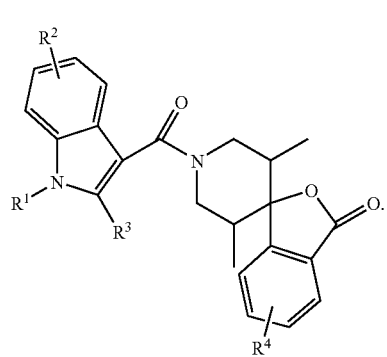

(I-g)

43. The compound of claim 42, wherein
R¹ is H,
  C$_{1-6}$-alkyl optionally substituted by CN,
  sulfonylaryl,
    —(CH$_2$)$_m$—R$^a$ wherein R$^a$ is:
      OR$^i$,
      CN,
      NR$^i$R$^{ii}$, or
      C$_{3-6}$-cycloalkyl, 3 to 6 membered-heterocycloalkyl, aryl or 5 or 6 membered heteroaryl, each of which is optionally substituted by one or more B,
    or —(CH$_2$)$_n$—(CO)—R$^b$, wherein R$^b$ is:
      C$_{1-6}$-alkoxy,
      NR$^i$R$^{ii}$, or
      6 membered-heterocycloalkyl, aryl, or 5 or 6 membered heteroaryl, each of which is optionally substituted by one or more B;
there is one or more R², wherein each R² is the same or different,
R² is one or more H, halo, or C$_{1-6}$-alkyl;
R³ is H,
  C$_{1-6}$-alkyl,
  or —(CO)—R$^c$, wherein R$^c$ is:
    C$_{1-6}$-alkyl or —(CH$_2$)$_n$—NR$^i$R$^{ii}$,
there is one or more R⁴, wherein each R⁴ is the same or different,
R⁴ is is one or more H, halo, or C$_{1-6}$-alkoxy optionally substituted by OH, or two R⁴ together with the phenyl ring to which they are attached form an oxo or dioxo bridge;
B is halo,
  CN,
  C$_{1-6}$-alkyl optionally substituted by CN or C$_{1-6}$-alkoxy,
  C$_{1-6}$-alkoxy,
  C$_{1-6}$-haloalkoxy,
  C$_{3-6}$-cycloalkyl,
  —C(O)O—C$_{1-6}$-alkyl,
  —(CR$^{iii}$R$^{iv}$)$_n$-phenyl, wherein the phenyl is optionally substituted by one or more substituent(s) selected from the group consisting of:
    halo, C$_{1-6}$-alkyl optionally substituted by CN or halo, and C$_{1-6}$-alkoxy;
R$^i$ and R$^{ii}$ are each independently H, C$_{1-6}$-alkyl, C$_{1-6}$-alkyl-NR$^{iii}$R$^{iv}$, —C(O)—C$_{1-6}$-alkyl, —S(O)$_2$—C$_{1-6}$-alkyl or OH;
R$^{iii}$ and R$^{iv}$ are each indepdently H or C$_{1-6}$-alkyl;
m is 1 to 6; and
n is 0 to 4;
or a pharmaceutically acceptable salt thereof.

44. The compound of claim 42, wherein
R$^1$ is H, or
—(CH$_2$)$_m$—R$^a$ wherein R$^a$ is aryl;
there is one or more R$^2$, wherein each R$^2$ is the same or different,
R$^2$ is one or more H or halo;
R$^3$ is H,
or C$_{1-6}$-alkyl;
R$^4$ is H;
R$^6$ is H;
or a pharmaceutically acceptable salt thereof.

45. The compound of claim 42, wherein the compound is selected from the group consisting of
(SS,RR)-1'-[(1-benzyl-2-methyl-1H-indol-3-yl)carbonyl]-3',5'-dimethyl-3H-spiro[2-benzofuran-1,4'-piperidin]-3-one;
(RS,SR)-1'-[(6-chloro-1H-indol-3-yl)carbonyl]-3',5'-dimethyl-3H-spiro[2-benzofuran-1,4'-piperidin]-3-one;
(RS,SR)-1'-[(1-benzyl-2-methyl-1H-indol-3-yl)carbonyl]-3',5'-dimethyl-3H-spiro[2-benzofuran-1,4'-piperidin]-3-one; and
(1r,3'R,5'S)-1'-[(1-benzyl-2-methyl-1H-indol-3-yl)carbonyl]-3',5'-dimethyl-3H-spiro[2-benzofuran-1,4'-piperidin]-3-one.

46. The compound of claim 1: having formula (I-h)

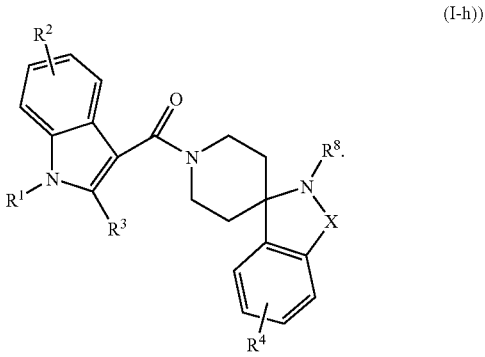

(I-h)

47. The compound of claim 46, wherein
R$^1$ is H,
C$_{1-6}$-alkyl optionally substituted by CN, sulfonylaryl,
—(CH$_2$)$_m$—R$^a$ wherein R$^a$ is:
OR$^i$,
CN,
NR$^i$R$^{ii}$, or
C$_{3-6}$-cycloalkyl, 3 to 6 membered-heterocycloalkyl, aryl or 5 or 6 membered heteroaryl, each of which is optionally substituted by one or more B,
or —(CH$_2$)$_n$—(CO)—R$^b$, wherein R$^b$ is:
C$_{1-6}$-alkoxy,
NR$^i$R$^{ii}$, or
6 membered-heterocycloalkyl, aryl, or 5 or 6 membered heteroaryl, each of which is optionally substituted by one or more B;
there is one or more R$^2$, wherein each R$^2$ is the same or different,
R$^2$ is one or more H, halo, or C$_{1-6}$-alkyl;
R$^3$ is H,
C$_{1-6}$-alkyl,
or —(CO)—R$^c$, wherein R$^c$ is:
C$_{1-6}$-alkyl or
—(CH$_2$)$_n$—NR$^i$R$^{ii}$,
there is one or more R$^4$, wherein each R$^4$ is the same or different,
R$^4$ is one or more H, halo, or C$_{1-6}$-alkoxy optionally substituted by OH, or two R$^4$ together with the phenyl ring to which they are attached form an oxo or dioxo bridge;
R$^8$ is H or C$_{1-6}$-alkyl;
X is CH$_2$ or C=O;
B is halo,
CN,
C$_{1-6}$-alkyl optionally substituted by CN or C$_{1-6}$-alkoxy,
C$_{1-6}$-alkoxy,
C$_{1-6}$-haloalkoxy,
C$_{3-6}$-cycloalkyl,
—C(O)O—C$_{1-6}$-alkyl,
—(CR$^{iii}$R$^{iv}$)$_n$-phenyl, wherein the phenyl is optionally substituted by one or more substituent(s) selected from the group consisting of:
halo, C$_{1-6}$-alkyl optionally substituted by CN or halo, and C$_{1-6}$-alkoxy;
R$^i$ and R$^{ii}$ are each indepdently H, C$_{1-6}$-alkyl, C$_{1-6}$-alkyl-NR$^{iii}$R$^{iv}$, —C(O)—C$_{1-6}$-alkyl, —S(O)$_2$—C$_{1-6}$-alkyl or OH;
R$^{iii}$ and R$^{iv}$ are each independently H or C$_{1-6}$-alkyl;
m is 1 to 6; and
n is 0 to 4;
or a pharmaceutically acceptable salt thereof.

48. The compound of claim 46, wherein
R$^1$ is H,
or —(CH$_2$)$_n$—(CO)—R$^b$, wherein R$^b$ is NR$^i$R$^{ii}$;
there is one or more R$^2$, wherein each R$^2$ is the same or different,
R$^2$ is one or more H or halo;
R$^3$ is H;
R$^4$ is H;
R$^8$ is H or C$_{1-6}$-alkyl;
X is CH$_2$ or C=O; and
R$^i$ and R$^{ii}$ are each indepdently H or C$_{1-6}$-alkyl;
or a pharmaceutically acceptable salt thereof.

49. The compound of claim 46, wherein said compound is selected from the group consisting of
1'-[(6-chloro-1H-indol-3-yl)carbonyl]spiro[isoindole-1,4'-piperidin]-3(2H)-one;
1'-[(6-chloro-1H-indol-3-yl)carbonyl]-2-methyl-2,3-dihydrospiro[isoindole-1,4'-piperidine];
1'-[(6-chloro-1H-indol-3-yl)carbonyl]-2,3-dihydrospiro[isoindole-1,4'-piperidine]; and
2-{6-chloro-3-[(3-oxo-2,3-dihydro-1'H-spiro[isoindole-1,4'-piperidin]-1'-yl)carbonyl]-1H-indol-1-yl}-N-methylacetamide.

50. A pharmaceutical composition comprising one or more compound of formula (I)

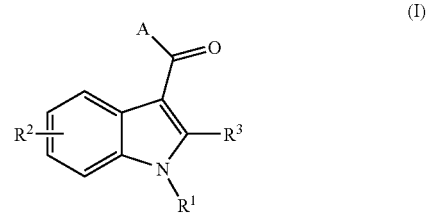

(I)

wherein
A is selected from the group consisting of (a), (b), (c), (d), (e), (f), (g) and (h):

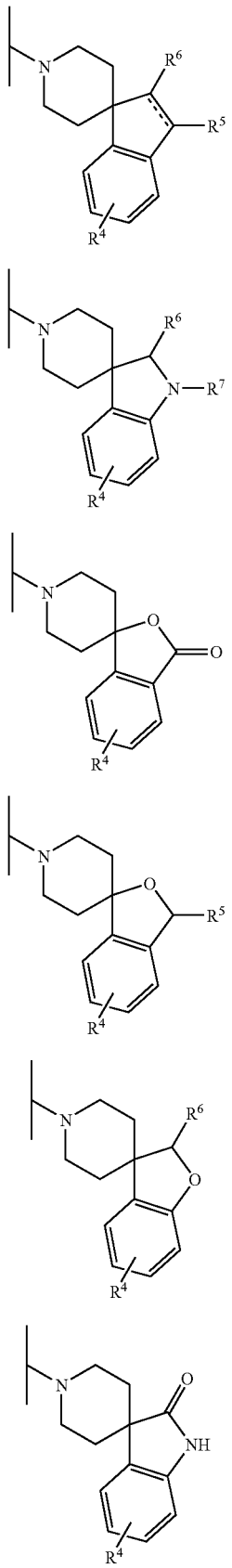

wherein in (a) the dotted line is an optional double bond;

R¹ is H,

C$_{1-6}$-alkyl optionally substituted by CN, aryl, 5 or 6 membered heteroaryl or sulfonylaryl, each of which is optionally substituted by one or more B, —(CH$_2$)$_m$—R$^a$ wherein R$^a$ is:

CN,

OR$^i$,

NR$^i$R$^{ii}$, or

C$_{3-6}$-cycloalkyl, 3 to 7 membered-heterocycloalkyl, aryl, or 5 or 6 membered heteroaryl, each of which is optionally substituted by one or more B, or —(CH$_2$)$_n$—(CO)—R$^b$ or —(CH$_2$)$_n$—(SO$_2$)—R$^b$, wherein R$^b$ is:

C$_{1-6}$-alkyl,

C$_{1-6}$-alkoxy,

C$_{3-6}$-cycloalkyl,

—(CH$_2$)$_m$—NR$^{iii}$R$^{iv}$,

NR$^i$R$^{ii}$, or

C$_{3-6}$-cycloalkyl, 4 to 7 membered-heterocycloalkyl, aryl, or 5 or 6 membered heteroaryl, each of which is optionally substituted by one or more B, or R¹ and R³ together with the indole ring to which they are attached form a 5 or 6 membered heterocycloalkyl which is optionally substituted by =O, C(O)O—C$_{1-6}$-alkyl or C$_{1-6}$-alkyl;

there is one or more R², wherein each R² is the same or different,

R² is one or more H, OH, halo, CN, nitro, C$_{1-6}$-alkyl optionally substituted by —NR$^{iii}$R$^{iv}$, C$_{1-6}$-alkoxy, —O—CH$_2$—C$_{2-6}$-alkenyl, or benzyloxy, or two R² together with the indole ring to which they are attached form an oxo or dioxo bridge;

R³ is H, halo,

—(CO)—R$^c$, wherein R$^c$ is:

C$_{1-6}$-alkyl,

—(CH$_2$)$_n$—NR$^i$R$^{ii}$,

—(CH$_2$)$_n$—NR$^{iii}$R$^{iv}$, or 5 or 6 membered heterocycloalkyl optionally substituted by C$_{1-6}$-alkyl, or $C_{1-6}$-alkyl or aryl, each of which is optionally substituted by
halo,
—O(CO)—$C_{1-6}$-alkyl, or
—NH(CO)$R^d$, wherein $R^d$ is $C_{1-6}$-alkyl optionally substituted by halo or nitro, or $R^d$ is aryl or a 5 or 6 membered heteroaryl, each of which is optionally substituted by halo, nitro, $C_{1-6}$-alkyl or $C_{1-6}$-haloalkyl;

there is one or more $R^4$, wherein each $R^4$ is the same or different, $R^4$ is one or more H, halo, $C_{1-6}$-alkyl or $C_{1-6}$-alkoxy optionally substituted by OH, or two $R^4$ together with the phenyl ring to which they are attached form an oxo or dioxo bridge;

$R^5$ is H, $C_{1-6}$-alkyl or aryl;

$R^6$ is H or $C_{1-6}$-alkyl;

$R^7$ is H or —$SO_2$—$R^e$ wherein $R^e$ is $C_{1-6}$-alkyl or aryl;

$R^8$ is H or $C_{1-6}$-alkyl;

X is $CH_2$ or C=O;

B is halo,
CN,
$NR^iR^{ii}$,
$C_{1-6}$-alkyl optionally substituted by CN, halo or $C_{1-6}$-alkoxy,
$C_{1-6}$-alkoxy,
$C_{1-6}$-haloalkoxy,
$C_{3-6}$-cycloalkyl,
—C(O)O—$C_{1-6}$-alkyl,
—C(O)$NR^iR^{ii}$,
—C(O)—$C_{1-6}$-alkyl,
—$S(O)_2$—$C_{1-6}$-alkyl, or
—$S(O)_2$—$NR^iR^{ii}$, $(CR^{iii}R^{iv})_n$-phenyl, or $(CR^{iii}R^{iv})_n$-5 or 6 membered heteroaryl wherein the phenyl or 5 or 6 membered heteroaryl moiety is optionally substituted by one or more substituent(s) selected from the group consisting of:
halo,
CN,
$NR^iR^{ii}$,
$C_{1-6}$-alkyl optionally substituted by CN, halo or $C_{1-6}$-alkoxy,
$C_{1-6}$-alkoxy,
$C_{1-6}$-haloalkoxy,
$C_{3-6}$-cycloalkyl,
—C(O)O—$C_{1-6}$-alkyl,
—C(O)—$NR^iR^{ii}$,
—C(O)—$C_{1-6}$-alkyl,
—$S(O)_2$—$C_{1-6}$-alkyl, and
—$S(O)_2$—$NR^iR^{ii}$;

$R^i$ and $R^{ii}$ are each independently H, $C_{1-6}$-alkyl, $C_{1-6}$-alkyl-$NR^{iii}R^{iv}$, —(CO)O—$C_{1-6}$-alkyl, —C(O)—$NR^{iii}R^{iv}$, —C(O)—$C_{1-6}$-alkyl, —$S(O)_2$—$C_{1-6}$-alkyl, —$S(O)_2$—$NR^{iii}R^{iv}$ or OH;

$R^{iii}$ and $R^{iv}$ are each independently H or $C_{1-6}$-alkyl;

m is 1 to 6; and n is 0 to 4;

or a pharmaceutically acceptable salt thereof and a pharmaceutically acceptable carrier.

* * * * *